US012788561B2

(12) United States Patent
Peleg et al.

(10) Patent No.: US 12,788,561 B2
(45) Date of Patent: Nov. 10, 2026

(54) VALVE LEAFLET TREATMENT SYSTEMS AND METHODS

(71) Applicant: Edwards Lifesciences Innovation (Israel) Ltd., Caesarea (IL)

(72) Inventors: Carmel Peleg, Pardes Hana-Karkur (IL); Yaron Herman, Givat Ada (IL); Gad Tennenbaum, Kiryat Ono (IL); Hannah Cohn, Tel Aviv (IL); Rami Rahamim Mazon, D.N.Modi'in (IL); Ido Halabi, Givatayim (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 690 days.

(21) Appl. No.: 18/317,005

(22) Filed: May 12, 2023

(65) Prior Publication Data

US 2023/0404758 A1 Dec. 21, 2023

Related U.S. Application Data

(63) Continuation of application No. PCT/IB2021/060436, filed on Nov. 11, 2021.

(Continued)

(51) Int. Cl.
*A61F 2/24* (2006.01)

(52) U.S. Cl.
CPC .......... *A61F 2/2463* (2013.01); *A61F 2/2466* (2013.01); *A61F 2/2469* (2013.01);

(Continued)

(58) Field of Classification Search
CPC ...... A61B 17/0469; A61B 2017/00243; A61B 2017/0427; A61B 2017/0437;

(Continued)

(56) References Cited

U.S. PATENT DOCUMENTS 3,604,488 A 9/1971 Wishart et al.
3,656,185 A 4/1972 Carpentier (Continued)

FOREIGN PATENT DOCUMENTS

CN 113331995 A 9/2021
EP 1034753 A1 9/2000

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Katherine M Shi
(74) *Attorney, Agent, or Firm* — Thomas C. Richardson

(57) ABSTRACT

An implant comprises a leaflet-augmentation patch, a patch anchor, and a cord. The patch comprises a flexible sheet, and a frame that supports the flexible sheet. The frame defines a spring configured to tension the cord. The cord couples the patch anchor to the patch in a manner in which anchoring the patch anchor to a first leaflet of a heart valve of a subject positions the patch to coapt with a second leaflet of the valve during ventricular systole. Other embodiments are also described.

23 Claims, 102 Drawing Sheets

Related U.S. Application Data

(60) Provisional application No. 63/113,430, filed on Nov. 13, 2020.

(52) U.S. Cl.
CPC ................ *A61F 2220/0016* (2013.01); *A61F 2220/0075* (2013.01)

(58) Field of Classification Search
CPC ...... A61B 2017/0441; A61B 2017/047; A61B 2017/0406; A61B 2017/0409; A61B 2017/0417; A61B 2017/0419; A61B 2017/0464; A61B 2017/0472; A61B 2017/0495; A61B 2017/0496; A61B 17/0401; A61F 2/2457; A61F 2/2463; A61F 2/2466; A61F 2/2469; A61F 2220/0016; A61F 2220/0075
See application file for complete search history.

(56) References Cited

U.S. PATENT DOCUMENTS 3,840,018 A 10/1974 Heifetz
3,881,366 A 5/1975 Bradley et al.
3,898,701 A 8/1975 La Russa
4,042,979 A 8/1977 Angell
4,118,805 A 10/1978 Reimels
4,214,349 A 7/1980 Munch
4,261,342 A 4/1981 Aranguren Duo
4,290,151 A 9/1981 Massana
4,434,828 A 3/1984 Trincia
4,473,928 A 10/1984 Johnson
4,602,911 A 7/1986 Ahmadi et al.
4,625,727 A 12/1986 Leiboff
4,712,549 A 12/1987 Peters et al.
4,778,468 A 10/1988 Hunt et al.
4,917,698 A 4/1990 Carpentier et al.
4,935,027 A 6/1990 Yoon
4,961,738 A 10/1990 Mackin
5,042,707 A 8/1991 Taheri
5,061,277 A 10/1991 Carpentier et al.
5,064,431 A 11/1991 Gilbertson et al.
5,104,407 A 4/1992 Lam et al.
5,108,420 A 4/1992 Marks
5,201,880 A 4/1993 Wright et al.
5,258,008 A 11/1993 Wilk
5,300,034 A 4/1994 Behnke et al.
5,325,845 A 7/1994 Adair
5,346,498 A 9/1994 Greelis et al.
5,383,852 A 1/1995 Stevens-Wright
5,449,368 A 9/1995 Kuzmak
5,450,860 A 9/1995 O'Connor
5,464,404 A 11/1995 Abela et al.
5,474,518 A 12/1995 Farrer Velazquez
5,477,856 A 12/1995 Lundquist
5,593,424 A 1/1997 Northrup, III
5,601,572 A 2/1997 Middleman et al.
5,626,609 A 5/1997 Zvenyatsky et al.
5,643,317 A 7/1997 Pavcnik et al.
5,669,919 A 9/1997 Sanders et al.
5,676,653 A 10/1997 Taylor et al.
5,683,402 A 11/1997 Cosgrove et al.
5,702,397 A 12/1997 Goble et al.
5,702,398 A 12/1997 Tarabishy
5,709,695 A 1/1998 Northrup, III
5,716,370 A 2/1998 Williamson, IV et al.
5,716,397 A 2/1998 Myers
5,728,116 A 3/1998 Rosenman
5,730,150 A 3/1998 Peppel et al.
5,749,371 A 5/1998 Zadini et al.
5,752,963 A 5/1998 Allard et al.
5,782,844 A 7/1998 Yoon et al.
5,810,882 A 9/1998 Bolduc et al.
5,824,066 A 10/1998 Gross
5,830,221 A 11/1998 Stein et al.
5,843,120 A 12/1998 Israel et al.
5,855,614 A 1/1999 Stevens et al.
5,876,373 A 3/1999 Giba et al.
5,935,098 A 8/1999 Blaisdell et al.
5,957,953 A 9/1999 DiPoto et al.
5,961,440 A 10/1999 Schweich, Jr. et al.
5,961,539 A 10/1999 Northrup, III et al.
5,984,959 A 11/1999 Robertson et al.
5,993,459 A 11/1999 Larsen et al.
6,042,554 A 3/2000 Rosenman et al.
6,045,497 A 4/2000 Schweich, Jr. et al.
6,050,936 A 4/2000 Schweich, Jr. et al.
6,059,715 A 5/2000 Schweich, Jr. et al.
6,074,341 A 6/2000 Anderson et al.
6,074,401 A 6/2000 Gardiner et al.
6,074,417 A 6/2000 Peredo
6,086,582 A 7/2000 Altman et al.
6,102,945 A 8/2000 Campbell
6,106,550 A 8/2000 Magovern et al.
6,110,200 A 8/2000 Hinnenkamp
6,132,390 A 10/2000 Cookston et al.
6,143,024 A 11/2000 Campbell et al.
6,159,240 A 12/2000 Sparer et al.
6,165,119 A 12/2000 Schweich, Jr. et al.
6,174,332 B1 1/2001 Loch et al.
6,183,411 B1 2/2001 Mortier et al.
6,187,040 B1 2/2001 Wright
6,210,347 B1 4/2001 Forsell
6,217,610 B1 4/2001 Carpentier et al.
6,228,032 B1 5/2001 Eaton et al.
6,231,602 B1 5/2001 Carpentier et al.
6,251,092 B1 6/2001 Qin et al.
6,296,656 B1 10/2001 Bolduc et al.
6,315,784 B1 11/2001 Djurovic
6,319,281 B1 11/2001 Patel
6,328,746 B1 12/2001 Gambale
6,332,893 B1 12/2001 Mortier et al.
6,355,030 B1 3/2002 Aldrich et al.
6,361,559 B1 3/2002 Houser et al.
6,368,348 B1 4/2002 Gabbay
6,402,780 B2 6/2002 Williamson, IV et al.
6,406,420 B1 6/2002 McCarthy et al.
6,406,493 B1 6/2002 Tu et al.
6,419,696 B1 7/2002 Ortiz et al.
6,451,054 B1 9/2002 Stevens
6,458,076 B1 10/2002 Pruitt
6,461,336 B1 10/2002 Larre
6,461,366 B1 10/2002 Seguin
6,470,892 B1 10/2002 Forsell
6,503,274 B1 1/2003 Howanec, Jr. et al.
6,524,338 B1 2/2003 Gundry
6,527,780 B1 3/2003 Wallace et al.
6,530,952 B2 3/2003 Vesely
6,533,772 B1 3/2003 Sherts et al.
6,537,314 B2 3/2003 Langberg et al.
6,547,801 B1 4/2003 Dargent et al.
6,554,845 B1 4/2003 Fleenor et al.
6,564,805 B2 5/2003 Garrison et al.
6,565,603 B2 5/2003 Cox
6,569,198 B1 5/2003 Wilson et al.
6,579,297 B2 6/2003 Bicek et al.
6,589,160 B2 7/2003 Schweich, Jr. et al.
6,592,593 B1 7/2003 Parodi et al.
6,602,288 B1 8/2003 Cosgrove et al.
6,602,289 B1 8/2003 Colvin et al.
6,613,078 B1 9/2003 Barone
6,613,079 B1 9/2003 Wolinsky et al.
6,619,291 B2 9/2003 Hlavka et al.
6,626,899 B2 9/2003 Houser et al.
6,626,917 B1 9/2003 Craig
6,626,930 B1 9/2003 Allen et al.
6,629,534 B1 10/2003 St. Goar et al.
6,629,921 B1 10/2003 Schweich, Jr. et al.
6,651,671 B1 11/2003 Donlon et al.
6,652,556 B1 11/2003 VanTassel et al.
6,682,558 B2 1/2004 Tu et al.
6,689,125 B1 2/2004 Keith et al.
6,689,164 B1 2/2004 Seguin

(56) References Cited

U.S. PATENT DOCUMENTS 6,695,866 B1 2/2004 Kuehn et al.
6,702,826 B2 3/2004 Liddicoat et al.
6,702,846 B2 3/2004 Mikus et al.
6,706,065 B2 3/2004 Langberg et al.
6,709,385 B2 3/2004 Forsell
6,709,456 B2 3/2004 Langberg et al.
6,711,444 B2 3/2004 Koblish
6,719,786 B2 4/2004 Ryan et al.
6,723,038 B1 4/2004 Schroeder et al.
6,726,716 B2 4/2004 Marquez
6,726,717 B2 4/2004 Alfieri et al.
6,749,630 B2 6/2004 McCarthy et al.
6,752,813 B2 6/2004 Goldfarb et al.
6,764,310 B1 7/2004 Ichihashi et al.
6,764,510 B2 7/2004 Vidlund et al.
6,764,810 B2 7/2004 Ma et al.
6,770,083 B2 8/2004 Seguin
6,786,924 B2 9/2004 Ryan et al.
6,786,925 B1 9/2004 Schoon et al.
6,790,231 B2 9/2004 Liddicoat et al.
6,797,001 B2 9/2004 Mathis et al.
6,797,002 B2 9/2004 Spence et al.
6,802,319 B2 10/2004 Stevens et al.
6,805,710 B2 10/2004 Bolling et al.
6,805,711 B2 10/2004 Quijano et al.
6,855,126 B2 2/2005 Flinchbaugh
6,858,039 B2 2/2005 McCarthy
6,884,250 B2 4/2005 Monassevitch et al.
6,893,459 B1 5/2005 Macoviak
6,908,478 B2 6/2005 Alferness et al.
6,908,482 B2 6/2005 McCarthy et al.
6,918,917 B1 7/2005 Nguyen et al.
6,926,730 B1 8/2005 Nguyen et al.
6,960,217 B2 11/2005 Bolduc
6,976,995 B2 12/2005 Mathis et al.
6,986,775 B2 1/2006 Morales et al.
6,989,028 B2 1/2006 Lashinski et al.
6,997,951 B2 2/2006 Solem et al.
7,004,176 B2 2/2006 Lau
7,007,798 B2 3/2006 Happonen et al.
7,011,669 B2 3/2006 Kimblad
7,011,682 B2 3/2006 Lashinski et al.
7,018,406 B2 3/2006 Seguin et al.
7,037,334 B1 5/2006 Hlavka et al.
7,077,850 B2 7/2006 Kortenbach
7,077,862 B2 7/2006 Vidlund et al.
7,087,064 B1 8/2006 Hyde
7,101,395 B2 9/2006 Tremulis et al.
7,101,396 B2 9/2006 Artof et al.
7,112,207 B2 9/2006 Allen et al.
7,118,595 B2 10/2006 Ryan et al.
7,125,421 B2 10/2006 Tremulis et al.
7,150,737 B2 12/2006 Purdy et al.
7,159,593 B2 1/2007 McCarthy et al.
7,166,127 B2 1/2007 Spence et al.
7,169,187 B2 1/2007 Datta et al.
7,172,625 B2 2/2007 Shu et al.
7,175,660 B2 2/2007 Cartledge et al.
7,186,262 B2 3/2007 Saadat
7,186,264 B2 3/2007 Liddicoat et al.
7,189,199 B2 3/2007 McCarthy et al.
7,192,443 B2 3/2007 Solem et al.
7,220,277 B2 5/2007 Arru et al.
7,226,467 B2 6/2007 Lucatero et al.
7,226,477 B2 6/2007 Cox
7,226,647 B2 6/2007 Kasperchik et al.
7,229,452 B2 6/2007 Kayan
7,238,191 B2 7/2007 Bachmann
7,288,097 B2 10/2007 Seguin
7,294,148 B2 11/2007 McCarthy
7,311,728 B2 12/2007 Solem et al.
7,311,729 B2 12/2007 Mathis et al.
7,314,485 B2 1/2008 Mathis
7,316,710 B1 1/2008 Cheng et al.
7,329,279 B2 2/2008 Haug et al.
7,329,280 B2 2/2008 Bolling et al.
7,335,213 B1 2/2008 Hyde et al.
7,361,190 B2 4/2008 Shaoulian et al.
7,364,588 B2 4/2008 Mathis et al.
7,377,941 B2 5/2008 Rhee et al.
7,390,329 B2 6/2008 Westra et al.
7,404,824 B1 7/2008 Webler et al.
7,431,692 B2 10/2008 Zollinger et al.
7,442,207 B2 10/2008 Rafiee
7,452,376 B2 11/2008 Lim et al.
7,455,690 B2 11/2008 Cartledge et al.
7,485,142 B2 2/2009 Milo
7,485,143 B2 2/2009 Webler et al.
7,500,989 B2 3/2009 Solem et al.
7,507,252 B2 3/2009 Lashinski et al.
7,510,575 B2 3/2009 Spenser et al.
7,510,577 B2 3/2009 Moaddeb et al.
7,527,647 B2 5/2009 Spence
7,530,995 B2 5/2009 Quijano et al.
7,549,983 B2 6/2009 Roue et al.
7,559,936 B2 7/2009 Levine
7,562,660 B2 7/2009 Saadat
7,563,267 B2 7/2009 Goldfarb et al.
7,563,273 B2 7/2009 Goldfarb et al.
7,569,062 B1 8/2009 Kuehn et al.
7,585,321 B2 9/2009 Cribier
7,588,582 B2 9/2009 Starksen et al.
7,591,826 B2 9/2009 Alferness et al.
7,604,646 B2 10/2009 Goldfarb et al.
7,608,091 B2 10/2009 Goldfarb et al.
7,608,103 B2 10/2009 McCarthy
7,618,449 B2 11/2009 Tremulis et al.
7,625,403 B2 12/2009 Krivoruchko
7,632,303 B1 12/2009 Stalker et al.
7,635,329 B2 12/2009 Goldfarb et al.
7,635,386 B1 12/2009 Gammie
7,655,015 B2 2/2010 Goldfarb et al.
7,666,204 B2 2/2010 Thornton et al.
7,682,319 B2 3/2010 Martin et al.
7,682,369 B2 3/2010 Seguin
7,686,822 B2 3/2010 Shayani
7,699,892 B2 4/2010 Rafiee et al.
7,704,269 B2 4/2010 St. Goar et al.
7,704,277 B2 4/2010 Zakay et al.
7,722,666 B2 5/2010 Lafontaine
7,736,388 B2 6/2010 Goldfarb et al.
7,748,389 B2 7/2010 Salahieh et al.
7,753,924 B2 7/2010 Starksen et al.
7,758,632 B2 7/2010 Hojeibane et al.
7,780,726 B2 8/2010 Seguin
7,871,368 B2 1/2011 Zollinger et al.
7,871,433 B2 1/2011 Lattouf
7,883,475 B2 2/2011 Dupont et al.
7,883,538 B2 2/2011 To et al.
7,892,281 B2 2/2011 Seguin et al.
7,927,370 B2 4/2011 Webler et al.
7,927,371 B2 4/2011 Navia et al.
7,942,927 B2 5/2011 Kaye et al.
7,947,056 B2 5/2011 Griego et al.
7,955,315 B2 6/2011 Feinberg et al.
7,955,377 B2 6/2011 Melsheimer
7,981,152 B1 7/2011 Webler et al.
7,992,567 B2 8/2011 Hirotsuka et al.
7,993,368 B2 8/2011 Gambale et al.
7,993,397 B2 8/2011 Lashinski et al.
8,012,201 B2 9/2011 Lashinski et al.
8,034,103 B2 10/2011 Burriesci et al.
8,052,592 B2 11/2011 Goldfarb et al.
8,057,493 B2 11/2011 Goldfarb et al.
8,062,355 B2 11/2011 Figulla et al.
8,070,804 B2 12/2011 Hyde et al.
8,070,805 B2 12/2011 Vidlund et al.
8,075,616 B2 12/2011 Solem et al.
8,100,964 B2 1/2012 Spence
8,123,801 B2 2/2012 Milo
8,142,493 B2 3/2012 Spence et al.
8,142,495 B2 3/2012 Hasenkam et al.
8,142,496 B2 3/2012 Berreklouw
8,147,542 B2 4/2012 Maisano et al.

(56) References Cited

U.S. PATENT DOCUMENTS

| | | | |
|---|---|---|---|
| 8,152,844 | B2 | 4/2012 | Rao et al. |
| 8,163,013 | B2 | 4/2012 | Machold et al. |
| 8,187,299 | B2 | 5/2012 | Goldfarb et al. |
| 8,187,324 | B2 | 5/2012 | Webler et al. |
| 8,202,315 | B2 | 6/2012 | Hlavka et al. |
| 8,206,439 | B2 | 6/2012 | Gomez Duran |
| 8,216,302 | B2 | 7/2012 | Wilson et al. |
| 8,231,671 | B2 | 7/2012 | Kim |
| 8,262,725 | B2 | 9/2012 | Subramanian |
| 8,265,758 | B2 | 9/2012 | Policker et al. |
| 8,277,502 | B2 | 10/2012 | Miller et al. |
| 8,287,584 | B2 | 10/2012 | Salahieh et al. |
| 8,287,591 | B2 | 10/2012 | Keidar et al. |
| 8,292,884 | B2 | 10/2012 | Levine et al. |
| 8,303,608 | B2 | 11/2012 | Goldfarb et al. |
| 8,323,334 | B2 | 12/2012 | Deem et al. |
| 8,328,868 | B2 | 12/2012 | Paul et al. |
| 8,333,777 | B2 | 12/2012 | Schaller et al. |
| 8,343,173 | B2 | 1/2013 | Starksen et al. |
| 8,343,174 | B2 | 1/2013 | Goldfarb et al. |
| 8,343,213 | B2 | 1/2013 | Salahieh et al. |
| 8,349,002 | B2 | 1/2013 | Milo |
| 8,353,956 | B2 | 1/2013 | Miller et al. |
| 8,357,195 | B2 | 1/2013 | Kuehn |
| 8,382,829 | B1 | 2/2013 | Call et al. |
| 8,388,680 | B2 | 3/2013 | Starksen et al. |
| 8,393,517 | B2 | 3/2013 | Milo |
| 8,419,825 | B2 | 4/2013 | Burgler et al. |
| 8,430,926 | B2 | 4/2013 | Kirson |
| 8,449,573 | B2 | 5/2013 | Chu |
| 8,449,599 | B2 | 5/2013 | Chau et al. |
| 8,454,686 | B2 | 6/2013 | Alkhatib |
| 8,460,370 | B2 | 6/2013 | Zakay |
| 8,460,371 | B2 | 6/2013 | Hlavka et al. |
| 8,475,491 | B2 | 7/2013 | Milo |
| 8,475,525 | B2 | 7/2013 | Maisano et al. |
| 8,480,732 | B2 | 7/2013 | Subramanian |
| 8,518,107 | B2 | 8/2013 | Tsukashima et al. |
| 8,523,940 | B2 | 9/2013 | Richardson et al. |
| 8,551,161 | B2 | 10/2013 | Dolan |
| 8,585,755 | B2 | 11/2013 | Chau et al. |
| 8,591,576 | B2 | 11/2013 | Hasenkam et al. |
| 8,608,797 | B2 | 12/2013 | Gross et al. |
| 8,628,569 | B2 | 1/2014 | Benichou et al. |
| 8,628,571 | B1 | 1/2014 | Hacohen et al. |
| 8,641,727 | B2 | 2/2014 | Starksen et al. |
| 8,652,202 | B2 | 2/2014 | Alon et al. |
| 8,652,203 | B2 | 2/2014 | Quadri et al. |
| 8,679,174 | B2 | 3/2014 | Ottma et al. |
| 8,685,086 | B2 | 4/2014 | Navia et al. |
| 8,728,097 | B1 | 5/2014 | Sugimoto et al. |
| 8,728,155 | B2 | 5/2014 | Montorfano et al. |
| 8,734,467 | B2 | 5/2014 | Miller et al. |
| 8,734,699 | B2 | 5/2014 | Heideman et al. |
| 8,740,920 | B2 | 6/2014 | Goldfarb et al. |
| 8,747,463 | B2 | 6/2014 | Fogarty et al. |
| 8,778,021 | B2 | 7/2014 | Cartledge |
| 8,784,481 | B2 | 7/2014 | Alkhatib et al. |
| 8,790,367 | B2 | 7/2014 | Nguyen et al. |
| 8,790,394 | B2 | 7/2014 | Miller et al. |
| 8,795,298 | B2 | 8/2014 | Hernlund et al. |
| 8,795,355 | B2 | 8/2014 | Alkhatib |
| 8,795,356 | B2 | 8/2014 | Quadri et al. |
| 8,795,357 | B2 | 8/2014 | Yohanan et al. |
| 8,808,366 | B2 | 8/2014 | Braido et al. |
| 8,808,368 | B2 | 8/2014 | Maisano et al. |
| 8,845,717 | B2 | 9/2014 | Khairkhahan et al. |
| 8,845,723 | B2 | 9/2014 | Spence et al. |
| 8,852,261 | B2 | 10/2014 | White |
| 8,852,272 | B2 | 10/2014 | Gross et al. |
| 8,858,623 | B2 | 10/2014 | Miller et al. |
| 8,864,822 | B2 | 10/2014 | Spence et al. |
| 8,870,948 | B1 | 10/2014 | Erzberger et al. |
| 8,870,949 | B2 | 10/2014 | Rowe |
| 8,888,843 | B2 | 11/2014 | Khairkhahan et al. |
| 8,889,861 | B2 | 11/2014 | Skead et al. |
| 8,894,702 | B2 | 11/2014 | Quadri et al. |
| 8,911,461 | B2 | 12/2014 | Traynor et al. |
| 8,911,494 | B2 | 12/2014 | Hammer et al. |
| 8,926,696 | B2 | 1/2015 | Cabiri et al. |
| 8,926,697 | B2 | 1/2015 | Gross et al. |
| 8,932,343 | B2 | 1/2015 | Alkhatib et al. |
| 8,932,348 | B2 | 1/2015 | Solem et al. |
| 8,940,044 | B2 | 1/2015 | Hammer et al. |
| 8,945,211 | B2 | 2/2015 | Sugimoto |
| 8,951,285 | B2 | 2/2015 | Sugimoto et al. |
| 8,951,286 | B2 | 2/2015 | Sugimoto et al. |
| 8,961,595 | B2 | 2/2015 | Alkhatib |
| 8,961,602 | B2 | 2/2015 | Kovach et al. |
| 8,979,922 | B2 | 3/2015 | Jayasinghe et al. |
| 8,992,604 | B2 | 3/2015 | Gross et al. |
| 9,005,273 | B2 | 4/2015 | Salahieh et al. |
| 9,011,520 | B2 | 4/2015 | Miller et al. |
| 9,011,530 | B2 | 4/2015 | Reich et al. |
| 9,023,100 | B2 | 5/2015 | Quadri et al. |
| 9,072,603 | B2 | 7/2015 | Tuval et al. |
| 9,107,749 | B2 | 8/2015 | Bobo et al. |
| 9,119,719 | B2 | 9/2015 | Zipory et al. |
| 9,125,632 | B2 | 9/2015 | Loulmet et al. |
| 9,125,742 | B2 | 9/2015 | Yoganathan et al. |
| 9,138,316 | B2 | 9/2015 | Bielefeld |
| 9,173,646 | B2 | 11/2015 | Fabro |
| 9,180,005 | B1 | 11/2015 | Lashinski et al. |
| 9,180,007 | B2 | 11/2015 | Reich et al. |
| 9,192,472 | B2 | 11/2015 | Gross et al. |
| 9,198,756 | B2 | 12/2015 | Aklog et al. |
| 9,226,825 | B2 | 1/2016 | Starksen et al. |
| 9,265,608 | B2 | 2/2016 | Miller et al. |
| 9,326,857 | B2 | 5/2016 | Cartledge et al. |
| 9,414,921 | B2 | 8/2016 | Miller et al. |
| 9,427,316 | B2 | 8/2016 | Schweich, Jr. et al. |
| 9,474,606 | B2 | 10/2016 | Zipory et al. |
| 9,526,613 | B2 | 12/2016 | Gross et al. |
| 9,561,104 | B2 | 2/2017 | Miller et al. |
| 9,579,090 | B1 | 2/2017 | Simms et al. |
| 9,693,865 | B2 | 7/2017 | Gilmore et al. |
| 9,730,793 | B2 | 8/2017 | Reich et al. |
| 9,788,941 | B2 | 10/2017 | Hacohen |
| 9,801,720 | B2 | 10/2017 | Gilmore et al. |
| 9,907,547 | B2 | 3/2018 | Gilmore et al. |
| 10,368,852 | B2 | 8/2019 | Gerhardt et al. |
| 2001/0021874 | A1 | 9/2001 | Carpentier et al. |
| 2002/0022862 | A1 | 2/2002 | Grafton et al. |
| 2002/0082525 | A1 | 6/2002 | Oslund et al. |
| 2002/0087048 | A1 | 7/2002 | Brock et al. |
| 2002/0103532 | A1 | 8/2002 | Langberg et al. |
| 2002/0120292 | A1 | 8/2002 | Morgan |
| 2002/0151916 | A1 | 10/2002 | Muramatsu et al. |
| 2002/0151970 | A1 | 10/2002 | Garrison et al. |
| 2002/0169358 | A1 | 11/2002 | Mortier et al. |
| 2002/0177904 | A1 | 11/2002 | Huxel et al. |
| 2002/0188301 | A1 | 12/2002 | Dallara et al. |
| 2002/0188350 | A1 | 12/2002 | Arru et al. |
| 2002/0198586 | A1 | 12/2002 | Inoue |
| 2003/0050693 | A1 | 3/2003 | Quijano et al. |
| 2003/0078465 | A1 | 4/2003 | Pai et al. |
| 2003/0078653 | A1 | 4/2003 | Vesely et al. |
| 2003/0083538 | A1 | 5/2003 | Adams et al. |
| 2003/0093148 | A1 | 5/2003 | Bolling et al. |
| 2003/0105519 | A1 | 6/2003 | Fasol et al. |
| 2003/0114901 | A1 | 6/2003 | Loeb et al. |
| 2003/0120340 | A1 | 6/2003 | Liska et al. |
| 2003/0144657 | A1 | 7/2003 | Bowe et al. |
| 2003/0167062 | A1 | 9/2003 | Gambale et al. |
| 2003/0171760 | A1 | 9/2003 | Gambale |
| 2003/0199974 | A1 | 10/2003 | Lee et al. |
| 2003/0204193 | A1 | 10/2003 | Gabriel et al. |
| 2003/0204195 | A1 | 10/2003 | Keane et al. |
| 2003/0229350 | A1 | 12/2003 | Kay |
| 2003/0229395 | A1 | 12/2003 | Cox |
| 2004/0002735 | A1 | 1/2004 | Lizardi et al. |
| 2004/0010287 | A1 | 1/2004 | Bonutti |
| 2004/0019359 | A1 | 1/2004 | Worley et al. |
| 2004/0019377 | A1 | 1/2004 | Taylor et al. |

(56) References Cited

U.S. PATENT DOCUMENTS

| | | | |
|---|---|---|---|
| 2004/0024451 | A1 | 2/2004 | Johnson et al. |
| 2004/0039442 | A1 | 2/2004 | St. Goar et al. |
| 2004/0044350 | A1 | 3/2004 | Martin et al. |
| 2004/0049211 | A1 | 3/2004 | Tremulis et al. |
| 2004/0059413 | A1 | 3/2004 | Argento |
| 2004/0068273 | A1 | 4/2004 | Fariss et al. |
| 2004/0106950 | A1 | 6/2004 | Grafton et al. |
| 2004/0111095 | A1 | 6/2004 | Gordon et al. |
| 2004/0122514 | A1 | 6/2004 | Fogarty et al. |
| 2004/0127982 | A1 | 7/2004 | Machold et al. |
| 2004/0133274 | A1 | 7/2004 | Webler et al. |
| 2004/0133374 | A1 | 7/2004 | Kattan |
| 2004/0138744 | A1 | 7/2004 | Lashinski et al. |
| 2004/0138745 | A1 | 7/2004 | Macoviak et al. |
| 2004/0148019 | A1 | 7/2004 | Vidlund et al. |
| 2004/0148020 | A1 | 7/2004 | Vidlund et al. |
| 2004/0148021 | A1 | 7/2004 | Cartledge et al. |
| 2004/0176788 | A1 | 9/2004 | Opolski |
| 2004/0181287 | A1 | 9/2004 | Gellman |
| 2004/0186566 | A1 | 9/2004 | Hindrichs et al. |
| 2004/0193191 | A1 | 9/2004 | Starksen et al. |
| 2004/0243227 | A1 | 12/2004 | Starksen et al. |
| 2004/0260317 | A1 | 12/2004 | Bloom et al. |
| 2004/0260344 | A1 | 12/2004 | Lyons et al. |
| 2004/0260393 | A1 | 12/2004 | Rahdert et al. |
| 2004/0260394 | A1 | 12/2004 | Douk et al. |
| 2004/0267358 | A1 | 12/2004 | Reitan |
| 2005/0004668 | A1 | 1/2005 | Aklog et al. |
| 2005/0010287 | A1 | 1/2005 | Macoviak et al. |
| 2005/0010787 | A1 | 1/2005 | Tarbouriech |
| 2005/0016560 | A1 | 1/2005 | Voughlohn |
| 2005/0049692 | A1 | 3/2005 | Numamoto et al. |
| 2005/0055038 | A1 | 3/2005 | Kelleher et al. |
| 2005/0055087 | A1 | 3/2005 | Starksen |
| 2005/0060030 | A1 | 3/2005 | Lashinski et al. |
| 2005/0065601 | A1 | 3/2005 | Lee et al. |
| 2005/0070999 | A1 | 3/2005 | Spence |
| 2005/0075654 | A1 | 4/2005 | Kelleher |
| 2005/0075727 | A1 | 4/2005 | Wheatley |
| 2005/0090827 | A1 | 4/2005 | Gedebou |
| 2005/0090834 | A1 | 4/2005 | Chiang et al. |
| 2005/0096740 | A1 | 5/2005 | Langberg et al. |
| 2005/0107871 | A1 | 5/2005 | Realyvasquez et al. |
| 2005/0119734 | A1 | 6/2005 | Spence et al. |
| 2005/0125002 | A1 | 6/2005 | Baran et al. |
| 2005/0125011 | A1 | 6/2005 | Spence et al. |
| 2005/0131533 | A1 | 6/2005 | Alfieri et al. |
| 2005/0137686 | A1 | 6/2005 | Salahieh et al. |
| 2005/0137688 | A1 | 6/2005 | Salahieh et al. |
| 2005/0137695 | A1 | 6/2005 | Salahieh et al. |
| 2005/0159728 | A1 | 7/2005 | Armour et al. |
| 2005/0159810 | A1 | 7/2005 | Filsoufi |
| 2005/0171601 | A1 | 8/2005 | Cosgrove et al. |
| 2005/0177180 | A1 | 8/2005 | Kaganov et al. |
| 2005/0177228 | A1 | 8/2005 | Solem et al. |
| 2005/0187568 | A1 | 8/2005 | Klenk et al. |
| 2005/0192596 | A1 | 9/2005 | Jugenheimer et al. |
| 2005/0203549 | A1 | 9/2005 | Realyvasquez |
| 2005/0203606 | A1 | 9/2005 | VanCamp |
| 2005/0216039 | A1 | 9/2005 | Lederman |
| 2005/0216079 | A1 | 9/2005 | MaCoviak |
| 2005/0222665 | A1 | 10/2005 | Aranyi |
| 2005/0234481 | A1 | 10/2005 | Waller |
| 2005/0240199 | A1 | 10/2005 | Martinek et al. |
| 2005/0251177 | A1 | 11/2005 | Saadat et al. |
| 2005/0256532 | A1 | 11/2005 | Nayak et al. |
| 2005/0267478 | A1 | 12/2005 | Corradi et al. |
| 2005/0273138 | A1 | 12/2005 | To et al. |
| 2005/0288778 | A1 | 12/2005 | Shaoulian et al. |
| 2006/0004442 | A1 | 1/2006 | Spenser et al. |
| 2006/0004443 | A1 | 1/2006 | Liddicoat et al. |
| 2006/0020326 | A9 | 1/2006 | Bolduc et al. |
| 2006/0020327 | A1 | 1/2006 | Lashinski et al. |
| 2006/0020333 | A1 | 1/2006 | Lashinski et al. |
| 2006/0020336 | A1 | 1/2006 | Liddicoat |
| 2006/0025787 | A1 | 2/2006 | Morales et al. |
| 2006/0025858 | A1 | 2/2006 | Alameddine |
| 2006/0030885 | A1 | 2/2006 | Hyde |
| 2006/0041319 | A1 | 2/2006 | Taylor et al. |
| 2006/0069429 | A1 | 3/2006 | Spence et al. |
| 2006/0074486 | A1 | 4/2006 | Liddicoat et al. |
| 2006/0085012 | A1 | 4/2006 | Dolan |
| 2006/0095009 | A1 | 5/2006 | Lampropoulos et al. |
| 2006/0106423 | A1 | 5/2006 | Weisel et al. |
| 2006/0116757 | A1 | 6/2006 | Lashinski et al. |
| 2006/0122633 | A1 | 6/2006 | To et al. |
| 2006/0129166 | A1 | 6/2006 | Lavelle |
| 2006/0142694 | A1 | 6/2006 | Bednarek et al. |
| 2006/0149280 | A1 | 7/2006 | Harvie et al. |
| 2006/0149368 | A1 | 7/2006 | Spence |
| 2006/0161265 | A1 | 7/2006 | Levine et al. |
| 2006/0173251 | A1 | 8/2006 | Govari et al. |
| 2006/0184240 | A1 | 8/2006 | Jimenez et al. |
| 2006/0184242 | A1 | 8/2006 | Lichtenstein |
| 2006/0195134 | A1 | 8/2006 | Crittenden |
| 2006/0206203 | A1 | 9/2006 | Yang et al. |
| 2006/0212048 | A1 | 9/2006 | Crainich |
| 2006/0241622 | A1 | 10/2006 | Zergiebel |
| 2006/0241656 | A1 | 10/2006 | Starksen et al. |
| 2006/0241748 | A1 | 10/2006 | Lee et al. |
| 2006/0247763 | A1 | 11/2006 | Slater |
| 2006/0259135 | A1 | 11/2006 | Navia et al. |
| 2006/0271175 | A1 | 11/2006 | Woolfson et al. |
| 2006/0276871 | A1 | 12/2006 | Lamson et al. |
| 2006/0282161 | A1 | 12/2006 | Huynh et al. |
| 2006/0287661 | A1 | 12/2006 | Bolduc et al. |
| 2006/0287716 | A1 | 12/2006 | Banbury et al. |
| 2007/0001627 | A1 | 1/2007 | Lin et al. |
| 2007/0010800 | A1 | 1/2007 | Weitzner et al. |
| 2007/0016287 | A1 | 1/2007 | Cartledge et al. |
| 2007/0016288 | A1 | 1/2007 | Gurskis et al. |
| 2007/0021781 | A1 | 1/2007 | Jervis et al. |
| 2007/0027533 | A1 | 2/2007 | Douk |
| 2007/0027536 | A1 | 2/2007 | Mihaljevic et al. |
| 2007/0032823 | A1 | 2/2007 | Tegg |
| 2007/0038221 | A1 | 2/2007 | Fine et al. |
| 2007/0038293 | A1 | 2/2007 | St.Goar et al. |
| 2007/0038296 | A1 | 2/2007 | Navia et al. |
| 2007/0039425 | A1 | 2/2007 | Wang |
| 2007/0049942 | A1 | 3/2007 | Hindrichs et al. |
| 2007/0049970 | A1 | 3/2007 | Belef et al. |
| 2007/0051377 | A1 | 3/2007 | Douk et al. |
| 2007/0055206 | A1 | 3/2007 | To et al. |
| 2007/0060922 | A1 | 3/2007 | Dreyfuss |
| 2007/0061010 | A1 | 3/2007 | Hauser et al. |
| 2007/0066863 | A1 | 3/2007 | Rafiee et al. |
| 2007/0078297 | A1 | 4/2007 | Rafiee et al. |
| 2007/0080188 | A1 | 4/2007 | Spence et al. |
| 2007/0083168 | A1 | 4/2007 | Whiting et al. |
| 2007/0083235 | A1 | 4/2007 | Jervis et al. |
| 2007/0100427 | A1 | 5/2007 | Perouse |
| 2007/0106328 | A1 | 5/2007 | Wardle et al. |
| 2007/0112359 | A1 | 5/2007 | Kimura et al. |
| 2007/0112422 | A1 | 5/2007 | Dehdashtian |
| 2007/0112425 | A1 | 5/2007 | Schaller et al. |
| 2007/0118151 | A1 | 5/2007 | Davidson |
| 2007/0118154 | A1 | 5/2007 | Crabtree |
| 2007/0118213 | A1 | 5/2007 | Loulmet |
| 2007/0118215 | A1 | 5/2007 | Moaddeb |
| 2007/0142907 | A1 | 6/2007 | Moaddeb et al. |
| 2007/0162111 | A1 | 7/2007 | Fukamachi et al. |
| 2007/0173931 | A1 | 7/2007 | Tremulis et al. |
| 2007/0198082 | A1 | 8/2007 | Kapadia et al. |
| 2007/0219558 | A1 | 9/2007 | Deutsch |
| 2007/0239208 | A1 | 10/2007 | Crawford |
| 2007/0244554 | A1 | 10/2007 | Rafiee et al. |
| 2007/0244556 | A1 | 10/2007 | Rafiee et al. |
| 2007/0255397 | A1 | 11/2007 | Ryan et al. |
| 2007/0255400 | A1 | 11/2007 | Parravicini et al. |
| 2007/0270755 | A1 | 11/2007 | Von Oepen et al. |
| 2007/0276437 | A1 | 11/2007 | Call et al. |
| 2007/0282375 | A1 | 12/2007 | Hindrichs et al. |
| 2007/0282429 | A1 | 12/2007 | Hauser et al. |
| 2007/0295172 | A1 | 12/2007 | Swartz |

(56) References Cited

U.S. PATENT DOCUMENTS

| | | | |
|---|---|---|---|
| 2007/0299424 | A1 | 12/2007 | Cumming et al. |
| 2008/0004697 | A1 | 1/2008 | Lichtenstein et al. |
| 2008/0027483 | A1 | 1/2008 | Cartledge et al. |
| 2008/0027555 | A1 | 1/2008 | Hawkins |
| 2008/0033460 | A1 | 2/2008 | Ziniti et al. |
| 2008/0035160 | A1 | 2/2008 | Woodson et al. |
| 2008/0039935 | A1 | 2/2008 | Buch et al. |
| 2008/0051703 | A1 | 2/2008 | Thornton et al. |
| 2008/0058595 | A1 | 3/2008 | Snoke et al. |
| 2008/0065011 | A1 | 3/2008 | Marchand et al. |
| 2008/0065204 | A1 | 3/2008 | Macoviak et al. |
| 2008/0071366 | A1 | 3/2008 | Tuval et al. |
| 2008/0086138 | A1 | 4/2008 | Stone et al. |
| 2008/0086203 | A1 | 4/2008 | Roberts |
| 2008/0091169 | A1 | 4/2008 | Heideman et al. |
| 2008/0091257 | A1 | 4/2008 | Andreas et al. |
| 2008/0097483 | A1 | 4/2008 | Ortiz et al. |
| 2008/0097523 | A1 | 4/2008 | Bolduc et al. |
| 2008/0103572 | A1 | 5/2008 | Gerber |
| 2008/0140116 | A1 | 6/2008 | Bonutti |
| 2008/0167713 | A1 | 7/2008 | Bolling |
| 2008/0167714 | A1 | 7/2008 | St. Goar et al. |
| 2008/0177380 | A1 | 7/2008 | Starksen et al. |
| 2008/0195126 | A1 | 8/2008 | Solem |
| 2008/0195200 | A1 | 8/2008 | Vidlund et al. |
| 2008/0208265 | A1 | 8/2008 | Frazier et al. |
| 2008/0221672 | A1 | 9/2008 | Lamphere et al. |
| 2008/0228030 | A1 | 9/2008 | Godin |
| 2008/0228223 | A1 | 9/2008 | Alkhatib |
| 2008/0234729 | A1 | 9/2008 | Page et al. |
| 2008/0262480 | A1 | 10/2008 | Stahler et al. |
| 2008/0262609 | A1 | 10/2008 | Gross et al. |
| 2008/0275300 | A1 | 11/2008 | Rothe et al. |
| 2008/0275469 | A1 | 11/2008 | Fanton et al. |
| 2008/0275551 | A1 | 11/2008 | Alfieri |
| 2008/0281353 | A1 | 11/2008 | Aranyi et al. |
| 2008/0281411 | A1 | 11/2008 | Berreklouw |
| 2008/0287862 | A1 | 11/2008 | Weitzner et al. |
| 2008/0288044 | A1 | 11/2008 | Osborne |
| 2008/0288062 | A1 | 11/2008 | Andrieu et al. |
| 2008/0294251 | A1 | 11/2008 | Annest et al. |
| 2008/0300537 | A1 | 12/2008 | Bowman |
| 2008/0300629 | A1 | 12/2008 | Surti |
| 2008/0312506 | A1 | 12/2008 | Spivey et al. |
| 2009/0024110 | A1 | 1/2009 | Heideman et al. |
| 2009/0028670 | A1 | 1/2009 | Garcia et al. |
| 2009/0043381 | A1 | 2/2009 | Macoviak et al. |
| 2009/0054723 | A1 | 2/2009 | Khairkhahan et al. |
| 2009/0054969 | A1 | 2/2009 | Salahieh et al. |
| 2009/0062866 | A1 | 3/2009 | Jackson |
| 2009/0076586 | A1 | 3/2009 | Hauser et al. |
| 2009/0076600 | A1 | 3/2009 | Quinn |
| 2009/0082797 | A1 | 3/2009 | Fung et al. |
| 2009/0088837 | A1 | 4/2009 | Gillinov et al. |
| 2009/0093877 | A1 | 4/2009 | Keidar et al. |
| 2009/0099650 | A1 | 4/2009 | Bolduc et al. |
| 2009/0105816 | A1 | 4/2009 | Olsen et al. |
| 2009/0125102 | A1 | 5/2009 | Cartledge et al. |
| 2009/0166913 | A1 | 7/2009 | Guo et al. |
| 2009/0171439 | A1 | 7/2009 | Nissl |
| 2009/0177266 | A1 | 7/2009 | Powell et al. |
| 2009/0177274 | A1 | 7/2009 | Scorsin et al. |
| 2009/0248148 | A1 | 10/2009 | Shaolian et al. |
| 2009/0254103 | A1 | 10/2009 | Deutsch |
| 2009/0264994 | A1 | 10/2009 | Saadat |
| 2009/0287231 | A1 | 11/2009 | Brooks et al. |
| 2009/0287304 | A1 | 11/2009 | Dahlgren et al. |
| 2009/0299409 | A1 | 12/2009 | Coe et al. |
| 2009/0326648 | A1 | 12/2009 | Machold et al. |
| 2010/0001038 | A1 | 1/2010 | Levin et al. |
| 2010/0010538 | A1 | 1/2010 | Juravic et al. |
| 2010/0023118 | A1 | 1/2010 | Medlock et al. |
| 2010/0030014 | A1 | 2/2010 | Ferrazzi |
| 2010/0030328 | A1 | 2/2010 | Seguin et al. |
| 2010/0042147 | A1 | 2/2010 | Janovsky et al. |
| 2010/0049213 | A1 | 2/2010 | Serina et al. |
| 2010/0063542 | A1 | 3/2010 | van der Burg et al. |
| 2010/0063550 | A1 | 3/2010 | Felix et al. |
| 2010/0076499 | A1 | 3/2010 | McNamara et al. |
| 2010/0094248 | A1 | 4/2010 | Nguyen et al. |
| 2010/0094314 | A1 | 4/2010 | Hernlund et al. |
| 2010/0106141 | A1 | 4/2010 | Osypka et al. |
| 2010/0114180 | A1 | 5/2010 | Rock et al. |
| 2010/0121349 | A1 | 5/2010 | Meier et al. |
| 2010/0121435 | A1 | 5/2010 | Subramanian et al. |
| 2010/0121437 | A1 | 5/2010 | Subramanian et al. |
| 2010/0130989 | A1 | 5/2010 | Bourque et al. |
| 2010/0130992 | A1 | 5/2010 | Machold et al. |
| 2010/0152845 | A1 | 6/2010 | Bloom et al. |
| 2010/0161043 | A1 | 6/2010 | Maisano et al. |
| 2010/0168845 | A1 | 7/2010 | Wright |
| 2010/0174358 | A1 | 7/2010 | Rabkin et al. |
| 2010/0179574 | A1 | 7/2010 | Longoria et al. |
| 2010/0217184 | A1 | 8/2010 | Koblish et al. |
| 2010/0217382 | A1 | 8/2010 | Chau et al. |
| 2010/0234935 | A1 | 9/2010 | Bashiri et al. |
| 2010/0249497 | A1 | 9/2010 | Peine et al. |
| 2010/0249908 | A1 | 9/2010 | Chau et al. |
| 2010/0249915 | A1 | 9/2010 | Zhang |
| 2010/0249920 | A1 | 9/2010 | Bolling et al. |
| 2010/0262232 | A1 | 10/2010 | Annest |
| 2010/0262233 | A1 | 10/2010 | He |
| 2010/0286628 | A1 | 11/2010 | Gross |
| 2010/0298929 | A1 | 11/2010 | Thornton et al. |
| 2010/0305475 | A1 | 12/2010 | Hinchliffe et al. |
| 2010/0324598 | A1 | 12/2010 | Anderson |
| 2011/0004210 | A1 | 1/2011 | Johnson et al. |
| 2011/0004298 | A1 | 1/2011 | Lee et al. |
| 2011/0009956 | A1 | 1/2011 | Cartledge et al. |
| 2011/0011917 | A1 | 1/2011 | Loulmet |
| 2011/0026208 | A1 | 2/2011 | Utsuro et al. |
| 2011/0029066 | A1 | 2/2011 | Gilad et al. |
| 2011/0035000 | A1 | 2/2011 | Nieminen et al. |
| 2011/0060407 | A1 | 3/2011 | Ketai et al. |
| 2011/0066231 | A1 | 3/2011 | Cartledge et al. |
| 2011/0067770 | A1 | 3/2011 | Pederson et al. |
| 2011/0071626 | A1 | 3/2011 | Wright et al. |
| 2011/0082538 | A1 | 4/2011 | Dahlgren et al. |
| 2011/0087146 | A1 | 4/2011 | Ryan et al. |
| 2011/0093002 | A1 | 4/2011 | Rucker et al. |
| 2011/0118832 | A1 | 5/2011 | Punjabi |
| 2011/0137410 | A1 | 6/2011 | Hacohen |
| 2011/0144576 | A1 | 6/2011 | Rothe et al. |
| 2011/0144703 | A1 | 6/2011 | Krause et al. |
| 2011/0202130 | A1 | 8/2011 | Cartledge et al. |
| 2011/0208283 | A1 | 8/2011 | Rust |
| 2011/0230941 | A1 | 9/2011 | Markus |
| 2011/0230961 | A1 | 9/2011 | Langer et al. |
| 2011/0238088 | A1 | 9/2011 | Bolduc et al. |
| 2011/0257433 | A1 | 10/2011 | Walker |
| 2011/0257633 | A1 | 10/2011 | Cartledge et al. |
| 2011/0264208 | A1 | 10/2011 | Duffy et al. |
| 2011/0276062 | A1 | 11/2011 | Bolduc |
| 2011/0288435 | A1 | 11/2011 | Christy et al. |
| 2011/0301498 | A1 | 12/2011 | Maenhout et al. |
| 2012/0053628 | A1 | 3/2012 | Sojka et al. |
| 2012/0053642 | A1 | 3/2012 | Lozier et al. |
| 2012/0065464 | A1 | 3/2012 | Ellis et al. |
| 2012/0078355 | A1 | 3/2012 | Zipory et al. |
| 2012/0078359 | A1 | 3/2012 | Li et al. |
| 2012/0089022 | A1 | 4/2012 | House et al. |
| 2012/0089125 | A1 | 4/2012 | Scheibe et al. |
| 2012/0095552 | A1 | 4/2012 | Spence et al. |
| 2012/0109155 | A1 | 5/2012 | Robinson et al. |
| 2012/0143226 | A1 | 6/2012 | Belson et al. |
| 2012/0143323 | A1 | 6/2012 | Hasenkam et al. |
| 2012/0150290 | A1 | 6/2012 | Gabbay |
| 2012/0158021 | A1 | 6/2012 | Morrill |
| 2012/0158023 | A1 | 6/2012 | Mitelberg et al. |
| 2012/0179086 | A1 | 7/2012 | Shank et al. |
| 2012/0191182 | A1 | 7/2012 | Hauser et al. |
| 2012/0226349 | A1 | 9/2012 | Tuval et al. |
| 2012/0239142 | A1 | 9/2012 | Liu et al. |
| 2012/0245604 | A1 | 9/2012 | Tegzes |

(56) References Cited

U.S. PATENT DOCUMENTS

2012/0271198 A1 10/2012 Whittaker et al.
2012/0296349 A1 11/2012 Smith et al.
2012/0296417 A1 11/2012 Hill et al.
2012/0310330 A1 12/2012 Buchbinder et al.
2012/0323313 A1 12/2012 Seguin
2013/0030522 A1 1/2013 Rowe et al.
2013/0046373 A1 2/2013 Cartledge et al.
2013/0053884 A1 2/2013 Roorda
2013/0079873 A1 3/2013 Migliazza et al.
2013/0085529 A1 4/2013 Housman
2013/0090724 A1 4/2013 Subramanian et al.
2013/0096673 A1 4/2013 Hill et al.
2013/0116776 A1 5/2013 Gross et al.
2013/0123910 A1 5/2013 Cartledge et al.
2013/0131791 A1 5/2013 Hlavka et al.
2013/0166017 A1 6/2013 Cartledge et al.
2013/0190863 A1 7/2013 Call et al.
2013/0204361 A1 8/2013 Adams et al.
2013/0218206 A1 8/2013 Gadlage
2013/0226289 A1 8/2013 Shaolian et al.
2013/0226290 A1 8/2013 Yellin et al.
2013/0231701 A1 9/2013 Voss et al.
2013/0268069 A1 10/2013 Zakai et al.
2013/0282059 A1 10/2013 Ketai et al.
2013/0289718 A1 10/2013 Tsukashima et al.
2013/0297013 A1 11/2013 Klima et al.
2013/0304093 A1 11/2013 Serina et al.
2013/0331930 A1 12/2013 Rowe et al.
2014/0067054 A1 3/2014 Chau et al.
2014/0081394 A1 3/2014 Keranen et al.
2014/0088368 A1 3/2014 Park
2014/0088646 A1 3/2014 Wales et al.
2014/0094826 A1 4/2014 Sutherland et al.
2014/0094903 A1 4/2014 Miller et al.
2014/0094906 A1 4/2014 Spence et al.
2014/0114390 A1 4/2014 Tobis et al.
2014/0135799 A1 5/2014 Henderson
2014/0142619 A1 5/2014 Serina et al.
2014/0142695 A1 5/2014 Gross et al.
2014/0148849 A1 5/2014 Serina et al.
2014/0155783 A1 6/2014 Starksen et al.
2014/0163615 A1 6/2014 Gadlage et al.
2014/0163670 A1 6/2014 Alon et al.
2014/0163690 A1 6/2014 White
2014/0188108 A1 7/2014 Goodine et al.
2014/0188140 A1 7/2014 Meier et al.
2014/0188215 A1 7/2014 Hlavka et al.
2014/0194976 A1 7/2014 Starksen et al.
2014/0207231 A1 7/2014 Hacohen et al.
2014/0243859 A1 8/2014 Robinson
2014/0243894 A1 8/2014 Groothuis et al.
2014/0243963 A1 8/2014 Sheps et al.
2014/0251042 A1 9/2014 Asselin et al.
2014/0275757 A1 9/2014 Goodwin et al.
2014/0276648 A1 9/2014 Hammer et al.
2014/0296962 A1 10/2014 Cartledge et al.
2014/0303649 A1 10/2014 Nguyen et al.
2014/0303720 A1 10/2014 Sugimoto et al.
2014/0309661 A1 10/2014 Sheps et al.
2014/0309730 A1 10/2014 Alon et al.
2014/0343668 A1 11/2014 Zipory et al.
2014/0350660 A1 11/2014 Cocks et al.
2014/0379006 A1 12/2014 Sutherland et al.
2015/0018940 A1 1/2015 Quill et al.
2015/0051697 A1 2/2015 Spence et al.
2015/0081014 A1 3/2015 Gross et al.
2015/0094800 A1 4/2015 Chawla
2015/0100116 A1 4/2015 Mohl et al.
2015/0112432 A1 4/2015 Reich et al.
2015/0127097 A1 5/2015 Neumann et al.
2015/0133997 A1 5/2015 Deitch et al.
2015/0182336 A1 7/2015 Zipory et al.
2015/0230919 A1 8/2015 Chau et al.
2015/0272586 A1 10/2015 Herman et al.
2015/0272734 A1 10/2015 Sheps et al.
2015/0282931 A1 10/2015 Brunnett et al.
2015/0351910 A1 12/2015 Gilmore et al.
2016/0008132 A1 1/2016 Cabiri et al.
2016/0029920 A1 2/2016 Kronstrom et al.
2016/0030034 A1 2/2016 Graul et al.
2016/0058557 A1 3/2016 Reich et al.
2016/0113767 A1 4/2016 Miller et al.
2016/0120642 A1 5/2016 Shaolian et al.
2016/0120645 A1 5/2016 Alon
2016/0158008 A1 6/2016 Miller et al.
2016/0242762 A1 8/2016 Gilmore et al.
2016/0256149 A1 9/2016 Sampson et al.
2016/0256274 A1 9/2016 Hayoz et al.
2016/0262755 A1 9/2016 Zipory et al.
2016/0302917 A1 10/2016 Schewel
2016/0317302 A1 11/2016 Madjarov et al.
2016/0346084 A1 12/2016 Taylor et al.
2016/0361058 A1 12/2016 Bolduc et al.
2016/0361168 A1 12/2016 Gross et al.
2016/0361169 A1 12/2016 Gross et al.
2017/0000609 A1 1/2017 Gross et al.
2017/0042670 A1 2/2017 Shaolian et al.
2017/0100119 A1 4/2017 Baird et al.
2017/0224489 A1 8/2017 Starksen et al.
2017/0245993 A1 8/2017 Gross et al.
2018/0008409 A1 1/2018 Kutzik et al.
2018/0049875 A1 2/2018 Iflah et al.
2018/0140420 A1 5/2018 Hayoz et al.
2018/0168803 A1 6/2018 Pesce et al.
2018/0214270 A1* 8/2018 Subramanian ........ A61F 2/2466
2018/0228608 A1 8/2018 Sheps et al.
2018/0256334 A1 9/2018 Sheps et al.
2018/0280019 A1 10/2018 Azar et al.
2018/0289480 A1 10/2018 D'ambra et al.
2018/0318080 A1 11/2018 Quill et al.
2018/0318083 A1 11/2018 Bolling et al.
2019/0029498 A1 1/2019 Mankowski et al.
2019/0038411 A1 2/2019 Alon
2019/0091445 A1 3/2019 House
2019/0111239 A1 4/2019 Bolduc et al.
2019/0117113 A1 4/2019 Curran
2019/0117400 A1 4/2019 Medema et al.
2019/0125325 A1 5/2019 Sheps et al.
2019/0151093 A1 5/2019 Keidar et al.
2019/0159898 A1 5/2019 Kutzik et al.
2019/0175344 A1 6/2019 Khairkhahan
2019/0175345 A1 6/2019 Schaffner et al.
2019/0175346 A1 6/2019 Schaffner et al.
2019/0183648 A1 6/2019 Trapp et al.
2019/0240023 A1 8/2019 Spence et al.
2019/0290260 A1 9/2019 Caffes et al.
2019/0290431 A1 9/2019 Genovese et al.
2019/0321049 A1 10/2019 Herman et al.
2019/0343633 A1 11/2019 Garvin et al.
2020/0015810 A1 1/2020 Piccirillo
2020/0015971 A1 1/2020 Brauon et al.
2020/0178956 A1 6/2020 Mitelberg et al.
2020/0289267 A1 9/2020 Peleg et al.
2020/0337840 A1 10/2020 Reich
2020/0390551 A1 12/2020 McCarthy
2021/0015475 A1 1/2021 Lau
2021/0052387 A1 2/2021 Greenan et al.
2021/0059820 A1 3/2021 Clark et al.
2021/0085461 A1 3/2021 Neumark et al.
2021/0093453 A1 4/2021 Peleg et al.
2021/0145584 A1 5/2021 Kasher et al.
2022/0071620 A1 3/2022 Brauon et al.
2022/0096232 A1 3/2022 Skaro et al.
2022/0110656 A1 4/2022 Azar et al.
2022/0142779 A1 5/2022 Sharon
2022/0176076 A1 6/2022 Keidar
2022/0233316 A1 7/2022 Sheps et al.
2022/0257196 A1 8/2022 Massmann
2022/0273436 A1 9/2022 Aviv et al.
2022/0313438 A1 10/2022 Chappel-Ram
2022/0323221 A1 10/2022 Sharon et al.
2023/0016867 A1 1/2023 Tennenbaum
2023/0218291 A1 7/2023 Zarbatany et al.

(56) References Cited

U.S. PATENT DOCUMENTS

| | | | |
|---|---|---|---|
| 2023/0320856 | A1 | 10/2023 | Zarbatany et al. |
| 2024/0008985 | A1 | 1/2024 | Yuan et al. |
| 2024/0099736 | A1 | 3/2024 | Elsheikh et al. |

FOREIGN PATENT DOCUMENTS

| | | | |
|---|---|---|---|
| EP | 3531975 | A1 | 9/2019 |
| WO | 9205093 | A1 | 4/1992 |
| WO | 9846149 | A1 | 10/1998 |
| WO | WO-2002085250 | A2 | 10/2002 |
| WO | 02085250 | A3 | 2/2003 |
| WO | 03047467 | A1 | 6/2003 |
| WO | 2007098512 | A1 | 9/2007 |
| WO | 2010000454 | A1 | 1/2010 |
| WO | WO-2012176195 | A2 | 12/2012 |
| WO | 2012176195 | A3 | 3/2013 |
| WO | 2014064964 | A1 | 5/2014 |
| WO | 2019145941 | A1 | 8/2019 |
| WO | 2019145947 | A1 | 8/2019 |
| WO | 2019182645 | A1 | 9/2019 |
| WO | 2019224814 | A1 | 11/2019 |
| WO | WO-2020226895 | A1 | 11/2020 |
| WO | 2020240282 | A2 | 12/2020 |
| WO | 2021014440 | A2 | 1/2021 |
| WO | 2021038559 | A1 | 3/2021 |
| WO | 2021038560 | A1 | 3/2021 |
| WO | 2022064401 | A2 | 3/2022 |
| WO | 2022090907 | A1 | 5/2022 |
| WO | 2022101817 | A2 | 5/2022 |
| WO | 2022153131 | A1 | 7/2022 |
| WO | 2022157592 | A1 | 7/2022 |
| WO | 2022172108 | A1 | 8/2022 |
| WO | 2022172149 | A1 | 8/2022 |
| WO | 2022200972 | A1 | 9/2022 |
| WO | 2022224071 | A1 | 10/2022 |
| WO | 2022229815 | A1 | 11/2022 |
| WO | 2022250983 | A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results 04yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

Alfieri O., et al., "Novel Suture Device for Beating-Heart Mitral Leaflet Approximation," The Annals of Thoracic Surgery, 2002, vol. 74, pp. 1488-1493.

* cited by examiner

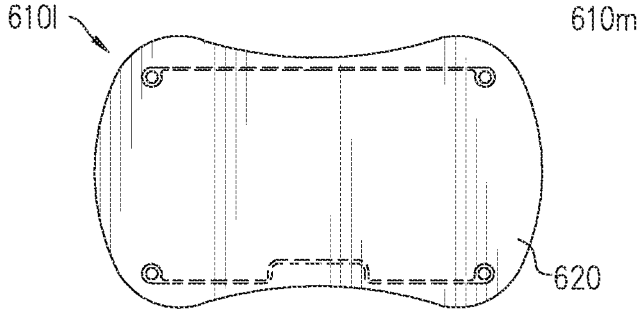
FIG. 37A
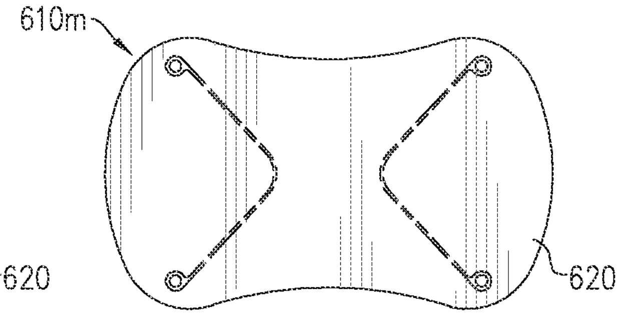
FIG. 37B
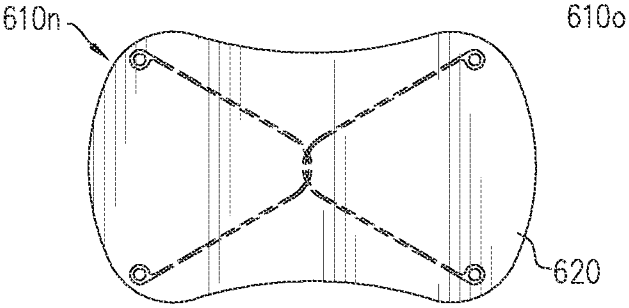
FIG. 37C
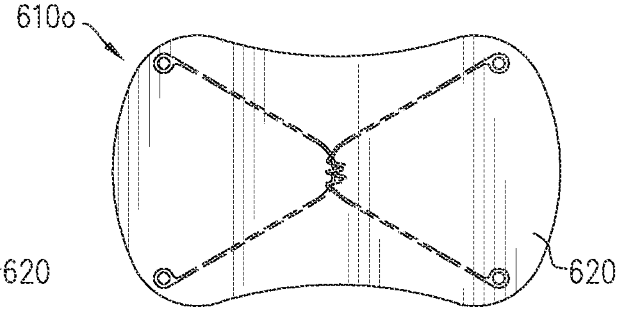
FIG. 37D
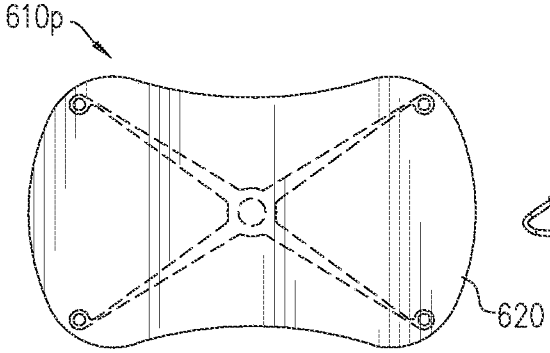
FIG. 37E
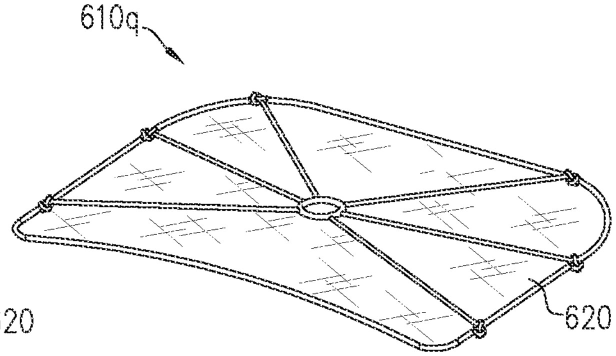
FIG. 37F
FIG. 37G
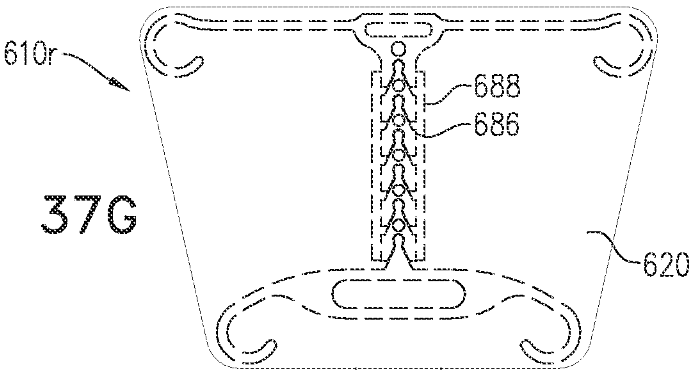

FIG. 43A
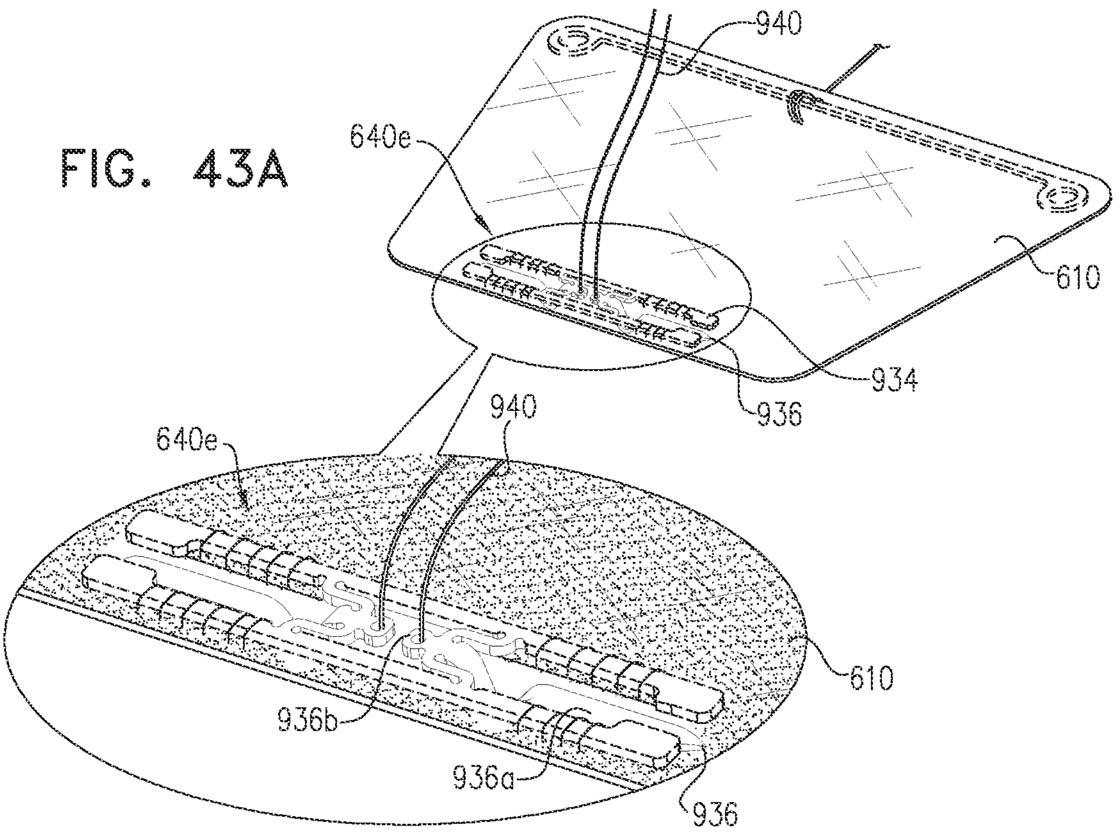
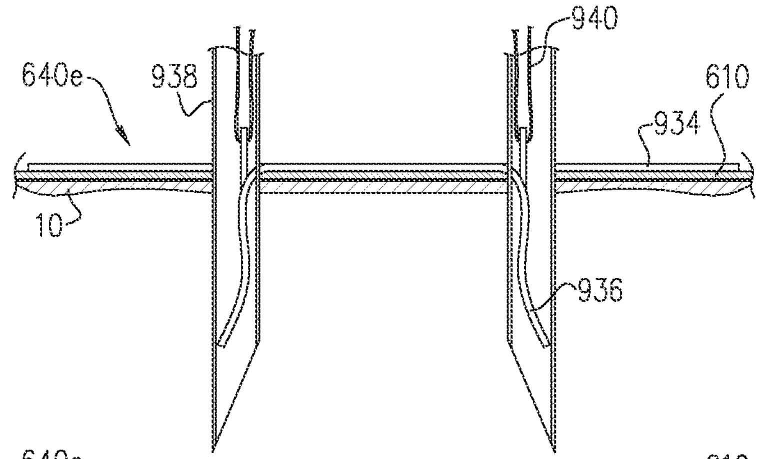
FIG. 43B
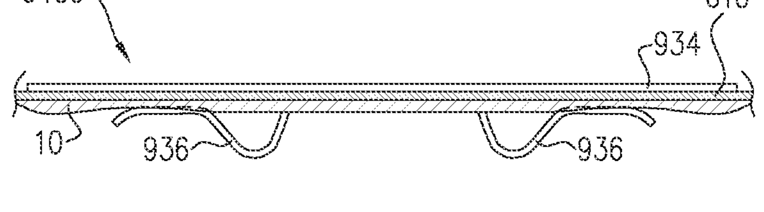
FIG. 43C

VALVE LEAFLET TREATMENT SYSTEMS AND METHODS

CROSS-REFERENCES TO RELATED APPLICATIONS

The present application is a Continuation of International Patent Application PCT/IB2021/060436 to Tennenbaum et al., filed Nov. 11, 2021, which published as WO 2022/101817, and which claims priority from Provisional U.S. Patent Application 63/113,430 to Tennenbaum et al., filed Nov. 13, 2020, and entitled "Valve leaflet treatment systems and methods."

Each of the above applications is incorporated by reference in its entirety for all purposes.

BACKGROUND

Ischemic heart disease can cause mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

Chronic or acute left ventricular dilatation can lead to papillary muscle displacement with increased leaflet tethering due to tension on chordae tendineae, as well as annular dilatation.

SUMMARY

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure can be included in the examples summarized here.

In some applications, systems and apparatuses are provided comprising leaflet patches (e.g., leaflet-augmentation patches), repair chords, and/or delivery tools for implantation thereof. The systems/apparatuses can comprise subvalvular apparatus and/or components. In some applications, the systems/apparatuses are provided for facilitating leaflet augmentation.

In some applications, the systems, apparatuses, and methods described herein can be used for providing artificial chordae tendineae and/or leaflet augmentation for the left side of the heart. In some applications, the systems, apparatuses, and methods described herein can be used for providing artificial chordae tendineae and/or leaflet augmentation for the right side of the heart. In some applications, the systems, apparatuses, and methods described herein can be used to adjust a length between two portions of the heart wall.

There is provided, in accordance with some applications, a system for use with a valve disposed between an atrium and a ventricle of a heart of a subject, the system including an implant comprising a patch (e.g., a leaflet-augmentation patch, etc.). For some applications, the patch includes a flexible sheet and a patch anchor.

The system can also include a downstream assembly that can include a winch coupled to a winch anchor. The system can also include a tether tethering the winch to the patch.

For some applications, the system further includes a delivery tool, having a distal portion transluminally advanceable to the heart while coupled to the implant. In some applications, the delivery tool includes a shaft, defining a longitudinal axis of the delivery tool. For some applications, the delivery tool includes a clasp that can include an upstream support and a downstream support. In some applications, the clasp is transitionable between an open state and a closed state.

For some applications, the open state is configured such that the upstream support and the downstream support are positioned away from each other, and the clasp is configured to receive a portion of a leaflet of the valve between the upstream support and the downstream support. In some applications, the closed state is a grasping state. In some applications, the clasp is configured to grasp the portion of the leaflet received between the upstream support and the downstream support by being transitioned from the open state toward the grasping state while the portion of the leaflet remains disposed between the upstream support and the downstream support.

For some applications, the system further includes a driver, configured to anchor the patch to the leaflet by driving the patch anchor through the leaflet while the portion of the leaflet remains grasped by the clasp For some applications, the system (e.g., the delivery tool, etc.) further includes a driveshaft subassembly that includes one or more driveshafts, extending through the shaft, and operatively coupled to the downstream assembly in a manner that configures the driveshaft subassembly: (1) to anchor the winch anchor to ventricular tissue of the heart by applying an anchoring force to the winch anchor, and (2) to actuate the winch independently of applying the anchoring force.

For some applications, the tether extends from the downstream assembly, alongside the shaft, past the clasp, and to the patch.

For some applications, the driver is disposed alongside the shaft, parallel with the shaft.

For some applications, the clasp, in both the open state and the grasping state, is disposed entirely laterally from the shaft.

For some applications, the driver is configured to anchor the patch to the leaflet by driving the patch anchor through the portion of the leaflet grasped by the clasp.

For some applications, the clasp is transitionable toward the open state subsequently to anchoring of the patch to the leaflet in order to release the portion of the leaflet, with the patch anchored thereto, from the clasp.

For some applications, in the grasping state, the upstream support and the downstream support are closer to each other than in the open state.

For some applications, the driveshaft subassembly includes a reference-force tube that extends through the shaft and is engaged with the downstream assembly, and the one or more driveshafts extend through the reference-force tube to the downstream assembly, and the driveshaft subassembly is configured to actuate the winch by applying torque to the winch while the reference-force tube provides a reference force to the downstream assembly.

For some applications, the downstream assembly and the delivery tool are configured to facilitate the delivery tool rotating the winch anchor with respect to the shaft without actuating the winch.

For some applications, the winch anchor includes a helical tissue-engaging element, the anchoring force includes torque, and the delivery tool is configured to anchor the winch anchor to the ventricular tissue by screwing the helical tissue-engaging element into the ventricular tissue by applying the torque to the winch anchor.

For some applications, the distal portion of the delivery tool is coupled to the implant in a manner that configures the driveshaft subassembly to screw the helical tissue-engaging element into the ventricular tissue by applying the torque to the winch anchor without rotating the winch with respect to the ventricular tissue.

For some applications, the distal portion of the delivery tool is coupled to the implant in a manner that configures the driveshaft subassembly to screw the helical tissue-engaging element into the ventricular tissue by applying the torque to the winch anchor without rotating the winch with respect to the shaft.

For some applications, the delivery tool includes a capsule coupled to a distal end of the shaft, the distal portion of the delivery tool being transluminally advanceable to the heart while the downstream assembly is housed within the capsule. In some applications, the capsule and the winch are shaped to inhibit rotation of the winch with respect to the shaft while the driveshaft subassembly screws the helical tissue-engaging element into the ventricular tissue.

For some applications, the capsule defines a track with which the winch is engaged while housed by the capsule. For some applications, the capsule and the downstream assembly configure the driveshaft subassembly to screw the helical tissue-engaging element into the ventricular tissue in a manner in which the downstream assembly advances distally out of the capsule, with the winch sliding linearly along the track.

For some applications, the track is a lateral opening in the capsule, and the winch defines an aperture through which the tether extends out of the winch to the patch. For some applications, protrusion of the aperture into the lateral opening configures the driveshaft subassembly to screw the helical tissue-engaging element into the ventricular tissue in a manner in which the downstream assembly advances distally out of the capsule, with the aperture of the winch sliding linearly along the lateral opening.

For some applications, the capsule includes a housing that houses the winch and that defines the lateral opening.

For some applications, the capsule includes a resilient shroud that shrouds the housing. For some applications, the shroud shrouds a distal region of the lateral opening, leaving a proximal region of the lateral opening exposed to define a window of the capsule, and the distal portion of the delivery tool is transluminally advanceable to the heart while the downstream assembly is housed within the capsule with the aperture exposed at the window.

For some applications, the shroud defines a slit that extends distally from the window, aligned with the lateral opening.

For some applications, protrusion of the aperture into the lateral opening configures the driveshaft subassembly to screw the helical tissue-engaging element into the ventricular tissue in a manner in which the downstream assembly advances distally out of the capsule, with the aperture of the winch transiently separating the shroud at the slit as the aperture slides linearly along the lateral opening.

For some applications, the implant includes an upstream assembly including the patch anchor coupled to the patch.

For some applications, the upstream assembly further includes a cord via which the patch anchor is coupled to the patch.

For some applications, the patch anchor has a sharpened tip, and is configured to be driven by the driver through the leaflet with the sharpened tip penetrating the leaflet.

For some applications, the delivery tool further includes a hollow needle, and the patch anchor is configured to be driven by the driver through the leaflet while disposed within the hollow needle.

For some applications, the delivery tool further includes a hollow needle configured to pierce the leaflet, and the driver is configured to drive the patch anchor out of the hollow needle while the hollow needle extends through the leaflet.

For some applications, the patch anchor includes a toggle that defines an eyelet partway along the toggle, the cord being attached to the patch anchor at the eyelet.

For some applications, the toggle is a first toggle, and the patch anchor further includes a second toggle that defines an eyelet partway along the second toggle. For some applications, the cord extends from the patch, through the eyelet of the second toggle, to the eyelet of the first toggle. For some applications, the first toggle and the second toggle are shaped such that tensioning of the cord arranges the first toggle and the second toggle into a cross.

For some applications, the toggle has a generally cylindrical outer surface, and the eyelet is sunken below the generally cylindrical outer surface.

For some applications, the eyelet extends transversely entirely through the toggle.

For some applications, the toggle is substantially tubular, having a lateral wall that defines a lumen.

For some applications, the eyelet is a cord eyelet, the toggle defines a lateral eyelet in the lateral wall, and the cord eyelet protrudes laterally from the lateral eyelet.

For some applications, the cord eyelet is defined by a wire.

For some applications, the wire is a spring wire, secured to the toggle by spring functionality of the spring wire.

For some applications, the wire is secured to the toggle by beads secured to ends of the wire and disposed in the lumen.

For some applications, the upstream assembly further includes a spring configured to tension the cord.

For some applications, the spring is a compression spring.

For some applications, the spring is a cantilever spring.

For some applications, the spring lies substantially flat with respect to the patch.

For some applications, the spring extends beyond the sheet of the patch.

For some applications, the spring extends out of a plane defined by the patch.

For some applications, the spring is configured to facilitate the driver driving the patch anchor through the leaflet by transiently straining in response to tension applied to the cord by the driver pushing the patch anchor away from the patch and through the leaflet.

For some applications, the spring is coupled to the sheet in a manner in which the patch transiently linearly contracts as the spring transiently strains.

For some applications, the spring is coupled to the sheet in a manner in which the spring slides across the sheet as the spring transiently strains.

For some applications, the patch has a lip and a root. For some applications, the driver is configured to anchor the root of the patch to the leaflet such that the lip of the patch extends toward an opposing leaflet of the valve. For some applications, the patch includes at least one frame that defines: a lip brace at the lip of the patch, and a root brace at the root of the patch.

For some applications, the spring is configured such that the transient straining consists substantially of transient compression of the spring between the lip brace and the root brace.

For some applications, the tether is attached to the lip brace and slidably coupled to the root brace, such that the tension applied to the cord transiently compresses the spring between the lip brace and the root brace by transiently drawing the lip brace toward the root brace.

For some applications, the patch defines, along a midline of the patch, a root-to-lip axis between the lip and the root, and the spring is configured such that the transient straining consists substantially of deflection of the spring with respect to the root-to-lip axis.

For some applications, the spring is configured such that the transient straining consists substantially of deflection of the spring toward the root-to-lip axis.

For some applications, the spring is a first spring, and the upstream assembly further includes a second spring, the first spring and the second spring configured such that the transient straining consists substantially of deflection of the first spring and the second spring toward each other.

For some applications, the cord extends back and forth between the first spring and the second spring.

For some applications, the at least one frame defines a patch-anchor support coupled to the root brace, the cord extending from the spring, through the patch-anchor support, to the patch anchor.

For some applications, the tether is connected to the lip brace.

For some applications, the spring is attached to the root brace.

For some applications, the spring is configured such that the transient straining consists substantially of transient deflection of the spring with respect to the root brace.

For some applications, the spring extends from the root brace to the lip brace.

For some applications, the spring extends from the root brace to the lip brace along a midline of the patch.

For some applications:

- the spring is a first spring, extending from the root brace to the lip brace along a first lateral edge of the patch, and
- the at least one frame defines a second spring, extending from the root brace to the lip brace along a second lateral edge of the patch.

For some applications, the spring does not extend to the lip brace.

For some applications, the clasp defines slot, and the driver is configured to anchor the patch to the leaflet by driving the patch anchor through the leaflet and the slot.

For some applications, the slot is defined by the downstream support of the clasp.

For some applications, the clasp defines a slot guard, configured to obstructing tissue of the heart from entering the slot.

For some applications, the patch is coupled to the patch anchor via a cord. For some applications, the slot guard is resilient and has a resting position in which it covers an entrance to the slot, thereby obstructing tissue of the heart from entering the slot. For some applications, the slot guard is transiently deflectable away from the slot by the cord, thereby facilitating exiting of the cord from the slot.

For some applications, the patch is coupled to the patch anchor via a cord. For some applications, the slot guard has a closed position in which it covers an entrance to the slot, thereby obstructing tissue of the heart from entering the slot and is reversibly retractable from the entrance to the slot, thereby facilitating exiting of the cord from the slot.

For some applications, the delivery tool further includes a capsule at a distal end of the shaft, the capsule configured to house the downstream assembly.

For some applications, the capsule includes a shroud formed from a resilient polymer.

For some applications, the capsule is shaped to define a lateral window therein.

For some applications, the capsule is shaped to define a narrow slit that extends between the lateral window and an open distal end of the capsule.

For some applications, the delivery tool has an extracorporeal proximal portion that includes a clasp controller operatively coupled to the clasp such that operation of the clasp controller transitions the clasp between the open state and the grasping state.

For some applications, the clasp controller is operatively coupled to the upstream support of the clasp such that operation of the clasp controller transitions the clasp between the open state and the grasping state via movement of the upstream support with respect to the shaft.

For some applications, the proximal portion further includes a driver controller operatively coupled to the driver such that operation of the driver controller induces the driver to drive the patch anchor through the leaflet.

For some applications, within the distal portion of the delivery tool the shaft has a proximal part and a distal part, and the proximal portion of the delivery tool further includes a shaft extender, operatively coupled to the shaft such that operation of the shaft extender reversibly extends the distal part of the shaft distally from the proximal part of the shaft.

For some applications, the clasp is coupled to the shaft such that extension of the distal part of the shaft distally from the proximal part of the shaft deflects the downstream support with respect to the shaft.

For some applications, the delivery tool includes a frame that defines the downstream support. For some applications, a first part of the frame is attached to the proximal part of the shaft, and a second part of the frame is attached to the distal part of the shaft, such that extension of the distal part of the shaft distally from the proximal part of the shaft folds the frame in a manner that deflects the downstream support with respect to the shaft.

For some applications, the clasp is coupled to the shaft such that extension of the distal part of the shaft distally from the proximal part of the shaft deflects both the downstream support and the upstream support with respect to the shaft.

For some applications, the clasp is coupled to the shaft such that extension of the distal part of the shaft distally from the proximal part of the shaft deflects both the downstream support and the upstream support with respect to the shaft without changing a disposition between the downstream support and the upstream support.

For some applications, the clasp is coupled to the shaft such that extension of the distal part of the shaft distally from the proximal part of the shaft deflects both the downstream support and the upstream support with respect to the shaft while the clasp remains in the grasping state.

For some applications, the proximal portion further includes an anchor controller configured such that, in at least one state of the delivery tool, the driveshaft subassembly operatively couples the anchor controller to the winch anchor such that operation of the anchor controller applies the anchoring force to the winch anchor.

For some applications, the proximal portion further includes a winch controller, the driveshaft subassembly operatively coupling the winch controller to the winch such that operation of the winch controller actuates the winch.

For some applications, the driveshaft subassembly includes a winch-control driveshaft via which the winch controller is operatively coupled to the winch. For some applications, the driveshaft subassembly includes an anchor-control driveshaft disposed through the winch-control driveshaft, and via which the anchor controller is operatively coupled to the anchor.

For some applications, the driveshaft subassembly includes a downstream-assembly-control driveshaft. For some applications, the driveshaft subassembly has an anchoring state in which the anchor controller is operatively coupled to the winch anchor via the downstream-assembly-control driveshaft such that operation of the anchor controller applies the anchoring force to the winch anchor.

For some applications, the driveshaft subassembly has a winching state in which the downstream-assembly-control driveshaft is: operatively uncoupled from the winch anchor such that operation of the anchor controller does not apply the anchoring force to the winch anchor, and operatively coupled to the winch such that rotation of the downstream-assembly-control driveshaft actuates the winch.

For some applications, in the anchoring state, the downstream-assembly-control driveshaft is disposed in a first axial position with respect to the downstream assembly. For some applications, in the winching state, the downstream-assembly-control driveshaft is disposed in a second, different, axial position with respect to the downstream assembly. For some applications, the delivery tool is transitionable between the anchoring state and the winching state via axial movement of the downstream-assembly-control driveshaft with respect to the downstream assembly.

For some applications, the first axial position is distal to the second axial position, and the delivery tool is transitionable from the anchoring state to winching state via proximal movement of the downstream-assembly-control driveshaft with respect to the downstream assembly.

For some applications, the delivery tool further includes a mount, configured to support the patch mounted thereon, and configured to carry the patch toward the clasp while the clasp is in the grasping state.

For some applications, the mount is configured to carry the patch toward the upstream support of the clasp by moving, with the patch mounted thereon, distally toward the clasp while the clasp is in the grasping state.

For some applications, the mount is configured to carry the patch toward the upstream support of the clasp by moving, with the patch mounted thereon, distally and laterally toward the clasp while the clasp is in the grasping state.

For some applications, the mount has a retracted position, the distal portion of the delivery tool being transluminally advanceable to the heart while the mount is in the retracted position with the patch mounted on the mount. For some applications, the mount has a primed position in which the mount is disposed closer to the clasp than in the retracted position. For some applications, the driver is configured to anchor the patch to the leaflet by, while the mount is in the primed position with the patch mounted on the mount, driving the patch anchor through the leaflet.

For some applications, the clasp is transitionable between the open state and the closed state while the mount remains in the retracted position.

For some applications, the delivery tool has an extracorporeal proximal portion that includes a mount controller operatively coupled to the mount such that operation of the mount controller moves the mount between the retracted position and the primed position.

For some applications, the delivery tool further includes a mount-control rod via which the mount controller is operatively coupled to the mount.

For some applications, the proximal portion further includes a driver controller operatively coupled to the driver such that operation of the driver controller induces the driver to drive the patch anchor through the leaflet.

For some applications, the mount-control rod is tubular, and the driver extends from the driver controller, through the mount-control rod.

For some applications, the extracorporeal proximal portion of the delivery tool further includes a clasp controller operatively coupled to the clasp such that operation of the clasp controller transitions the clasp between the open state and the grasping state.

For some applications, the delivery tool further includes a clasp-control wire via which the clasp controller is operatively coupled to the mount.

For some applications, the mount controller is configured to, while the clasp is in the grasping state, move the mount between the retracted position and the primed position by sliding the mount over and along the clasp-control wire toward the clasp.

For some applications, the clasp controller is configured to, while the mount is in the retracted position, transition the clasp from the grasping state to the open state by retracting the clasp-control wire through the mount.

For some applications, the delivery tool further includes one or more wraps, the distal portion of the delivery tool being transluminally advanceable to the heart while the mount is in the retracted position with the patch held against the mount by the one or more wraps wrapped around the patch and the mount.

For some applications, the distal portion of the delivery tool is transluminally advanceable to the heart while the mount is in the retracted position with the patch held against the mount by the one or more wraps wrapped around the patch, the mount, and the shaft.

For some applications, the delivery tool further includes one or more spring-loaded brackets configured to hold the wraps taut.

For some applications, the delivery tool further includes a rod that cooperates with the spring-loaded brackets to hold the wraps taut, and that is retractable to release the wraps.

For some applications, in the retracted position, the mount curves in an arc partway around the shaft.

For some applications, the mount has a convex outer surface, and the patch is mounted on the mount in a manner in which the patch lies in a curve against the convex outer surface of the mount.

For some applications, the mount is shaped to house the patch anchor while the patch is mounted on the mount.

For some applications, the patch anchor is coupled to the patch, and the system is configured such that housing of the patch anchor by the mount secures the patch to the mount.

For some applications, the patch is coupled to the patch anchor via a cord and is secured to a surface of the mount by the patch anchor being disposed in a groove defined in the surface of the mount, the groove being shaped to: facilitate sliding of the patch anchor along the groove, and obstruct the patch anchor from exiting the groove laterally.

For some applications, the driver is configured to anchor the patch to the leaflet by, while the mount is in the primed position with the patch mounted on the mount, driving the patch anchor along the groove, out of an end of the groove, and through the leaflet.

For some applications, the cord extends from the patch anchor, laterally out of the groove to the patch.

For some applications, within the distal portion of the delivery tool the shaft is telescopic, and the delivery tool has a delivery state in which: the shaft is telescopically extended, the clasp faces distally, and the distal portion of the delivery tool is transluminally advanceable to the heart.

For some applications, in the delivery state, the downstream support is deflected distally compared to in the open state.

For some applications, in the delivery state, the downstream support is disposed adjacent to, and substantially parallel with, the shaft.

For some applications, in the delivery state, the clasp is closed.

For some applications, the delivery tool has a contracted state in which the shaft is telescopically contracted, and the clasp faces proximally.

For some applications, the distal portion of the delivery tool is configured to be advanced downstream through the valve while in the contracted state.

For some applications, in the contracted state, the clasp is closed.

For some applications, in the contracted state, the downstream support is deflected proximally compared to in the open state.

For some applications, in the contracted state, the clasp extends further laterally from the shaft than in the open state.

For some applications, the proximal portion of the delivery tool further includes a shaft extender, operatively coupled to the shaft such that operation of the shaft extender reversibly extends a distal part of the shaft distally from a proximal part of the shaft.

For some applications, the clasp is coupled to the shaft such that extension of the distal part of the shaft distally from the proximal part of the shaft deflects the downstream support with respect to the shaft.

For some applications, the flexible sheet includes a first woven layer including weft yarns and warp yarns, and a second woven layer including weft yarns and warp yarns, and is affixed to the first woven layer such that the weft yarns of the first woven layer are offset with respect to the weft yarns of the second woven layer.

For some applications, the second woven layer is affixed to the first woven layer such that the weft yarns of the first woven layer are offset with respect to the weft yarns of the second woven layer by 5-30 degrees.

For some applications, the patch has a lip and a root, the driver is configured to anchor the root of the patch to the leaflet such that the lip of the patch extends toward an opposing leaflet of the valve, and the patch defines a root-to-lip axis along a midline of the patch from the root to the lip. For some applications, the weft yarns of the first woven layer and the weft yarns of the second woven layer are offset with respect to each other, and with respect to the root-to-lip axis by 5-40 degrees.

For some applications, the patch is substantially trapezoid.

For some applications, the patch has a lip and a root, the driver is configured to anchor the root of the patch to the leaflet such that the lip of the patch extends toward an opposing leaflet of the valve, and the lip is longer than the root.

For some applications, the patch anchor is disposed approximately midway along the root of the patch, and the patch further includes auxiliary anchors at lateral corners of the root of the patch. For some applications, each auxiliary anchor has a support region attached to the patch, and an arm region elastically deflectable away from the support region. For some applications, the arm region is configured to: pierce the leaflet and/or sandwich the leaflet against the support region.

For some applications, the driver is configured to anchor the patch to the leaflet by, while the portion of the leaflet remains grasped by the clasp, driving the patch anchor through both the patch and the leaflet.

For some applications, the patch anchor includes a tubular staple having a central tubular portion and two lateral tubular portions, one of the lateral tubular portions at either end of the central tubular portion.

For some applications, the driver includes two parallel needles, one of the parallel needles disposed within each of the lateral tubular portions, thereby restraining the lateral tubular portions in parallel with each other. For some applications, the driver is configured to anchor the patch to the leaflet by advancing the needles and the lateral tubular portions through both the patch and the leaflet while the lateral tubular portions are in parallel with each other, and to deploy the tubular staple by retracting the needles out of the lateral tubular portions.

For some applications, the patch anchor includes a frame, attached to the patch and an arm, flexibly coupled to the frame. For some applications, the driver is configured to anchor the patch to the leaflet by advancing the arm through the leaflet while the arm is constrained in an anchoring position, and subsequently, releasing the arm such that the arm responsively moves against the leaflet and toward the frame.

For some applications, the delivery tool further includes a retrieval line, releasably coupled to the anchor such that tensioning the retrieval line returns the arm toward the anchoring position.

For some applications, the arm is flexibly coupled to the frame such that an axis of pivoting of the arm with respect to the frame is transverse to a long axis of the frame.

For some applications, the arm is flexibly coupled to the frame such that an axis of pivoting of the arm with respect to the frame is parallel with a long axis of the frame.

For some applications, the delivery tool further includes a retrieval line, releasably coupled to the anchor such that tensioning the retrieval line facilitates de-anchoring of the patch anchor from the leaflet.

For some applications, the retrieval line is releasably coupled to the anchor such that tensioning the retrieval line facilitates de-anchoring of the patch anchor from the leaflet by reorienting the patch anchor.

For some applications, the retrieval line is releasably coupled to the anchor such that tensioning the retrieval line facilitates de-anchoring of the patch anchor from the leaflet by reshaping the patch anchor.

For some applications, the winch anchor includes a helical tissue-engaging element.

For some applications: the winch anchor further includes a head, a flange, and barbs. For some applications, the helical tissue-engaging element is screwable through the flange such that the head moves toward the flange. For some applications, the barbs are articulatably coupled to the head such that, as the head moves toward the flange, the barbs slide over the flange in a manner in which the flange urges the barbs progressively radially outward.

For some applications, the winch anchor includes a tissue-engaging element that includes a barb structure that includes barbs and a lance structure that includes a lance, relative axial movement between the barb structure and the lance structure inducing radial expansion of the barbs.

For some applications, the tissue-engaging element further includes an overtube within which the barb structure and the lance structure are axially slidable.

For some applications, the lance structure is disposed substantially within the barb structure.

For some applications, the barb structure is disposed substantially within the lance structure.

For some applications, the winch anchor includes a tissue-engaging element that includes multiple lances, configured to be advanced into the ventricular tissue and to automatically deflect laterally within the ventricular tissue. For some applications, the tissue-engaging element includes multiple sleeves, each of the sleeves configured to be advanced, within the ventricular tissue, over and along a corresponding one of the multiple lances.

For some applications, the lances are more rigid than the sleeves.

There is provided, in accordance with some applications, a system and/or an apparatus for use with a valve disposed between an atrium and a ventricle of a heart of a subject, the valve having a first leaflet and a second leaflet. The system/apparatus includes an implant that includes a patch (e.g., a leaflet augmentation patch, etc.), a patch anchor, and a cord. For some applications, the patch includes a flexible sheet and a frame that supports the flexible sheet and defines a spring. For some applications, the cord couples the patch anchor to the patch in a manner in which anchoring the patch anchor to the first leaflet positions the patch to coapt with the second leaflet during ventricular systole, the spring being configured to tension the cord.

For some applications, the implant includes an upstream assembly that includes the patch and the patch anchor. For some applications, the implant further includes a downstream assembly including a winch coupled to a winch anchor that is configured to anchor the downstream assembly to tissue of the ventricle; and a tether, tethering the winch to the patch.

For some applications, the spring is a compression spring.

For some applications, the spring is a cantilever spring.

For some applications, the spring lies substantially flat with respect to the patch.

For some applications, the spring extends out of a plane defined by the patch.

For some applications, the spring extends beyond the sheet of the patch.

For some applications, the patch anchor has a sharpened tip, and is configured to be driven through the leaflet with the sharpened tip penetrating the leaflet.

For some applications, the patch anchor is configured to be driven through the leaflet while disposed within a hollow needle.

For some applications, the spring is configured to facilitate driving of the patch anchor through the leaflet by transiently straining in response to tension applied to the cord by pushing the patch anchor away from the patch and through the leaflet.

For some applications, the spring is coupled to the sheet in a manner in which the patch transiently linearly contracts as the spring transiently strains.

For some applications, the spring is coupled to the sheet in a manner in which the spring slides across the sheet as the spring transiently strains.

For some applications, the patch has a lip and a root, and the cord couples the patch anchor to the patch in a manner in which anchoring the patch anchor to the first leaflet positions the patch such that the lip of the patch extends toward the second leaflet. For some applications, the frame defines: a lip brace at the lip of the patch and a root brace at the root of the patch.

For some applications, the spring is configured such that the transient straining consists substantially of transient compression of the spring between the lip brace and the root brace.

For some applications, the patch defines, along a midline of the patch, a root-to-lip axis between the lip and the root, and the spring is configured such that the transient straining consists substantially of deflection of the spring with respect to the root-to-lip axis.

For some applications, the spring is configured such that the transient straining consists substantially of deflection of the spring toward the root-to-lip axis.

For some applications, the spring is a first spring, and the frame further includes a second spring, the first spring and the second spring configured such that the transient straining consists substantially of deflection of the first spring and the second spring toward each other.

For some applications, the cord extends back and forth between the first spring and the second spring.

For some applications, the at least one frame defines a patch-anchor support coupled to the root brace, the cord extending from the spring, through the patch-anchor support, to the patch anchor.

For some applications, the spring is attached to the root brace.

For some applications, the spring is configured such that the transient straining consists substantially of transient deflection of the spring with respect to the root brace.

For some applications, the spring extends from the root brace to the lip brace.

For some applications, the spring extends from the root brace to the lip brace along a midline of the patch.

For some applications, the spring is a first spring, extending from the root brace to the lip brace along a first lateral edge of the patch, and the at least one frame defines a second spring, extending from the root brace to the lip brace along a second lateral edge of the patch.

For some applications, the spring does not extend to the lip brace.

For some applications, the patch anchor includes a toggle that defines an eyelet substantially midway along the toggle, the cord being attached to the patch anchor at the eyelet.

For some applications, the system/apparatus further includes a retrieval line, coupled to the patch anchor at substantially an end of the toggle, and configured to de-anchor the patch anchor from the first leaflet upon tensioning of the retrieval line.

For some applications, the toggle is a first toggle, the patch anchor further includes a second toggle that defines an eyelet partway along the second toggle, the cord extends from the patch, through the eyelet of the second toggle, to the eyelet of the first toggle, and the first toggle and the second toggle are shaped such that tensioning of the cord arranges the first toggle and the second toggle into a cross.

For some applications, the toggle has a generally cylindrical outer surface, and the eyelet is sunken below the generally cylindrical outer surface.

For some applications, the eyelet extends transversely entirely through the toggle.

For some applications, the toggle is substantially tubular, having a lateral wall that defines a lumen.

For some applications, the lateral wall defines two lateral holes adjacent each other, the eyelet being defined by a part of the lateral wall disposed between the two lateral holes.

There is provided, in accordance with some applications, a system for use with a valve disposed between an atrium and a ventricle of a heart of a subject, the system including an implant and a delivery tool. For some applications, the implant includes a tether, a winch, and a winch anchor coupled to the winch. For some applications, the winch includes a housing and a spool disposed therein. For some applications, the tether extends from the winch, and the spool is operatively coupled to the tether such that actuation of the winch tensions the tether.

For some applications, the delivery tool has a distal portion transluminally advanceable to the heart while coupled to the implant. For some applications, the delivery tool includes a driveshaft subassembly, including a reference-force tube, coupled to the housing and a driveshaft. For some applications, the driveshaft extends through the reference-force tube.

For some applications, the driveshaft has an anchoring state and a winching state. For some applications, in the anchoring state, the driveshaft is operatively coupled to the winch anchor such that rotation of the driveshaft applies an anchoring force to the winch anchor, and operatively uncoupled from the winch such that rotation of the driveshaft does not actuate the winch. For some applications, in the winching state, the driveshaft is operatively uncoupled from the winch anchor such that rotation of the driveshaft does not apply the anchoring force to the winch anchor, and operatively coupled to the winch such that rotation of the driveshaft actuates the winch.

For some applications, in the anchoring state, the is disposed in a first axial position with respect to the winch. For some applications, in the winching state, the driveshaft is disposed in a second, different, axial position with respect to the winch. For some applications, the delivery tool is transitionable between the anchoring state and the winching state via axial movement of the driveshaft with respect to the winch.

For some applications, the first axial position is distal to the second axial position, and the delivery tool is transitionable from the anchoring state to winching state via proximal movement of the driveshaft with respect to the winch.

There is provided, in accordance with some applications, a method for manufacturing a leaflet-augmentation patch for implantation in a heart of a subject, the method including: to a provisional frame assembly that includes a root brace, a lip brace, and one or more splints, connecting the root brace to the lip brace, securing a flexible sheet such that (i) a root edge of the flexible sheet is secured to the root brace, and (ii) a lip edge of the flexible sheet is secured to the lip brace; and subsequently, removing the splints from the provisional frame assembly.

For some applications, the splints are connected to the root brace and the lip brace via frangible connections, and removing the splints from the provisional frame assembly includes breaking the frangible connections.

For some applications, the method further includes attaching flexible ties between the root brace and the lip brace before removing the splints from the provisional frame assembly.

For some applications, the flexible sheet is a first flexible sheet, securing the flexible sheet to the provisional frame assembly includes securing the flexible sheet to a first side of the provisional frame assembly. For some applications, the method further includes, prior to removing the splints from the provisional frame assembly, securing a second flexible sheet to a second side of the provisional frame assembly, thereby sandwiching the provisional frame assembly between the first flexible sheet and the second flexible sheet. For some applications, removing the splints from the provisional frame assembly includes removing the splints from between the first flexible sheet and the second flexible sheet.

For some applications, securing the second flexible sheet to the provisional frame assembly includes securing the second flexible sheet to the provisional frame assembly such that: (i) a root edge of the second flexible sheet is secured to the root brace and to the root edge of the first flexible sheet, and (ii) a lip edge of the second flexible sheet is secured to the lip brace and to the lip edge of the second flexible sheet.

For some applications, removing the splints from the provisional frame assembly includes removing the splints from between a lateral edge of the first flexible sheet and a lateral edge of the second flexible sheet.

For some applications, the method further includes, subsequently to removing the splints from between the lateral edge of the first flexible sheet and the lateral edge of the second flexible sheet, securing the lateral edge of the first flexible sheet to the lateral edge of the second flexible sheet.

The above method(s) can be performed on a living animal or on a simulation, such as on a cadaver, cadaver heart, simulator (e.g., with the body parts, heart, tissue, etc. being simulated), etc.

There is provided, in accordance with some applications, a system for use with a valve disposed between an atrium and a ventricle of a heart of a subject, the system including: an implant and a delivery system or delivery tool. For some applications, the delivery system/tool includes, at a distal portion of the delivery system/tool, a shaft, a clasp, a rail, a mount, and a driver.

For some applications, the shaft defines (or extends along) a longitudinal axis of the delivery tool.

For some applications, the clasp includes a first support and a second support. For some applications, the clasp has an open state in which the first support and the second support are positioned away from each other, and in which the clasp is configured to receive a portion of a leaflet of the valve between the first support and the second support. For some applications, the clasp has a grasping state, the clasp being configured to grasp the portion of the leaflet received between the first support and the second support by being transitioned from the open state toward the grasping state while the portion of the leaflet remains disposed between the first support and the second support.

For some application, the rail is coupled to the clasp such that altering tension in the rail transitions the clasp between the open state and the grasping state.

For some applications, the implant is mounted on the mount, and the mount is slidable over and along the rail.

For some applications, the distal portion of the delivery tool is transluminally advanceable to the heart while the implant is mounted on the mount.

For some applications, the delivery tool is configured to grasp the portion of the leaflet by transitioning the clasp toward the grasping state by altering the tension in the rail.

For some applications, the delivery tool is further configured to, while the portion of the leaflet remains grasped by the clasp: slide the mount over and along the rail to the clasp such that the mount carries the implant to the clasp, and anchor the implant to the leaflet while the mount remains disposed at the clasp.

For some applications, the delivery tool is configured to subsequently release the portion of the leaflet by reversing the alteration of the tension in the rail.

For some applications, the rail is coupled to the first support. For some applications, the clasp is configured to move toward the grasping state by deflection of at least the first support away from the shaft, such that the rail extends obliquely away from the shaft to the clasp. For some applications, the delivery tool is configured to slide the mount over and along the rail obliquely away from the shaft to the clasp such that the mount carries the implant obliquely away from the shaft to the clasp.

There is provided, in accordance with some applications, a method, including grasping a leaflet of an atrioventricular valve of a heart of a patient using a leaflet-grasping element. The leaflet-grasping element can include an elongate helical coil. In some applications, grasping a leaflet is done by corkscrewing the elongate helical coil to an edge of the leaflet in a manner in which a length of the elongate helical coil is in alignment with the edge of the leaflet.

In some applications, the method also includes extending at least one longitudinal member from the leaflet-grasping element down through a ventricle of the heart of the patient. In some applications, the method includes coupling the longitudinal member to a papillary muscle of the heart.

In some applications, the elongate helical coil includes nitinol.

In some applications, positioning a pad at the edge of the leaflet and corkscrewing the elongate helical coil includes corkscrewing the elongate helical coil through the pad and through tissue of the edge of the leaflet.

In some applications, the method further includes stabilizing the leaflet prior to grasping the leaflet.

In some applications, stabilizing the leaflet includes supporting the leaflet from a ventricular surface of the leaflet by pushing against the ventricular surface using a pronged structure.

In some applications, stabilizing the leaflet includes clamping the leaflet from an atrial surface and from a ventricular surface by positioning a first clamping element at the atrial surface and a second clamping element at the ventricular surface.

In some applications, positioning the first and second clamping elements includes pivoting the first and second clamping elements in place using a hinge.

In some applications, positioning the first and second clamping elements includes sliding the first clamping element longitudinally toward the second clamping element.

The above method(s) can be performed on a living animal or on a simulation, such as on a cadaver, cadaver heart, simulator (e.g., with the body parts, heart, tissue, etc. being simulated), etc.

There is provided, in accordance with some applications, a method, including grasping a leaflet of an atrioventricular valve of a heart of a patient using a leaflet-grasping element. In some applications, the leaflet-grasping element includes a first snap element and a second snap element. In some applications, grasping a leaflet is done by positioning (a) the first snap element at an atrial surface of the leaflet and (b) the second snap element at a ventricular surface of the leaflet, and by the positioning, snapping the leaflet.

In some applications, the method further comprises extending at least one longitudinal member from the leaflet-grasping element down through a ventricle of the heart of the patient. In some applications, the method further comprises coupling the longitudinal member to a papillary muscle of the heart.

In some applications, snapping the leaflet includes snapping the leaflet by trapping a portion of the leaflet between the first and second snap elements.

In some applications, snapping the leaflet includes puncturing the leaflet with a portion of the first snap element and passing the portion of the first snap element through a space defined by the second snap element.

In some applications, the portion of the first snap element includes first and second legs that are (a) compressible responsively to force applied to the first and second legs by a wall of the second snap element that defines the space and (b) expandable once distal portions of the first and second legs emerge from within the space. In some applications, passing the portion of the first snap includes facilitating compressing and expanding of the first and second legs. In some applications, snapping the leaflet includes locking in place the first snap element with respect to the second snap element responsively to the expanding of the first and second legs of the first snap element.

In some applications, the portion of the first snap element includes a barb, and the second snap element is shaped so as to define a wall defining the space. In some applications, the wall is (a) expandable responsively to movement of the barb through the space and (b) compressible once a distal end of the barb emerges from within the space. In some applications, passing the portion of the first snap includes facilitating expanding and compressing of the wall of the second snap element.

In some applications, snapping the leaflet includes locking in place the first snap element with respect to the second snap element responsively to the compressing of the wall of the second snap element first and second legs of the first snap element.

In some applications, the method further includes stabilizing the leaflet prior to grasping the leaflet.

In some applications, stabilizing the leaflet includes supporting the leaflet from a ventricular surface of the leaflet by pushing against the ventricular surface using a pronged structure.

In some applications, stabilizing the leaflet includes clamping the leaflet from an atrial surface and from a ventricular surface of the leaflet by positioning a first clamping element at the atrial surface and a second clamping element at the ventricular surface.

In some applications, positioning the first and second clamping elements includes pivoting the first and second clamping elements in place using a hinge.

In some applications, positioning the first and second clamping elements includes sliding the first clamping element longitudinally toward the second clamping element.

The above method(s) can be performed on a living animal or on a simulation, such as on a cadaver, cadaver heart, simulator (e.g., with the body parts, heart, tissue, etc. being simulated), etc.

There is provided, in accordance with some applications, a system and/or apparatus for repairing a leaflet of an atrioventricular valve of a patient, the system/apparatus including a primary longitudinal member configured to be coupled at a first end to tissue surrounding a ventricle of a heart of the patient and two or more secondary longitudinal members. In some applications, each of the two or more secondary longitudinal members having a first end that is configured to be coupled to a respective location of the leaflet.

In some applications, a force-distributing member is coupled to a second end of the primary longitudinal member and to respective second ends of the two or more secondary longitudinal members in a manner in which the force-distributing member is positioned between the leaflet and the tissue surrounding the ventricle of the heart.

In some applications, the force-distributing member is configured to distribute tension forces between the primary longitudinal member and the two or more secondary longitudinal members.

In some applications, the force-distributing member includes a planar force-distributing member.

In some applications, the force-distributing member includes a symmetrical force-distributing member.

In some applications, the force-distributing member is shaped so as to define two or more vertices for coupling of each of the respective second ends of the two or more secondary longitudinal members, wherein the two or more vertices are spaced apart at a distance in a manner in which a corresponding distance is maintained between the first ends of the two or more secondary longitudinal members at the leaflet.

In some applications, the system/apparatus further includes a cinching device coupled to the primary longitudinal member, wherein the cinching device is configured to control tension of the primary longitudinal member.

In some applications, the force-distributing member is shaped so as to define a respective opening at coupling sites where the force-distributing member is coupled (a) to the second end of the primary longitudinal member and (b) to the respective second ends of the two or more secondary longitudinal members.

In some applications, the primary longitudinal member and the two or more secondary longitudinal members pass through the respective openings in a manner in which creates slidable coupling between the force-distributing member and (1) the primary longitudinal member and (2) the two or more secondary longitudinal members.

In some applications, the primary longitudinal member and the two or more secondary longitudinal members and are locked in place with respect to the force-distributing member using a respective lock that is couplable to the second end of the primary longitudinal member and to the respective second ends of the two or more secondary longitudinal members.

In some applications, the slidable coupling facilitates distribution of the tension forces between the primary longitudinal member and the two or more secondary longitudinal members.

There is provided, in accordance with some applications, a method for repairing a leaflet of an atrioventricular valve of a patient, the method including coupling a first end of a primary longitudinal member to tissue surrounding a ventricle of a heart of the patient, coupling respective first ends of two or more secondary longitudinal members to respective locations of the leaflet, and distributing tension forces between the primary longitudinal member and the two or more secondary longitudinal members using a force-distributing member.

In some applications, the force-distributing member is coupled to a second end of the primary longitudinal member and to respective second ends of the two or more secondary longitudinal members, in a manner in which the force-distributing member is positioned between the leaflet and the tissue surrounding the ventricle of the heart.

In some applications, coupling the primary longitudinal member at the first end to tissue surrounding the ventricle includes coupling the first end of the primary longitudinal member to a papillary muscle.

In some applications, coupling the primary longitudinal member at the first end to tissue surrounding the ventricle includes coupling the first end of the primary longitudinal member to a wall of the ventricle.

In some applications, the force-distributing member includes a planar force-distributing member.

In some applications, the force-distributing member includes a symmetrical force-distributing member.

In some applications, the force-distributing member is shaped so as to define two or more vertices for coupling of each of the respective second ends of the two or more secondary longitudinal members, wherein the two or more vertices are spaced apart at a distance in a manner in which a corresponding distance is maintained between the first ends of the two or more secondary longitudinal members at the leaflet.

In some applications, the method further includes cinching the primary longitudinal member and by the cinching, controlling tension of the primary longitudinal member.

In some applications the force-distributing member is shaped so as to define a respective opening at coupling sites where the force-distributing member is coupled (a) to the second end of the primary longitudinal member and (b) to the respective second ends of the two or more secondary longitudinal members.

In some applications, the primary longitudinal member and the two or more secondary longitudinal members pass through the respective openings in a manner in which creates slidable coupling between the force-distributing member and (1) the primary longitudinal member and (2) the two or more secondary longitudinal members.

In some applications, the primary longitudinal member and the two or more secondary longitudinal members and are locked in place with respect to the force-distributing member using a respective lock that is couplable to the second end of the primary longitudinal member and to the respective second ends of the two or more secondary longitudinal members.

In some applications, distributing the tension forces between the primary longitudinal member and the two or more secondary longitudinal members includes facilitating the slidable coupling.

The above method(s) can be performed on a living animal or on a simulation, such as on a cadaver, cadaver heart, simulator (e.g., with the body parts, heart, tissue, etc. being simulated), etc.

There is provided, in accordance with some applications, a method, including implanting a tube in a muscle of a ventricle of a heart of a patient, passing a longitudinal member through the tube, securing the longitudinal member with respect to itself, and by the securing, facilitating slidable coupling between a first portion of the longitudinal member and the tube and between the first portion of the longitudinal member and the muscle.

In some applications, the method also includes fastening a second portion of the longitudinal member to a leaflet of a heart valve of the patient.

In some applications, implanting the tube in the muscle of the ventricle includes implanting the tube in a papillary muscle.

In some applications, securing the longitudinal member with respect to itself includes securing the longitudinal member with a lock.

In some applications, securing the longitudinal member with respect to itself includes securing the longitudinal member with a crimp, and the method further includes adjusting a tension of the longitudinal member using the crimp.

In some applications, the method further includes adjusting a tension of the longitudinal member prior to the securing the longitudinal member.

In some applications, the method further includes adjusting a tension of the longitudinal member subsequently to the securing the longitudinal member.

In some applications, implanting the tube includes implanting a tube having free ends following the implanting.

In some applications, implanting the tube includes implanting a tube having free ends, and the method further includes coupling the free ends of the tube to form a closed loop.

In some applications, implanting the tube includes implanting a tube having free ends, wherein the tube has a shape-memory which enables the tube to assume a closed loop, and implanting the tube includes enabling the free ends to close to form the tube into the closed loop.

In some applications, implanting the tube includes delivering the tube in a straight configuration within an overtube, passing the overtube through the muscle, and removing the overtube to leave the tube within the muscle.

In some applications, the tube has a shape-memory, and removing the overtube includes allowing the tube to assume a predetermined shape.

In some applications, allowing the tube to assume the predetermined shape includes allowing the tube to assume a curved shape.

In some applications, allowing the tube to assume the predetermined shape includes allowing the tube to assume a closed loop.

In some applications, allowing the tube to assume the predetermined shape includes allowing free ends of the tube to lock together.

In some applications, allowing the tube to assume the predetermined shape includes allowing free ends of the tube to deform, and allowing the free ends of the tube to deform includes allowing the free ends to form anchors against an external surface of the muscle.

The above method(s) can be performed on a living animal or on a simulation, such as on a cadaver, cadaver heart, simulator (e.g., with the body parts, heart, tissue, etc. being simulated), etc.

There is provided, in accordance with some applications, a method, including helically stitching a middle section of a longitudinal member to an edge of a single leaflet of an atrioventricular valve of a heart of a patient.

In some applications, the method includes subsequently, extending a first portion of the longitudinal member into a ventricle of the heart, the first portion being downstream of the middle section of the longitudinal member.

In some applications, the method includes coupling a first end of the longitudinal member to tissue surrounding the ventricle.

In some applications, coupling the first end of the longitudinal member to the tissue surrounding the ventricle includes coupling the first end of the longitudinal member to a papillary muscle.

In some applications, the method further includes coupling a second end of the longitudinal member to the leaflet.

In some applications, the method further includes:

- extending a second portion of the longitudinal member into the ventricle of the heart, the second portion being upstream of the middle section of the longitudinal member; and
- coupling a second end of the longitudinal member to tissue surrounding the ventricle.

In some applications, coupling the second end of the longitudinal member to the tissue surrounding the ventricle includes coupling the second end of the longitudinal member to a papillary muscle.

In some applications, the first end of the longitudinal member is coupled to a helical tissue anchor. In some applications, helically stitching includes passing the helical tissue anchor helically with respect to tissue of the leaflet. In some applications, coupling the first end of the longitudinal member to the tissue surrounding the ventricle includes corkscrewing the helical tissue anchor into the tissue surrounding the ventricle.

In some applications, coupling the first end of the longitudinal member to the tissue surrounding the ventricle includes corkscrewing the helical tissue anchor into a papillary muscle.

In some applications, the method further includes coupling a second end of the longitudinal member to the leaflet.

In some applications, the method further includes extending a second portion of the longitudinal member into the ventricle of the heart, the second portion being upstream of the middle section of the longitudinal member, and coupling a second end of the longitudinal member to tissue surrounding the ventricle.

In some applications, coupling the second end of the longitudinal member to the tissue surrounding the ventricle includes coupling the second end of the longitudinal member to a papillary muscle.

In some applications, coupling the second end of the longitudinal member to tissue surrounding the ventricle includes anchoring the second end of the longitudinal member using a tissue anchor.

In some applications, anchoring the second end of the longitudinal member using the tissue anchor includes anchoring the second end of the longitudinal member using a helical tissue anchor.

The above method(s) can be performed on a living animal or on a simulation, such as on a cadaver, cadaver heart, simulator (e.g., with the body parts, heart, tissue, etc. being simulated), etc.

There is provided, in accordance with some applications, a method, including passing at least a portion of a leaflet-tissue-anchor through tissue of a leaflet of an atrioventricular heart valve of a heart of a patient, the leaflet-tissue anchor being coupled to a longitudinal member. In some applications, during the passing, a free end of the longitudinal member is disposed outside the patient.

In some applications, the method includes subsequently to the passing of the leaflet-tissue anchor, passing a ventricle-tissue-anchor along the longitudinal member and toward tissue surrounding a ventricle of the heart.

In some applications, the method includes coupling the ventricle-tissue-anchor to tissue surrounding the ventricle.

In some applications, the method includes adjusting tension of the longitudinal member.

In some applications, passing the leaflet-tissue-anchor through tissue of the leaflet includes puncturing the leaflet.

In some applications, puncturing the leaflet includes puncturing the leaflet with a portion of the leaflet-tissue-anchor.

In some applications, puncturing the leaflet includes advancing a needle through the leaflet prior to the passing of the leaflet-tissue-anchor through the tissue of the leaflet.

The above method(s) can be performed on a living animal or on a simulation, such as on a cadaver, cadaver heart, simulator (e.g., with the body parts, heart, tissue, etc. being simulated), etc.

There is provided, in accordance with some applications, a system and/or apparatus, including an elongate tool for facilitating leaflet augmentation and repair of chordae tendineae.

In some applications, the elongate tool includes a central tube shaped so as to define a side-slot and at least one needle slidable within a lumen of the central tube. In some applications, the elongate tool includes a lower structural element configured for positioning at a ventricular surface of a leaflet of a valve of a heart of a patient. In some applications, the elongate tool includes at least one needle-stabilizing element moveable along a longitudinal axis of the central tube to abut an atrial surface of the leaflet and to grasp a portion of the leaflet between the at least one needle-stabilizing element and the lower structural element.

In some applications, the system/apparatus includes a leaflet-augmentation patch deliverable through the central tube. The leaflet-augmentation patch can be the same as or similar to any of the leaflet-augmentation patches described herein. In some applications, the leaflet-augmentation patch includes a flap (e.g., a planar flap, non-planar flap, flat flap, thin flap, elongate flap, etc.) configured to emerge from the side-slot of the central tube. In some applications, the leaflet-augmentation patch includes at least one tensioning member coupled to the flap.

In some applications, the leaflet-augmentation patch includes at least one locking element comprising a locking element proximal end and a locking element distal end. In some applications, the at least one locking element is coupled to a first end of the at least one tensioning member. In some applications, the at least one locking element is deliverable through a respective one of the at least one needle of the elongate tool to lock in place the flap with respect to the leaflet.

In some applications, the at least one locking element includes a “T”-shaped locking element which is compressible within the at least one needle and expandable once deployed from within the needle.

In some applications, the at least one tensioning member is configured to be coupled to tissue surrounding a ventricle of the heart.

In some applications, the system/apparatus further includes at least one longitudinal member coupled to the at least one tensioning member, wherein the at least one longitudinal member is coupled at a first end thereof to the at least one tensioning member, and wherein a second end of the at least one longitudinal member is configured to be coupled to tissue surrounding a ventricle of the heart.

In some applications, the at least one tensioning member is threaded with respect to the flap.

In some applications, the at least one tensioning member has shape-memory, and the at least one tensioning member deforms the flap from a compressed configuration to an expanded configuration.

In some applications, the at least one locking element includes an elongated rod-like (e.g., tubular) locking element, configured to flip from a vertical orientation when the at least one rod-like locking element is disposed within the at least one needle, to a lateral orientation, having its longitudinal axis parallel to a ventricular surface of the leaflet, when the at least one rod-like locking element is deployed from within the at least one needle, and is pressed against the ventricular surface of the leaflet.

In some applications, the at least one tensioning member includes fabric or polymeric thread.

In some applications, the leaflet-augmentation patch further includes a support frame coupled to the flap.

In some applications, the support frame has shape-memory, and the support frame is configured to deform the flap from a compressed configuration to an expanded configuration.

In some applications, the at least one needle includes a beveled tip, wherein the beveled tip includes a sharp distal tip portion and a blunt proximal tip portion.

In some applications, the system/apparatus further includes at least one pull member extending through the central tube, and releasably coupled to the at least one locking element.

In some applications, the at least one locking element includes an eyelet, wherein the at least one pull member is looped through the eyelet of the at least one locking element, such that one stand of the pull member extends from one side of the eyelet, and another stand of the pull member extends from the other side of the eyelet.

In some applications, the system/apparatus further includes a U-shaped loop, the at least one locking element includes first and second locking elements, and the U-shaped loop is attached at ends of tails thereof to the first and second locking elements, wherein the at least one pull member is looped through the U-shaped loop, such that one stand of the pull member extends from one side of the U-shaped loop, and another stand of the pull member extends from the other side of the U-shaped loop.

In some applications, the at least one locking element includes an expandable locking element, configured to transition from an elongated configuration in a free state thereof, to an expanded configuration when the locking element distal end approximates the locking element proximal end.

In some applications, the system/apparatus further includes at least one longitudinal member, wherein the at least one tensioning member is coupled at its first end to the locking element distal end, and at a second end thereof to the at least one longitudinal member.

In some applications, the system/apparatus further includes a pull member which extends through the central tube and is releasably coupled to the flap at an end of the flap which is opposite to the second end of the at least one tensioning member.

In some applications, the locking element proximal end is tapering radially inward in a proximal direction.

In some applications, the locking element further comprises a constrictor attached to the locking element proximal end, wherein the constrictor is tapering radially inward in a proximal direction.

There is provided, in accordance with some applications, a method, including positioning between leaflets of an atrioventricular valve of a heart of a patient a portion of an elongate tool for facilitating leaflet augmentation and repair of chordae tendineae.

In some applications, the elongate tool includes a central tube shaped so as to define a side-slot and at least one needle slidable within a lumen of the central tube. In some applications, the elongate tool includes a lower structural element configured for positioning at a ventricular surface of a leaflet of a valve of a heart of a patient. In some applications, the elongate tool includes at least one needle-stabilizing element moveable along a longitudinal axis of the central tube.

In some applications, the method includes positioning the lower structural element at the ventricular surface of the leaflet.

In some applications, the method includes grasping the leaflet between the at least one needle-stabilizing element and the lower structural element by moving the at least one needle-stabilizing element along the longitudinal axis, and by the moving, abutting an atrial surface of the leaflet with the at least one needle-stabilizing element.

In some applications, the method includes delivering through the central tube a leaflet-augmentation patch. The leaflet-augmentation patch can be the same as or similar to any of the leaflet-augmentations patches described herein. In some applications, the leaflet-augmentation patch includes a flap (e.g., a planar flap, non-planar flap, flat flap, thin flap, elongate flap, etc.) configured to emerge from the side-slot of the central tube. In some applications, the leaflet-augmentation patch includes at least one tensioning member coupled to the flap. In some applications, the leaflet-augmentation patch includes at least one locking element coupled to respective first ends of the at least one tensioning member.

In some applications, the method includes passing the flap through the side-slot of the central tube and out of the tube, and by the passing, enabling the flap to deform to an expanded configuration.

In some applications, the method includes locking the flap to the leaflet by delivering the at least one locking element through the at least one needle of the elongate tool.

In some applications, the at least one locking element includes a "T"-shaped locking element, and the delivering the at least one locking element includes delivering the "T"-shaped locking element within the at least one needle in a compressed state and pushing the "T"-shaped locking element out of the needle thereby enabling expanding of the "T"-shaped locking element.

In some applications, the at least one tensioning member has shape-memory, and enabling the flap to deform to the expanded configuration includes enabling the flap to deform via the shape-memory of the at least one tensioning member.

In some applications, the method further includes: extending at least one longitudinal member from the flap into a ventricle of the heart; and coupling the at least one longitudinal member to tissue surrounding the ventricle.

In some applications, extending the at least one longitudinal member includes applying tension to the at least one longitudinal member, and enabling the flap to deform to the expanded configuration includes enabling the flap to deform by the applying the tension.

In some applications, coupling the at least one longitudinal member to the tissue surrounding the ventricle includes coupling the at least one longitudinal member to a papillary muscle.

In some applications, coupling the at least one longitudinal member to the tissue surrounding the ventricle includes coupling the at least one longitudinal member to a wall of the ventricle.

In some applications, the method further includes extending the at least one tensioning member from the flap into a ventricle of the heart, and coupling the at least one tensioning member to tissue surrounding the ventricle.

In some applications, extending the at least one tensioning member includes applying tension to the at least one tensioning member, and enabling the flap to deform to the expanded configuration includes enabling the flap to deform by the applying the tension.

In some applications, coupling the at least one tensioning member to the tissue surrounding the ventricle includes coupling the at least one tensioning member to a papillary muscle.

In some applications, coupling the at least one tensioning member to the tissue surrounding the ventricle includes coupling the at least one tensioning member to a wall of the ventricle.

In some applications, the at least one locking element includes an elongated rod-like locking element, and the delivering the at least one locking element includes delivering the rod-like locking element within the at least one needle in a vertical orientation and deploying the rod-like locking element from within the needle thereby enabling the rod-like locking element to assume a lateral orientation.

In some applications, the leaflet-augmentation patch further includes a support frame which has shape-memory, wherein enabling the flap to deform to the expanded configuration includes enabling the flap to deform via the shape-memory of the support frame.

In some applications, the method further includes simultaneously pulling two stands of at least one pull member which is looped through an eyelet of the at least one locking element.

In some applications, the method further includes pulling one strand of at least one pull member which is looped through an eyelet of the at least one locking element, while allowing another strand of the pull member, extending from an opposite side of the eyelet, to move toward the eyelet, so as to release the at least one pull member from the eyelet.

In some applications, the at least one locking element includes first and second locking elements, and the method further includes simultaneously pulling two stands of a pull member which is looped through a U-shaped loop, wherein the U-shaped loop is coupled to the first and second locking elements.

In some applications, the at least one locking element includes first and second locking elements, and the method further includes pulling one strand of a pull member which is looped through a U-shaped loop coupled to the first and second locking elements, while allowing another strand of the pull member, extending from an opposite side of the U-shaped loop, to move toward the U-shaped loop, so as to release the pull member from the U-shaped loop.

In some applications, the at least one locking element includes an expandable locking element, and delivering the at least one locking element comprises delivering the expandable locking element within the at least one needle in a free state and deploying the expandable locking element from within the needle, thereby enabling the expandable locking element to assume an expanded state upon application of tension on the at least one tensioning member, which is attached to a locking element distal end.

In some applications, the method further comprises pulling at least one longitudinal member coupled to the at least one tensioning member in a proximal direction, until the leaflet-augmentation patch transitions to a folded state, thereby allowing the at least one expandable locking element to transition to the free state.

In some applications, the method includes simultaneously pulling both strands of the pull member and the at least one longitudinal member in a proximal direction.

In some applications, the method further comprises pulling one strand of a pull member which is coupled to the flap, while allowing another strand of the pull member to move toward the flap, so as to release the pull member from the flap.

The above method(s) can be performed on a living animal or on a simulation, such as on a cadaver, cadaver heart, simulator (e.g., with the body parts, heart, tissue, etc. being simulated), etc.

There is provided, in accordance with some applications, a method, including delivering an elongate tool between leaflets of an atrioventricular valve of a heart of a patient such that a side-slot in the elongate tool is disposed between the leaflets and positioning the elongate tool such that a single leaflet is moved within the side-slot in the elongate tool.

In some applications, the method includes passing two ends of a longitudinal member through at least one lumen of the elongate tool in a section of the tool that is disposed within a ventricle of the heart.

In some applications, the method includes puncturing the leaflet from a ventricular surface of the leaflet and passing the two ends of the longitudinal member through the leaflet and toward an atrium of the heart such that a bight of the longitudinal member is disposed at the ventricular surface of the leaflet.

In some applications, the method includes pulling the two ends of the longitudinal member with the tool from an atrial surface of the leaflet and toward the ventricle.

In some applications, the method includes coupling the two ends of the longitudinal member to tissue surrounding the ventricle.

In some applications, coupling the two ends of the longitudinal member to the tissue surrounding the ventricle includes coupling the two ends of the longitudinal member to a papillary muscle.

In some applications, coupling the two ends of the longitudinal member to the tissue surrounding the ventricle includes coupling the two ends of the longitudinal member to a wall of the ventricle.

In some applications, each of the two ends of the longitudinal member is coupled to a respective needle, and each needle passes through a respective lumen of the tool.

In some applications, the tool is shaped so as to define respective lumens for respective portions of the longitudinal member, and passing two ends of the longitudinal member includes passing each end of the longitudinal member through a respective lumen of the tool.

In some applications, each of the two ends of the longitudinal member is coupled to a needle, and each needle passes through a respective lumen of the tool.

The above method(s) can be performed on a living animal or on a simulation, such as on a cadaver, cadaver heart, simulator (e.g., with the body parts, heart, tissue, etc. being simulated), etc.

There is provided, in accordance with some applications, a method, including delivering an elongate docking-element-delivery tool between leaflets of an atrioventricular valve of a heart of a patient and coupling a docking element to tissue surrounding a ventricle of the heart. In some applications, the docking element is shaped so as to define a receptacle.

In some applications, the method includes delivering a tissue-anchor-delivery tool to an atrial surface of a leaflet of the leaflets of the atrioventricular valve.

In some applications, the method includes puncturing tissue of the leaflet.

In some applications, the method includes passing (a) a tissue anchor coupled to a first end of a longitudinal member, and (b) a first portion of the longitudinal member through the leaflet via the tissue-anchor-delivery tool into the ventricle.

In some applications, the method includes coupling the tissue anchor and the first end of the longitudinal member to the docking element by advancing the tissue anchor further and into the receptacle of the docking element; and In some applications, the method includes locking a second end of a longitudinal member to the leaflet.

In some applications, the tissue anchor includes one or more expandable protrusions which are compressed during passing of the tissue anchor, and the docking element is shaped so as to define one or more openings.

In some applications, coupling the tissue anchor and the first end of the longitudinal member to the docking element includes aligning the one or more expandable protrusions of the tissue anchor with the one or more openings of the docking element, and by the aligning enabling expanding of the one or more protrusions through the one or more openings and locking of the tissue anchor to the docking element.

In some applications, coupling the docking element to the tissue surrounding the ventricle includes coupling the docking element to a papillary muscle.

In some applications, coupling the docking element to the tissue surrounding the ventricle includes coupling the docking element to a wall of the ventricle.

In some applications, the method further includes adjusting tension of the longitudinal member.

In some applications, adjusting the tension includes adjusting the tension by the locking of the second end of the longitudinal member to the leaflet.

In some applications, adjusting the tension includes adjusting the tension subsequently to the locking of the second end of the longitudinal member to the leaflet by: engaging the longitudinal member with a tension-adjusting tool; pulling on the longitudinal member with the tension-adjusting tool; and locking in place the longitudinal member in order to secure tension applied to the longitudinal member.

The above method(s) can be performed on a living animal or on a simulation, such as on a cadaver, cadaver heart, simulator (e.g., with the body parts, heart, tissue, etc. being simulated), etc.

There is provided, in accordance with some applications, a system and/or apparatus, including at least one curved rigid element having a distal pointed tip configured to puncture cardiac tissue from an atrial surface of an atrioventricular valve of a heart of a patient, toward a ventricular surface of the atrioventricular valve, and subsequently, from the ventricular surface toward an atrial surface of a native leaflet of the atrioventricular valve.

In some applications, the system/apparatus includes a prosthetic leaflet patch configured to augment the native leaflet, the prosthetic leaflet patch configured to be coupled to the distal pointed tip of the curved rigid element.

In some applications, the system/apparatus includes at least one longitudinal member extending from a portion of the prosthetic leaflet patch at a first end thereof and configured at a second end thereof to be coupled to tissue surrounding a ventricle of the heart.

In some applications, the at least one longitudinal member includes a plurality of longitudinal members.

In some applications, the at least one curved rigid element includes a metal.

In some applications, the at least one curved rigid element includes two curved rigid elements coupled together by a bridge.

In some applications, the distal pointed tip includes a plurality of barbs configured to ensnare the prosthetic leaflet.

In some applications, the distal pointed tip includes a plurality of barbs, and the prosthetic leaflet patch includes a coupling configured to engage with and be coupled to the plurality of barbs.

In some applications, the distal pointed tip includes a plurality of barbs, and the prosthetic leaflet patch includes a socket configured to surround the plurality of barbs.

In some applications, the system/apparatus further includes a tissue anchor coupled to the second end of the longitudinal member.

In some applications, the tissue anchor includes a pointed tip configured to penetrate the tissue surrounding the ventricle.

In some applications, the tissue anchor includes a ring configured to surround the tissue surrounding the ventricle.

In some applications, the tissue anchor includes a cuff configured to surround the tissue surrounding the ventricle.

There is provided, in accordance with some applications, a method, including puncturing cardiac tissue from an atrial surface of an atrioventricular valve of a heart of a patient with a distal pointed tip of at least one curved rigid element, passing the distal pointed tip toward a ventricular surface of the atrioventricular valve, puncturing a ventricular surface of a native leaflet of the atrioventricular valve with the distal pointed tip, and passing the distal pointed tip from the ventricular surface of the native leaflet toward an atrial surface of the native leaflet.

In some applications, the method includes augmenting the native leaflet by coupling a prosthetic leaflet patch to the distal pointed tip.

In some applications, the method includes extending at least one longitudinal member coupled at a first end thereof to the prosthetic leaflet patch into a ventricle of the heart of the patient.

In some applications, the method includes coupling a second end of the at least one longitudinal member to tissue surrounding the ventricle.

In some applications, puncturing the cardiac tissue from the atrial surface includes puncturing tissue of an annulus of the atrioventricular valve.

In some applications, coupling the second end of the at least one longitudinal member to tissue surrounding the ventricle includes coupling the second end of the longitudinal member to tissue of a wall of the ventricle.

In some applications, coupling the second end of the longitudinal member to tissue surrounding the ventricle includes coupling the second end of the longitudinal member to tissue of a papillary muscle.

In some applications, the at least one curved rigid element includes a metal.

In some applications, the at least one curved rigid element includes two curved rigid elements coupled together by a bridge, each of the two curved rigid elements has a respective distal pointed tip, puncturing the cardiac tissue includes puncturing the cardiac tissue with the distal pointed tips of the two curved rigid elements, and coupling the prosthetic leaflet patch includes coupling the prosthetic leaflet patch to the distal pointed tips of the two curved rigid elements.

In some applications, coupling the prosthetic leaflet patch to the distal pointed tip includes ensnaring the prosthetic leaflet patch with a plurality of barbs coupled to the distal pointed tip.

In some applications, coupling the prosthetic leaflet patch to the distal pointed tip includes coupling a coupling of the prosthetic leaflet patch to a plurality of barbs coupled to the pointed distal tip.

In some applications, extending the at least one longitudinal member includes extending a plurality of longitudinal members into the ventricle and coupling the second end of the longitudinal member to tissue surrounding the ventricle includes coupling respective second ends of the plurality of longitudinal members to tissue surrounding the ventricle.

In some applications, coupling the second end of the longitudinal member to the tissue surrounding the ventricle includes coupling the second end of the longitudinal member using a tissue anchor coupled to the second end of the longitudinal member.

In some applications, coupling the second end of the longitudinal member includes penetrating the tissue surrounding the ventricle with a pointed tip of the tissue anchor.

In some applications, coupling the second end of the longitudinal member includes surrounding the tissue surrounding the ventricle with the tissue anchor.

In some applications, coupling the second end of the longitudinal member includes surrounding the tissue surrounding the ventricle with a cuff of the tissue anchor.

The above method(s) can be performed on a living animal or on a simulation, such as on a cadaver, cadaver heart, simulator (e.g., with the body parts, heart, tissue, etc. being simulated), etc.

There is provided, in accordance with some applications, a system and/or apparatus, including a frame shaped so as to define a central ring coupled to a plurality of struts arranged circumferentially with respect to the central ring and a tissue anchor coupled to the central ring of the frame, the tissue anchor configured to be coupled to a portion of cardiac tissue of a patient.

In some applications, the system/apparatus also includes a polymer sheet coupled to the frame configured to increase contact between the frame and the portion of cardiac tissue.

In some applications, the system/apparatus includes wherein, the frame is expandable from within a sheath used to deliver the frame and collapsible around the tissue anchor in order to enhance coupling between the tissue anchor and the portion of cardiac tissue.

In some applications, each one of the plurality of struts is shaped so as to define a petal shape.

In some applications, the tissue anchor includes a helical tissue anchor.

In some applications, the frame includes a material having shape memory, and the frame is self-collapsible due to the shape memory.

In some applications, the frame is collapsible around the tissue anchor upon a force applied to the frame, in a vector toward the tissue anchor.

In some applications, the frame is collapsible around the tissue anchor upon a force applied to the frame by the polymer sheet, in a vector toward the tissue anchor.

In some applications, the frame is collapsible upon application of tension to the central ring.

In some applications, the system/apparatus further includes at least one longitudinal element coupled at a first end thereof to the central ring, and the frame is collapsible in response to tension applied to the longitudinal member.

In some applications, the central ring is shaped so as to define a loop extending away from a circumference of the central ring, and the first end of the longitudinal member is coupled to the loop.

In some applications, the system/apparatus further includes a leaflet-tissue-anchor coupled to a second end of the longitudinal member, and the second end the longitudinal member is configured to be coupled to tissue of a leaflet of a heart of the patient via the leaflet-tissue-anchor.

There is provided, in accordance with some applications, a method, including delivering within a ventricle of a heart of a patient a distal end portion of a sheath housing a frame shaped so as to define a central ring coupled to a plurality of struts arranged circumferentially with respect to the central ring and a tissue anchor coupled to the central ring of the frame. In some applications, the sheath also houses a polymer sheet coupled to the frame configured to increase contact between the frame and the portion of cardiac tissue. In some applications, during the delivering the frame and the polymer sheet are in a compressed state.

In some applications, the method includes exposing the frame, the tissue anchor, and the polymer sheet from within the sheath such that the frame and the polymer sheet expand from the compressed state into an expanded state.

In some applications, the method includes coupling the tissue anchor to a portion of cardiac tissue, and by the coupling, facilitating collapsing of the frame and the polymer sheet around the portion of the cardiac tissue.

In some applications, each one of the plurality of struts is shaped so as to define a petal shape.

In some applications, coupling the tissue anchor to the portion of cardiac tissue includes coupling the tissue anchor to a papillary muscle.

In some applications, coupling the tissue anchor to the portion of cardiac tissue includes coupling the tissue anchor to a portion of a wall of the ventricle.

In some applications, the tissue anchor includes a helical tissue anchor, and coupling the tissue anchor to the portion of cardiac tissue includes driving the helical tissue anchor into the portion of cardiac tissue.

In some applications, the frame includes a material having shape memory, and exposing the frame includes allowing the frame to self-expand.

In some applications, the frame includes a material having shape memory, and facilitating collapsing of the frame includes allowing the frame to self-collapse around the portion of cardiac tissue.

In some applications, facilitating collapsing of the frame includes facilitating exposing of the frame to a force applied to the frame, in a vector toward the tissue anchor.

In some applications, facilitating collapsing of the frame includes facilitating exposing of the frame to a force applied to the frame by the polymer sheet, in a vector toward the tissue anchor.

In some applications, facilitating collapsing of the frame includes applying tension to the central ring.

In some applications, at least one longitudinal element is coupled at a first end thereof to the central ring, and facilitating collapsing of the frame includes applying tension to the central ring by applying tension to the longitudinal member.

In some applications, the central ring is shaped so as to define a loop extending away from a circumference of the central ring, and the first end of the longitudinal member is coupled to the loop.

In some applications, the method further includes coupling a second end of the longitudinal member to tissue of a leaflet of a heart of the patient.

The above method(s) can be performed on a living animal or on a simulation, such as on a cadaver, cadaver heart, simulator (e.g., with the body parts, heart, tissue, etc. being simulated), etc.

The present invention will be more fully understood from the following detailed description of examples thereof, taken together with the drawings, in which:

BRIEF DESCRIPTION OF THE DRAWINGS

FIGS. 36A-K and 37A-G are schematic illustrations of various patches, in accordance with some applications;

FIGS. 39, 40, 41A-B, 42A-D, 43A-C, 44, 45A-C, 46A-B, 47A-C, 48A-B, 49A-D, 50A-C, 51A-E, 52A-B, and 53A-B are schematic illustrations of various patch anchors and techniques for use therewith, in accordance with some applications;

DETAILED DESCRIPTION

Figure 1A:
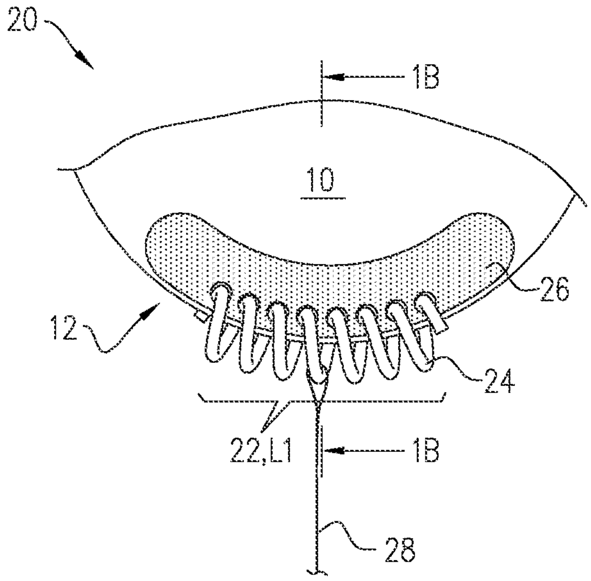
FIGS. 1A-B are schematic illustrations of an example of a leaflet-grasping element, in accordance with some applications.
Figure 1B:
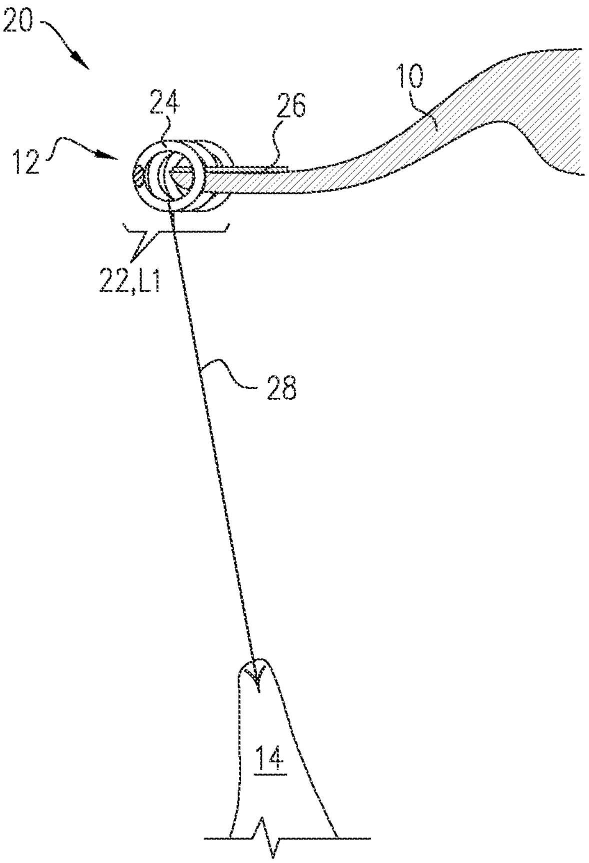

Reference is now made to FIGS. 1A-B, which are schematic illustrations of a system 20 comprising a leaflet-grasping element 22 which can comprise an elongate helical coil 24, in accordance with some applications. Leaflet-grasping element 22 is shown as a helical coil 24 by way of illustration and not limitation, and can comprise staples, clips, spring-loaded anchors, or other tissue anchors known in the art. Leaflet-grasping element 22 is configured to grasp a leaflet 10 of an atrioventricular valve of a heart of a patient. For some applications, the atrioventricular valve includes a mitral valve. For some applications, the atrioventricular valve includes a tricuspid valve.

Helical coil 24 comprises a flexible material (e.g., metal such as nitinol, or a fabric such as a braided fabric). For some applications, a leading end of helical coil 24 comprises a sharp tip configured to puncture tissue of leaflet 10. Helical coil 24 is corkscrewed to an edge 12 of leaflet 10 in a manner in which a length L1 the elongate helical coil 24 is in alignment, e.g., runs along or is generally parallel, with edge 12 of leaflet 10.

At least one longitudinal member 28 extends from leaflet-grasping element 22 down through a ventricle of the heart and is coupled to ventricular tissue of the heart such as a papillary muscle 14 of the heart or a ventricular wall e.g., using any suitable tissue anchor known in the art such as a pledget, knot, clip, helical tissue anchor, or barb. For some applications, longitudinal member 28 is coupled to helical coil 24. Longitudinal member 28 can function as artificial chordae tendineae. For some applications, longitudinal member 28 comprises a suture. For some applications, longitudinal member 28 comprises a flexible and/or super-elastic material, e.g., ePTFE, nitinol, PTFE, polyester, stainless steel, or cobalt chrome. In some applications, longitudinal member 28 is coated with polytetrafluoroethylene (PTFE). In some applications, longitudinal member 28 comprises at least one wire/suture portion and at least one portion that comprises an elongate tensioning coil. For example, longitudinal member 28 can comprise an elongate coil between two wire/suture portions.

For some applications, a support pad 26 is coupled to edge 12 of leaflet 10 prior to corkscrewing of helical coil 24. Coil 24 is corkscrewed with respect to pad 26. Pad 26 is configured to distribute forces of coil 24 on edge 12 of leaflet 10. Pad 26 can comprise a fabric, synthetic material, rubber, or a metal such as nitinol.

For some applications, system 20 does not comprise helical coil 24. Instead, support pad 26 and a coiled needle is used to deliver a suture in a coiled manner with respect to edge 12 of leaflet 10. In such a manner a suture can be helically sutured to leaflet 10. Following the helical suturing of the suture to the leaflet, the coiled needle can be removed from the body of the patient. Support pad 26 distributes the force of the helically-disposed suture on edge 12 of leaflet 10. In such a manner, support pad 26 prevents tearing of tissue of leaflet 10.

Figure 2A:
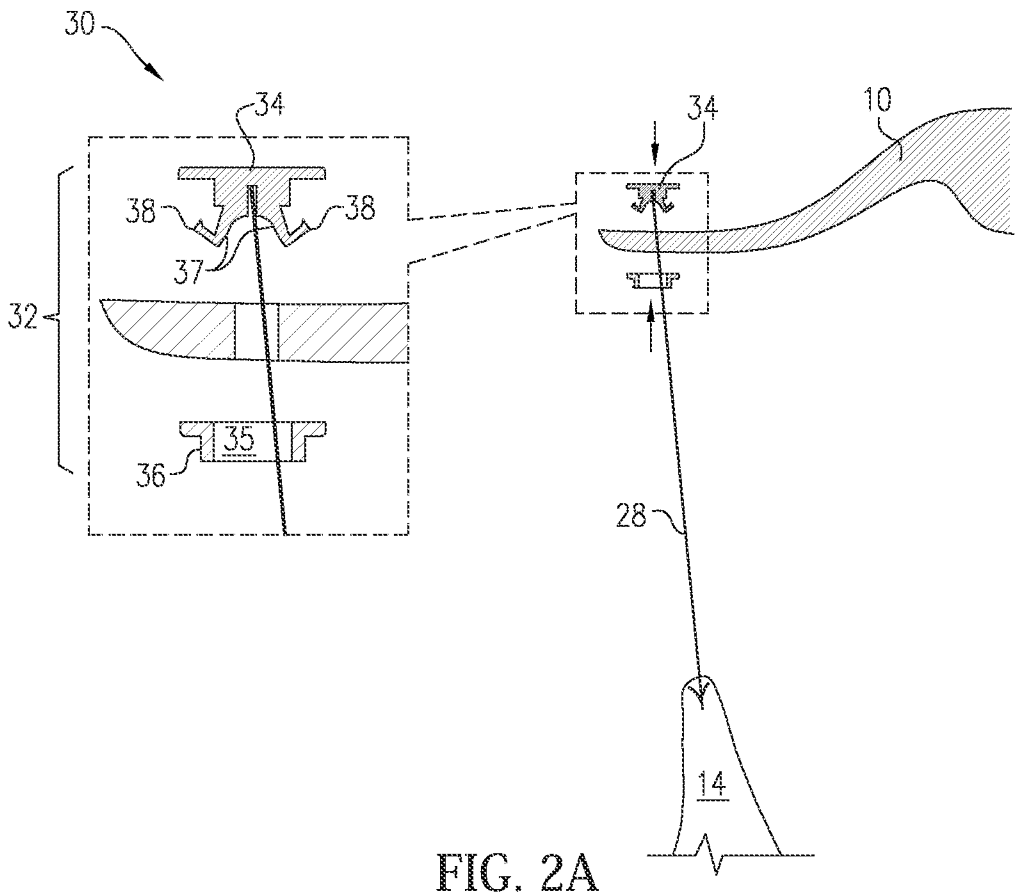
FIGS. 2A-B and 3A-C are schematic illustrations of examples of respective leaflet-grasping elements comprising first and second snap elements, in accordance with some applications.
Figure 2B:
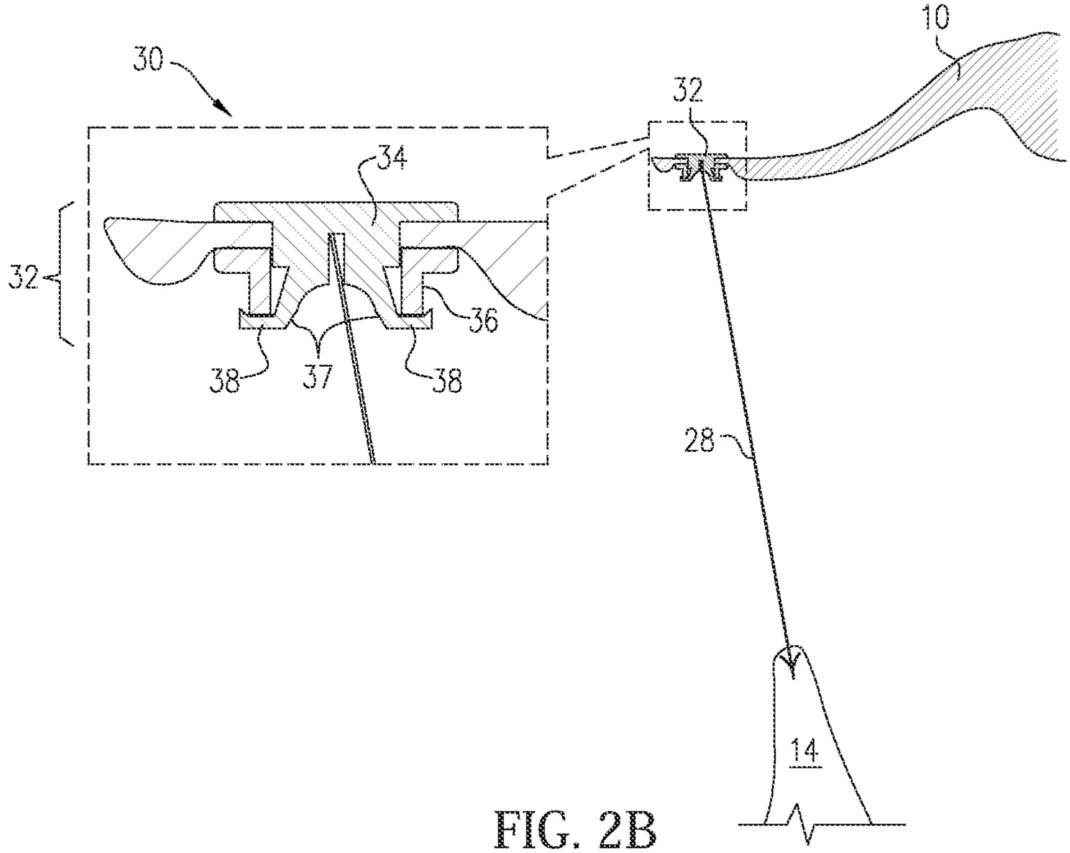

Reference is now made to FIGS. 2A-B, which are schematic illustrations of a system 30 comprising a leaflet-grasping element 32 which comprises a first snap element 34 and a second snap element 36, in accordance with some applications. Leaflet-grasping element 32 is shown as a snap fastener by way of illustration and not limitation, and can comprise staples, clips, spring-loaded anchors, or other tissue anchors known in the art. Leaflet-grasping element 32 is configured to grasp leaflet 10 of an atrioventricular valve of a heart of a patient. For some applications, the atrioventricular valve includes a mitral valve. For some applications, the atrioventricular valve includes a tricuspid valve.

First and second snap elements 34 and 36 comprise a biocompatible metal such as nitinol or stainless steel.

First snap element 34 is positioned at an atrial surface of leaflet 10 and second snap element 36 is positioned at a ventricular surface of leaflet 10. By the positioning of elements 34 and 36, tissue of leaflet 10 is grasped or snapped between elements 34 and 36. For some applications, by snapping elements 34 and 36 together, a portion of tissue of leaflet 10 is trapped between the first and second snap elements 34 and 36, e.g., without puncturing tissue of leaflet 10.

Longitudinal member 28 extends from leaflet-grasping element 32 down through a ventricle of the heart and is coupled to a papillary muscle 14 of the heart e.g., using any suitable tissue anchor known in the art. Longitudinal member 28 functions as artificial chordae tendineae. For some applications, as shown, longitudinal member 28 is coupled to first snap element 34. For some applications, longitudinal member 28 is coupled to second snap element 36.

First snap element 34 comprises an upper element or upper planar element which provides anchoring to element 34 as the upper element abuts tissue of leaflet 10. As shown, snap element 34 punctures leaflet 10 with a portion of first snap element 34 which comprises first and second legs 37 that are passable through a space 35 defined by second snap element 36. Second snap element 36 is shown as a generally cylindrical element by way of illustration and not limitation. Each leg 37 is shaped so as to define a respective distal portion 38 that is disposed angularly with respect to leg 37. Legs 37 are (a) compressible responsively to force applied to first and second legs 37 by a wall of second snap element 36 that defines space 35, and (b) expandable once distal portions 38 of first and second legs 37 emerge from within space 35. Due to the angular disposition of portions 38 with respect to legs 37, portions 38 slide within space 35 and in the absence of force applied thereto by the wall of second snap element 36, legs 37 expand such that distal portion assume a larger dimension than space 35, as shown in FIG. 2B, thereby locking in place first snap element 34 with respect to second snap element 36.

Figure 3A:
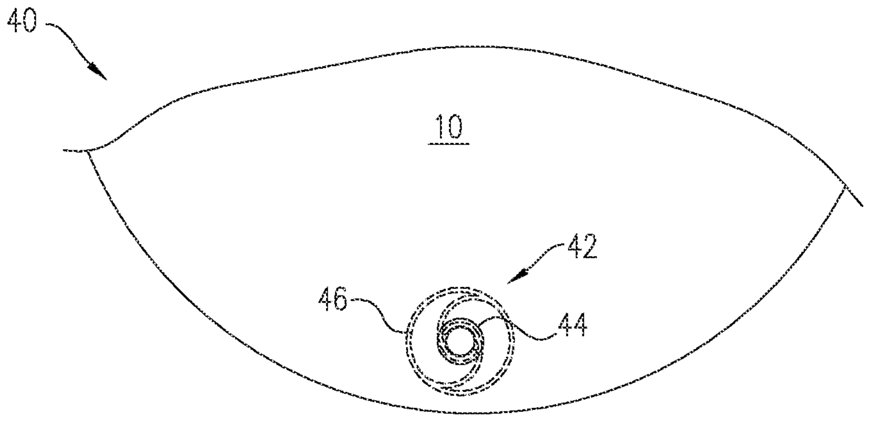
Figure 3B:
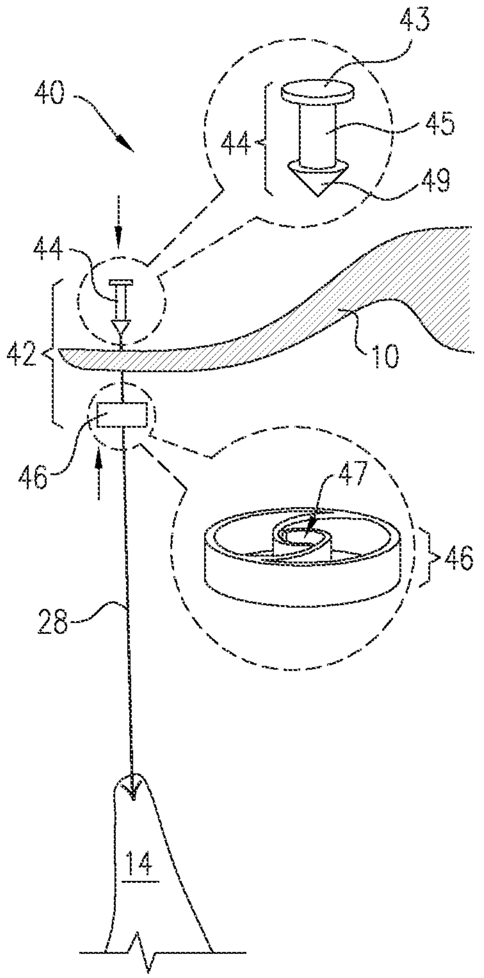
Figure 3C:
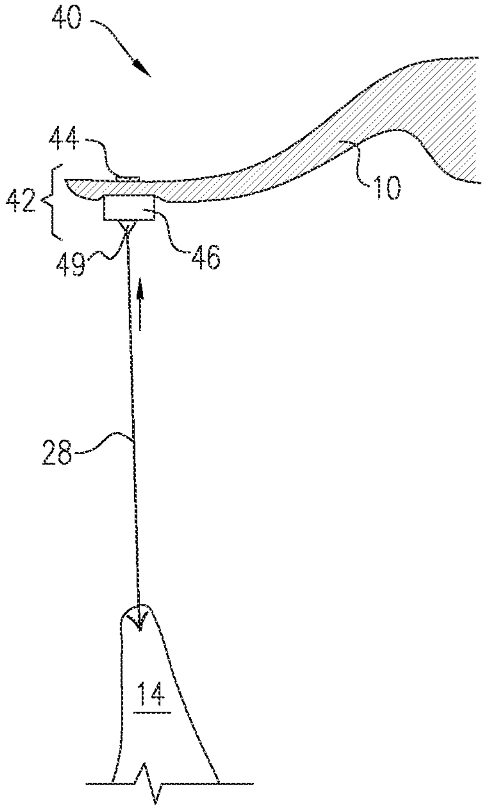

Reference is now made to FIGS. 3A-B, which are schematic illustrations of a system 40 comprising a leaflet-grasping element 42 which comprises a first snap element 44 and a second snap element 46, in accordance with some applications. Leaflet-grasping element 42 is shown as a snap fastener by way of illustration and not limitation, and can comprise staples, clips, spring-loaded anchors, or other tissue anchors known in the art. Leaflet-grasping element 42 is configured to grasp leaflet 10 of an atrioventricular valve of a heart of a patient. For some applications, the atrioventricular valve includes a mitral valve. For some applications, the atrioventricular valve includes a tricuspid valve.

First and second snap elements 44 and 46 comprise a biocompatible metal such as nitinol or stainless steel.

First snap element 44 is positioned at an atrial surface of leaflet 10 and second snap element 46 is positioned at a ventricular surface of leaflet 10. By the positioning of elements 44 and 46, tissue of leaflet 10 is grasped or snapped between elements 44 and 46. For some applications, by snapping elements 44 and 46 together, a portion of tissue of leaflet 10 is trapped between the first and second snap elements 44 and 46, e.g., without puncturing tissue of leaflet 10.

Longitudinal member 28 extends from leaflet-grasping element 42 down through a ventricle of the heart and is coupled to a papillary muscle 14 of the heart e.g., using any suitable tissue anchor known in the art. Longitudinal member 28 functions as artificial chordae tendineae. For some applications, as shown, longitudinal member 28 is coupled to first snap element 44. For some applications, longitudinal member 28 is coupled to second snap element 46.

First snap element 44 comprises an upper element or upper planar element which provides anchoring to element 44 as the upper element abuts tissue of leaflet 10. As shown, snap element 44 punctures leaflet 10 with a portion of first snap element 44 which comprises a barb that is passable through a space 47 defined by second snap element 46. Second snap element 46 is shown as a generally disc-shaped element having internal structure comprising a wall shaped as a swirl or a coil, by way of illustration and not limitation. As the barb of snap element 44 passes through space 47, the wall of second snap element 46 expands to accommodate the width of the barb during movement of the barb with respect to second snap element 46. Once the barb of first snap element 44 passes through second snap element and the barb emerges from within space 47, the wall of second snap element 46 compresses in order to lock in place first snap element with respect to second snap element.

Figure 4A:
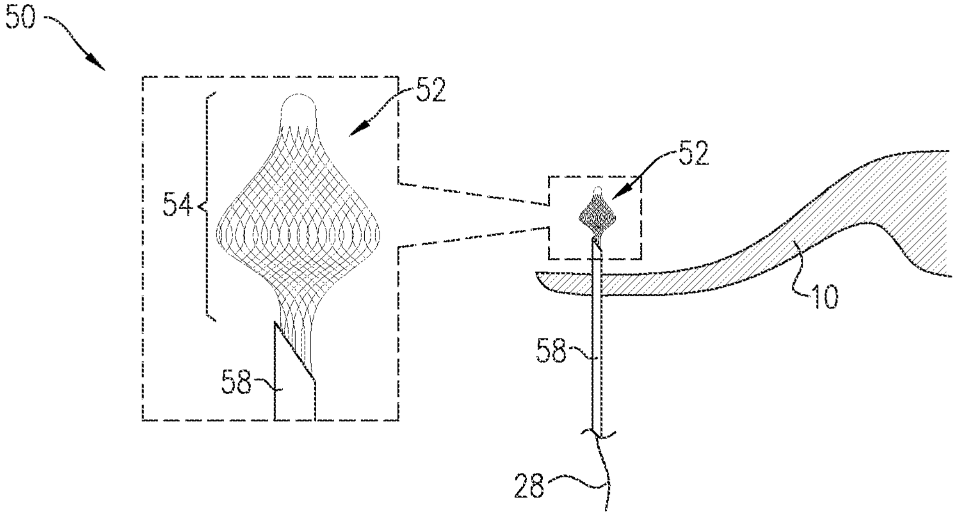
FIGS. 4A-C are schematic illustrations of an example of a leaflet-grasping element comprising an hourglass-shaped element, in accordance with some applications.
Figure 4B:
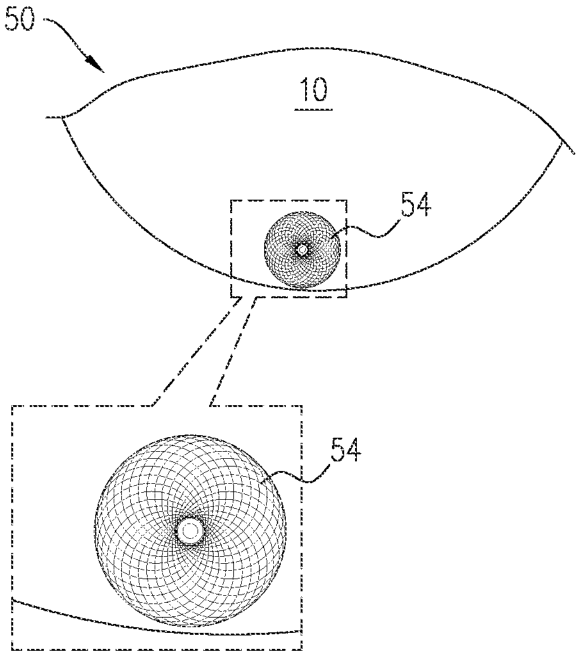
Figure 4C:
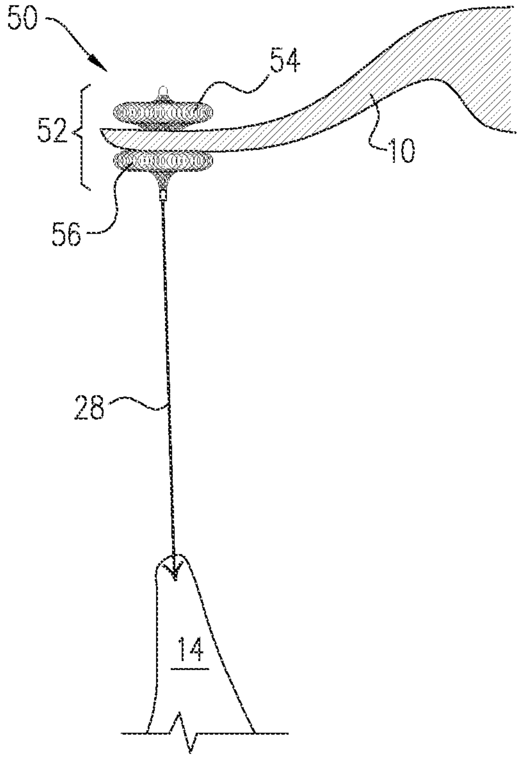

Reference is now made to FIGS. 4A-C, which are schematic illustrations of a system 50 comprising a leaflet-grasping element 52 which comprises an hourglass-shaped element comprising a braided, flexible material (e.g., metal such as nitinol, or a fabric such as a braided fabric). In a resting state of element 52, element is shaped as shown in FIG. 4C, i.e., element 52 is shaped so as to define an upper disc 54 and a lower disc 56. In the absence of force applied to element 52, element assumes the shape as shown in FIG. 4C. Due to the braided material of element 52, when element is linearly pulled straight and constrained within a needle 58, element 52 assumes a narrow, longer configuration than in the resting state of element 52. For some applications, leaflet-grasping element 52 self-expands to the configuration shown in FIG. 4C.

As shown in FIG. 4A, element 52 is deployable from within needle 58 following puncturing of leaflet 10 by a sharp end of needle 58. As shown, needle 58 can be delivered from within the ventricle and puncture leaflet 10 from the ventricular surface such that upper disc 54 is deployed, expanded, and positioned against the atrial surface of leaflet 10. Once upper disc 54 is positioned, needle 58 is retracted and pulls slightly on disc 54 such that it remains in place. Needle 58 is then further retracted in order to expose lower disc 56 such that lower disc 56 is deployed, expanded, and positioned against the ventricular surface of leaflet 10. It is to be noted that needle 58 can also approach leaflet 10 from within the atrium. In such a manner, lower disc 56 is delivered to the ventricular surface of leaflet 10 first, mutatis mutandis.

In order to lock in place the final shape of element 52, a crimp can be attached to lower disc 56. Alternatively or additionally, element 52 remains in place with a ratchet.

By the positioning of discs 54 and 56, tissue of leaflet 10 is grasped between discs 54 and 56.

Longitudinal member 28 extends from leaflet-grasping element 52 down through a ventricle of the heart and is coupled to a papillary muscle 14 of the heart e.g., using any suitable tissue anchor known in the art. Longitudinal member 28 functions as artificial chordae tendineae. For some applications, as shown, longitudinal member 28 is coupled to lower disc 56.

Figure 5A:
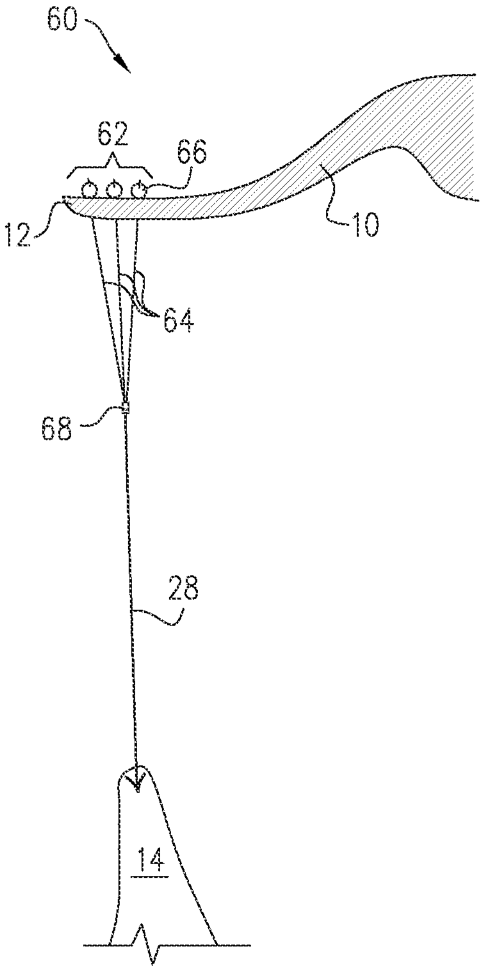
FIGS. 5A-B and 6A-C are schematic illustrations of examples of a leaflet-grasping element comprising a plurality of secondary sutures coupled to a primary suture, in accordance with some applications.
Figure 5B:
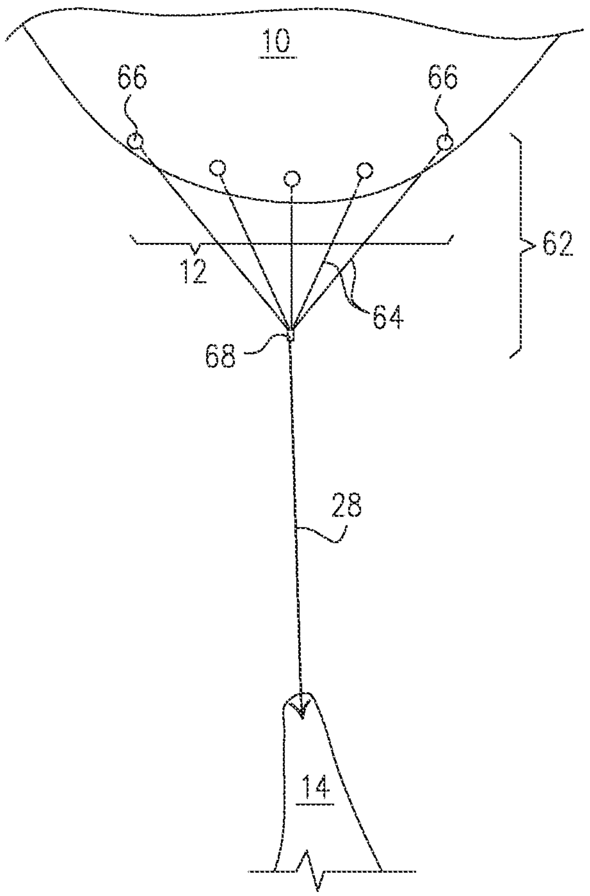

Reference is now made to FIGS. 5A-B, which are schematic illustrations of a system 60 comprising a leaflet-grasping element 62 which comprises a plurality of longitudinal members 64 distributed along edge 12 of leaflet, in accordance with some applications. For some applications, each of the plurality of longitudinal members 64 is sutured to tissue of leaflet 10. Each of the plurality of longitudinal members 64 is coupled at a first end to a portion of tissue of leaflet 10 using a suture knot or a respective locking element 66, e.g., a bead or a crimp. The second ends of each of the plurality of longitudinal members 64 are coupled together using a coupler 68, e.g., a bead, which couples the plurality of longitudinal members 64 to longitudinal member 28. As such, longitudinal member 28 defines a primary longitudinal member, while the plurality of longitudinal members 64 define secondary longitudinal members 64.

Each of the plurality of longitudinal members 64 is coupled to a respective portion of leaflet 10 in a manner in which the plurality of longitudinal members 64 of leaflet-grasping element 62 fan out with respect to leaflet 10 and forces are distributed along edge 12 of leaflet 10.

Reference is now made to FIGS. 1A-B and 5A-B. It is to be noted that leaflet-grasping element 62 can be used in combination with support pad 26 of FIGS. 1A-B in order to distribute forces of the plurality of longitudinal members 64 on edge 12 of leaflet 10. Pad 26 can comprise a fabric, synthetic material, rubber, or a metal such as nitinol.

At least one longitudinal member 28 extends from leaflet-grasping element 62 down through a ventricle of the heart and is coupled to a papillary muscle 14 of the heart e.g., using any suitable tissue anchor known in the art. Longitudinal member 28 functions as artificial chordae tendineae. Longitudinal member 28 and secondary longitudinal members 64 comprise a flexible and/or superelastic material, e.g., ePTFE, nitinol, PTFE, polyester, stainless steel, or cobalt chrome. In some applications, longitudinal member 28 and secondary longitudinal members 64 are coated with polytetrafluoroethylene (PTFE) or with PTFE. In some applications, longitudinal member 28 and secondary longitudinal members 64 comprise sutures. In some applications, longitudinal member 28 comprises at least one wire/suture portion and at least one portion that comprises an elongate tensioning coil. For example, longitudinal member 28 can comprise an elongate coil between two wire/suture portions.

Figure 6A:
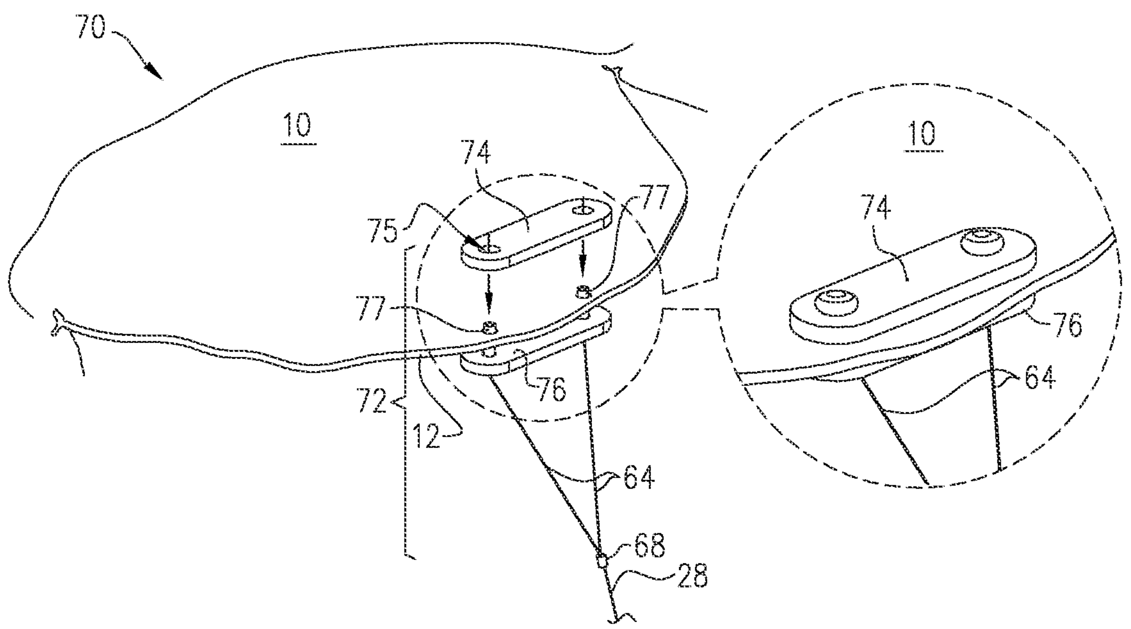
Figure 6B:
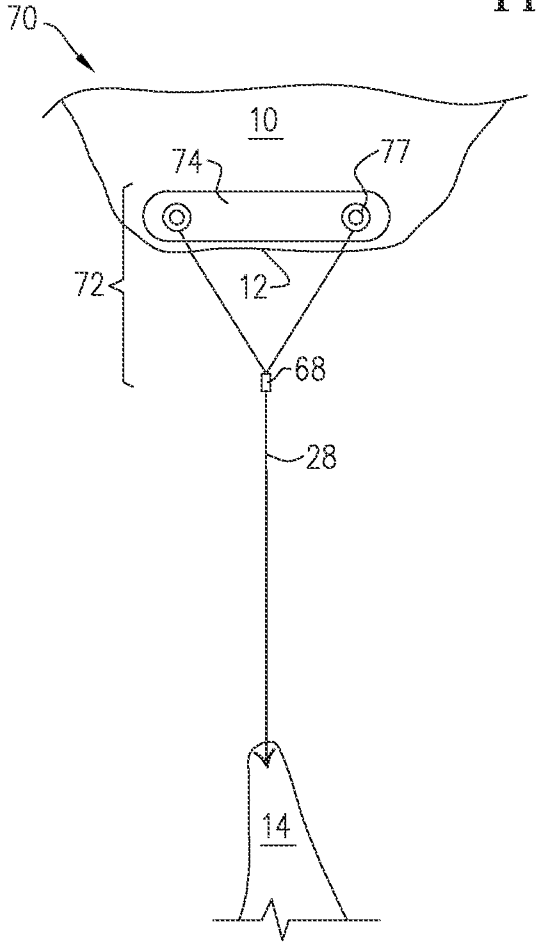
Figure 6C:
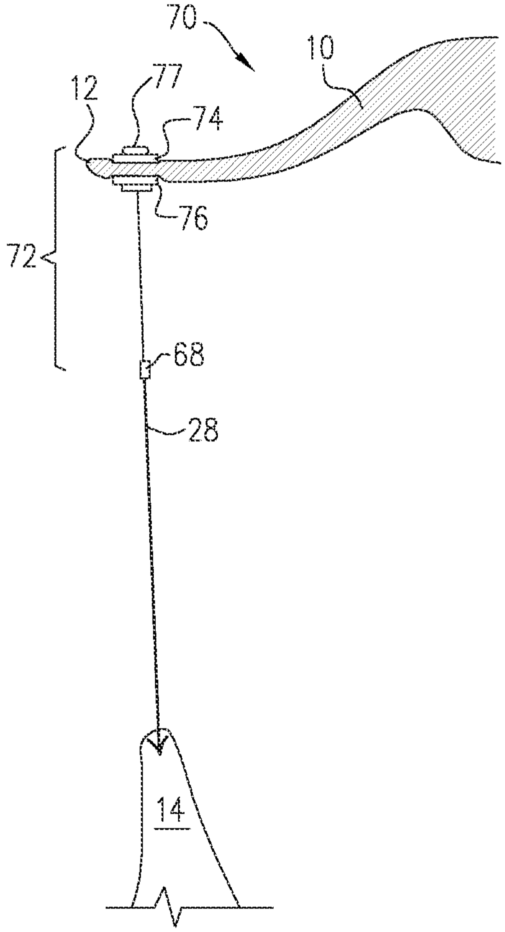

Reference is now made to FIGS. 6A-C, which are schematic illustrations of a system 70 comprising a leaflet-grasping element 72 which comprises a plurality of longitudinal members 64 distributed along edge 12 of leaflet 10, in accordance with some applications. As shown, element 72 comprises two longitudinal members 64. It is to be noted that any suitable number of longitudinal members 64 can be used. Leaflet-grasping element 72 comprises a first snap element 74 and a second snap element 76. For some applications, as shown, first and second snap elements 74 and 76 comprise respective plates. For some applications, the plates comprise metal plates, and for some applications, the metal plates are covered in fabric. Leaflet-grasping element 72 is shown as a snap fastener by way of illustration and not limitation, and can comprise staples, clips, spring-loaded anchors, or other tissue anchors known in the art. Leaflet-grasping element 72 is configured to grasp leaflet 10 of an atrioventricular valve of a heart of a patient. For some applications, the atrioventricular valve includes a mitral valve. For some applications, the atrioventricular valve includes a tricuspid valve.

First snap element 74 is positioned at an atrial surface of leaflet 10 and second snap element 76 is positioned at a ventricular surface of leaflet 10. By the positioning of elements 74 and 76, tissue of leaflet 10 is grasped or snapped between elements 74 and 76. For some applications, by snapping elements 74 and 76 together, a portion of tissue of leaflet 10 is trapped between the first and second snap elements 74 and 76, e.g., without puncturing tissue of leaflet 10.

First and second snap elements 74 and 76 comprise a biocompatible metal such as nitinol or stainless steel.

First snap element 74 comprises an upper element or upper planar element which provides anchoring to element 74 as the upper element or upper planar element abuts tissue of leaflet 10. As shown, second snap element 76 punctures leaflet 10 with respective protrusions 77 of second snap element 76. Protrusions 77 are passable through a respective space 75 defined by first snap element 74. Once protrusions 77 of second snap element 76 fit within spaces 75 of first snap element 74, as shown in FIG. 6B, first snap element 74 is locked in place with respect to second snap element 76.

It is to be noted that first snap element 74 can comprise protrusions 77 while second snap element 76 can be shaped so as to define spaces 75.

It is to be noted that for some applications, protrusions 77 do not puncture tissue of leaflet 10, rather protrusions 77 trap tissue of leaflet 10 between first and second snap elements 74 and 76.

Each of the plurality of longitudinal members 64 is coupled at a first end to second snap element 76. The second ends of each of the plurality of longitudinal members 64 are coupled together using a coupler 68, e.g., a bead, which couples the plurality of longitudinal members 64 to longitudinal member 28. As such, longitudinal member 28 defines a primary longitudinal member, while the plurality of longitudinal members 64 define secondary longitudinal members 64.

Each of the plurality of longitudinal members 64 is coupled to a respective portion of leaflet 10 in a manner in which the plurality of longitudinal members 64 of leaflet-grasping element 62 fan out with respect to leaflet 10 and forces are distributed along edge 12 of leaflet 10.

At least one longitudinal member 28 extends from leaflet-grasping element 62 down through a ventricle of the heart and is coupled to a papillary muscle 14 of the heart e.g., using any suitable tissue anchor known in the art. Longitudinal member 28 functions as artificial chordae tendineae. Longitudinal member 28 and secondary longitudinal members 64 comprise a flexible and/or superelastic material, e.g., ePTFE, nitinol, PTFE, polyester, stainless steel, or cobalt chrome. In some applications, longitudinal member 28 and secondary longitudinal members 64 are coated with polytetrafluoroethylene (PTFE) or with PTFE. In some applications, longitudinal member 28 and secondary longitudinal members 64 comprise sutures. In some applications, longitudinal member 28 comprises at least one wire/suture portion and at least one portion that comprises an elongate tensioning coil. For example, longitudinal member 28 can comprise an elongate coil between two wire/suture portions.

Figure 7A:
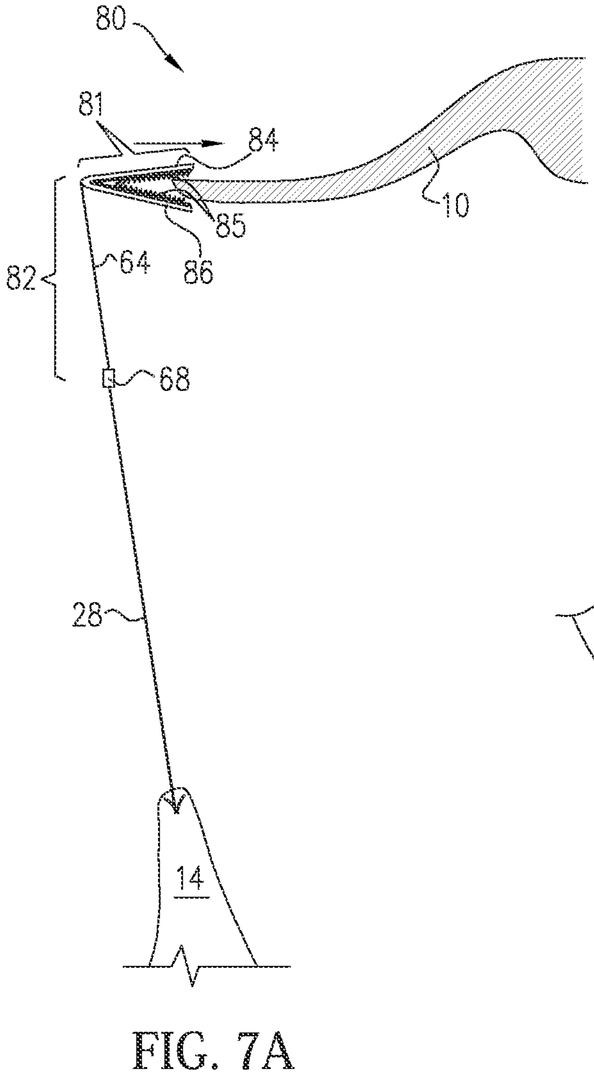
FIGS. 7A-B are schematic illustrations of an example of a leaflet-grasping element comprising a clamp, in accordance with some applications.
Figure 7B:
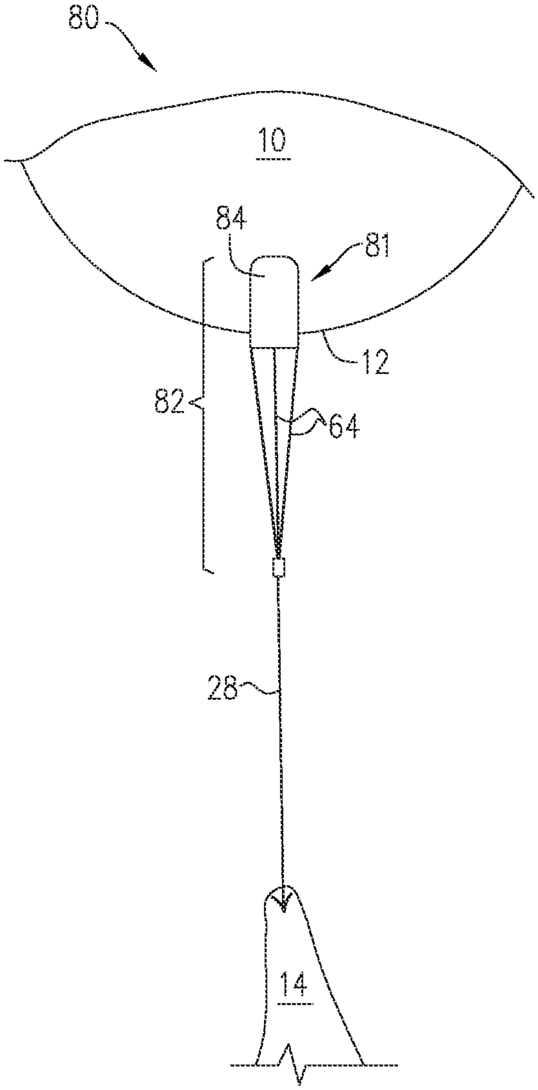

Reference is now made to FIGS. 7A-B, which are schematic illustrations of a system 80 comprising a leaflet-grasping element 82 which comprises a plurality of longitudinal members 64 distributed along edge 12 of leaflet, in accordance with some applications. As shown, element 82 comprises three longitudinal members 64. It is to be noted that any suitable number of longitudinal members 64 can be used. Leaflet-grasping element 82 comprises clamp 81 comprising an upper jaw 84 and a lower jaw 86. Leaflet-grasping element 82 is shown as a clamp by way of illustration and not limitation, and can comprise staples, clips, spring-loaded anchors, or other tissue anchors known in the art. Leaflet-grasping element 82 is configured to grasp leaflet 10 of an atrioventricular valve of a heart of a patient. For some applications, the atrioventricular valve includes a mitral valve. For some applications, the atrioventricular valve includes a tricuspid valve.

Each of upper jaw 84 and lower jaw 86 comprises a plurality of teeth 85 configured to grip tissue of leaflet 10 with or without puncturing tissue of leaflet 10. Teeth 85 increase friction between clamp 81 and tissue of leaflet 10.

Upper jaw 84 of clamp 81 is positioned at an atrial surface of leaflet 10 and lower jaw 86 is positioned at a ventricular surface of leaflet 10. By the positioning of jaws 84 and 86, tissue of leaflet 10 is grasped or snapped between jaws 84 and 86. For some applications, by closing jaws 84 and 86 together, a portion of tissue of leaflet 10 is trapped between the first and second jaws 84 and 86, e.g., without puncturing tissue of leaflet 10.

Clamp 81 comprises a biocompatible metal such as nitinol or stainless steel.

Upper jaw 84 comprises a broad element or broad planar element which provides anchoring to jaw 84 as the broad element or broad planar element abuts tissue of leaflet 10. Lower jaw 86 comprises a broad element or broad planar element which provides anchoring to jaw 86 as the broad element or broad planar element abuts tissue of leaflet 10. Since clamp 81 is broad, forces from longitudinal members 64 and from longitudinal member 28 are distributed along edge 12 of leaflet 10. Once jaws 84 and 86 clamp together and teeth 85 grip tissue of leaflet 10, clamp 81 is locked in place with respect leaflet 10.

It is to be noted that for some applications, teeth 85 do not puncture tissue of leaflet 10, rather teeth 85 trap tissue of leaflet 10 between upper and lower jaws 84 and 86.

Each of the plurality of longitudinal members 64 is coupled at a first end to lower jaw 86. The second ends of each of the plurality of longitudinal members 64 are coupled together using a coupler 68, e.g., a bead, which couples the plurality of longitudinal members 64 to longitudinal member 28. As such, longitudinal member 28 defines a primary longitudinal member, while the plurality of longitudinal members 64 define secondary longitudinal members 64.

Each of the plurality of longitudinal members 64 is coupled to a respective portion of leaflet 10 in a manner in which the plurality of longitudinal members 64 of leaflet-grasping element 62 fan out with respect to leaflet 10 and forces are distributed along edge 12 of leaflet 10.

At least one longitudinal member 28 extends from leaflet-grasping element 62 down through a ventricle of the heart and is coupled to a papillary muscle 14 of the heart e.g., using any suitable tissue anchor known in the art. Longitudinal member 28 functions as artificial chordae tendineae. Longitudinal member 28 and secondary longitudinal members 64 comprise a flexible and/or superelastic material, e.g., ePTFE, nitinol, PTFE, polyester, stainless steel, or cobalt chrome. In some applications, longitudinal member 28 and secondary longitudinal members 64 are coated with polytetrafluoroethylene (PTFE) or with PTFE. In some applications, longitudinal member 28 and secondary longitudinal members 64 comprise sutures. In some applications, longitudinal member 28 comprises at least one wire/suture portion and at least one portion that comprises an elongate tensioning coil. For example, longitudinal member 28 can comprise an elongate coil between two wire/suture portions.

Figure 8:
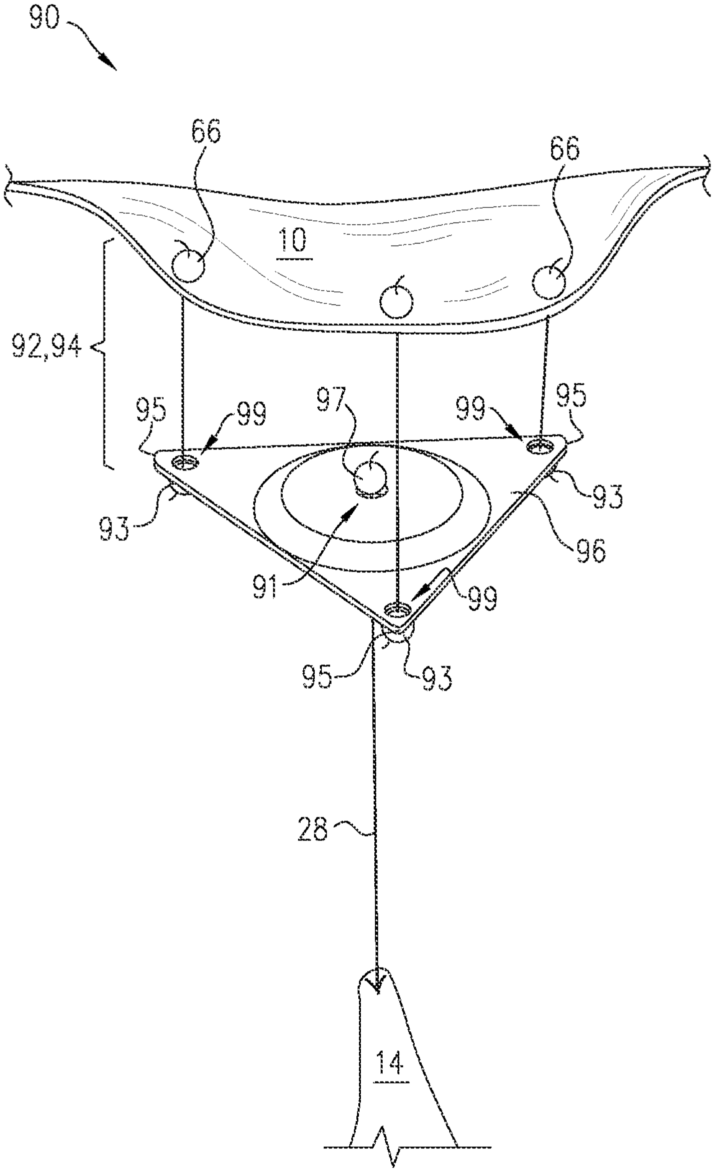
FIG. 8 is a schematic illustration of an example of a leaflet-grasping element comprising a force-distributing member, in accordance with some applications.

Reference is now made to FIG. 8, which is a schematic illustration of a system 90 comprising a leaflet-grasping element 92 which comprises a plurality of longitudinal members 64 distributed along edge 12 of leaflet, and a force-distributing member 96, in accordance with some applications. As shown, element 92 comprises three longitudinal members 64. It is to be noted that any suitable number of longitudinal members 64 can be used, e.g., two member 64 or more. Force-distributing member 96 comprises a biocompatible metal such as nitinol or stainless steel. For some applications, force-distributing member 96 comprises a plastic or rubber.

Longitudinal member 28 defines a primary longitudinal member, while the plurality of longitudinal members 64 define secondary longitudinal members 64. Each of the plurality of longitudinal members 64 is coupled at a first end to leaflet 10 using a locking element 66, e.g., a bead, a pledget, or a crimp, which couples the plurality of longitudinal members 64 to leaflet 10. A second end of each of the plurality of longitudinal members 64 is coupled to force-distributing member 96, e.g., using a respective locking element 93, e.g., a bead, a pledget, or a crimp. A first end of longitudinal member 28 is coupled to tissue surrounding the ventricle, e.g., to papillary muscle 14, as shown, e.g., using any suitable tissue anchor known in the art. For some applications, the second end of longitudinal member 28 is coupled to tissue of the wall of the ventricle, e.g., using any suitable tissue anchor known in the art. A second end of longitudinal member 28 is coupled to force-distributing member 96. Force-distributing member 96 is positioned within the ventricle between leaflet 10 and the tissue surrounding the ventricle of the heart. Force-distributing member 96 is configured to distribute tension forces between primary longitudinal member 28 and secondary longitudinal members 64.

For some applications, force-distributing member 96 comprises a force-distributing member (e.g., a planar force-distributing member, etc.). For some applications, force-distributing member 96 is symmetrical. For some applications, force-distributing member 96 is shaped so as to define two or more vertices 95 for coupling of each of the respective second ends of secondary longitudinal members 64. The two or more vertices 95 are spaced apart at a distance in a manner in which a corresponding distance is maintained between the first ends of secondary longitudinal members 64 at leaflet 10. As shown, force-distributing member 96 is shaped as a triangle with three vertices 95.

Force-distributing member 96 is shaped so as to define an opening 91 at a coupling site (e.g., at the center of force-distributing member 96) where force-distributing member 96 is coupled to the second end of primary longitudinal member 28. A locking element 97, e.g., a bead or a pledget, is used to lock longitudinal member 28 with respect to force-distributing member 96. For some applications, system 90 comprises a cinching device, a crimp, or ratchet coupled to longitudinal member 28, e.g., on longitudinal member 28 or in place of locking element 97. Tension of longitudinal member 28 is controlled by the cinching device, by the crimp, or by the ratchet in a manner in which longitudinal member 28 functions as an artificial chordae tendineae. Force-distributing member 96 is shaped so as to define respective openings 99 at coupling sites (e.g., at vertices 95) where force-distributing member 96 is coupled to the respective second ends of secondary longitudinal members 64.

Primary longitudinal member 28 and secondary longitudinal members 64 pass through the respective openings 91 and 99 in a manner in which creates slidable coupling between force-distributing member 96 and (i) primary longitudinal member 28 and (ii) secondary longitudinal members 64. The slidable coupling facilitates distribution of the tension forces between primary longitudinal member 28 and secondary longitudinal members 64 such that forces are also distributed along leaflet 10. The slidable coupling enables force-distributing member 96 to compensate for the differential tensions on each of longitudinal members 64. That is, force-distributing member 96 compensates for slack on one of members 64 while a second member 64 may be more tense. In such a manner, force-distributing member 96 enhances the durability of longitudinal members 28 and 64 over time because the forces are distributed over longitudinal members 28 and 64 equally such that no one of longitudinal members 28 and 64 experiences a greater tension than the other.

Reference is now made to FIGS. 1A-B and 8. It is to be noted that leaflet-locking elements 66 can be used in combination with support pad 26 of FIGS. 1A-B in order to distribute forces of the plurality of longitudinal members 64 on edge 12 of leaflet 10. Pad 26 can comprise a fabric, synthetic material, rubber, or a metal such as nitinol.

Each of the plurality of longitudinal members 64 is coupled to a respective portion of leaflet 10 in a manner in which the plurality of longitudinal members 64 of leaflet-grasping element 92 fan out with respect to leaflet 10 and forces are distributed along edge 12 of leaflet 10.

Locking elements 66 are shown as beads by way of illustration and not limitation, and can comprise staples, clips, spring-loaded anchors, or other tissue anchors known in the art. Leaflet-grasping element 92 is configured to grasp leaflet 10 of an atrioventricular valve of a heart of a patient. For some applications, the atrioventricular valve includes a mitral valve. For some applications, the atrioventricular valve includes a tricuspid valve.

The plurality of secondary longitudinal members 64, together with force-distributing member 96 collectively define a location-distributing element 94 which enables distribution of the plurality of secondary longitudinal members 64 at respective locations along edge 12 of leaflet 10 in a manner in which tension forces on leaflet 10 are distributed.

Longitudinal members 64 and 28 extend from leaflet 10 down through a ventricle. Longitudinal member 28 functions as artificial chordae tendineae. Longitudinal member 28 and secondary longitudinal members 64 comprise a flexible and/or superelastic material, e.g., ePTFE, nitinol, PTFE, polyester, stainless steel, or cobalt chrome. In some applications, longitudinal member 28 and secondary longitudinal members 64 are coated with polytetrafluoroethylene (PTFE) or with PTFE. In some applications, longitudinal member 28 and secondary longitudinal members 64 comprise sutures. In some applications, longitudinal member 28 comprises at least one wire/suture portion and at least one portion that comprises an elongate tensioning coil. For example, longitudinal member 28 can comprise an elongate coil between two wire/suture portions.

Figure 9:
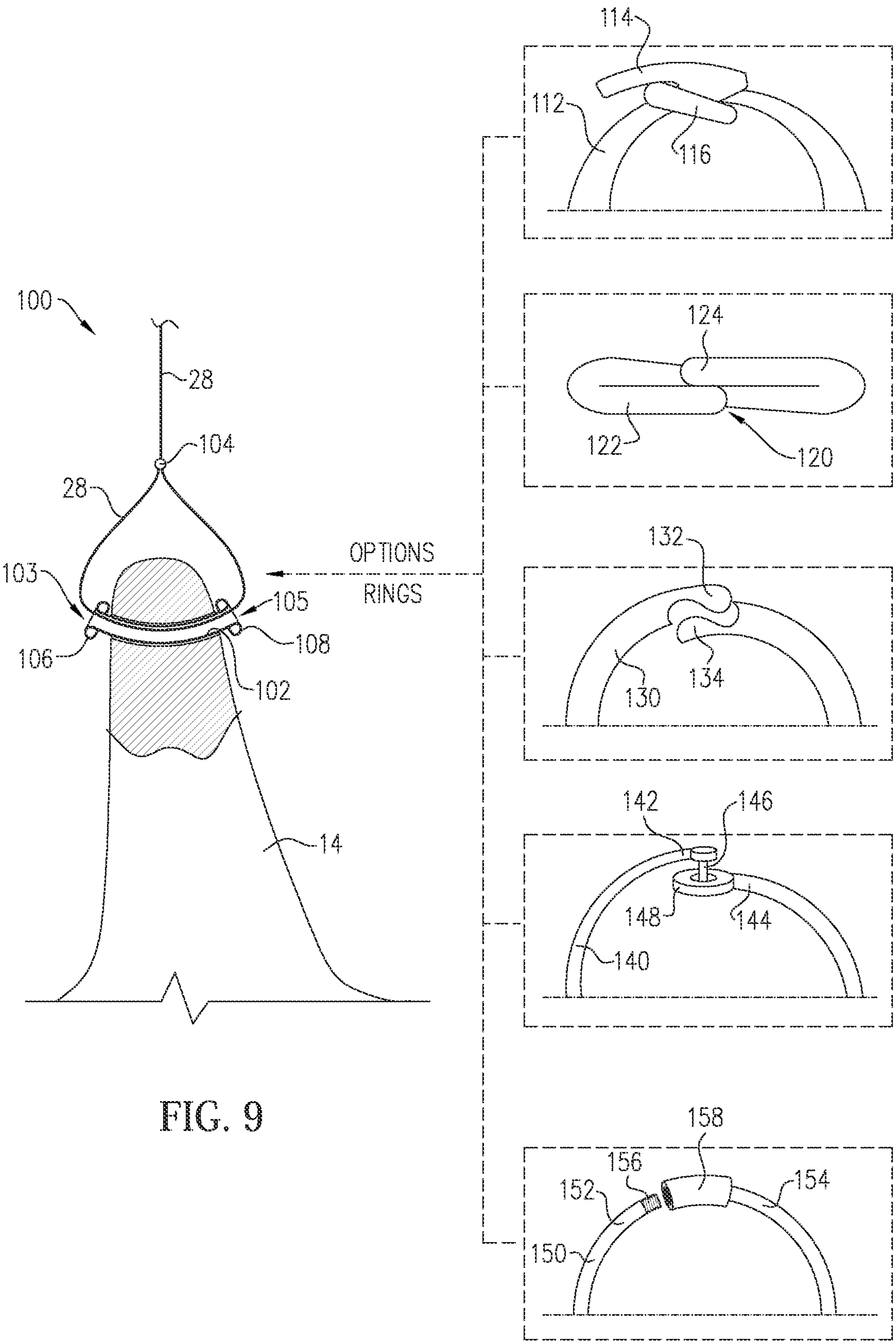
FIG. 9 is a schematic illustration of respective examples of ventricular muscle tube configured to facilitate slidable coupling of a longitudinal member, in accordance with some applications.

Reference is now made to FIG. 9, which is a schematic illustration of a system 100 comprising respective tubes implanted at muscle of the ventricle of the heart of the patient, e.g., papillary muscle 14, the tube facilitates slidable coupling between a first portion of longitudinal member 28 and the tube, and between first portion of longitudinal member 28 and papillary muscle 14, in accordance with some applications. A second end portion of longitudinal member 28 (not shown) is coupled, e.g., fastened, to leaflet 10, e.g., using any coupling described herein. A tension of longitudinal member 28 can be adjusted in a direction that is between leaflet 10 and papillary muscle 14.

As shown, longitudinal member 28 is secured to itself using a lock 104 which prevents longitudinal member 28 from decoupling from the tube while facilitating sliding coupling between longitudinal member 28 and the tube. For some applications, lock 104 comprises a bead. For some applications, lock 104 comprises a ratchet or a crimp which facilitates adjusting of tension of longitudinal member 28. For some applications, the tension of longitudinal member 28 is adjusted prior to securing longitudinal member 28. For some applications, the tension of longitudinal member 28 is adjusted subsequently to securing longitudinal member 28, e.g., at a stage later than initial implantation.

An overtube (not shown) is used to deliver the tube in a straight configuration to muscle 14. The overtube passes through muscle 14 and delivers the tube in the straight configuration. Once the tube is implanted in muscle 14, the overtube is removed leaving the tube within the muscle. Once free from within the overtube, the tube is formed into its final shape as shown in FIG. 9. The overtube approaches papillary muscle 14 from the side, i.e., not from the top, and in such a manner, implantation of the tube in muscle 14 does not interfere with the native chordae tendineae. Additionally, implanting from the side and not using a helical anchor at the top of muscle 14 reduces and eliminates torque on muscle 14. Additionally, the slidable coupling between longitudinal member 28 and the tube provides flexibility to system 100 and reduces stress on tissue of muscle 14 during (i) initial adjustment of tension of longitudinal member 28, (ii) subsequent adjustment of tension of longitudinal member 28, and (iii) pulling forces on longitudinal member 28 on muscle 14 in the vector that is defined between muscle 14 and leaflet 10. That is, the angle of implantation is different from the vector of pulling forces of longitudinal member 28 on muscle 14.

Once longitudinal member 28 is coupled to leaflet 10, tension of longitudinal member 28 is adjusted in the direction that is between leaflet 10 and papillary muscle 14. That is, the angle of implantation of the tube is at a nonzero angle, e.g., perpendicular, with respect to the direction of tension applied to longitudinal member 28. Additionally, once longitudinal member 28 is fixed to muscle 14 via the tube implanted therein, force can be applied to longitudinal member 28 and to muscle 14 from any direction since longitudinal member 28 is slidably coupled to muscle 14 via the tube.

For some applications, the tube is formed into the predetermined final shape as shown in the various examples in FIG. 9. For some applications, the tube comprises a shape-memory material, e.g., nitinol, which enables the tube to assume the predetermined final shape as shown in the various examples in FIG. 9. That is, once the overtube is removed, the tube is allowed to assume the predetermined shape.

As shown, longitudinal member 28 is looped with respect to papillary muscle 14 by passing through the tube. In such a manner, a loop at the first portion of longitudinal member 28 is created. The loop of longitudinal member 28 alleviates tension of longitudinal member 28 on the tissue of papillary muscle 14.

For some applications, the tube comprises a partial ring tube 102 having free ends 103 and 105 and shaped so as to define a lumen. During implantation, tube 102 is implanted within tissue of muscle 14. Tube 102 is delivered in a straight configuration and once free from the overtube used to deliver tube 102, tube 102 curves into the predetermined curved shape. Once free ends 103 and 105 are exposed from within muscle 14, the free ends deform such that anchors, e.g., wings 106 and 108, abut against an external surface of muscle 14.

For some applications, the tube comprises a tube 112 having ends 114 and 116 that close to form a closed loop. For some applications, ends 114 and 116 are manually closed by the operating physician. For some applications, tube 112 has shape-memory which enables ends 114 and 116 to close to form tube 112 into a closed loop. During implantation, tube 112 is implanted within tissue of muscle 14. Tube 112 is delivered in a straight configuration and once free from the overtube used to deliver tube 112, tube 112 curves into the predetermined curved shape. Once ends 114 and 116 are exposed from within muscle 14, ends 114 and 116 deform such ends 114 and 116 clasp together and tube 112 self-locks. Ends 114 and 116 form an embrace lock. For some applications, longitudinal member 28 slides within a lumen of tube 112. For some applications, longitudinal member 28 is looped around a portion of tube 112.

For some applications, the tube comprises a tube 120 having ends 122 and 124 that close to form a closed loop. For some applications, ends 122 and 124 are manually closed by the operating physician. For some applications, tube 120 has shape-memory which enables ends 122 and 124 to close to form tube 120 into a closed loop. During implantation, tube 120 is implanted within tissue of muscle 14. Tube 120 is delivered in a straight configuration and once free from the overtube used to deliver tube 120, tube 120 curves into the predetermined curved shape. Once ends 122 and 124 are exposed from within muscle 14, ends 122 and 124 deform such ends 122 and 124 clasp together and tube 120 self-locks. Ends 122 and 124 form an overlapping lock where ends 122 and 124 are disposed adjacent each other similar to a keyring. For some applications, longitudinal member 28 slides within a lumen of tube 120. For some applications, longitudinal member 28 is looped around a portion of tube 120.

For some applications, the tube comprises a tube 130 having ends 132 and 134 that close to form a closed loop. For some applications, ends 132 and 134 are manually closed by the operating physician. For some applications, tube 130 has shape-memory which enables ends 132 and 134 to close to form tube 130 into a closed loop. During implantation, tube 130 is implanted within tissue of muscle 14. Tube 130 is delivered in a straight configuration and once free from the overtube used to deliver tube 130, tube 130 curves into the predetermined curved shape. Once ends 132 and 134 are exposed from within muscle 14, ends 132 and 134 deform such ends 132 fit together and tube 130 self-locks. Ends 132 and 134 form a pushable lock where ends 132 and 134 are disposed adjacent each other similar to a carabiner or a shackle. For some applications, longitudinal member 28 slides within a lumen of tube 130. For some applications, longitudinal member 28 is looped around a portion of tube 130.

For some applications, the tube comprises a tube 140 having ends 142 and 144 that close to form a closed loop. For some applications, ends 142 and 144 are manually closed by the operating physician. For some applications, tube 140 has shape-memory which enables ends 142 and 144 to close to form tube 140 into a closed loop. During implantation, tube 140 is implanted within tissue of muscle 14. Tube 140 is delivered in a straight configuration and once free from the overtube used to deliver tube 140, tube 140 curves into the predetermined curved shape. Once ends 142 and 144 are exposed from within muscle 14, ends 142 and 144 deform such ends 142 fit together and tube 140 self-locks. End 142 comprises a post 146 which fits within a ring 148 of end 144. For some applications, longitudinal member 28 slides within a lumen of tube 140. For some applications, longitudinal member 28 is looped around a portion of tube 140.

For some applications, the tube comprises a tube 150 having ends 152 and 154 that close to form a closed loop. For some applications, ends 152 and 154 are manually closed by the operating physician. For some applications, tube 150 has shape-memory which enables ends 152 and 154 to close to form tube 150 into a closed loop. During implantation, tube 150 is implanted within tissue of muscle 14. Tube 150 is delivered in a straight configuration and once free from the overtube used to deliver tube 150, tube 150 curves into the predetermined curved shape. Once ends 152 and 154 are exposed from within muscle 14, ends 152 and 154 deform such ends 152 fit together and tube 150 self-locks. End 152 comprises a screw 156 which is threaded within and fits within a housing 158 of end 154. For some applications end 152 comprises a barb (not shown) which ensnares an internal surface of housing 158. For some applications, longitudinal member 28 slides within a lumen of tube 150. For some applications, longitudinal member 28 is looped around a portion of tube 150.

Reference is now made to FIGS. 10A-E, which are schematic illustrations of a system 160 comprising a leaflet-grasping element 162 comprising protrusions 168 functioning as a staple, in accordance with some applications. Leaflet-grasping element 162 is coupled to longitudinal member 28. Leaflet-grasping element 162 is configured to be coupled to edge 12 of leaflet 10. Leaflet-grasping element 162 comprises a first snap element 164 and a second snap element 166. For some applications, as shown, first and second snap elements 164 and 166 comprise respective plates. For some applications, the plates comprise metal plates, and for some applications, the metal plates are covered in fabric. Leaflet-grasping element 162 is shown as a snap fastener by way of illustration and not limitation, and can comprise staples, clips, spring-loaded anchors, or other tissue anchors known in the art. Leaflet-grasping element 162 is configured to grasp leaflet 10 of an atrioventricular valve of a heart of a patient. For some applications, the atrioventricular valve includes a mitral valve. For some applications, the atrioventricular valve includes a tricuspid valve.

First snap element 164 is positioned at an atrial surface of leaflet 10 and second snap element 166 is positioned at a ventricular surface of leaflet 10. By the positioning of elements 164 and 166, tissue of leaflet 10 is grasped or snapped between elements 164 and 166. For some applications, by snapping elements 164 and 166 together, a portion of tissue of leaflet 10 is trapped between the first and second snap elements 164 and 166.

For some applications, first and second snap elements 164 and 166 comprise a biocompatible metal such as nitinol or stainless steel.

Figure 10A:
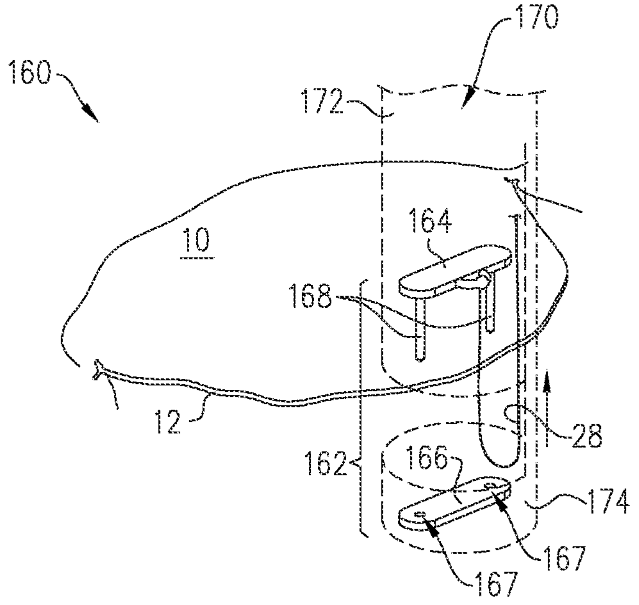
FIGS. 10A-E are schematic illustrations of an example of a leaflet-grasping element comprising a staple, in accordance with some applications.
Figure 10B:
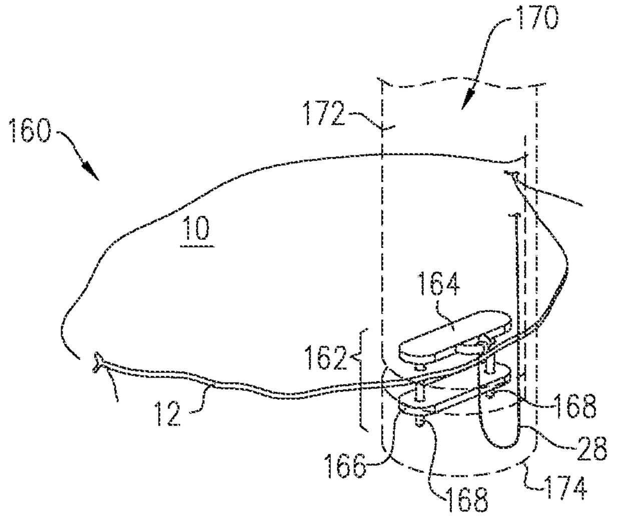

A delivery tool 170 is used to deliver first and second snap elements 164 and 166 to edge 12 of leaflet 10. Delivery tool 170 comprises an elongate tube having a static tubular element 172 and a moveable tubular element 174 which are connected together by a longitudinal element, e.g., by a track, which facilitates movement of moveable tubular element 174 with respect to static tubular element 172. Static tubular element 172 holds first snap element 164 and moveable tubular element 174 holds second snap element 166. As shown in FIG. 10A, static tubular element 172 and moveable tubular element 174 are distanced from each other in order to enable positioning of edge 12 of leaflet 10 between tubular elements 172 and 174 and between snap elements 164 and 166. Additionally, the distancing of tubular elements 172 and 174 keeps first and second snap elements 164 and 166 apart. As shown in FIG. 10B, moveable tubular element 174 is moved closer to static tubular element 172, in order to enable grasping of edge 12 of leaflet 10 between tubular elements 172 and 174 and between snap elements 164 and 166. For some applications, the moving of moveable tubular element 174 brings together first and second snap elements 164 and 166 such that they snap together.

First snap element 164 comprises an upper element or upper planar element which provides anchoring to element 164 as the upper element or upper planar element abuts tissue of leaflet 10. As shown, first snap element 164 punctures leaflet 10 with respective protrusions 168 of first snap element 164. Protrusions 168 are passable through a respective space 167 defined by second snap element 166. Once protrusions 168 of first snap element 164 fit within spaces 167 of second snap element 166, as shown in FIG. 10B, first snap element 164 is locked in place with respect to second snap element 166.

For some applications, second snap element 166 can comprise protrusions 168 while second first element 164 can be shaped so as to define spaces 167.

Figure 10C:
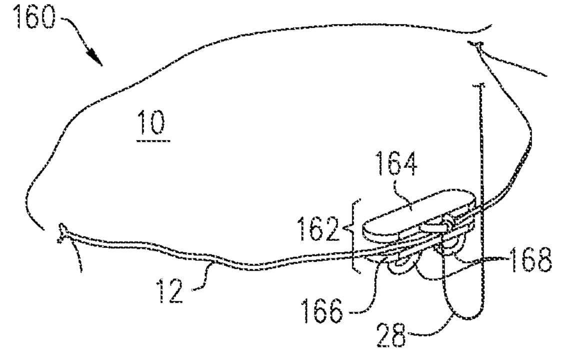

Once protrusions 168 puncture tissue of leaflet 10, and fit within spaces 167, excess portions of protrusions 168 downstream of second snap element 166 are deformed and curve back toward second snap element 166 in order to lock in place first and second snap elements 164 and 166, as shown in FIG. 10C. In such a manner, leaflet-grasping element 162 functions as a staple. For some applications, the operating physician manually deforms protrusions 168 such that they curve upward. For some applications, protrusions 168 comprise a shape-memory material in which, in the absence of force applied to protrusions 168, protrusions 168 curve upward.

Figure 10D:
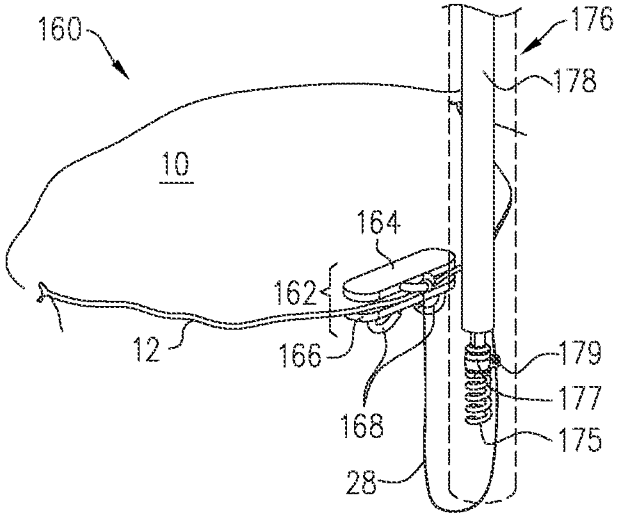
Figure 10E:
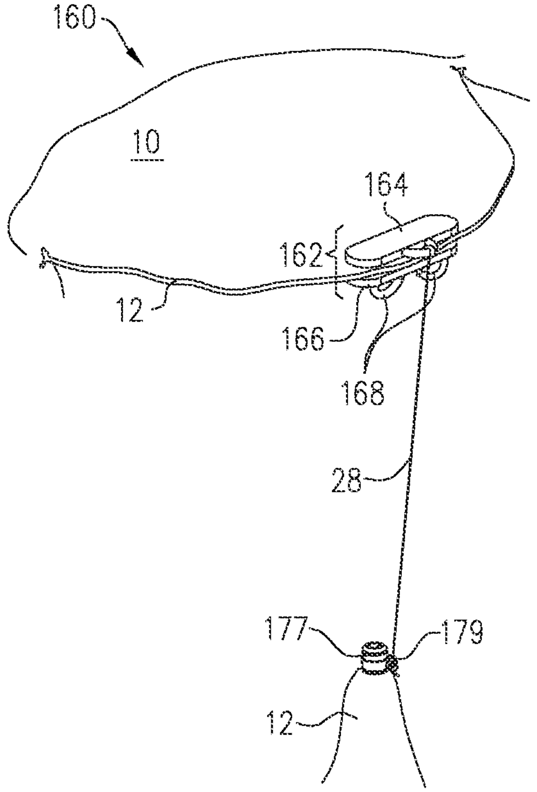

For some applications, longitudinal member 28 is coupled at a first end to first snap element 164. It is to be noted that longitudinal member 28 can be coupled instead to second snap elements 166. Longitudinal member 28 extends upstream of the valve such that a second end of longitudinal member 28 is accessible from outside the body (FIG. 10C). An anchor-delivery tool 176 is threaded along longitudinal member 28, as shown in FIG. 10D, in order to deliver a tissue anchor 175 to papillary muscle 14. Anchor 175 comprises an anchor head 177 shaped so as to define an eyelet 179 for threading anchor 175 with respect to longitudinal member 28. An anchor driver 178 is reversibly coupled to anchor 175 so as to deploy the anchor into papillary muscle 14. As shown, anchor 175 comprises a helical anchor by way of illustration and not limitation. Anchor 175 can comprise any suitable anchor, e.g., the tubes shown hereinabove with reference to FIG. 9. Once longitudinal member 28 is anchored to muscle 14, tension of member 28 can be adjusted, and longitudinal member 28 is locked in place with respect to muscle 14, e.g., using a bead or a lock or a crimp.

For some applications, at least one longitudinal member 28 extends from leaflet-grasping element 162 down through a ventricle of the heart and is coupled to a papillary muscle 14 of the heart e.g., using any suitable tissue anchor known in the art. Longitudinal member 28 functions as artificial chordae tendineae. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises a suture. In some applications, longitudinal member 28 comprises at least one wire/suture portion and at least one portion that comprises an elongate tensioning coil. For example, longitudinal member 28 can comprise an elongate coil between two wire/suture portions.

Figure 11A:
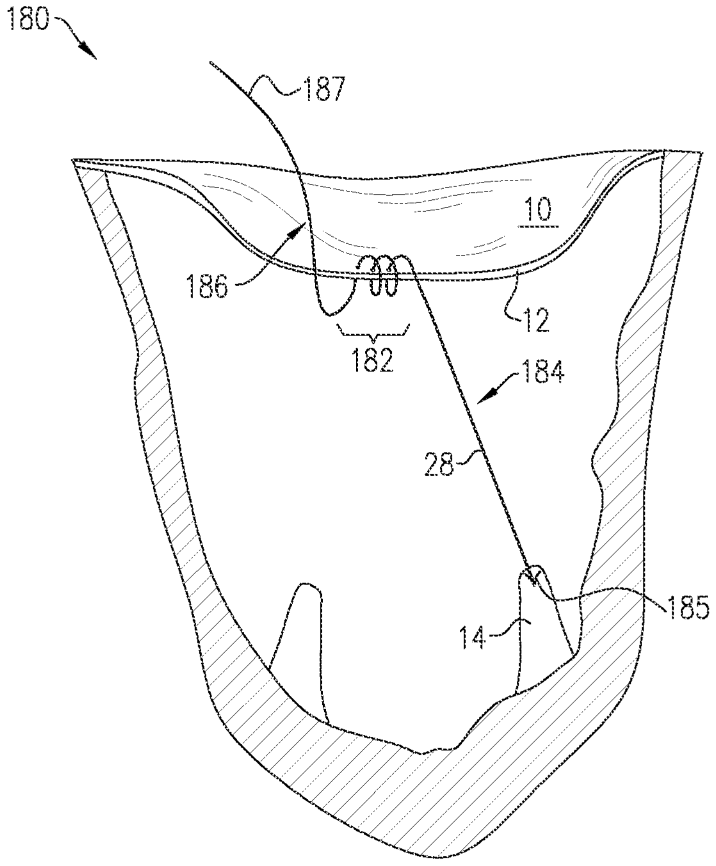
FIGS. 11A-B and 12A-C are schematic illustrations of an example of helically suturing an edge of a leaflet, in accordance with some applications.
Figure 11B:
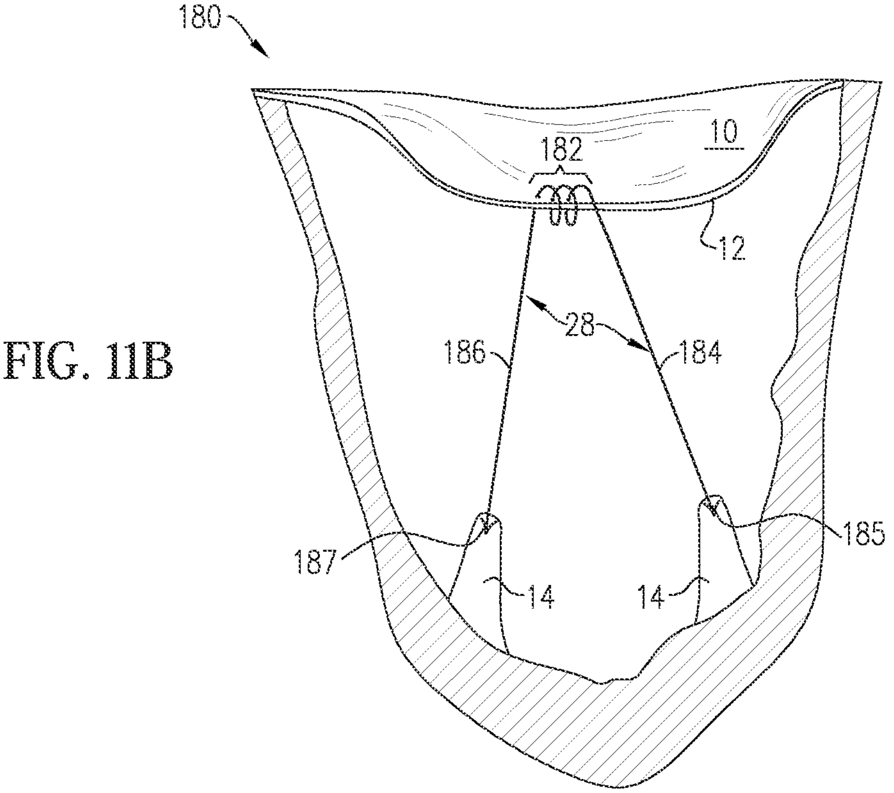

Reference is now made to FIGS. 11A-B, which are schematic illustrations of a system 180 for creating a helical stitch at the edge of a single leaflet 10, in accordance with some applications. A middle section 182 of longitudinal member 28 is helically sutured to edge 12 of leaflet 10, as shown in FIG. 11B. As such, middle section 182 defines a leaflet-grasping element. The helical stitch is created using a suture needle or any other rigid element that is coupled to a first end 185 of longitudinal member 28 and is woven multiple times helically with respect to edge 12 of leaflet 10. As the rigid element or suture needle passes helically through the tissue of leaflet 10, it threads portions of longitudinal member 28 through leaflet 10, thereby helically suturing longitudinal member 28 to leaflet 10. After suturing middle section 182, a first portion 184 of longitudinal member 28 is then extended into the ventricle. First portion 184 is downstream of middle section 182 of longitudinal member 28. First end 185 of longitudinal member 28 is then coupled to tissue surrounding the ventricle, e.g., papillary muscle 14 as shown in FIG. 11A. For example, first end 185 is knotted to muscle 14 or held in place with a lock or a crimp. For some applications, first end 185 is coupled to a tissue anchor, e.g., a barb or a helical tissue anchor or any other suitable tissue anchor known in the art.

For some applications, a second end 187 of longitudinal member 28 is coupled to leaflet 10, e.g., by being knotted to leaflet 10 or by being held in place with a bead, or a lock, or a crimp (configuration not shown). Optionally, a second portion 186 of longitudinal member 28 that is upstream of middle section 182 is then extended into the ventricle. Second end 187 of longitudinal member 28 is then coupled to tissue surrounding the ventricle, e.g., a second papillary muscle 14 as shown in FIG. 11B. For example, second end 187 is knotted to muscle 14 or held in place with a lock or a crimp. For some applications, second end 187 is coupled to a tissue anchor, e.g., a barb or a helical tissue anchor or any other suitable tissue anchor known in the art. For some applications, a tissue anchor, e.g., a barb, or a helical tissue anchor, or any other suitable tissue anchor known in the art, is threaded along second portion 186 in order to couple second end 187 to the tissue of muscle 14.

Prior to anchoring second end 187, longitudinal member 28 is pulled in order to adjust a tension of longitudinal member 28. Locking second end 187 of longitudinal member 28 maintains tension applied to longitudinal member 28.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Figure 12C:
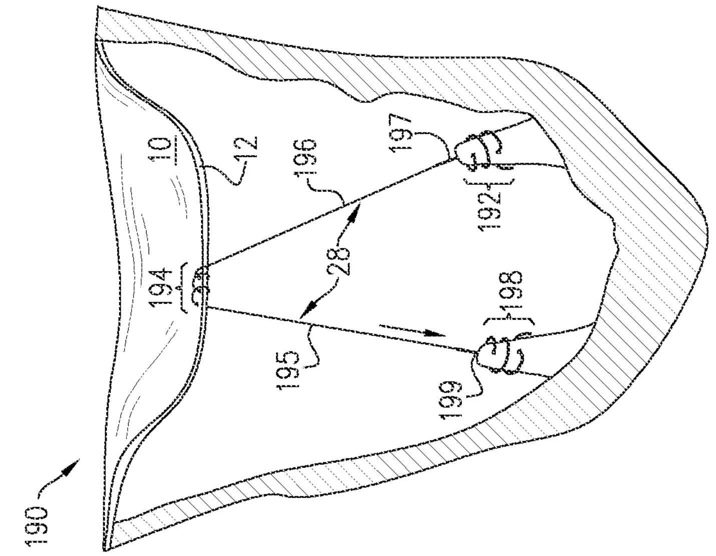
Figure 12B:
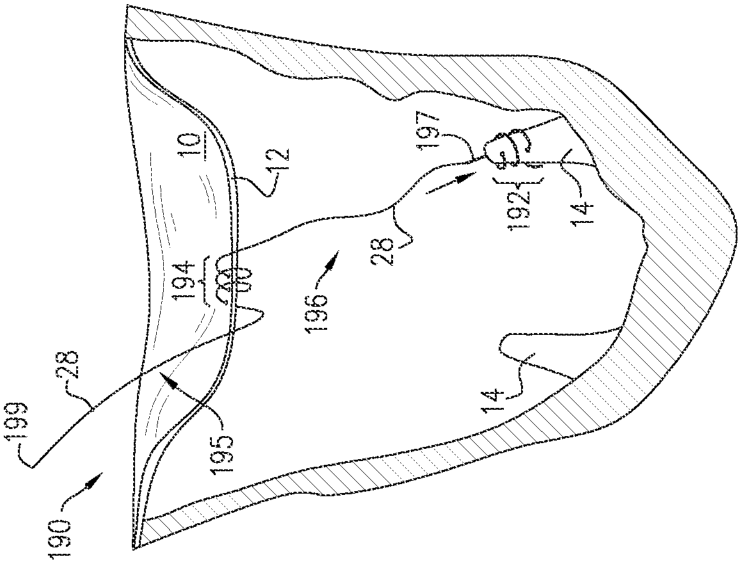
Figure 12A:
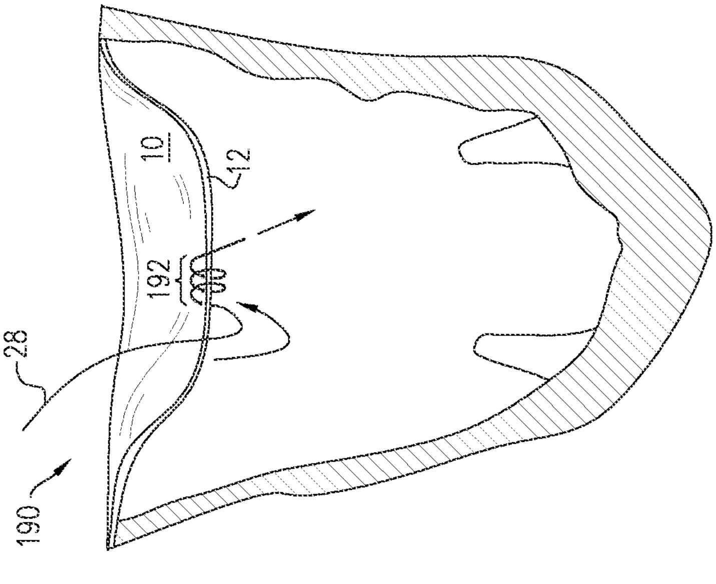

Reference is now made to FIGS. 12A-C, which are schematic illustrations of a system 190 for creating a helical stitch at the edge of a single leaflet 10, in accordance with some applications. A middle section 194 of longitudinal member 28 is helically sutured to edge 12 of leaflet 10, as shown in FIG. 12B. As such, middle section 194 defines a leaflet-grasping element. The helical stitch is created using a suture needle or any other rigid element, e.g., a helical tissue anchor 192, that is coupled to a first end 197 of longitudinal member 28 and is woven multiple times helically with respect to edge 12 of leaflet 10. As helical anchor 192 passes helically through the tissue of leaflet 10 (as shown in FIG. 12A), it threads portions of longitudinal member 28 through leaflet 10, thereby helically suturing longitudinal member 28 to leaflet 10. After suturing middle section 194, a first portion 196 of longitudinal member 28 is then extended into the ventricle. First portion 196 is downstream of middle section 194 of longitudinal member 28. First end 197 of longitudinal member 28 is then coupled to tissue surrounding the ventricle, e.g., papillary muscle 14 using helical anchor 192, as shown in FIG. 12B.

For some applications, a second end 199 of longitudinal member 28 is coupled to leaflet 10, e.g., by being knotted to leaflet 10 or by being held in place with a bead, or a lock, or a crimp (configuration not shown). Optionally, a second portion 195 of longitudinal member 28 that is upstream of middle section 194 is then extended into the ventricle. Second end 199 of longitudinal member 28 is then coupled to tissue surrounding the ventricle, e.g., a second papillary muscle 14 as shown in FIG. 12C. For example, second end 199 is knotted to muscle 14 or held in place with a lock or a crimp (configuration not shown). For some applications, second end 199 is coupled to a tissue anchor, e.g., a barb or a helical tissue anchor 198 or any other suitable tissue anchor known in the art. For some applications, a tissue anchor, e.g., a barb, or a helical tissue anchor 198, or any other suitable tissue anchor known in the art, is threaded along second portion 195 in order to couple second end 199 to the tissue of muscle 14.

Prior to anchoring second end 199, longitudinal member 28 is pulled in order to adjust a tension of longitudinal member 28. Locking second end 199 of longitudinal member 28 maintains tension applied to longitudinal member 28.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Figure 13:
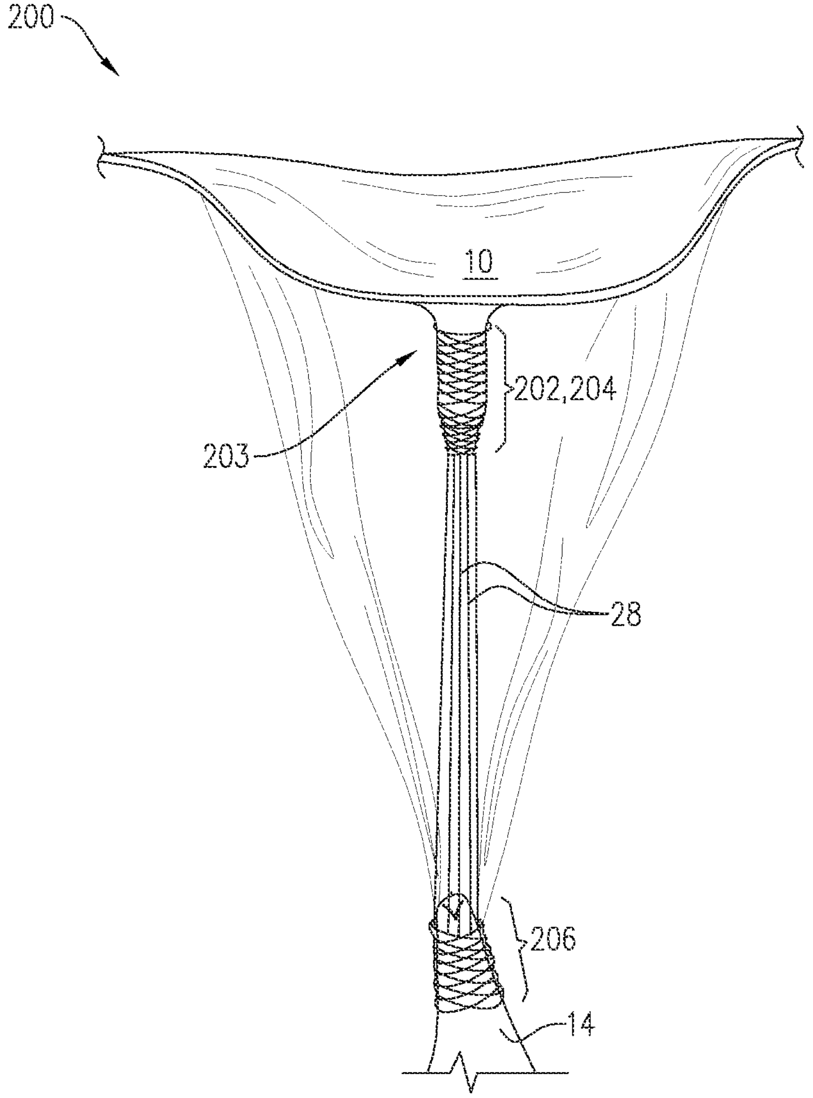
FIG. 13 is a schematic illustration of an example of a leaflet-grasping element comprising a stent, in accordance with some applications.

Reference is now made to FIG. 13, which is a schematic illustration of a system 200 for grasping leaflet 10 using a leaflet-grasping element 202 that comprises a stent element 204 that is configured to surround a juncture 203 between native chordae tendineae and leaflet 10, in accordance with some applications. Stent element 204 comprises struts which are collectively formed in a manner in which stent element 204 is configured to tighten its grip on tissue the more stent element 204 is pulled longitudinally. As stent element 204 is pulled longitudinally, it increases in length and decreases in width in order to increase its grip on tissue. Stent element 204 is coupled to one or more (e.g., a plurality, as shown) longitudinal members 28 at respective first ends of longitudinal members 28. Each second end of longitudinal members 28 is coupled to a second stent element 206 which is configured to surround a papillary muscle 14. Stent element 206 comprises struts which are collectively formed in a manner in which stent element 206 is configured to tighten its grip on tissue the more stent element 206 is pulled longitudinally. As stent element 206 is pulled longitudinally, it increases in length and decreases in width in order to increase its grip on tissue.

In such a manner, stent elements 204 and 206 grasp tissue without puncturing or causing damage to tissue. For some applications, stent elements 204 and 206 function as latching end effectors.

In some applications, each of stent elements 204 and 206 is shaped as a semi-tubular stent having a "C"-shaped cross-section so that stent elements 204 and 206 can be positioned around tissue. For some applications, each of stent elements 204 and 206 comprises a cuff. Stent elements 204 and 206 are then fixed in place using a ratchet or any suitable lock. For some applications, stent elements 204 and 206 have overlapping elements which lock in place once elements 204 and 206 surround tissue. For some applications, stent elements 204 and 206 comprise barbs which help fix stent elements 204 and 206 to tissue.

Stent elements 204 and 206 can be placed over ruptured or intact native chordae tendineae. Longitudinal member(s) 28 function as artificial chordae tendineae. Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Tension of longitudinal member 28 is controlled by pulling distally on second stent element 206.

Figure 14A:
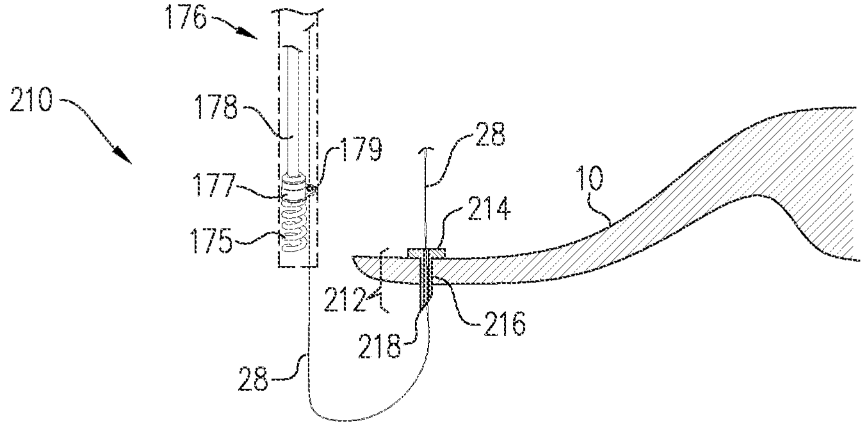
FIGS. 14A-C, 15A-B, and 16A-C are schematic illustrations of respective examples of leaflet-grasping elements which are configured to pass through tissue of the leaflet, in accordance with some applications.
Figure 14B:
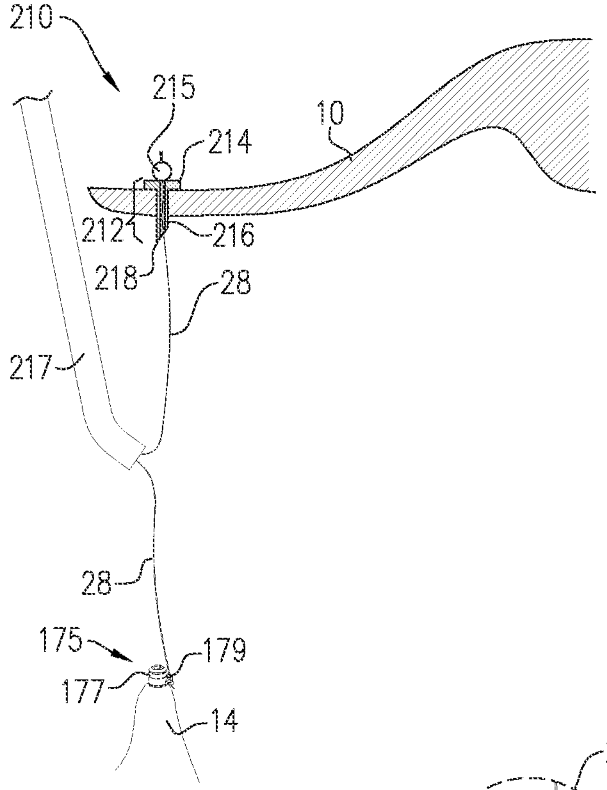
Figure 14C:
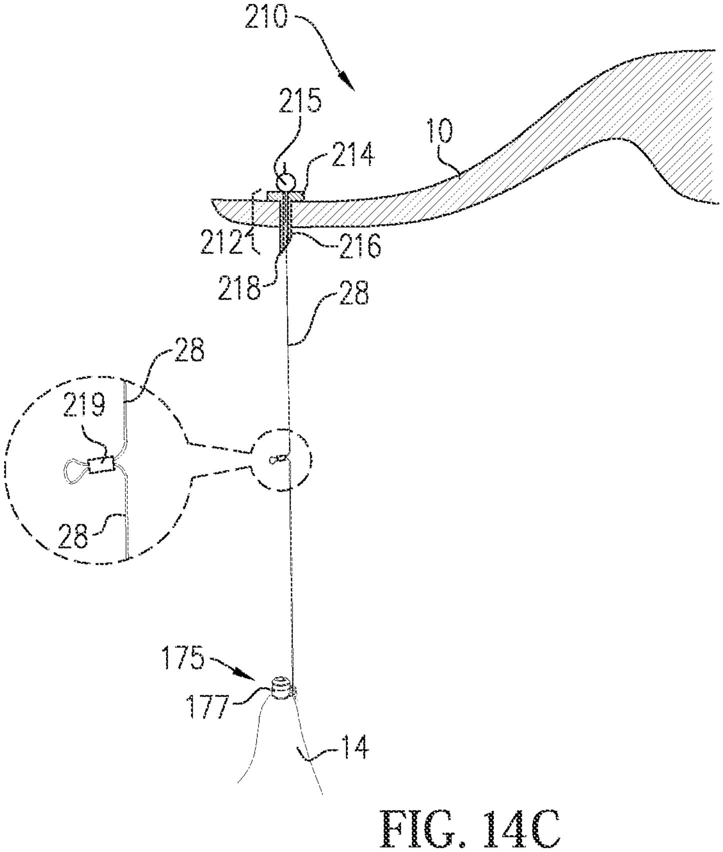

Reference is now made to FIGS. 14A-C, which are schematic illustrations of a system 210 for grasping leaflet 10 by passing a leaflet-tissue-anchor 212 through leaflet 10, in accordance with some applications. Leaflet-tissue-anchor 212 defines a leaflet-grasping element. As shown, leaflet-tissue-anchor 212 is shaped so as to define an upper element or planar upper element 214 coupled to an elongate longitudinal element 216. Elongate longitudinal element 216 is disposed at a nonzero angle, e.g., perpendicularly, with respect to upper element or planar upper element 214. A distal end of elongate longitudinal element 216 is shaped so as to define a pointed distal tip 218 that is configured to puncture tissue of leaflet 10. Leaflet-tissue-anchor 212 can comprise a rigid biocompatible material, e.g., nitinol or stainless steel. For some applications, leaflet-tissue-anchor 212 can comprise a plastic.

Leaflet-tissue-anchor 212 is initially anchored to leaflet 10 by puncturing leaflet 10 from an atrial surface using tip 218. A portion of leaflet-tissue-anchor 212, i.e., elongate longitudinal element 216 is passed through tissue of leaflet 10.

As shown, leaflet-tissue-anchor 212 is shaped so as to define an elongate lumen for passage therethrough of longitudinal member 28. It is to be noted that for some applications, leaflet-tissue-anchor 212 is not shaped to as to define the lumen, e.g., leaflet-tissue-anchor 212 is solid, and longitudinal member 28 is coupled to leaflet-tissue-anchor 212 at elongate longitudinal element 216. In either application, following the anchoring of leaflet-tissue-anchor 212 to leaflet 10, longitudinal member 28 extends upstream of the valve such that an end of longitudinal member 28 is accessible from outside the body. An anchor-delivery tool 176 is threaded along longitudinal member 28, as shown in FIG. 14A, and as described hereinabove with reference to FIG. 10D, in order to deliver a tissue anchor 175 (e.g., a ventricle-tissue-anchor) to papillary muscle 14. Anchor 175 comprises an anchor head 177 shaped so as to define an eyelet 179 for threading anchor 175 with respect to longitudinal member 28. An anchor driver 178 is reversibly coupled to anchor 175 so as to deploy the anchor into papillary muscle 14. As shown, anchor 175 comprises a helical anchor by way of illustration and not limitation. Anchor 175 can comprise any suitable anchor, e.g., the tubes shown hereinabove with reference to FIG. 9.

Once longitudinal member 28 is anchored to muscle 14, tension of member 28 can be adjusted, and longitudinal member 28 is locked in place with respect to muscle 14 using a lock, e.g., a bead or a lock or a crimp, and with respect to leaflet 10 using a lock 215, e.g., a bead or a lock or a crimp. As shown in FIG. 14B, a tension-adjusting tool 217 is then introduced within the ventricle and grabs longitudinal member 28, e.g., using a snare, and facilitates pulling, cinching, and crimping of longitudinal member 28. Longitudinal member is then locked in place with a lock 219, e.g., a bead or a crimp.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Figure 15A:
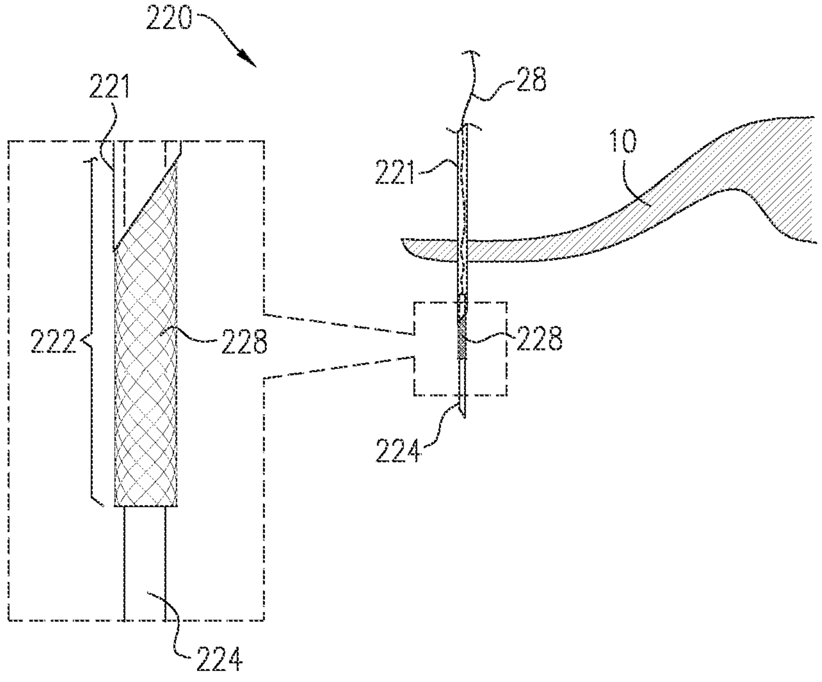
Figure 15B:
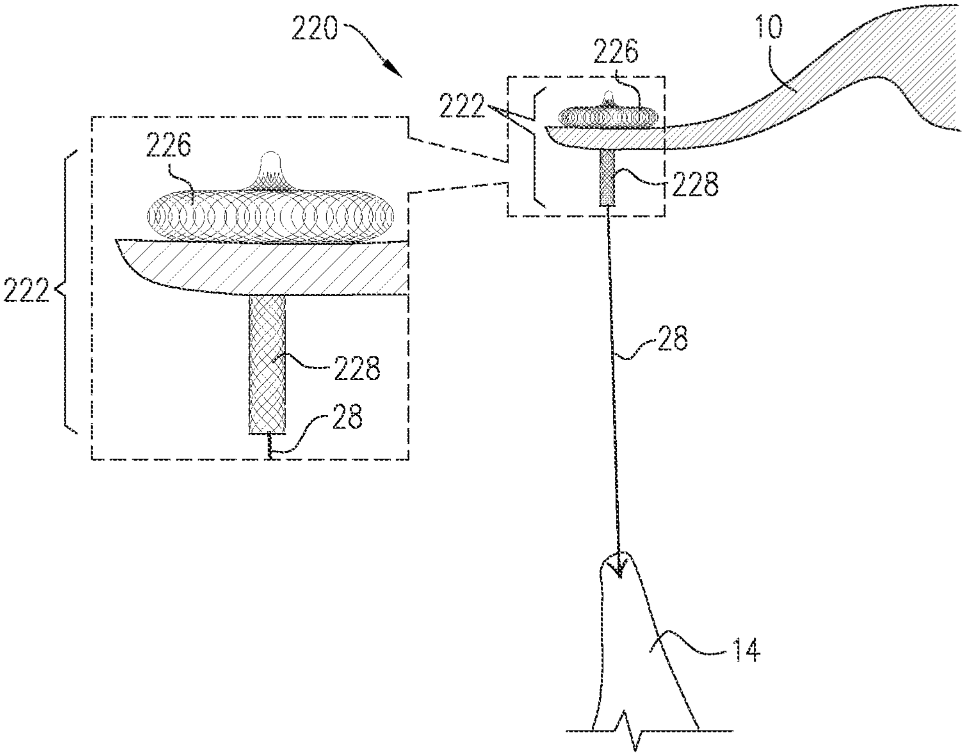

Reference is now made to FIGS. 15A-B, which are schematic illustrations of a system 220 for grasping leaflet 10 by passing a leaflet-tissue-anchor 222 through leaflet 10, in accordance with some applications. Leaflet-tissue-anchor 222 defines a leaflet-grasping element. As shown in FIG. 15B, leaflet-tissue-anchor 222, in its resting state, is shaped so as to define an upper element or planar upper element 226 and an elongate longitudinal element 228. Elongate longitudinal element 228 is disposed at a nonzero angle, e.g., perpendicularly, with respect to upper element or planar upper element 226. For some applications, leaflet-tissue-anchor 222 comprises a biocompatible metal, e.g., nitinol or stainless steel, that comprises a plurality of struts which are arranged so as to impart flexibility, compressibility, and expandability to leaflet-tissue-anchor 222. For some applications, leaflet-tissue-anchor 222 comprises a fabric which comprises a plurality of woven strands. For some applications, leaflet-tissue-anchor 222 comprises a plastic which comprises a plurality of woven strands. For some applications, in its resting state, leaflet-tissue-anchor 222 can be shaped so as to define an hourglass shape, i.e., leaflet-tissue-anchor 222 can comprise a lower element or lower planar lower element similar to upper element or planar upper element 226.

Leaflet-tissue-anchor 222 is compressible within a delivery tube 221, as shown in FIG. 15A. A needle 224 is positioned distally to leaflet-tissue-anchor 222 and is exposed from within tube 221 such that needle 224 punctures and passes through leaflet 10. Tube 221 passes through the puncture in leaflet 10 such that tube passes a portion of leaflet-tissue-anchor 222, e.g., elongate longitudinal element 228, through leaflet 10. Tube 221 is then retracted fully to expose upper element or planar upper element 226 at the atrial surface of leaflet 10 so that upper element or planar upper element 226 expands against the atrial surface.

For some applications, needle 224 is passed through the ventricle and arrives at papillary muscle 14 where it punctures muscle 14 and delivers a tissue anchor, e.g., ventricle-tissue-anchor, to muscle 14. For some applications, needle 224 itself is an anchor, e.g., a barb and remains implanted.

For some applications, leaflet-tissue-anchor 222 is shaped so as to define an elongate lumen for passage therethrough of longitudinal member 28. It is to be noted that for some applications, leaflet-tissue-anchor 222 is not shaped to as to define the lumen, and longitudinal member 28 is coupled to leaflet-tissue-anchor 222 at elongate longitudinal element 228.

For some applications, following anchoring of leaflet-tissue-anchor 222 to leaflet 10, longitudinal member 28 is anchored to tissue surrounding the ventricle, e.g., papillary muscle 14. For some applications, longitudinal member extends upstream of the valve such that an end of longitudinal member 28 is accessible from outside the body and anchor-delivery tool is threaded along longitudinal member 28, as described hereinabove with reference to FIG. 14A, and as described hereinabove with reference to FIG. 10D, in order to deliver a tissue anchor to papillary muscle 14. The anchor at muscle 14 can comprise a helical anchor by way of illustration and not limitation. The anchor can comprise any suitable anchor, e.g., the tubes shown hereinabove with reference to FIG. 9.

Once longitudinal member 28 is anchored to muscle 14, tension of member 28 can be adjusted, and longitudinal member 28 is locked in place using a lock, e.g., a bead or a lock or a crimp, in order to maintain tension on longitudinal member 28.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Figure 16A:
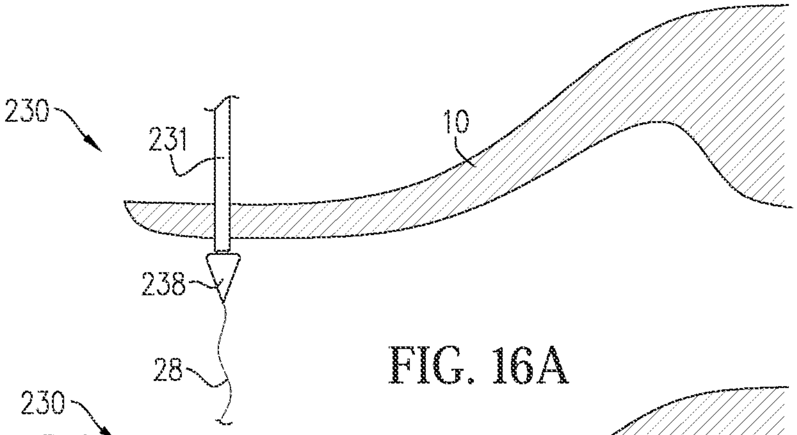
Figure 16B:
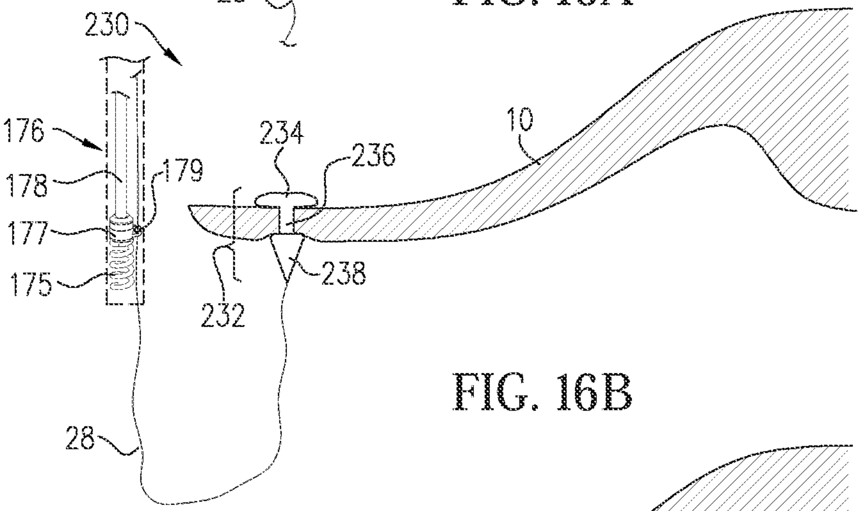
Figure 16C:
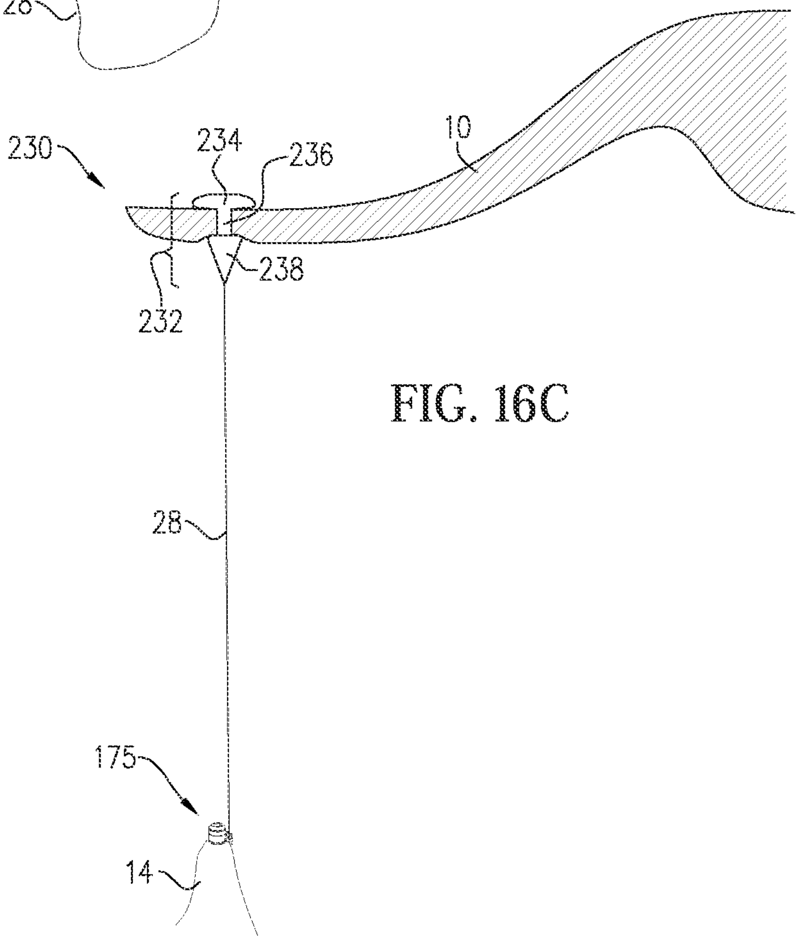

Reference is now made to FIGS. 16A-C, which are schematic illustrations of a system 230 for grasping leaflet 10 by passing a leaflet-tissue-anchor 232 through leaflet 10, in accordance with some applications. Leaflet-tissue-anchor 232 defines a leaflet-grasping element. As shown in FIG. 16B, leaflet-tissue-anchor 232, in its resting state, is shaped so as to define an upper element or planar upper element 234, an elongate longitudinal element 236 disposed distally to upper element or planar upper element 234, and a distal structural element 238. Elongate longitudinal element 236 is disposed at a nonzero angle, e.g., perpendicularly, with respect to upper element or planar upper element 234. Distal structural element 238 is shaped so as to define a tapered element, e.g., a cone, having a distal pointed tip. For some applications, distal structural element 238 is configured to puncture and pass through tissue of leaflet 10. Alternatively or additionally, a needle can be used to puncture leaflet 10 in advance of passing distal structural element 238 through leaflet 10 (e.g., needle 224 as shown in FIGS. 15A-B, and as described hereinabove with reference to FIG. 10D). For applications in which the needle is used in advance of passing anchor 232 through leaflet 10, distal structural element 238 can be shaped to assume any other shape, e.g., a planar disc, etc., in a manner in which anchor 232 assumes an hourglass configuration.

For some applications, leaflet-tissue-anchor 232 comprises a biocompatible metal, e.g., nitinol or stainless steel, that comprises a plurality of struts which are arranged so as to impart flexibility, compressibility, and expandability to leaflet-tissue-anchor 232. For some applications, leaflet-tissue-anchor 232 comprises a fabric which comprises a plurality of woven strands. For such applications, distal structural element 238 can comprise a rigid material capable of puncturing and passing through leaflet 10. Alternatively or additionally, a needle can be used to puncture leaflet 10 in advance of passing distal structural element 238 through leaflet 10. For some applications, leaflet-tissue-anchor 232 comprises a plastic which comprises a plurality of woven strands. For some applications, in its resting state, leaflet-tissue-anchor 232 can be shaped so as to define an hourglass shape, i.e., leaflet-tissue-anchor 232 can comprise a lower element or planar lower element similar to upper element or planar upper element 234.

Leaflet-tissue-anchor 232 is compressible within a delivery tube 231, as shown in FIG. 16A. As shown, distal structural element 238 of leaflet-tissue-anchor 232 is exposed from within tube 231 such that distal structural element 238 punctures and passes through leaflet 10. Tube 231 passes through the puncture in leaflet 10 such that tube passes a portion of leaflet-tissue-anchor 232, e.g., distal structural element 238 and elongate longitudinal element 236, through leaflet 10. Tube 231 is then retracted fully to expose upper element or planar upper element 234 at the atrial surface of leaflet 10 so that upper element or planar upper element 234 expands against the atrial surface.

As shown, longitudinal member 28 is coupled to leaflet-tissue-anchor 232 at distal structural element 238. For some applications, leaflet-tissue-anchor 232 is shaped so as to define an elongate lumen for passage therethrough of longitudinal member 28 (configuration not shown).

Following the anchoring of leaflet-tissue-anchor 232 to leaflet 10, longitudinal member 28 extends upstream of the valve such that an end of longitudinal member 28 is accessible from outside the body. An anchor-delivery tool 176 is threaded along longitudinal member 28, as shown in FIG. 16B, and as described hereinabove with reference to FIG. 10D, in order to deliver a tissue anchor 175 (e.g., ventricle-tissue-anchor) to papillary muscle 14. Anchor 175 comprises an anchor head 177 shaped so as to define an eyelet 179 for threading anchor 175 with respect to longitudinal member 28. An anchor driver 178 is reversibly coupled to anchor 175 so as to deploy the anchor into papillary muscle 14. As shown, anchor 175 comprises a helical anchor by way of illustration and not limitation. Anchor 175 can comprise any suitable anchor, e.g., the tubes shown hereinabove with reference to FIG. 9.

Once longitudinal member 28 is anchored to muscle 14, tension of member 28 can be adjusted, and longitudinal member 28 is locked in place using a lock, e.g., a bead or a lock or a crimp, in order to maintain tension of longitudinal member 28.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Figure 17A:
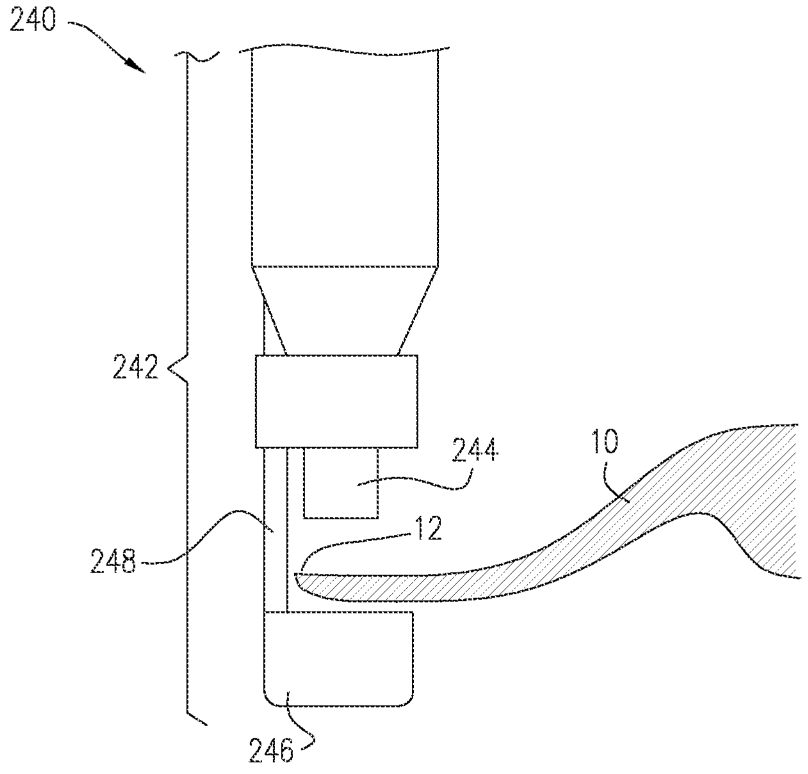
FIGS. 17A-B, 18A-B, and 19A-B are schematic illustrations of respective examples of leaflet-stabilizing elements which are configured to hold and stabilize the leaflet, in accordance with some applications.
Figure 17B:
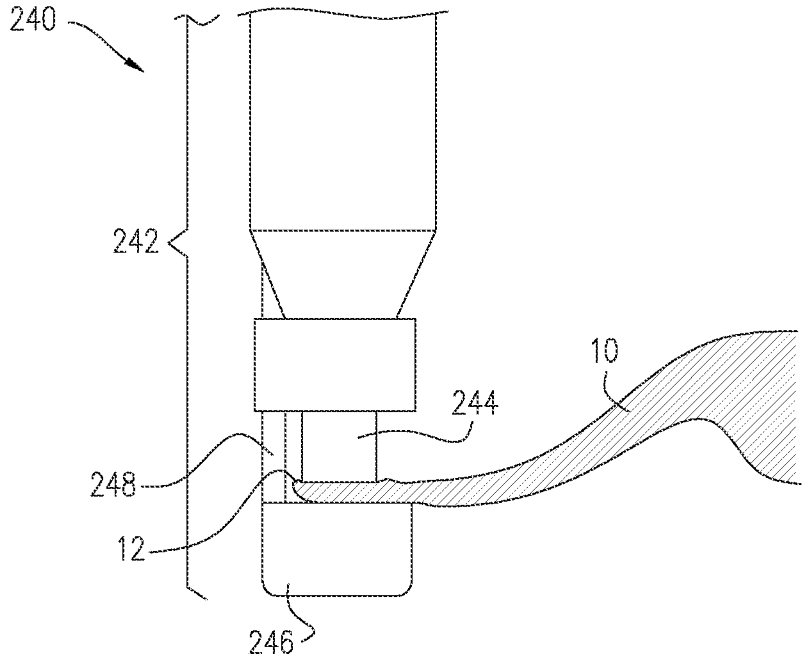

Reference is now made to FIGS. 17A-B, which are schematic illustrations of a system 240 comprising a leaflet-stabilizing element 242 which is configured to hold and stabilize leaflet 10, in accordance with some applications. Leaflet-stabilizing element 242 is configured to be passed between leaflets of an atrioventricular valve and grasp edge 12 of leaflet so as to hold and stabilize leaflet 10 as procedures are performed on leaflet 10 such as grasping the leaflet, clamping the leaflet, and/or puncturing the leaflet using any of the leaflet-grasping elements described herein or any other tool used on leaflet 10 known in the art. Leaflet-stabilizing element 242 is configured to provide a counter-force to leaflet 10 during the procedure, e.g., by providing temporary tension and/or tone to leaflet 10. Once the procedure on leaflet 10 has been completed, the grip of leaflet-stabilizing element 242 on leaflet 10 is released, and leaflet-stabilizing element 242 is removed from the body of the patient.

Leaflet-stabilizing element 242 comprises an elongate tube having a static tubular element 244 and a moveable tubular element 246 which are connected together by a longitudinal element 248, e.g., by a track, which facilitates movement of moveable tubular element 246 with respect to static tubular element 244. As shown in FIG. 17A, static tubular element 244 and moveable tubular element 246 are distanced from each other in order to enable positioning of edge 12 of leaflet 10 between tubular elements 244 and 246. As shown in FIG. 17B, moveable tubular element 246 is moved closer to static tubular element 244, in order to enable grasping of edge 12 of leaflet 10 between tubular elements 244 and 246. This movement can be controlled by the operating physician outside the body of the patient. The grasp of leaflet-stabilizing element 242 is reversible. In some applications, moveable tubular element 246 is slidable longitudinally toward static tubular element 244.

Figure 18A:
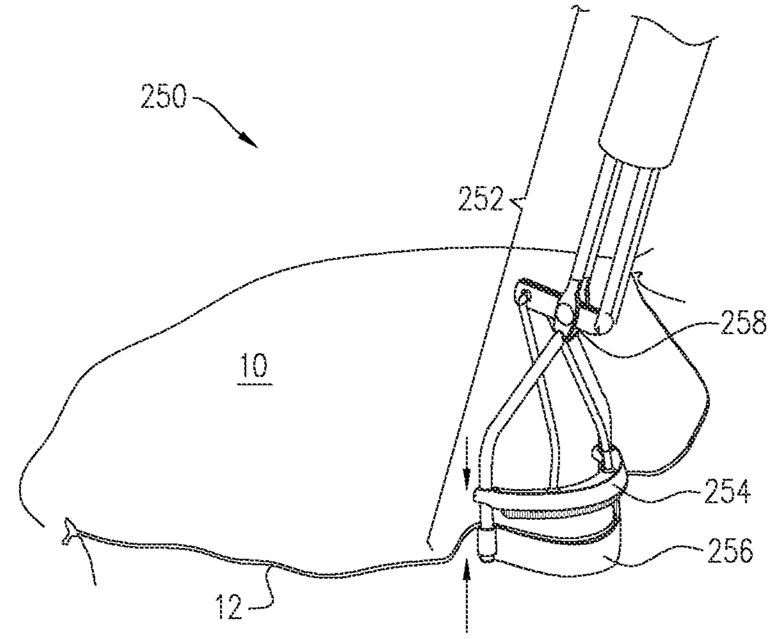
Figure 18B:
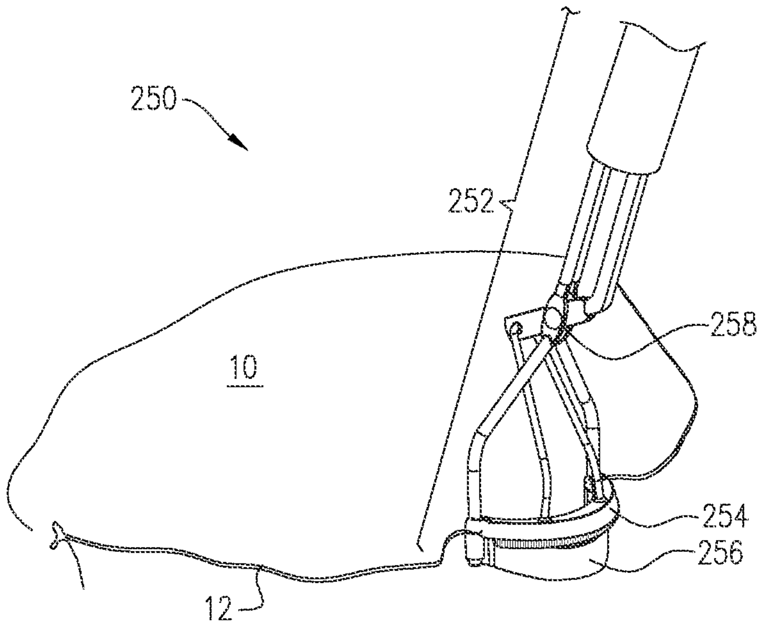

Reference is now made to FIGS. 18A-B, which are schematic illustrations of a system 250 comprising a leaflet-stabilizing element (e.g., a clasp) 252 which is configured to hold and stabilize leaflet 10, in accordance with some applications. Leaflet-stabilizing element 252 is configured to be passed between leaflets of an atrioventricular valve and grasp edge 12 of leaflet so as to hold and stabilize leaflet 10 as procedures are performed on leaflet 10 such as grasping the leaflet, clamping the leaflet, and/or puncturing the leaflet using any of the leaflet-grasping elements described herein or any other tool used on leaflet 10 known in the art. Leaflet-stabilizing element 252 is configured to provide a counter-force to leaflet 10 during the procedure, e.g., by providing temporary tension and/or tone to leaflet 10. Once the procedure on leaflet 10 has been completed, the grip of leaflet-stabilizing element 252 on leaflet 10 is released, and leaflet-stabilizing element 252 is removed from the body of the patient.

Leaflet-stabilizing element 252 comprises an elongate tube having an upper clamping element (e.g., an upstream support) 254 and a lower clamping element 256 (e.g., a downstream support) which are connected together by a hinge 258, which facilitates movement, e.g., by pivoting, of upper and lower clamping elements 254 and 256. As shown in FIG. 18A, upper and lower clamping elements 254 and 256 are distanced from each other in order to enable positioning of edge 12 of leaflet 10 between upper and lower clamping elements 254 and 256. As shown in FIG. 18B, upper and lower clamping elements 254 and 256 are moved together in order to enable grasping of edge 12 of leaflet 10 between upper and lower clamping elements 254 and 256. This movement can be controlled by the operating physician outside the body of the patient. The grasp of leaflet-stabilizing element 252 is reversible.

Figure 19A:
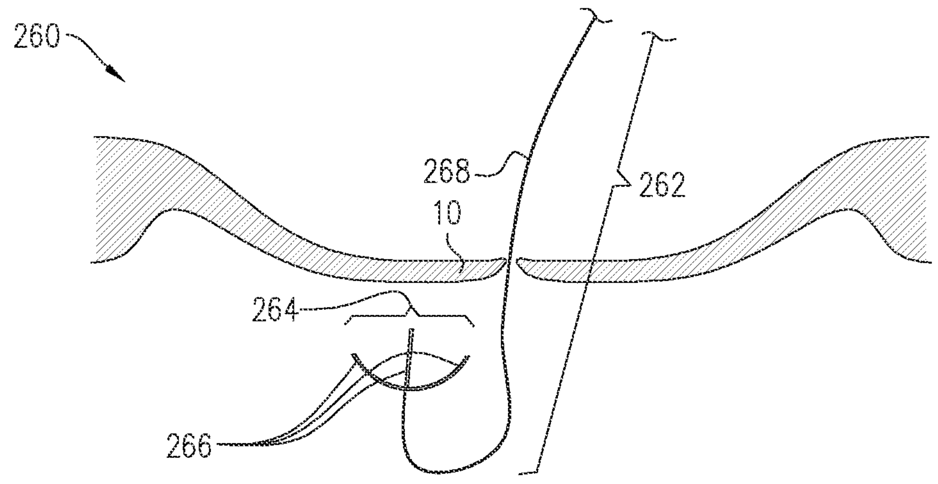
Figure 19B:
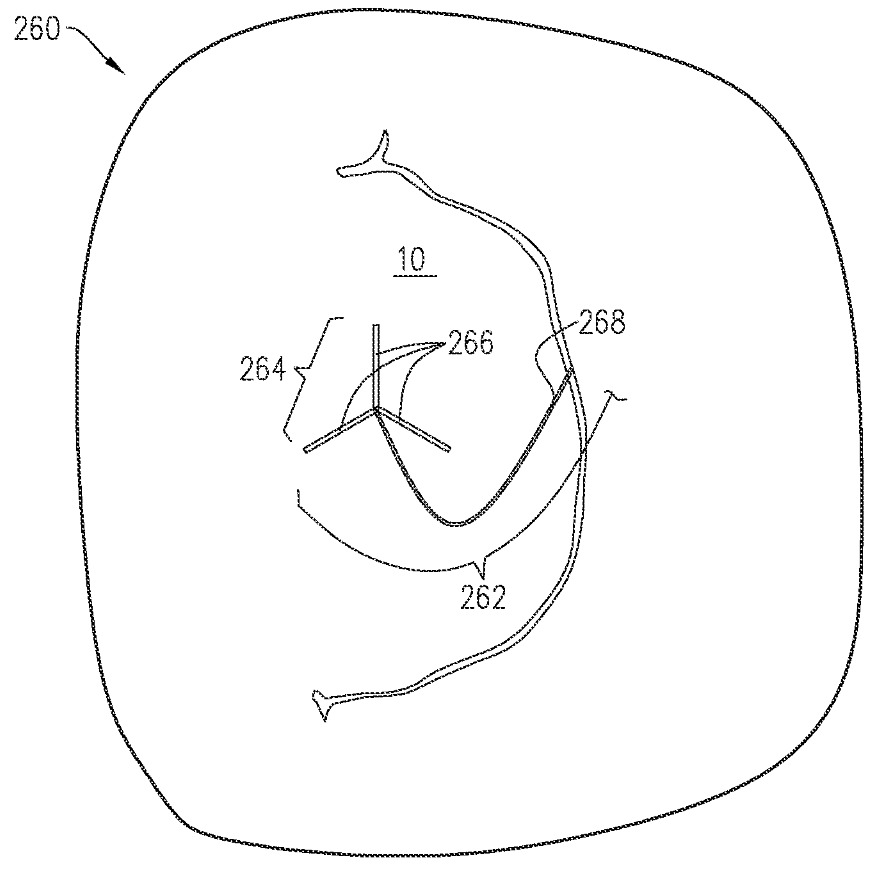

Reference is now made to FIGS. 19A-B, which are schematic illustrations of a system 260 comprising a leaflet-stabilizing element (e.g., a clasp) 262 which is configured to hold and stabilize leaflet 10, in accordance with some applications. Leaflet-stabilizing element 262 is configured to be passed between leaflets of an atrioventricular valve and grasp edge 12 of leaflet so as to hold and stabilize leaflet 10 as procedures are performed on leaflet 10 such as grasping the leaflet, clamping the leaflet, and/or puncturing the leaflet using any of the leaflet-grasping elements described herein or any other tool used on leaflet 10 known in the art. Leaflet-stabilizing element 262 is configured to provide a counter-force to leaflet 10 during the procedure, e.g., by providing temporary tension and/or tone to leaflet 10. Once the procedure on leaflet 10 has been completed, the grip of leaflet-stabilizing element 262 on leaflet 10 is released, and leaflet-stabilizing element 262 is removed from the body of the patient.

Leaflet-stabilizing element 262 comprises an elongate wire 268 that is coupled at a distal end to an expandable support 264. Elongate wire 268 extends outside the body of the patient and a proximal end is accessible from outside the body of the patient by an operating physician who controls movement of wire 268 in order to properly position expandable support 264. For some applications, expandable support 264 and wire 268 are deliverable to the valve within a delivery tube. For such applications, expandable support 264 is compressible within the delivery tube. Expandable support 264 comprises a flexible material, e.g., plastic, nitinol, or stainless steel. Expandable support 264 is shaped so as to define a plurality of fingers 266 which are configured to fan from each other and increase surface area contact between expandable support 264 and leaflet 10.

Wire 268 is delivered between leaflets of the valve such that expandable support 264 is positioned within the ventricle. For applications in which expandable support 264 is deliverable within a tube, the tube is retracted to expose expandable support 264 within the ventricle. In either application, once inside the ventricle, fingers 266 of expandable support fan from each other and have a curved state, as shown in FIG. 19A. The operating physician then pulls proximally on wire 268 in order to draw expandable support toward the ventricular surface of leaflet 10, as shown in FIG. 19B. Grip on wire 268 is maintained in order to press fingers 266 against the ventricular surface of leaflet 10 in a manner in which stability is provided to leaflet 10 from the ventricular surface of leaflet 10. As fingers 266 press against the ventricular surface of leaflet 10, fingers 266 lengthen and straighten. As long as wire 268 is pulled proximally, support 264 supports leaflet 10. Once the procedure on leaflet 10 is completed, the operating physician releases the tension on wire 268 and grip on the ventricular surface of leaflet 10 is released. Wire 268 is then pulled so that support 264 a wire 268 are removed from within the body of the patient.

Figure 20C:
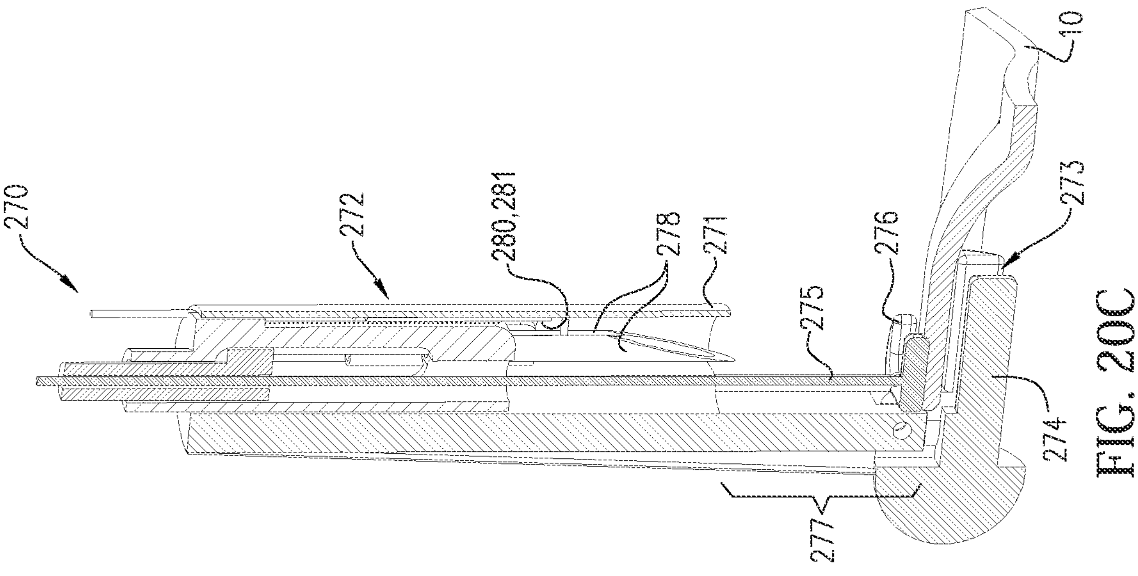
FIGS. 20A-I, 21A-C, 22A-B, 23A-E, 24A-D, and 25A-F are schematic illustrations of respective examples of a leaflet-augmentation and chordae tendineae repair device, in accordance with some applications.

Reference is now made to FIGS. 20A-I, which are schematic illustrations of a system 270 comprising an elongate tool 272 for facilitating leaflet-augmentation, in accordance with some applications. Tool 272 comprises a central tube 271 having a central longitudinal axis. Central tube 271 is shaped so as to define a side-slot 277. Tool 272 comprises at least one needle 278 which is slidable within a lumen of central tube 271. FIG. 20C shows an exemplary implementation of a tool 272 comprising two needles, namely first and second needles 278 that are slidable within a lumen of central tube 271. Tool 272 comprises a lower structural element 274 (i.e., a downstream support) that is configured for positioning at the ventricular surface of leaflet 10 in a manner that leaflet 10 is positioned within side-slot 277. Tool 272 comprises at least one needle-stabilizing element 276 (e.g., an upstream support), which is movable along the longitudinal axis of central tube 271. FIG. 20C shows an exemplary implementation of a tool 272 comprising first and second needle-stabilizing elements 276 that are moveable along the longitudinal axis of central tube 271.

Figure 20B:
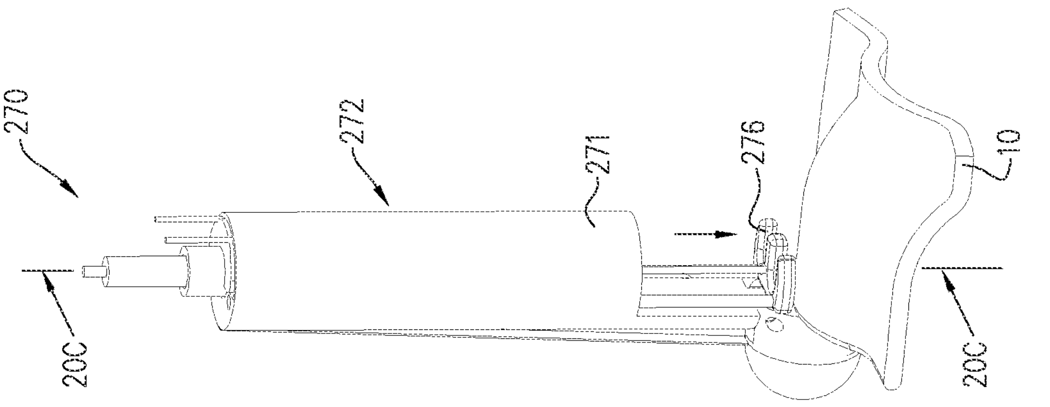
Figure 20A:
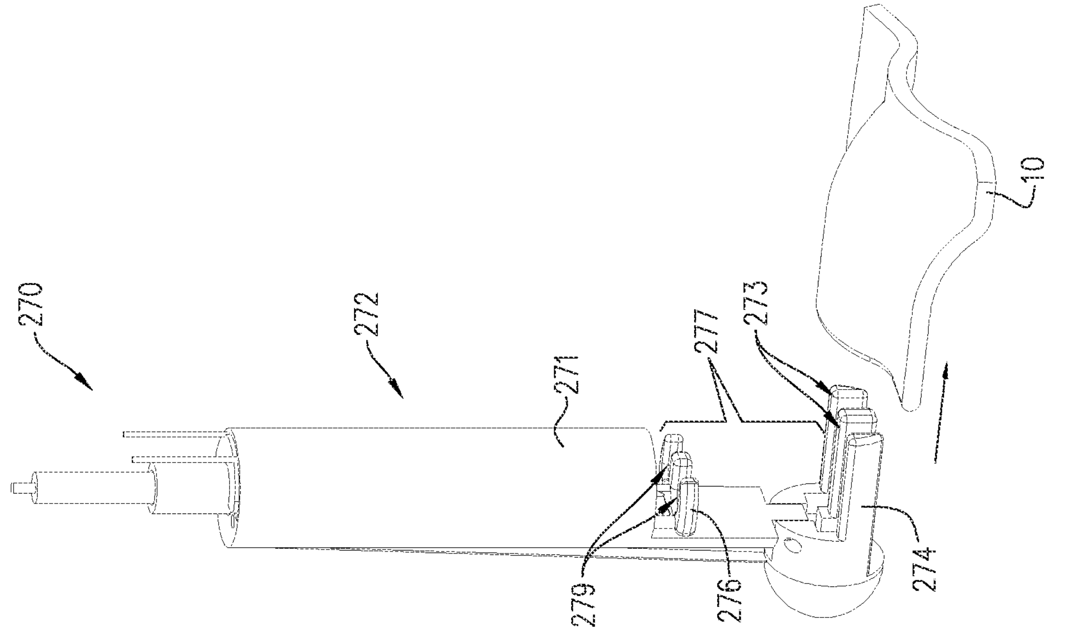

FIG. 20A shows tool 272 approaching leaflet 10. In FIG. 20B, first and second needle-stabilizing elements 276 are moved distally by pushing distally respective shafts coupled to first and second needle-stabilizing elements 276. In FIG. 20C, first and second needle-stabilizing elements 276 are pushed enough that a portion of the edge of leaflet 10 is grasped between first and second needle-stabilizing elements 276 and lower structural element 274. Thus, needle-stabilizing elements 276 and lower structural element 274 collectively define a clasp configured to grasp a portion of leaflet 10 in order to facilitate anchoring of an anchor to the portion of the leaflet. At this point, needles 278 have not yet moved distally.

Figure 23A:
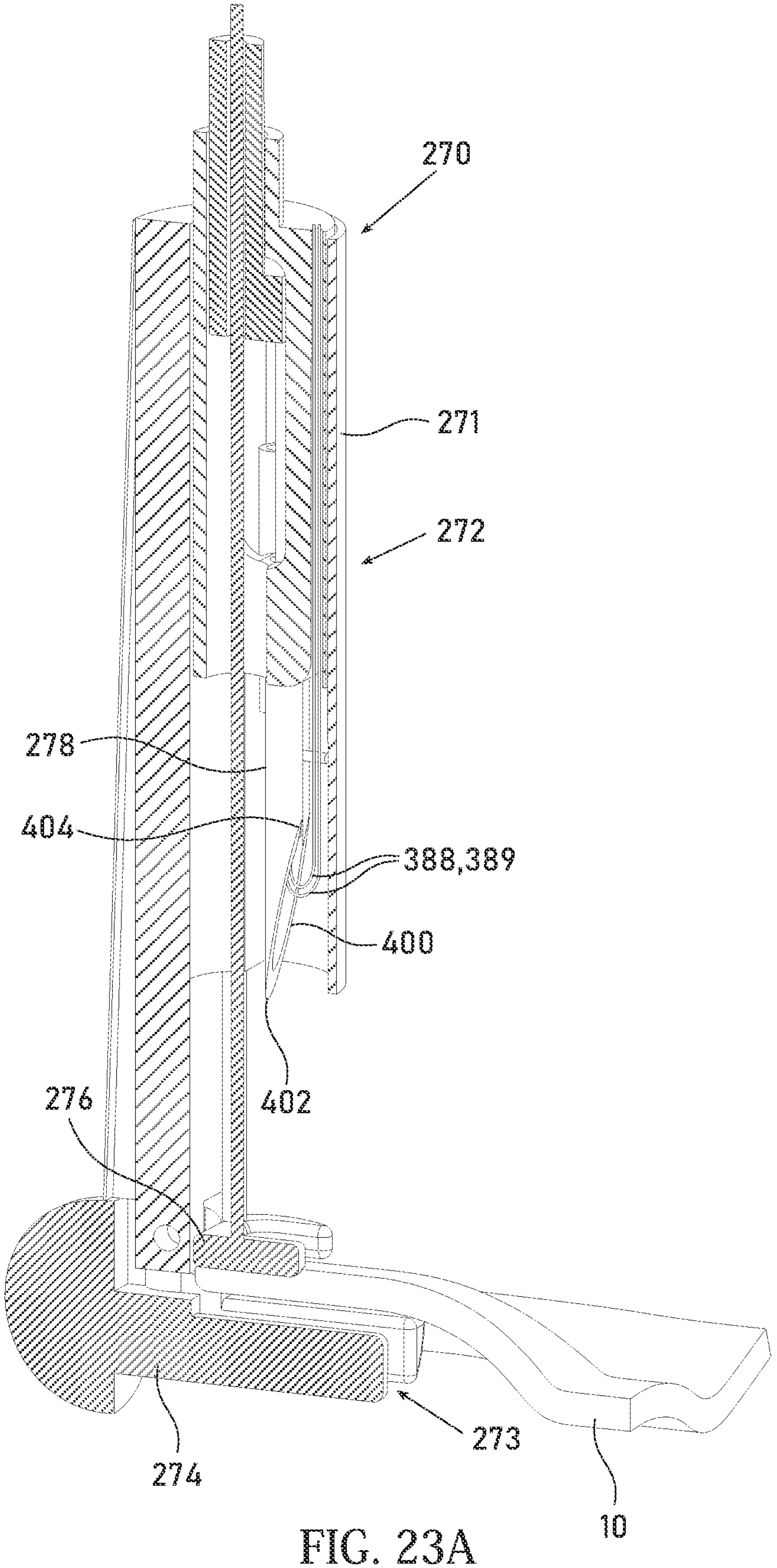
Figure 23B:
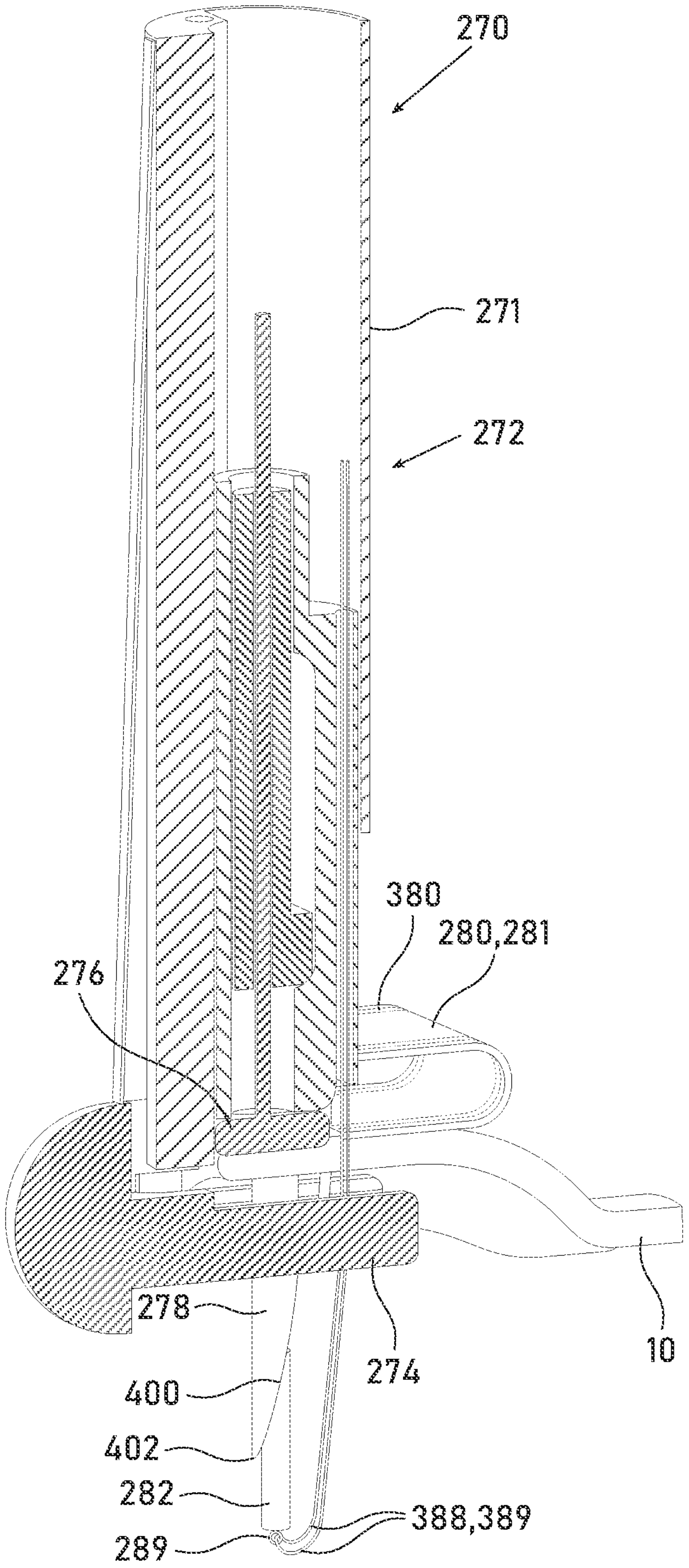

Each needle 278 comprises a sharp distal tip. In some implementations, each needle 278 comprises a beveled tip 400 (see for example in FIG. 23A), which includes a sharp distal tip portion 402, and a proximal tip portion 404.

Figure 20E:
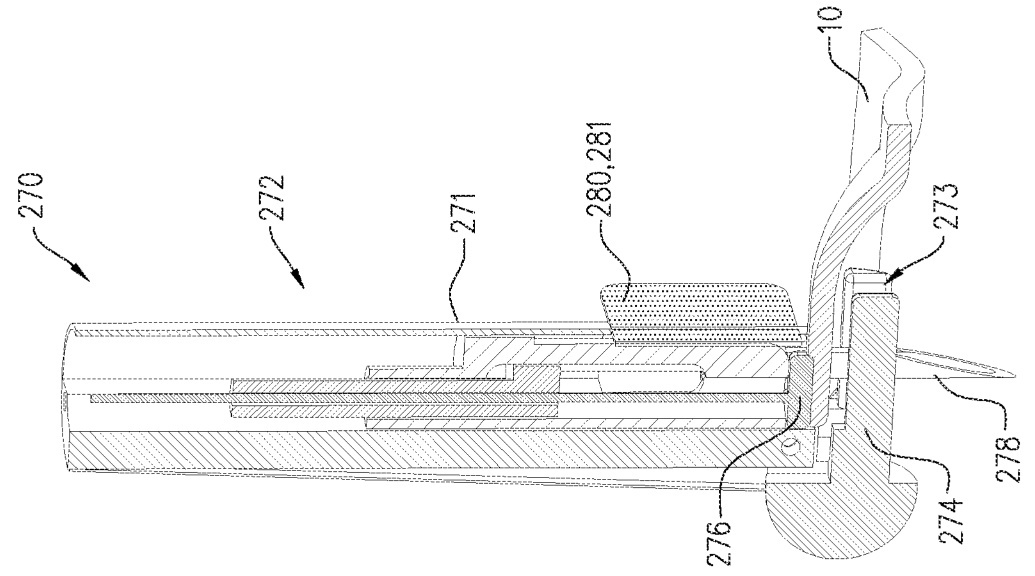
Figure 20D:
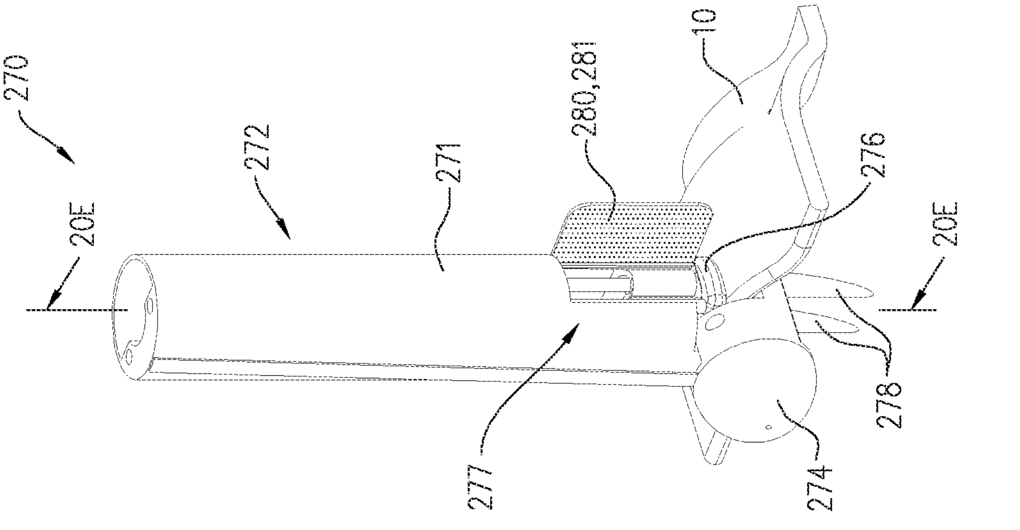

In FIG. 20D, needles 278 are passed distally by sliding needles 278 within the lumen of central tube 271. The distal tip portions 402 of needles 278 pass through respective openings 279 (openings 279 are shown in FIG. 20A) in first and second needle-stabilizing elements 276 such that first and second needle-stabilizing elements 276 loosely fit around and stabilize needles 278 as needles 278 pass through first and second needle-stabilizing elements 276. The distal tip portions 402 of needles 278 puncture tissue of leaflet 10. Continued distal pushing of needles 278 passes needles 278 through tissue of leaflet 10 and through respective slots 273 (slots 273 are shown in FIG. 20A) in lower structural element 274.

Central tube 271 is configured to facilitate delivery to leaflet 10 of a flap 281 (e.g., a planar flap, non-planar flap, flat flap, thin flap, elongate flap, etc.) of a leaflet-augmentation patch 280. Flap 281 is coupled to needles 278 such that the pushing of needles 278 distally brings (e.g., carries) flap 281 distally and to side-slot 277 of tube 271. Patch 280 (e.g., flap 281 thereof) is then exposed from within tube 271 via side-slot 277 (FIG. 20D).

FIG. 20E is a cross-sectional side-view of tool 272 as shown in the configuration shown in FIG. 20D.

Flap 281 comprises a flexible sheet of biocompatible material that mechanically resembles or emulates native tissue of leaflet 10 in a manner in which flap 281 can augment leaflet 10 and enhance the function of leaflet 10 and coaptation of leaflet 10 with the opposing leaflet. For some applications, flap 281 comprises tissue, e.g., pericardial tissue. For some applications, flap 281 comprises a sheet of a polymer such as polyethylene, expanded polytetrafluoroethylene, or polyethylene terephthalate, e.g., a sheet of a fabric of such a polymer. For some applications, flap 281 comprises organic and/or inorganic material that collectively provide the characteristics of flexibility, shape-memory durability, impermeability, and peri-implant tissue growth stimulation.

Figure 20G:
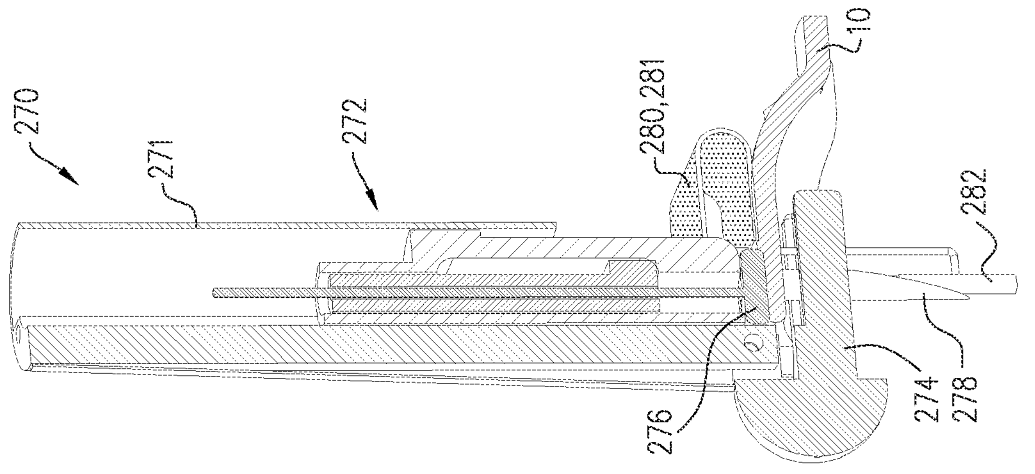
Figure 20F:
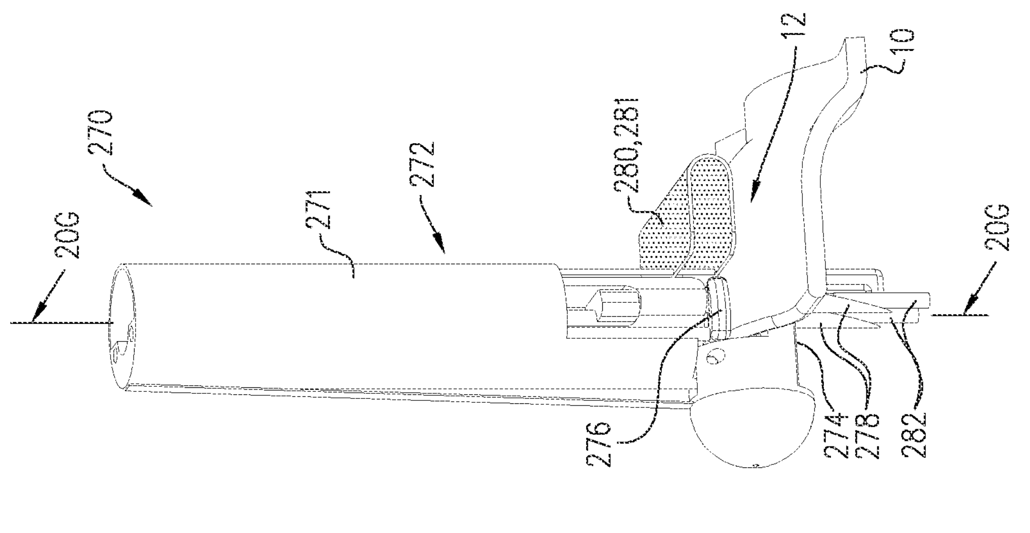
Figure 20I:
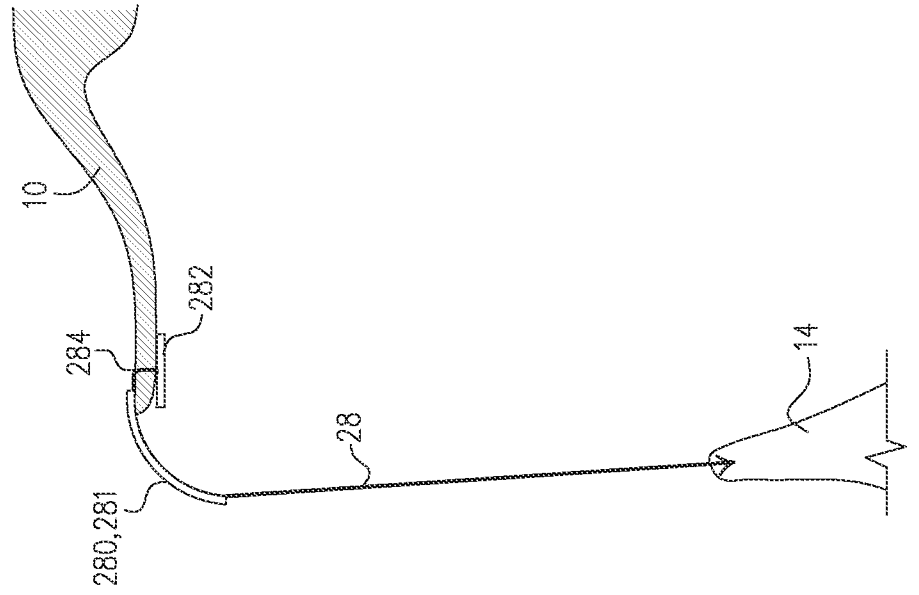
Figure 20H:
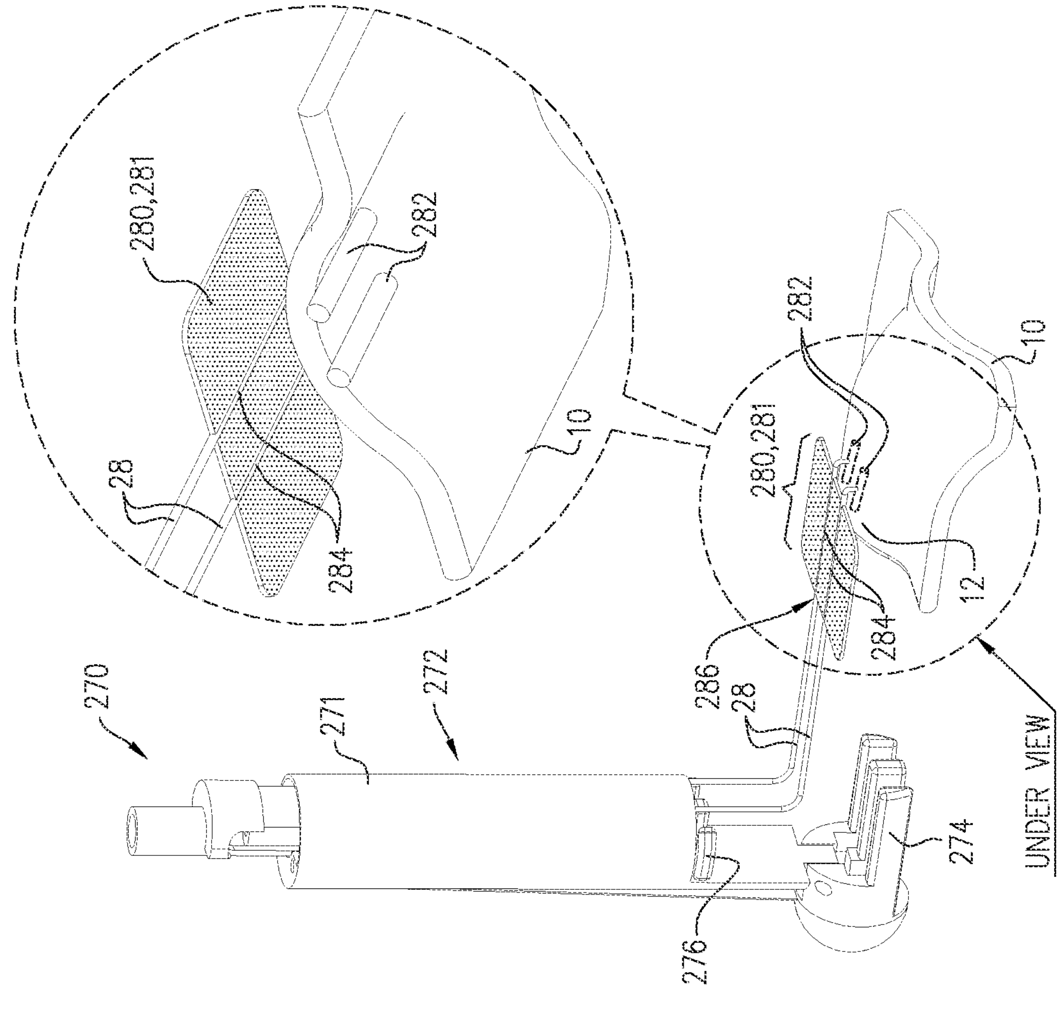

In FIG. 20F, flap 281 is moved distally and assumes a folded state at edge 12 of leaflet 10. Patch 280 comprises at least one tensioning member coupled to flap 281. FIG. 20H shows an exemplary implementation of a patch 280 comprising two tensioning members (e.g., cords) 284, namely first and second flap-deforming elements, which are coupled to flap 281. For some applications, tensioning members 284 are threaded with respect to flap 281. The tensioning members 284 can be threaded through flap 281 following various threading or stitching patterns, including threading through the thickness of the flap 281 through at least one point of penetration, threading in an in-and-out stitch pattern, and the like. For some applications, tensioning members 284 extend through channels formed within flap 281. For some applications, tensioning members 284 comprise fabric or polymeric threads.

Tensioning members 284 are coupled at their respective ends to respective first ends of longitudinal members 28 (e.g., tethers) at juncture 286, i.e., at an edge of flap 281. For some applications, each juncture 286 comprises a coupling member to which both the tensioning member 284 and the respective longitudinal member 28 are attached, such as an eyelet or ring member. For some applications, tensioning members 284 are knotted to, or loosely knotted to, flap 281 at juncture 286. For some applications, both tensioning members 284 are coupled to a single longitudinal member 28. Longitudinal members 28 are pulled into the ventricle and respective second ends of longitudinal members 28 are coupled to tissue surrounding the ventricle, e.g., a wall of the ventricle or papillary muscle 14, as shown in FIG. 20I.

For some applications, tensioning members 284 can be further utilized to help flap 281 transition from the folded state shown in FIGS. 20F-G to the expanded configuration shown in FIG. 20H, thereby serving as flap-deforming elements. For some applications, tensioning members 284 comprise a shape-memory material, e.g., nitinol. that has shape-memory which helps flap 281 self-expand and transition from the folded state shown in FIGS. 20F-G to the expanded configuration shown in FIG. 20H. For some applications, tensioning members 284 comprise wires.

For some applications, by pulling on longitudinal members 28, tension is applied to tensioning members 284 to help deform flap 281 into the expanded configuration. For some applications, tensioning members extend beyond juncture 286 and function as longitudinal members 28. That is, tensioning members 284 are longer than patch 280 and are pulled into the ventricle. Respective second ends of tensioning members 284 are coupled to tissue surrounding the ventricle, e.g., a wall of the ventricle or papillary muscle 14. By pulling on tensioning members 284, tension is applied to flap 281 by tensioning members 284 to help deform flap 281 into the expanded configuration. At least one locking element (e.g., a patch anchor or a stopper) can pass through the at least one needle 278 toward the ventricular surface of the leaflet 10. The at least one locking element can assume a variety of shapes, configured to press against the ventricular surface of the leaflet 10 and prevent spontaneous disengagement between the at least one locking element and the leaflet 10. For some applications, locking elements 282 can comprise any suitable anchor and can comprise any suitable crimping or collapsing features. For some applications, the at least one locking element comprises a rod-like locking element 282 (e.g., a toggle anchor), as illustrated in the example of FIGS. 20F-G, showing two rod-like elements, namely first and second locking elements 282. Rod-like locking element 282 can be tubular.

In FIGS. 20F-G, first and second locking elements 282 are pushed through to the ventricular surface of leaflet 10 by passing through needles 278. Each of locking elements 282 is coupled to a respective first end of the respective first and second tensioning members 284. For some applications, rod-like locking elements 282 comprise an elongated element configured to flip from a substantially vertical orientation, in which the longitudinal axis is substantially orthogonal to the atrial or ventricular surface of leaflet 10, and is parallel to the longitudinal axis of needle 278, while the locking elements 282 are disposed within the needles 278 during penetration through leaflet 10, and a substantially lateral orientation, in which the longitudinal axis of locking elements 282 is substantially parallel with the ventricular surface of leaflet 10, once the locking elements 282 are deployed from within the needles 278 and are pressed against the ventricular surface of leaflet 10.

For some applications, locking elements 282 comprise "T"-shaped locking elements which are compressible when delivered within the respective lumens of hollow needles 278 and expandable to the "T"-shape once pushed out of and exposed from within needles 278. Once expanded at the ventricular surface of leaflet 10, the at least one locking elements, such as rod-like locking elements 282, locks in place flap or planar flap 281 with respect to leaflet 10. For example, the at least one locking element can assume a helical configuration once deployed from a straight configuration as the at least one locking element is disposed within needles 278.

Tool 272 is then pulled away from leaflet 10, as shown in FIG. 20H, thereby pulling longitudinal members 28, which can further facilitate, for some applications, straightening and expanding of flap 281. Tool 272 is then moved within the ventricle in order to pull and bring longitudinal members 28 within the ventricle. Longitudinal members 28 are then coupled to tissue surrounding the ventricle, e.g., papillary muscle 14, as shown in FIG. 20I.

Flap 281 is illustrated as a substantially rectangular flap by way of illustration and not limitation. For example, and as described hereinbelow with respect to patch 610, flap 281 can be substantially trapezoid. For some applications, flap 281 has a flap inner edge 390 (e.g., a root edge), defined as the edge disposed over leaflet 10, facing the annulus, and a flap free edge (e.g., a lip) 394, defined as the opposite edge of flap 281, spaced away from (e.g., disposed beyond) edge 12 of leaflet 10. Flap 281 can further define flap side edges (i.e., lateral edges) 392 extending between the flap inner edge 390 and the flap free edge 394. For some applications, junctures 286 are position at, or in the vicinity of, flap free edge 394. For some applications, junctures 286 are coupled to flap free edge 394. Ultimately, system 270 provides an atraumatic device which facilitates leaflet augmentation aimed at facilitating or enhancing coaptation and apposition of the leaflets of the valve in order to treat regurgitation. Additionally, system 270 provides artificial chordae tendineae, i.e., longitudinal members 28 and/or tensioning members 284. The combination of both leaflet augmentation, such as via attachment of leaflet augmentation path 280 to a leaflet 10, and an artificial chordae tendineae, such as longitudinal members 28, provided by a single system 270, may be advantageous over partial solutions that provide only leaflet augmentation of artificial chordae tendineae functionalities, or system that require separate procedures, performed for each, and utilizing different systems.

It is to be noted that a suture can be sutured to leaflet 10 and patch 280 can be slid over the suture. For example, the suture positioned at leaflet 10 using tool 272 can be first coupled to leaflet 10 and patch 280 can be slid along the suture to either the atrial or ventricular surfaces of leaflet 10.

Figure 21A:
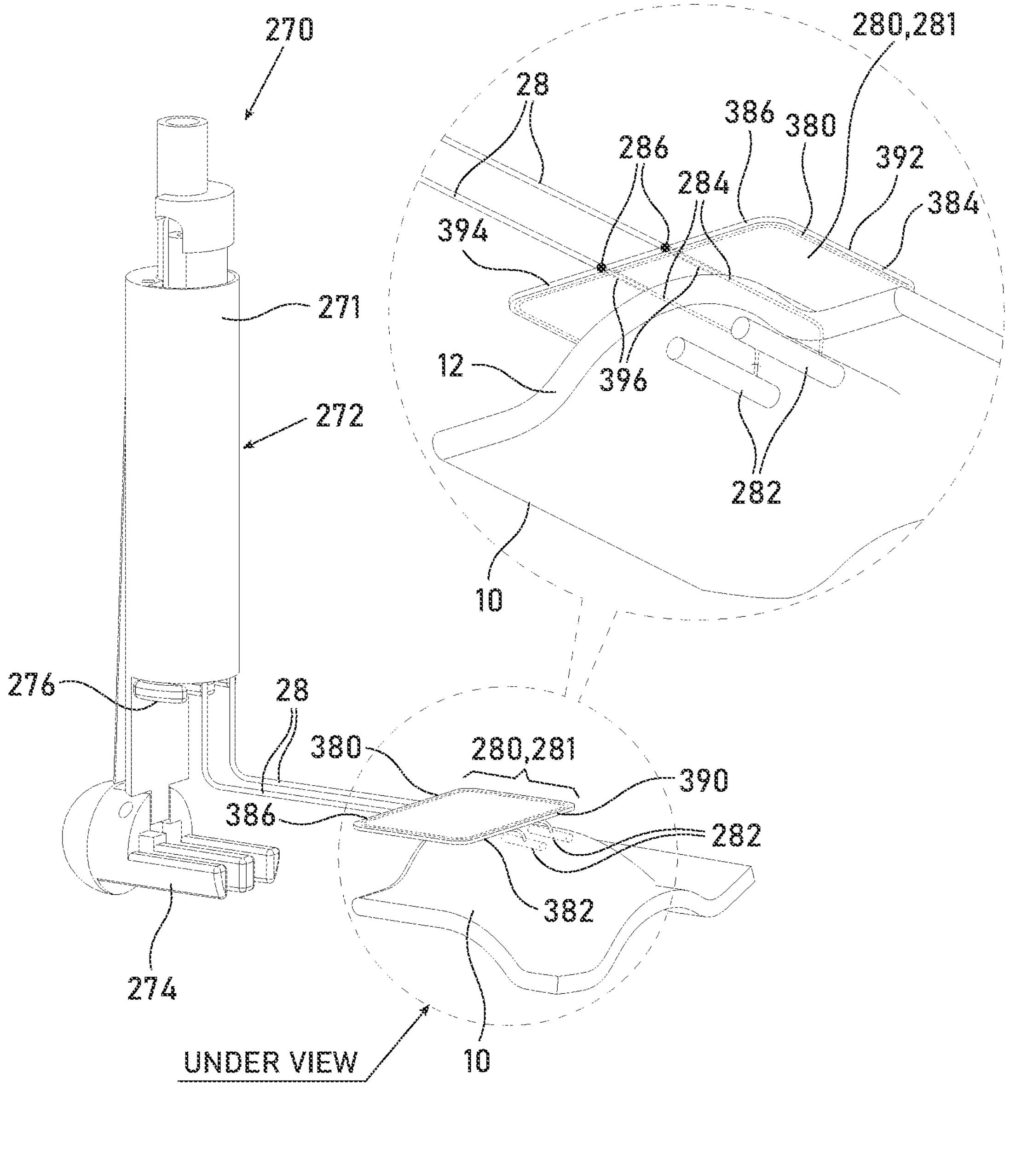
Figure 21B:
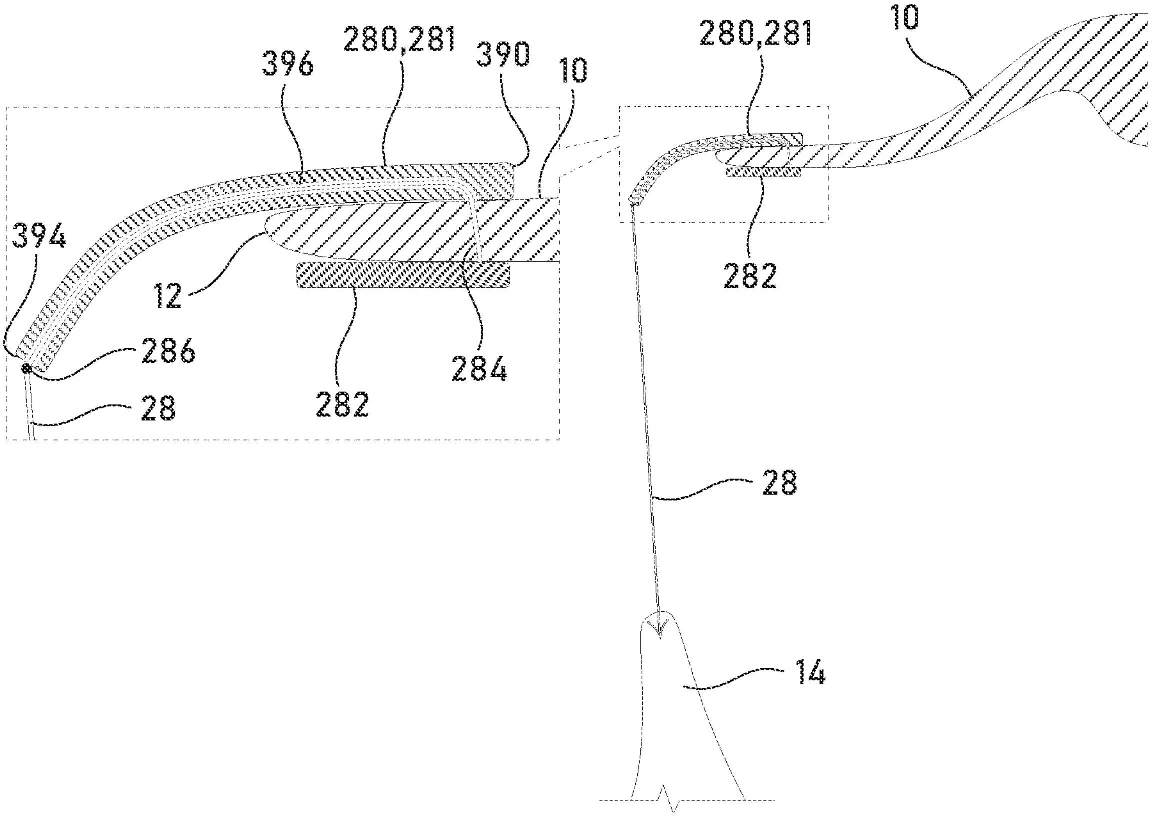
Figure 21C:
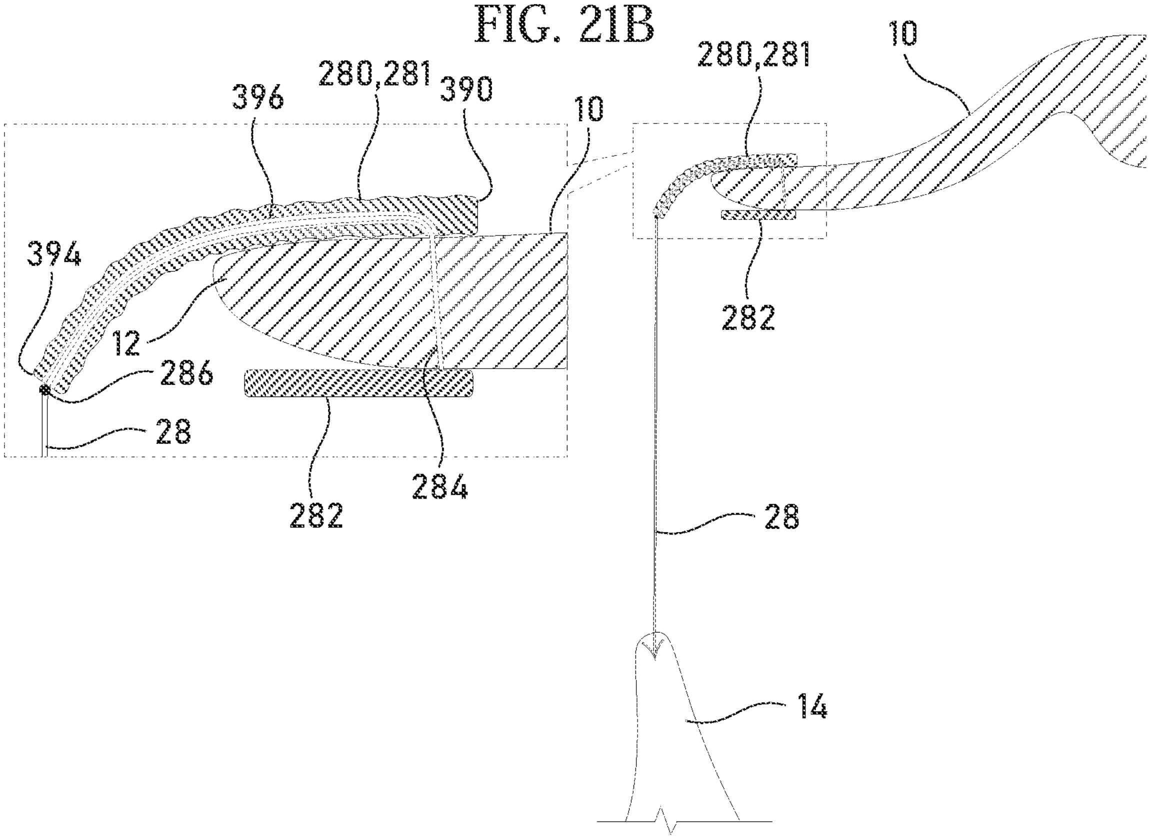

Reference is now made to FIGS. 21A-C, which are schematic illustrations of additional exemplary configurations and applications of a leaflet augmentation patch 280 of system 270. For some applications, leaflet augmentation patch 280 comprises a support frame 380, coupled to the flap 281, preferably following the edges of the flap 281. For some applications, the support frame can include a polymeric wire frame or a stainless-steel wire frame, which adds support to flap 281. For some applications, support frame 380 is configured to help flap 281 transition from the folded state (such as the state shown in FIGS. 20F-G) to the expanded configuration (such as the configuration shown in FIG. 21A), thereby serving as flap-deforming element. For some applications, the support frame 380 comprises a shape-memory material, e.g., nitinol, that has shape-memory which helps flap 281 self-expand and transition from the folded state (also termed the compressed configuration) to the expanded configuration. Support frame 380 is illustrated as a substantially rectangular frame by way of illustration and not limitation. For some applications, support frame 380 comprises a frame inner edge 382, coupled to flap 281 along flap inner edge 390, and a frame free edge 386, coupled to flap 281 along flap free edge 394. Frame 380 can further define frame side edges 384 extending between the frame inner edge 382 and the frame free edge 386. For some applications, junctures 286 are position at, or in the vicinity of, frame free edge 386. For some applications, junctures 286 are coupled to frame free edge 386.

As mentioned hereinabove, the at least one tensioning member 284 can be coupled to the flap 281 in various manners. For some applications, as shown in FIGS. 21A-C, the tensioning members 284 extend through channels 396 formed within and along the flap 281. For some applications, the at least one tensioning member 284 can be a suture (e.g., a single filament suture or a multi-filament suture), a flexible wire (e.g., a metal wire formed from stainless steel, Nitinol or other suitable metals), a cable (e.g., a braided cable formed from metal or polymeric strands), a strip of material (e.g., a polymer or metal strip), or any other similar materials that can be bent and placed under stress (e.g., in tension) between the juncture 286, at which the tensioning member 284 is coupled to the longitudinal member 28, and its opposite end, at which the tensioning member 284 is coupled to the locking element 282.

As shown in FIG. 21B, when the longitudinal members 28 are pulled in the distal direction, tension is applied to the tensioning members 284, which in turn transfers said pulling force to the locking elements 282, pressing them against the ventricular surface of leaflet 10. This advantageously serves to alleviate tension of longitudinal member 28 from flap 281.

For some applications, leaflet-augmentation patch 280 can comprise a spring which is configured to compress and shorten any excess length of leaflet-augmentation patch 280 and/or of tensioning members 284. For some applications, support frame 380 further serves as a spring-biased member configured to compress and shorten any excess length of leaflet-augmentation patch 280 and/or of tensioning members 284.

FIG. 21C shows the leaflet-augmentation patch 280 coupled to a leaflet having a thickness that is larger than that of the leaflet illustrated in FIG. 21C. Since each tensioning member 284 is placed under tension between both ends thereof (i.e., between its attachment to the longitudinal member 28 at juncture 286, and its attachment to the locking element), its total length remains unchanged, regardless of the thickness of the leaflet 10 it extends through. Thus, a thicker leaflet results in a smaller portion of the length of the tensioning member 284 extending through or along, the flap 281. This may result, as shown in FIG. 21C, in shortening of the flap 281 between the juncture 286 and the atrial surface of the leaflet 10, relative to the length of the flap 281 in FIG. 21B. The support frame 380 can be configured to enable shortening of the flap 281 when placed under compressive forces between the juncture 286 and the region at which the tensioning member 284 extends through the leaflet 10 and the flap 281, and to extend or allow extension of the flap 281 in the absence of such forces. For example, support frame 380 can comprise a compression spring.

Figure 22A:
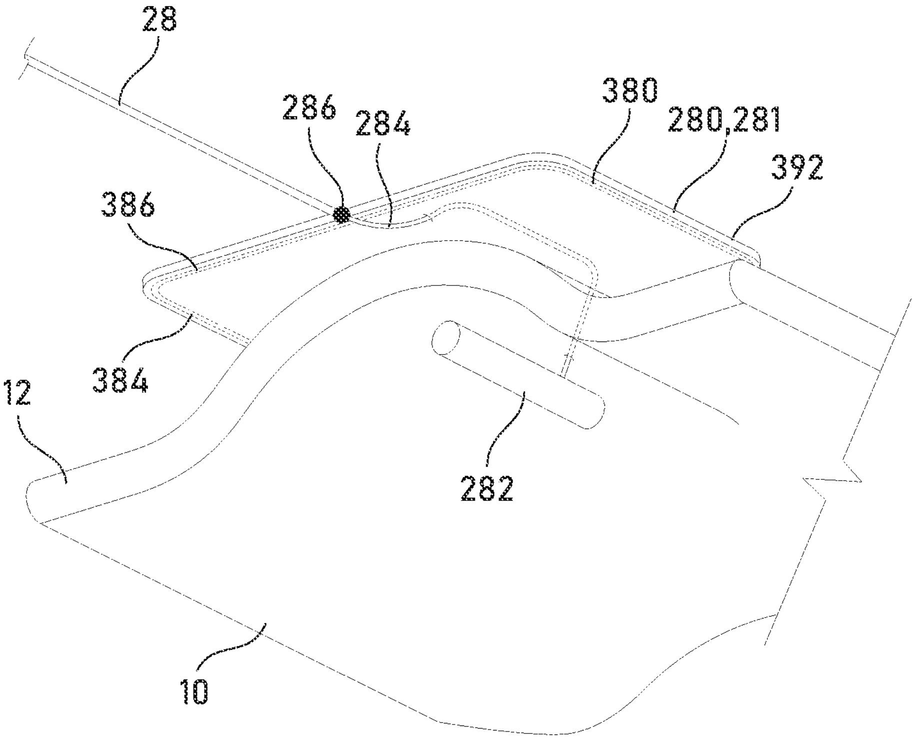
Figure 22B:
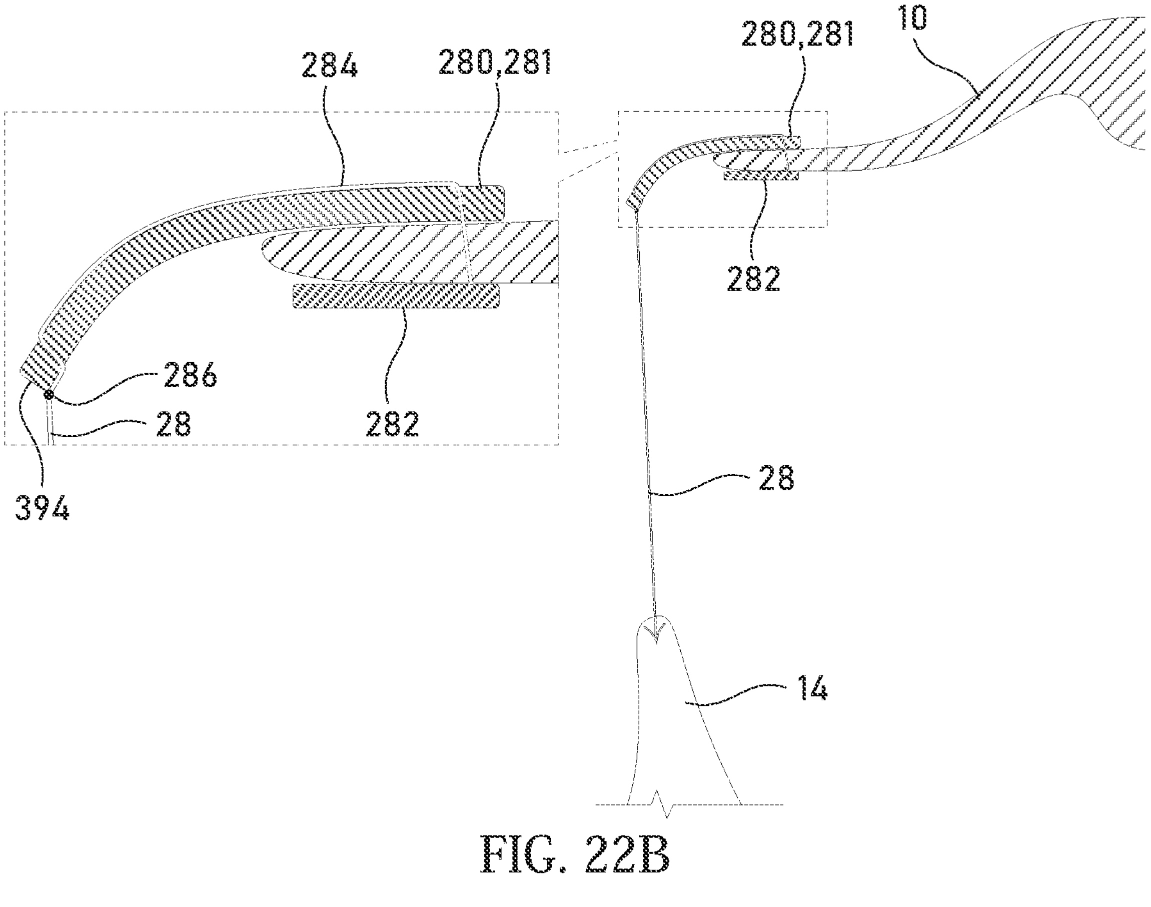

Reference is now made to FIGS. 22A-B, which are schematic illustrations of additional exemplary applications and configurations of a leaflet augmentation patch 280 of system 270. For some applications, the at least one tensioning member comprises a single locking element 282, as shown in FIG. 22A. In such applications, the elongate tool 272 can include a single needle 278 through which the tensioning member 284 can be advanced, a single needle-stabilizing element 276, a single tensioning member 284 coupled at one end to the locking element 282, at the opposite end to a single longitudinal members 28 (e.g., at a single juncture 286). It is to be understood that any other implementation of system 270 and leaflet augmentation patch 280, e.g., those disclosed with respect to FIGS. 20A-21C, FIGS. 23A-26E, and FIGS. 31A-66D, can be implemented with a single locking element (i.e., a single patch anchor), as well as with more than two locking elements (i.e., more than two patch anchors), mutatis mutandis.

FIGS. 22A-B further demonstrate, by way of illustration and not limitation, another configuration for coupling a tensioning member 284 to the flap 281, wherein the tensioning member 284 can extend from the locking element, through the leaflet 10, toward and through the flap 281, extending further therefrom over a portion of the flap 281 along an upper surface thereof, and then penetrate through the flap 281 toward the underside of the flap 281, to connect with longitudinal members 28 at junction 286. It is to be understood that any coupling configuration between tensioning member 284 and flap 281, including the back-and-forth suturing shown in FIGS. 22A-B or extension through channels 396 shown in FIGS. 21A-C, can be used in combination with any other example of system 270 and leaflet augmentation patch 280 disclosed with respect to FIGS. 20A-25F, mutatis mutandis.

Attachment of leaflet augmentation patch 280 to leaflet 10 can be executed and viewed under fluoroscopy or other imaging modalities. During such procedures, it may become desirable to retrieve the leaflet augmentation patch 280, for example if its position is unsuitable with respect to the leaflet 10. For some applications, the system 270 further comprises a patch retrieval mechanism, configured to facilitate retrieval of leaflet augmentation patch 280 after it is coupled to leaflet 10 via at least one locking element, such as locking elements 282.

Reference is now made to FIGS. 23A-E, which are schematic illustrations of a of system 270 comprising a patch retrieval mechanism for facilitating retrieval of leaflet augmentation patch 280, in accordance with some applications. According to some applications, the system 270 further comprises at least one pull member (e.g., a retrieval line) 388 releasably coupled, directly or indirectly, to the at least one locking elements. The at least one pull member 388 can comprise a polymeric or textile thread, a flexible wire, or a flexible cable.

As shown in FIG. 22, pull member 388 extends through a lumen of the central tube 271, and can be movable through the central tube 271 along its central longitudinal axis. According to some applications, each locking element, such as rod-like locking element 282, comprises an eyelet 289 attached to one end thereof, through which a respective pull member 388 is looped (see FIG. 23B).

According to some applications, central tube 271 is a multi-lumen tube, comprising at least two lumens: a lumen through which longitudinal members 28 can extend, and another lumen through which pull members 388 can extend, so as to avoid any potential entanglement between longitudinal members 28 and pull members 388 extending longitudinally through the central tube 271.

While locking elements 282 are retained within needles 278, pull members 388 can extend from the eyelets 289 of locking elements 282, over the edge of beveled tips 400 of needles 278, and back through a lumen of central tube 271, for example so as to extend outside the body of the patient, such that the proximal ends of pull members 388 are accessible from outside the body of the patient by an operating physician who controls movement of pull members 388. According to some applications, the distal tip portion 402 of each beveled tip 400 of needle 278 is sharp, which the proximal tip portion 404 remains blunt, thereby reducing or eliminating risk of accidently cutting the portion of the pull member 388 folded thereover.

Figure 23D:
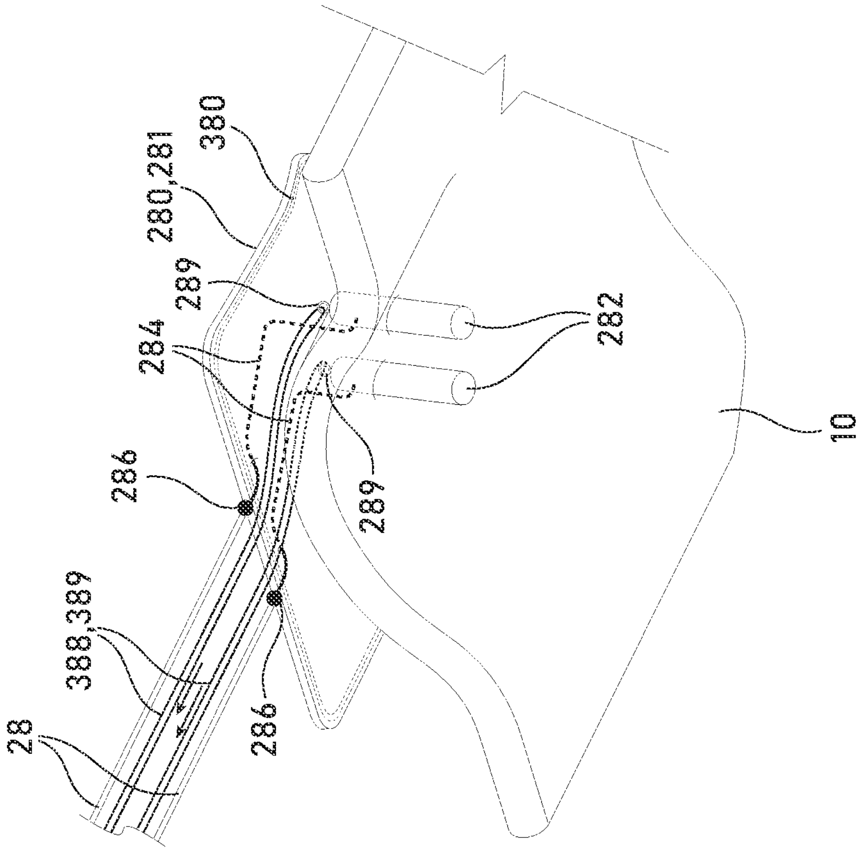
Figure 23C:
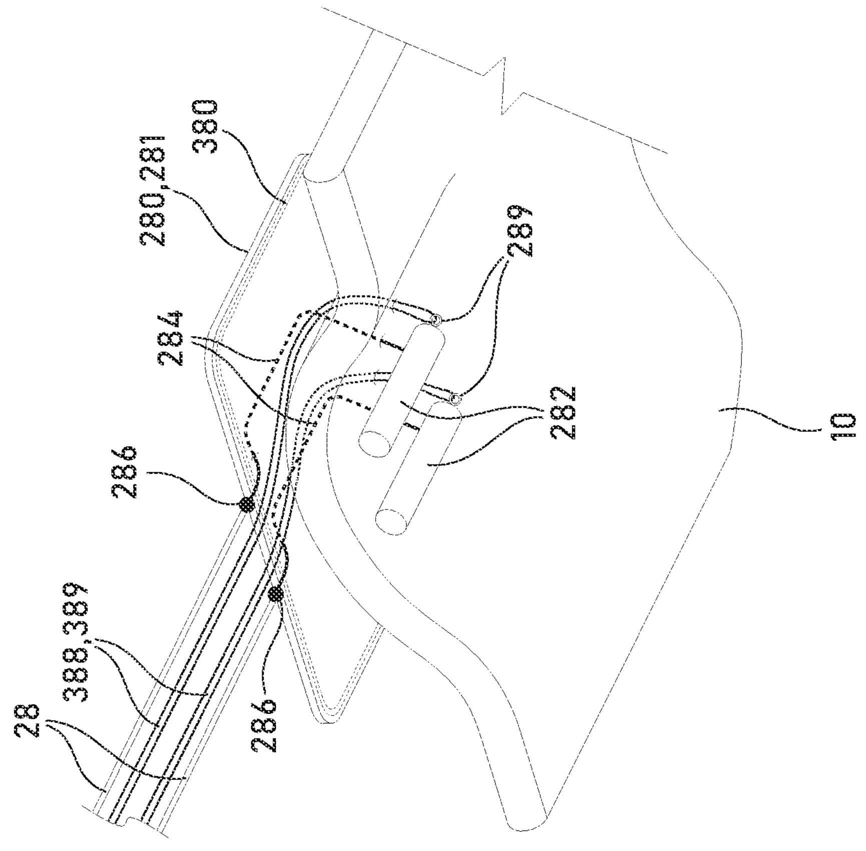

FIG. 23C shows the leaflet augmentation patch 280 is an expanded configuration, coupled to leaflet 10, while the pull members 388 and the longitudinal members 28 still extend toward the central tube 271. The elongate tool 272 and central tube 271 are not shown in FIG. 23C, but it is to be understood that at the stage shown in FIG. 23C, the elongate tool 272 and central tube 271 have been moved away from the leaflet 10, to a position similar to that shown in FIG. 20H, for example. As shown, each of the pull members 388 is looped through a respective eyelet 289, such that one strand 389 of each pull member 388 extends from one side of the respective eyelet 289, and another strand 389 extends from the other side of the same eyelet 289. All strands 389 extend from the eyelets 289, through leaflet 10 and toward the central tube (271), between the atrial surface of leaflet 10 and lower surface of flap 281.

FIG. 23D shows a potential follow-up step of retrieving the leaflet augmentation patch 280, for example if its position over leaflet 10 is determined to be inadequate. As shown, both strands 389 of each pull member 388 are pulled in a proximal direction, which serves to reorient the locking elements 282 from a locking orientation shown in FIG. 23C, to a non-parallel, i.e., angled or even orthogonal orientation, with respect to leaflet 10. Applying further pull force on the pull members 388, and more specifically, on both strands 389 of each pull member 388, serves to pull the locking elements 282 through leaflet 10, and eventually pull the patch 280 there-along, toward and potentially into elongate tool 272. Proximally oriented pull force can be applied to the longitudinal members 28, in parallel to the pull force applied to the pull members 388, to further facilitate patch retrieval.

Figure 23E:
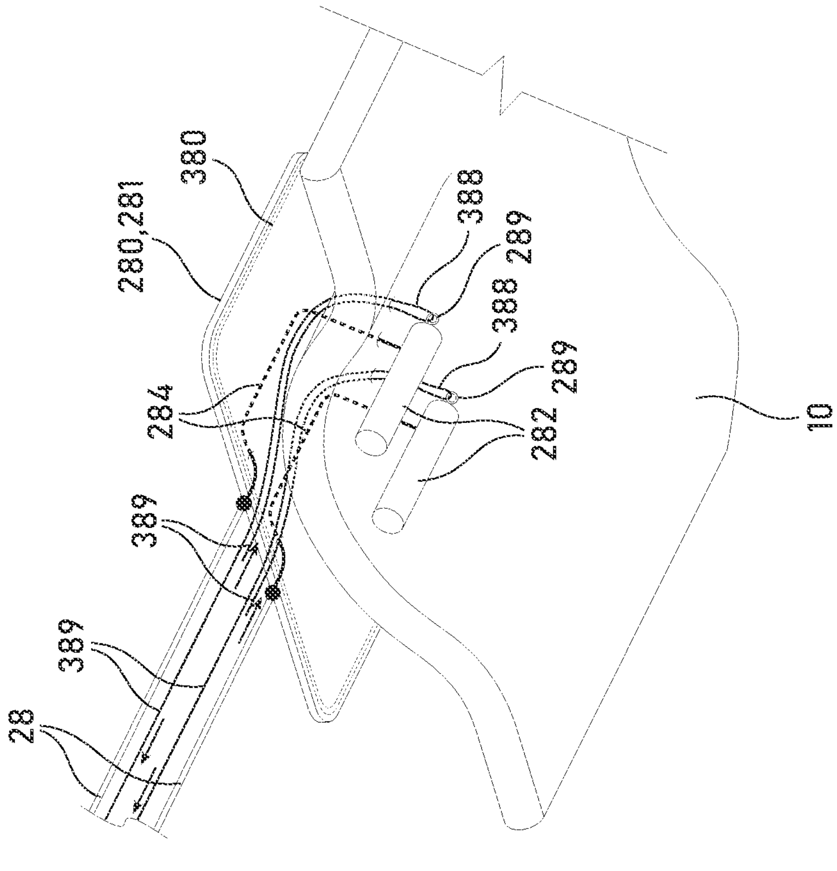

FIG. 23E shows an alternative follow-up step to FIG. 23C, in which the pull members 388 can be decoupled from the locking elements 282 and retrieved, if the position of patch 280 over leaflet 10 is adequate, and retrieval thereof is not required. In such instances, one strand 389 of each pull member 388 can be pulled proximally, while the other strand is free to move distally toward the eyelet 289, until it is released from the eyelet 289, such that the pull member 388 is no longer looped through the eyelet 289, and can be retrieved therefrom.

Figure 24A:
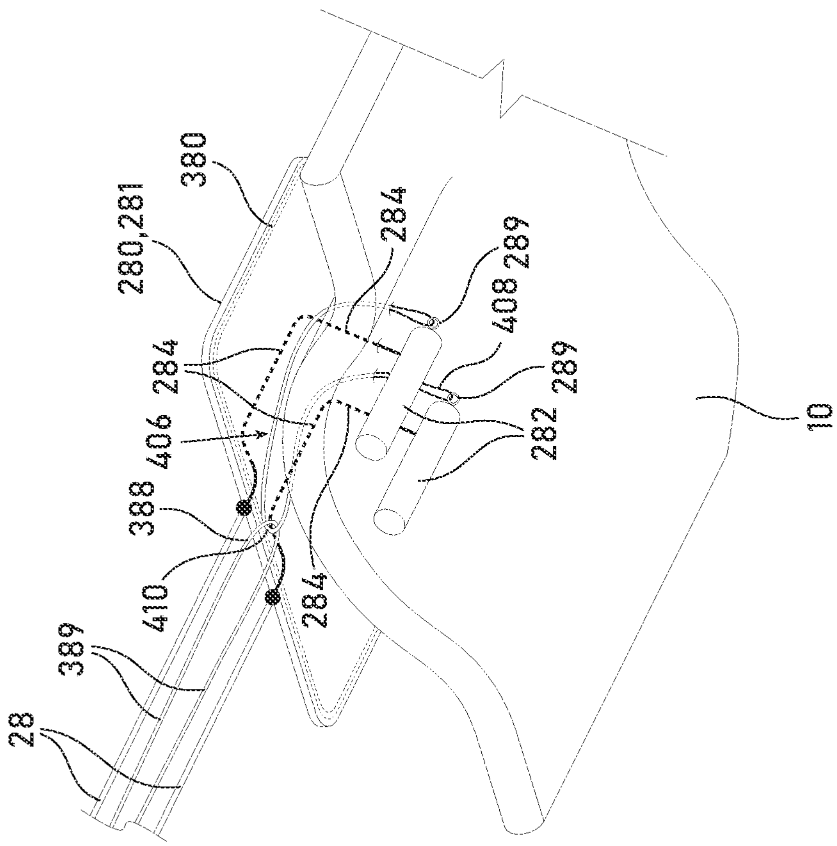
Figure 24C:
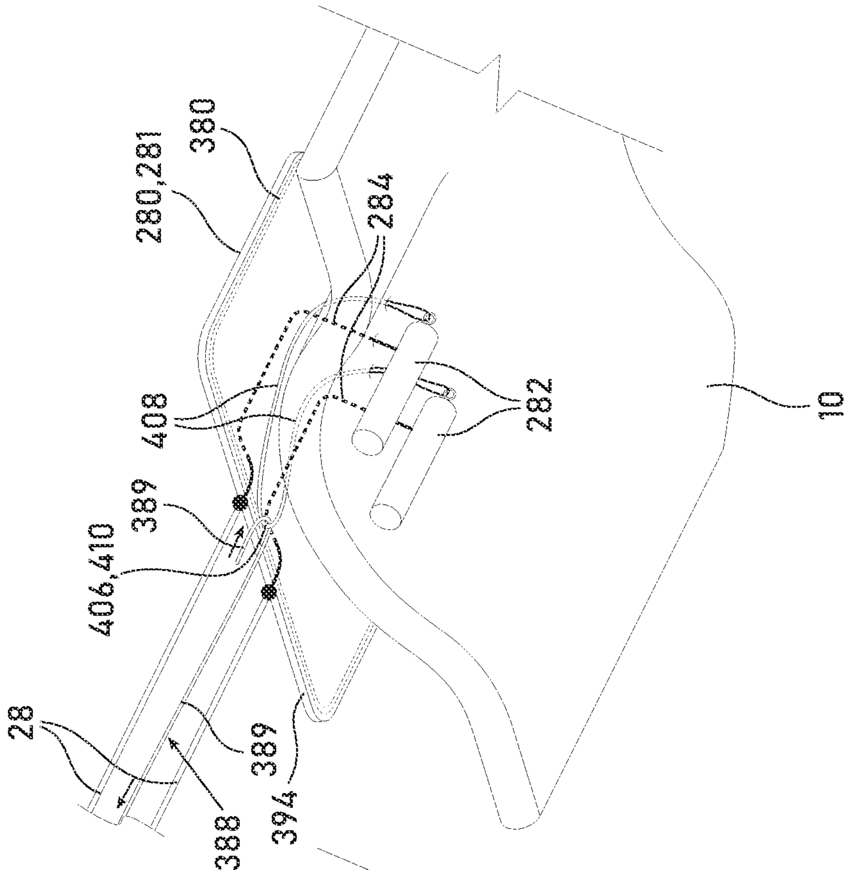
Figure 24B:
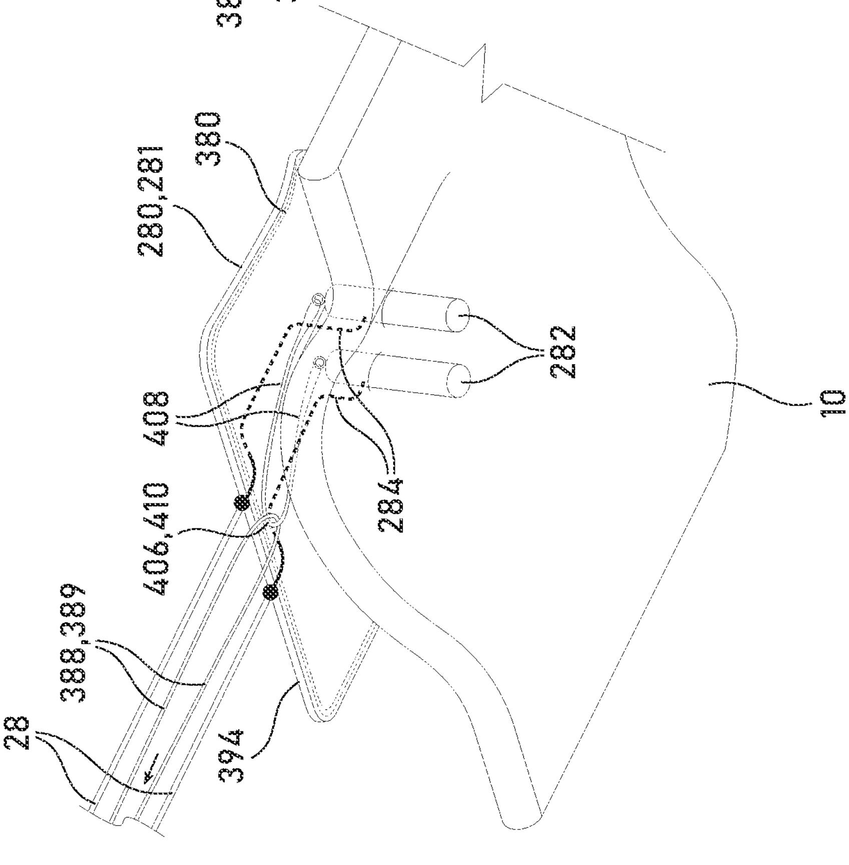

Reference is now made to FIGS. 24A-C, which are schematic illustrations of a of another retrieval mechanism for facilitating retrieval of leaflet augmentation patch 280, in accordance with some applications. According to some implementations, as shown in FIG. 24A, a single pull member 388 can be coupled to a U-shaped loop 406, attached to first and second locking elements 282. As shown, a U-shaped loop 406 can comprise first and second tails 408 attached at their ends to first and second locking elements 282, and a central bight portion 410 defined between the tails 408, over which the pull member 388 is looped. In this configuration, one strand 389 extends from one side of the U-shaped loop 406, and another strand extends from the other side of the U-shaped loop 406.

First and second U-shaped tails 408 can be coupled to first and second locking elements via eyelets 289 or be attached directly thereto in any number of methods known in the art, such as suturing, gluing, welding, and the like. First and second tails 408 of extend from the locking elements 282, through the thickness of leaflet 10, and toward the central tube (271), between the atrial surface of leaflet 10 and lower surface of flap or planar flap 281.

FIG. 24B shows a potential follow-up step of retrieving the leaflet augmentation patch 280, for example if its position over leaflet 10 is determined to be inadequate. As shown, both strands 389 are pulled simultaneously in a proximal direction, which pulls the U-shaped loop 406 there-along and serves to reorient the locking elements 282 from a locking orientation shown in FIG. 24A, to a non-parallel, i.e., angled or even orthogonal orientation, with respect to leaflet 10. Applying further pull force on the pull member 388, and more specifically, on both strands 389, serves to pull the locking elements 282 through leaflet 10, and eventually pull the patch 280 there-along, toward, and potentially into elongate tool 272. Proximally oriented pull force can be applied to the longitudinal members 28, in parallel to the pull force applied to the pull member 388, to further facilitate patch retrieval.

FIG. 24C shows an alternative follow-up step to FIG. 24A, in which the pull member 388 can be decoupled from the U-shaped loop 406 and retrieved, if the position of patch 280 over leaflet 10 is adequate, and retrieval thereof is not required. In such instances, one strand 389 can be pulled proximally, while the other strand is free to move distally toward the bight portion 410 of U-shaped loop 406, until it is released therefrom, such that the pull member 388 is no longer looped through the U-shaped loop 406 and can be retrieved therefrom.

Figure 24D:
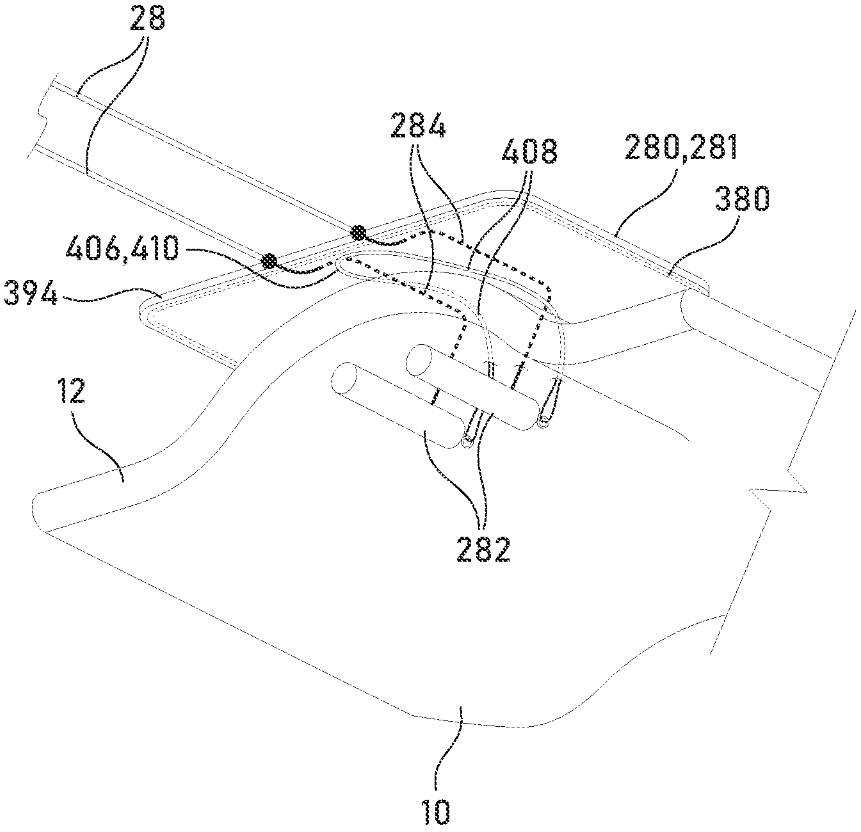

FIG. 24D shows leaflet-augmentation patch 280 coupled to leaflet 10 after retrieval of pull member 388 therefrom. Preferably, the U-shaped loop 406 is dimensioned such that central bight portion 410 does not extend beyond the free edge 394 of the flap 281, resulting in the entire U-shaped loop 406 being concealed beneath flap 281.

In implementations utilizing more than one locking element 282, the configuration shown in FIGS. 24A-C can be advantageous over that shown in FIGS. 23A-E, requiring a smaller number of pull members 388 than need to be maneuvered during the procedure. For example, a patch 280 coupled to leaflet 10 via two locking elements 282, may require a single pull member 388 when a U-shaped loop 406 as shown in FIGS. 24A-C is utilized, instead of two pull members 388 that need to be pulled simultaneously in the configuration shown in FIGS. 23A-E.

Reference is now made to FIGS. 25A-F, which are schematic illustrations of another type of a system 270 with a retrieval mechanism for facilitating retrieval of leaflet augmentation patch 280, in accordance with some applications. According to some applications, the at least one locking element is provided in the form of at least one expandable locking element 283. Expandable locking element 283 can comprise a braided member.

Figure 25A:
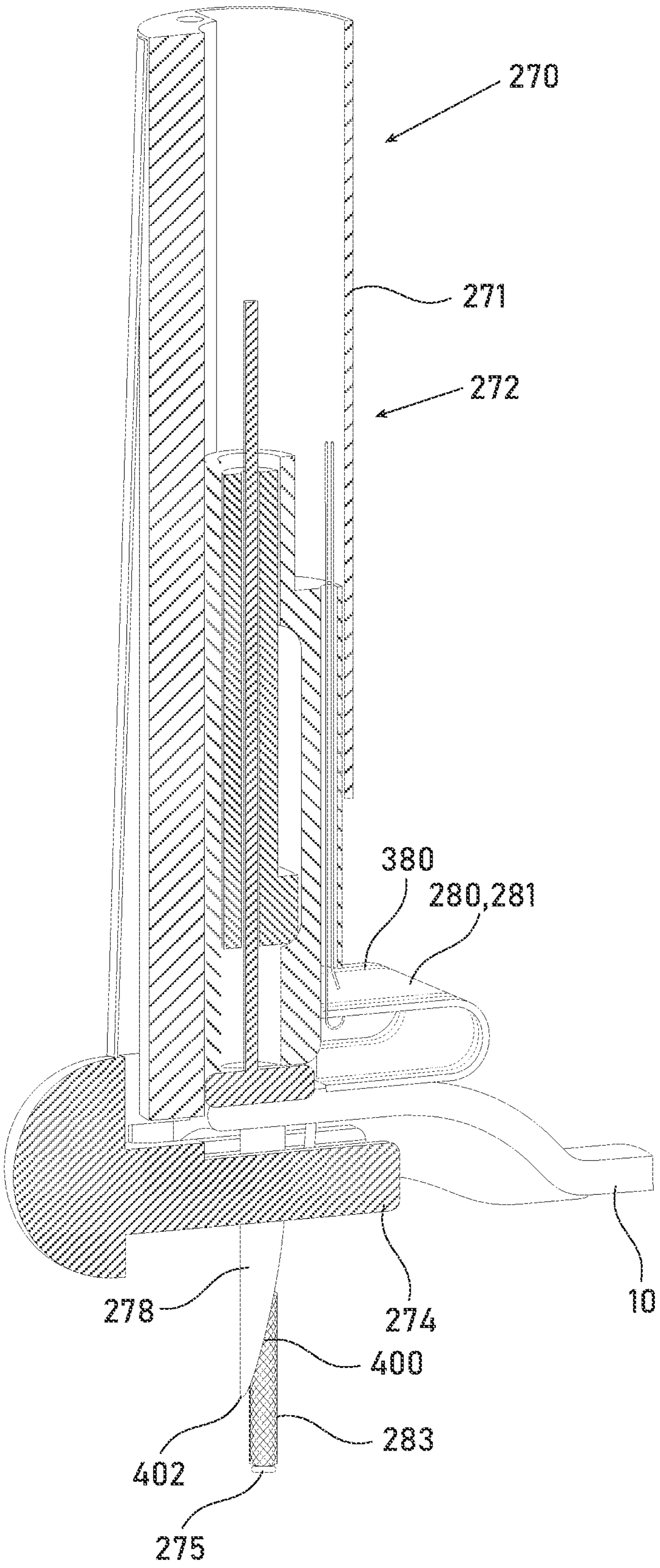

As shown in FIG. 25A, expandable locking element 283, in its resting state, is shaped so as to define an elongate longitudinal (e.g., tubular) element. When disposed within needle 278, expandable locking element 283 is in its free state, and may not assume an expanded state due to the restriction of the surrounding inner walls of needle 278. For some applications, expandable locking element 283 comprises a biocompatible metal, e.g., nitinol or stainless steel, that comprises a plurality of struts which are arranged so as to impart flexibility, compressibility, and expandability to expandable locking element 283. For some applications, expandable locking element 283 comprises a fabric which comprises a plurality of woven strands. For some applications, expandable locking element 283 comprises a plastic which comprises a plurality of woven strands.

Each type of locking element, including rod-like locking element 282 and expandable locking element 283, comprises a locking element proximal end 285 and a locking element distal end 287.

Each tensioning member 284 is coupled at one end thereof to a respective distal end 287 of a locking element 283, and at its opposite end to longitudinal member 28 at juncture 286. In the illustrated example, tensioning member is shown to be sutured through the flap 281 at two penetration points. However, it will be clear that any other coupling configuration between tensioning members 284 and flap 281 is contemplated.

Figure 25B:
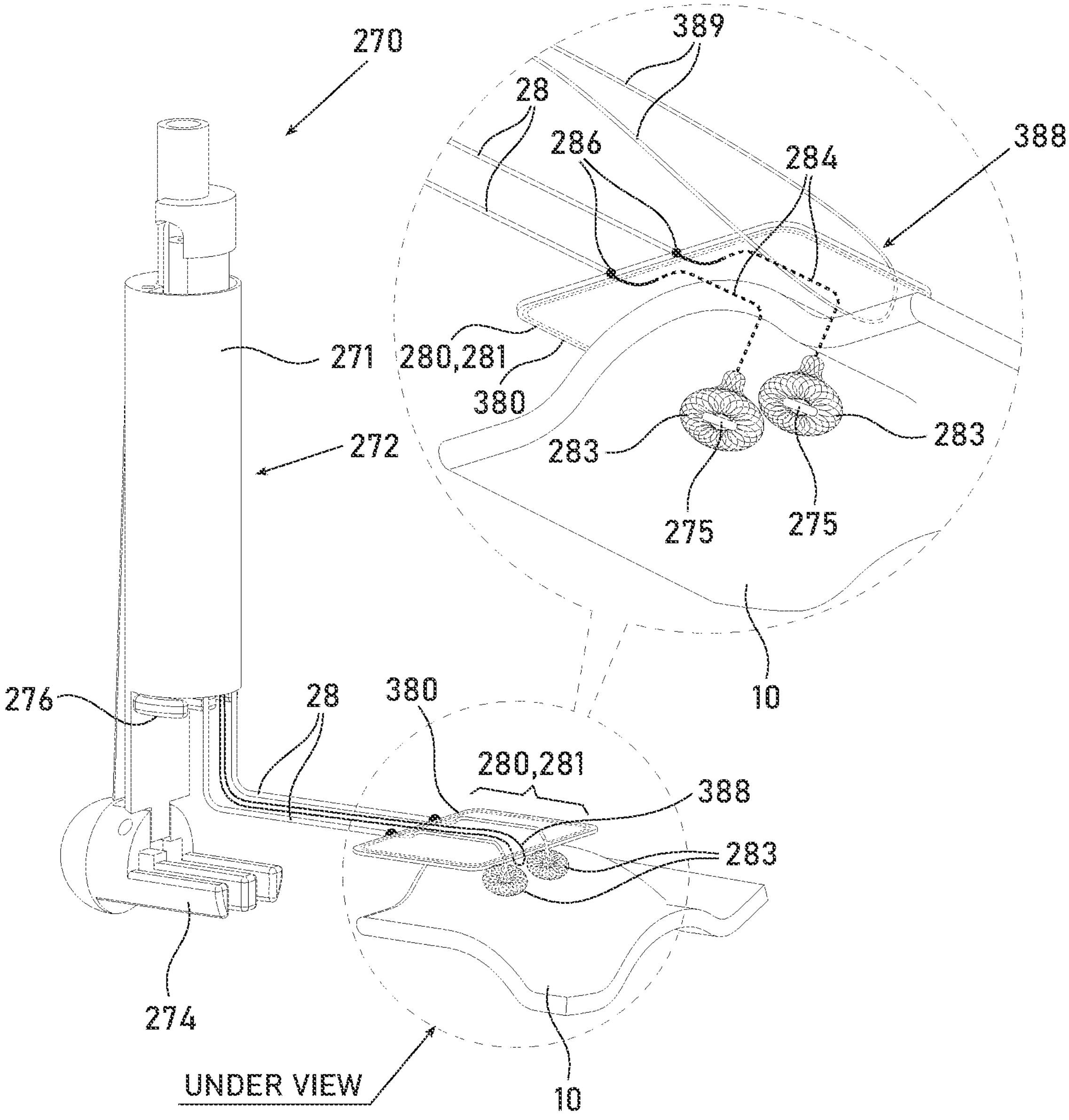

The length of each tensioning member 284 is chosen such that once the flap or planar flap 281 assumes the expanded configuration shown in FIG. 25B, the locking element distal end 287 is proximally pulled, by the tensioning member 284 applying a pulling force thereto, toward the ventricular surface of leaflet 10, forcing the expandable locking element 283 to assume an expanded orientation or configuration (e.g., an expanded substantially planar, disc-like, etc. orientation/configuration), having an external maximal diameter larger than the diameter of the expandable locking element 283 in a free state thereof.

For some applications, an end of tensioning member 284 can be directly coupled to locking element distal end 287, for example by welding, suturing, gluing and the like. For some applications, an end of tensioning member 284 comprises a biasing element 275 extending beyond the diameter of locking element distal end 287 in the free state of expandable locking element 283, such that when the tensioning member 284 is tensioned, the biasing element 275 is pressed against locking element distal end 287 while being pulled proximally, thereby transitioning the expandable locking element 283 to an expanded orientation or configuration (e.g., a substantially planar, disc-like, etc. orientation/configuration), pressed between the biasing element 275 and the ventricular surface of leaflet 10. Biasing element 275 can be in the form of an elongated rod, a disc, a washer, a plat, and the like, which can be either attached to locking element distal end 287 (e.g., sutured, glued, and/or welded thereto), or disposed below (i.e., distal to) locking element distal end 287.

According to some implementations, system 270 further comprises a pull member 388 releasably coupled to a portion of flap 281 opposite to the juncture 286, for example, coupled to a portion of the flap 281 in the vicinity of flap inner edge 390. For some applications, pull member 388 is sutured through a portion of flap 281 opposite to the juncture 286, for example, sutured through the thickness of flap 281 in the vicinity of flap inner edge 390.

Figure 25C:
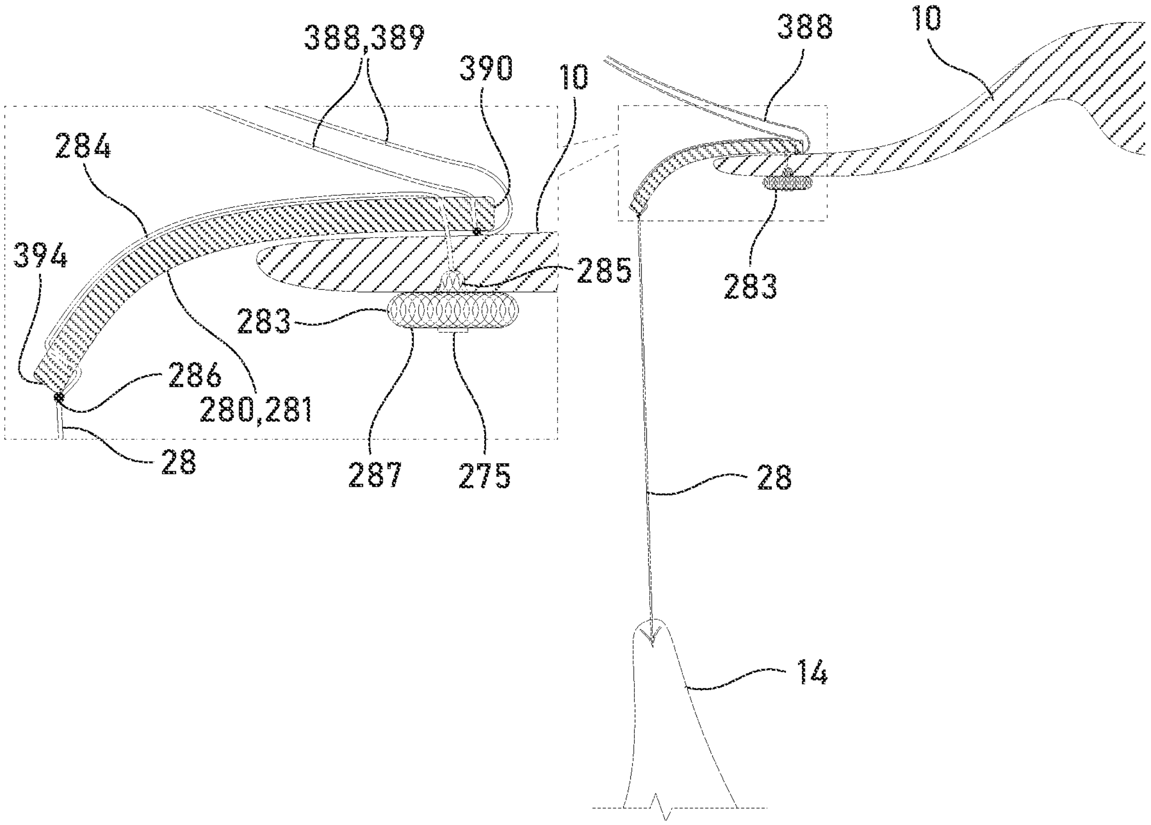
Figure 25D:
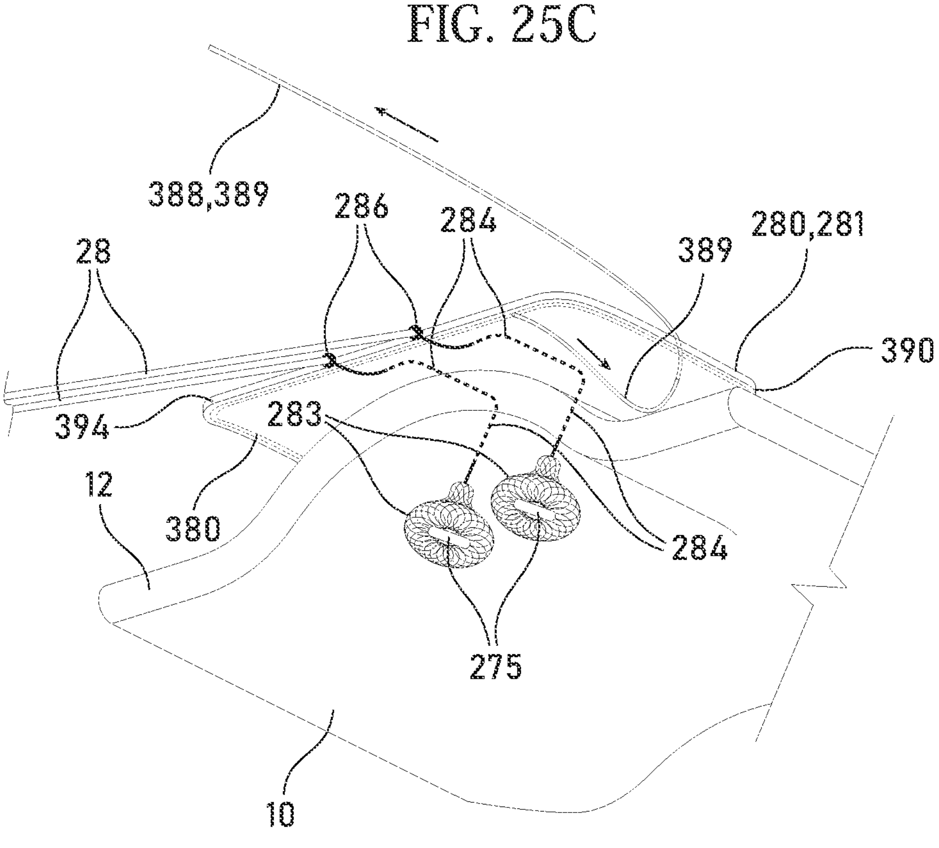
Figure 25E:
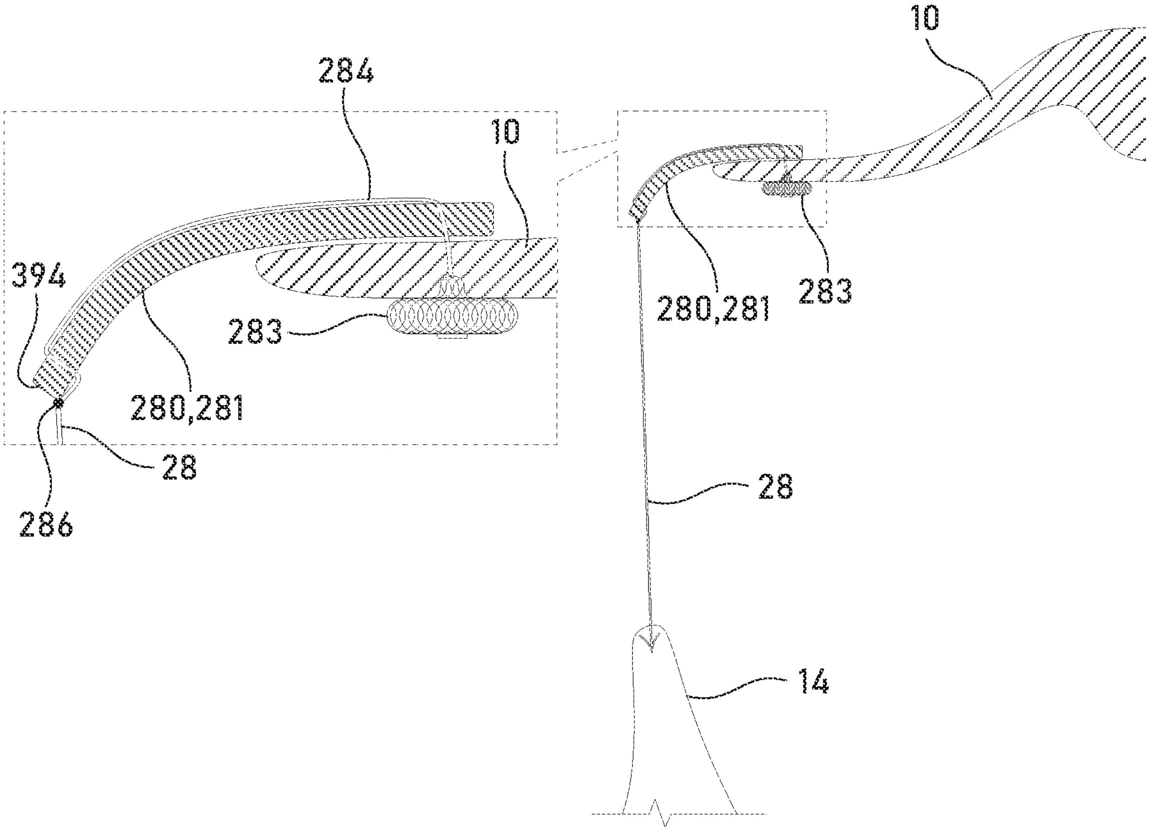

FIG. 25D shows a potential follow-up step in which the pull member 388 can be decoupled from the flap 281 and retrieved, if the position of patch 280 over leaflet 10 is adequate, and retrieval thereof is not required. In such instances, one strand 389 can be pulled proximally, while the other end portion is free to move distally toward the flap 281, until it is released therefrom, such that the pull member 388 is no longer threaded through flap 281 and can be retrieved therefrom. FIG. 25E shows the leaflet-augmentation patch 280 coupled to leaflet 10 after removal of pull member 388 therefrom.

Figure 25F:
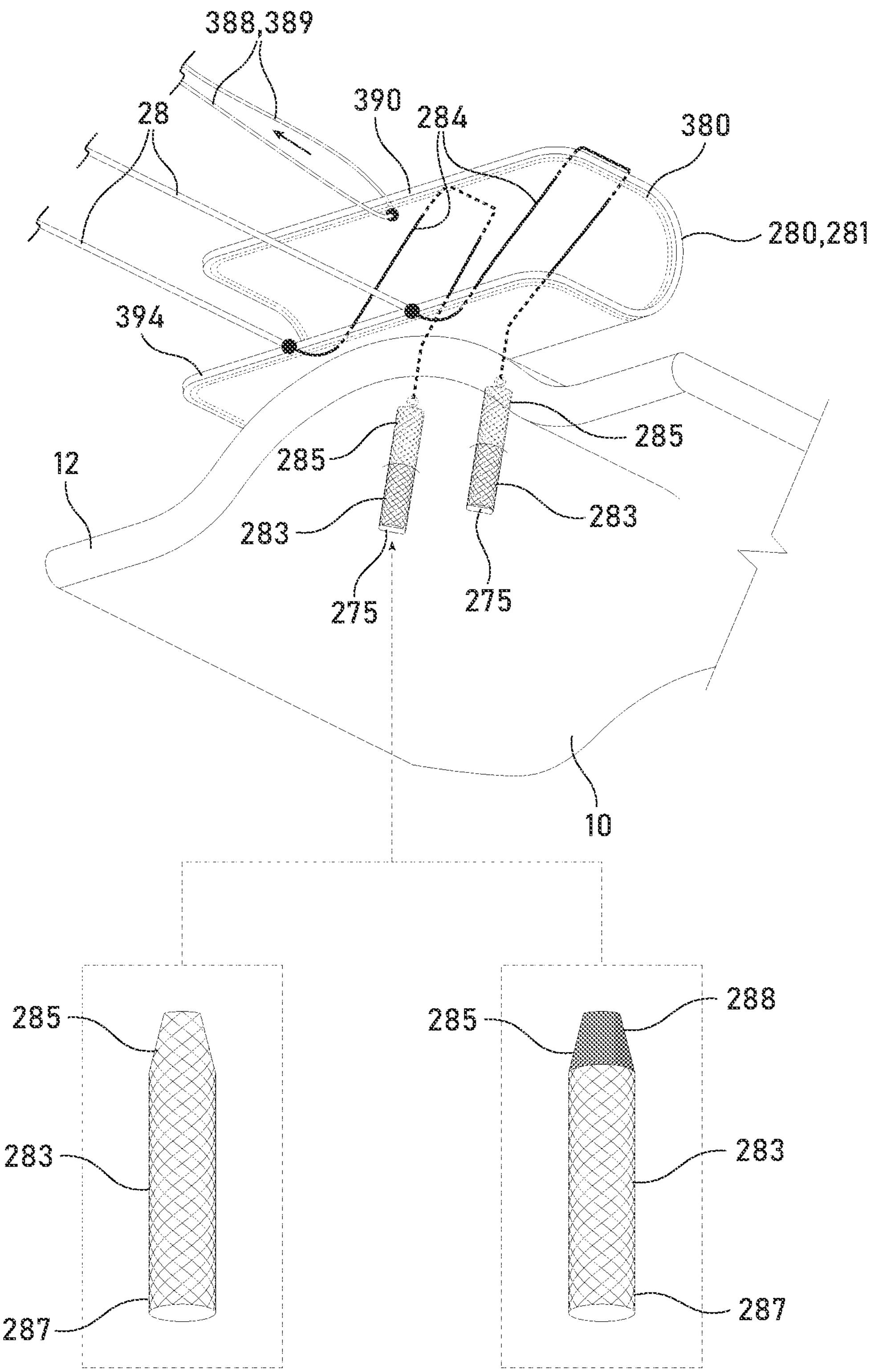

FIG. 25F shows an alternative follow-up step of retrieving the leaflet augmentation patch 280, for example if its position over leaflet 10 is determined to be inadequate. As shown, first the longitudinal members 28 are pulled proximally, for example toward elongate tool 272, so as to transition the flap 281 to a folded U-shaped state shown in FIG. 25E. For some applications, the elongate tool 272 can be repositioned over leaflet 10 in a position that will transition flap 281 to a desired folded state, upon application of a proximal pull force to longitudinal members 28.

Transitioning the flap 281 to a folded state approximates the flap free edge 394 to the inner edge 390, such that the tensioning members 284 are no longer tensioned therebetween, resulting in the expandable locking elements 283 being free to assume a free state thereof, transitioning to their elongate longitudinal shape. In this state, both ends of the flap 281 can be pulled toward elongate tool 272 by applying proximally oriented pull forces on the tensioning members 284 and the pull member 388 simultaneously, during which locking elements 283 are pulled through leaflet 10, allowing retrieval of leaflet augmentation patch 280.

FIG. 25F further illustrates two examples of expandable locking elements 283, in which the locking element proximal end 285 is shaped to assume a tapering shape, configured to facilitate retraction of the locking element 283 through leaflet 10. For some applications, the locking element proximal end 285 is shaped to have a conical or frustoconical shape, tapering in the proximal direction. This can be achieved by heat-setting or otherwise shape-setting the struts of the locking element proximal end 287 to taper radially inward in the proximal direction. For some applications, the locking element 283 comprises a constrictor 288 attached to the locking element proximal end 287. The constrictor 288 is shaped as a conical or frustoconical ring, tapering radially inward in the proximal direction.

While illustrated for an expandable locking element 283, it is to be understood that any other type of a locking element, including rod-like locking element 282, can have a tapering locking element proximal end, either by shape-forming locking element, or coupling a constrictor (288) thereto, mutatis mutandis. By virtue of the locking element being tapered along its proximal end, the locking element proximal end acts as an expanding wedge mechanism to pull the locking element through the thickness of leaflet 10, so as to facilitate retrieval of leaflet-augmentation patch (280) according to any of the mechanisms described in conjunction with FIGS. 23A-D, 24A-D, and/or 25A-F, mutatis mutandis.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Figure 26A:
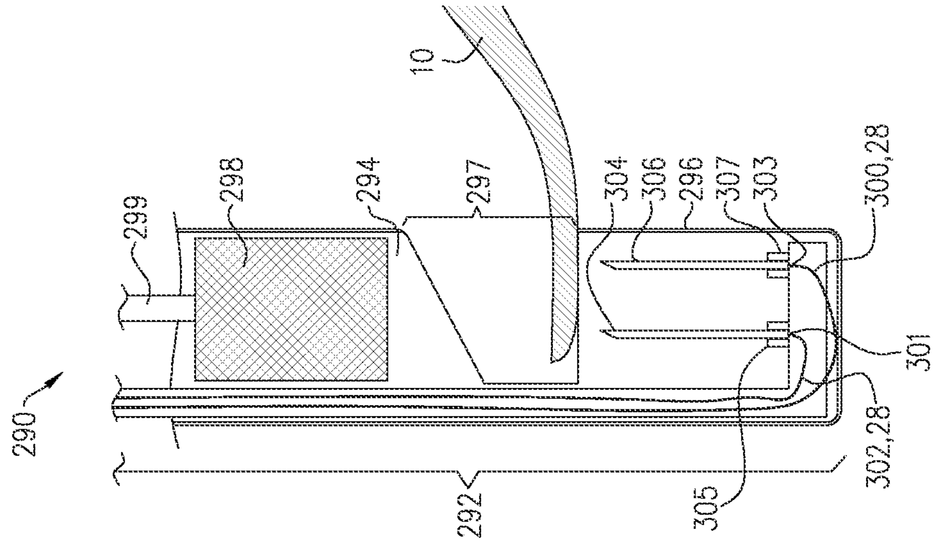
FIGS. 26A-E are schematic illustrations of an example of implantation of artificial chordae tendineae, in accordance with some applications.

Reference is now made to FIGS. 26A-E, which are schematic illustrations of a system 290 for implantation of artificial chordae tendineae using an elongate implantation tool 292, in accordance with some applications. Elongate implantation tool 292 comprises an upper tubular section 294 and a lower tubular section 296. Tool 292 is shaped so as to define a side-slot 297 between upper and lower tubular sections 294 and 296. Tool 292 is delivered between leaflets of the atrioventricular valve such that side-slot 297 is disposed between the leaflets. As shown in FIG. 26A, tool 292 is positioned and maneuvered such that a single leaflet 10 is moved within side-slot 297 of tool 292, upper tubular section 294 is disposed within the atrium, and lower tubular section 296 is disposed within the ventricle.

Tool 292 carries within its lumen longitudinal member 28, which functions as an artificial chordae tendineae. Longitudinal member 28 extends through tool 292 such that first and second ends 301 and 303 are disposed within lower tubular section 296. Each end 301 and 303 of longitudinal member 28 is coupled to a respective needle 304 and 306. Lower tubular section 296 is shaped so as to define needle holders 305 and 307 which are configured to each hold a respective needle 304 and 306. Respective portions 300 and 302 of longitudinal member 28 extend from respective ends 301 and 303 of longitudinal member 28. For some applications, tool 292 is shaped so as to define respective lumens (not shown) for passage therethrough of respective portions 300 and 302 of longitudinal member and/or for passage therethrough of respective needles 304 and 306.

Figure 26B:
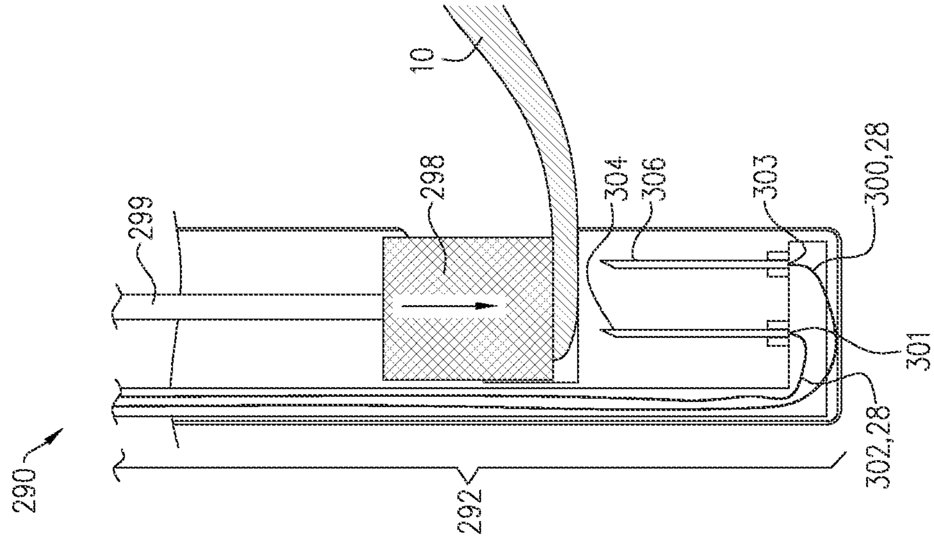

Tool 292 comprises a needle-receiver 298 which is disposed within a lumen of and slidable with respect to upper tubular section 294. Needle-receiver 298 can comprise plastic or rubber which is penetrable by needles 304 and 306. For some applications, needle-receiver 298 is shaped so as to define respective lumens for receiving each of needles 304 and 306. Needle-receiver 298 is moveable within the lumen of upper tubular section 294 by a rod 299 coupled to needle-receiver 298. As shown in FIG. 26B, needle-receiver 298 is moved by rod 299 toward a distal end of upper tubular section 294, and to an atrial surface of leaflet 10.

Figure 26C:
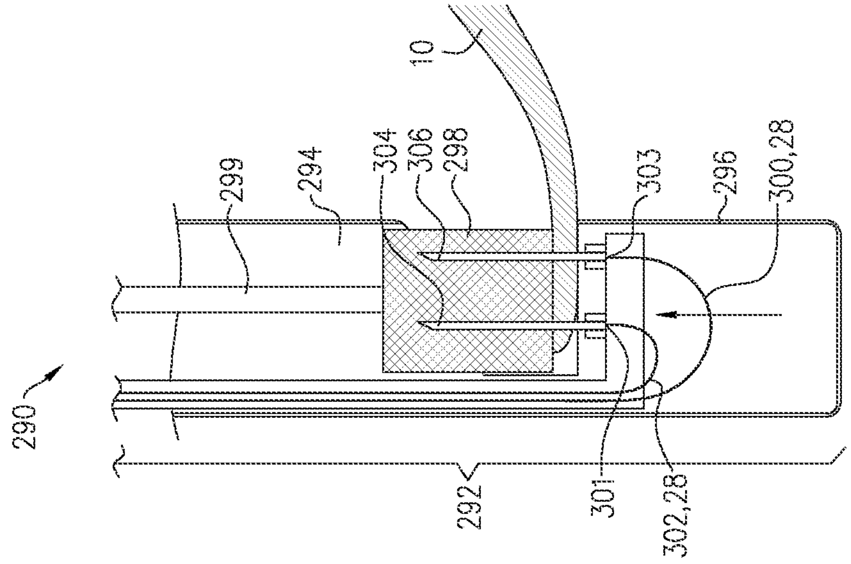

As shown in FIG. 26C, tool 292 moves needles 304 and 306 upward by moving needle holders 305 and 307 proximally and in parallel toward a ventricular surface of leaflet 10 such that needles 304 and 306 puncture leaflet 10 from the ventricular surface and pass through leaflet 10 toward the atrium of the heart. Needle-receiver 298 receives needles 304 and 306. As shown in FIG. 26D, needle-receiver 298 then moves proximally in order to thread portions 300 and 302 of longitudinal member 28 through leaflet 10 such that a bight 308 of longitudinal member 28 is disposed at the ventricular surface of leaflet 10.

Figure 26E:
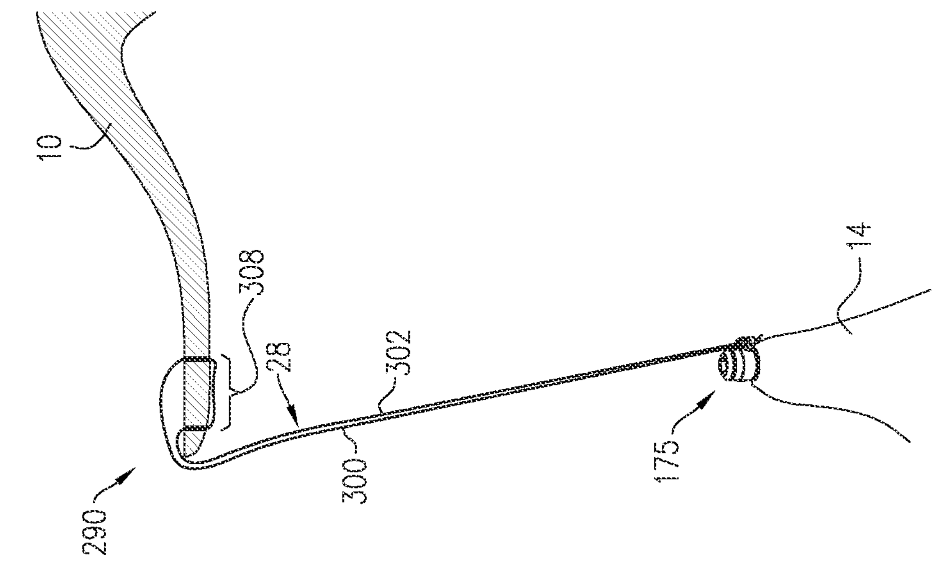
Figure 26D:
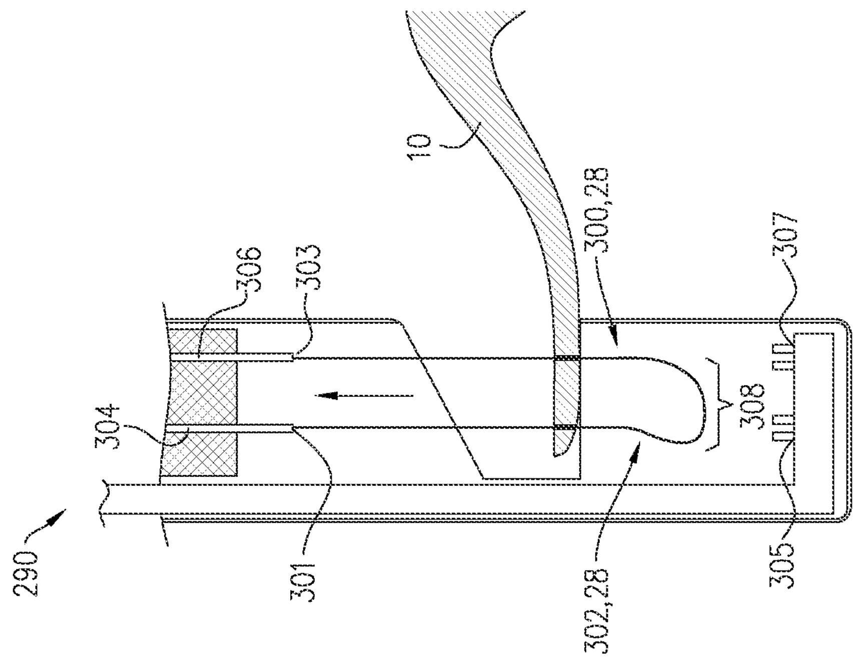

Tool 292 is then pulled away from leaflet 10 thereby pulling longitudinal member 28 with it such that portions 300 and 302 overhang the lip of leaflet 10, as shown in FIG. 26E. Ends 301 and 303 are coupled to tissue surrounding the ventricle, e.g., papillary muscle 14, as shown. As shown, longitudinal member 28 is coupled to muscle 14 via a tissue anchor 175. Anchor 175 can comprise any suitable anchor, e.g., the tubes shown hereinabove with reference to FIG. 9. Once longitudinal member 28 is anchored to muscle 14, tension of member 28 can be adjusted, and longitudinal member 28 is locked in place with respect to muscle 14, e.g., using a bead or a lock or a crimp. For some applications, longitudinal member 28 can be sutured to or otherwise knotted to muscle 14.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

The systems and leaflet augmentation patches described with respect to FIGS. 20A-26E, as well as their features and components (individually or as subassemblies), can be used in combination with or in place of systems and leaflet augmentation patches described with respect to FIGS. 31A-66D, mutatis mutandis. Furthermore, the systems and leaflet augmentation patches described with respect to FIGS. 20A-26E, as well as their features and components (individually or as subassemblies), can be modified to include features and/or components of systems and leaflet augmentation patches described with respect to FIGS. 31A-66D, mutatis mutandis.

Reference is now made to FIGS. 27A-D, which are schematic illustrations of a system 310 or implantation of artificial chordae tendineae using a docking element 312, in accordance with some applications. An elongate docking-element-delivery tool 313 is delivered between the leaflets of the atrioventricular valve. Tool 313 comprises an oversheath 311 shaped so as to define a lumen which houses docking element 312 during delivery of docking element 312 to tissue surrounding the ventricle so as to enable atraumatic delivery of docking element 312 to the tissue. As shown, docking element 312 is coupled to tissue of papillary muscle 14. It is to be noted that docking element 312 can be coupled to tissue of the wall of the ventricle.

Docking element 312 is shaped so as to define a tubular element shaped so as to define a receptacle having a lumen therethrough. For some applications, docking element 312 is shaped so as to define a receptacle with any suitable shape. Docking element 312 is shaped so as to define a pointed distal tip 314 which punctures through tissue of muscle 14. It to be noted that docking element 312 can comprise any suitable tissue anchor, e.g., a helical anchor, a clip, or a barb. For some applications, parts of docking element 312 can surround papillary muscle 14, e.g., as described hereinabove with reference to FIG. 13. Docking element 312 is shaped so as to define one or more openings 316.

Figure 27A:
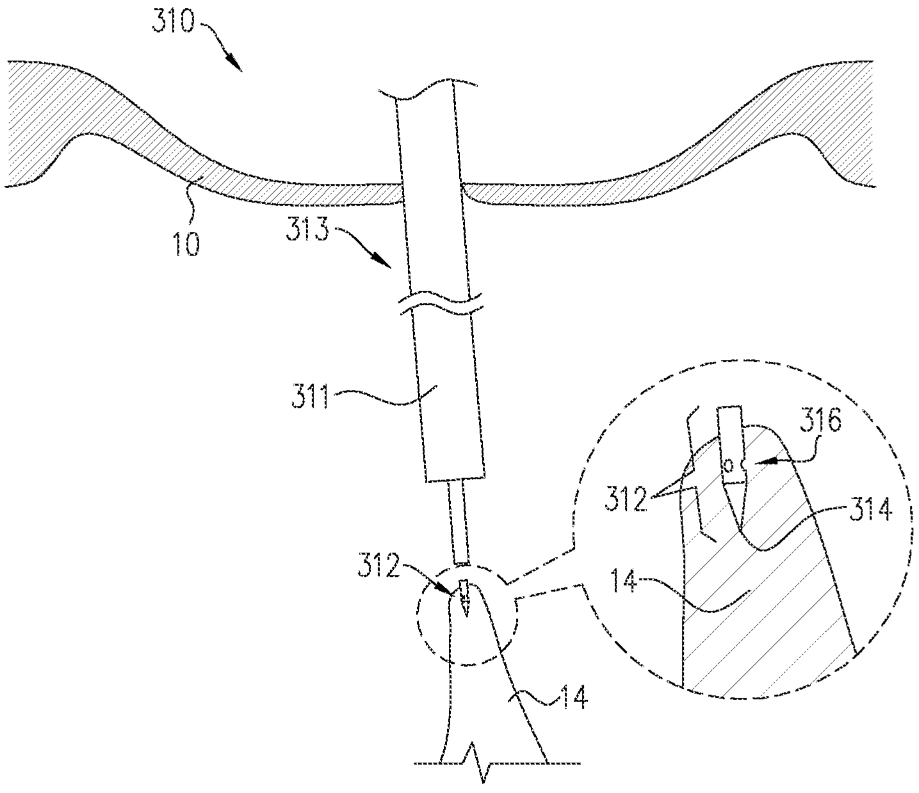
FIGS. 27A-D are schematic illustrations of an example of implantation of artificial chordae tendineae using a docking element, in accordance with some applications.
Figure 27B:
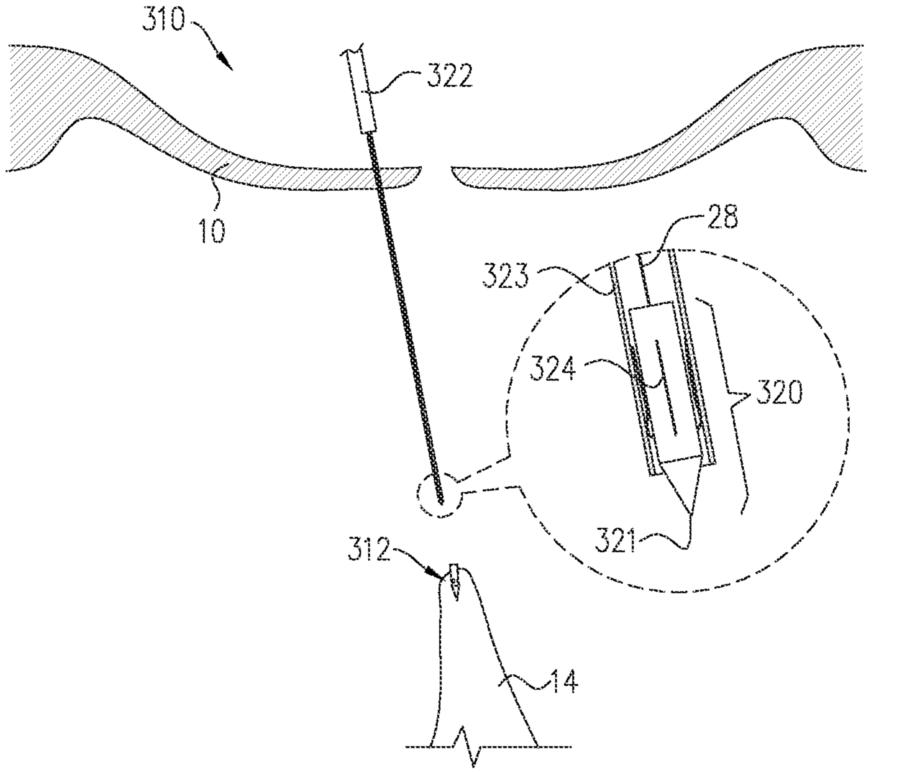

As shown in FIG. 27B, a tissue-anchor-delivery tool 322 is delivered to an atrial surface of leaflet 10. Tool 322 carries within its lumen a tissue anchor 320 shaped so as to define a tubular element and a pointed distal tip 321. Tip 321 is configured to puncture and pass through tissue of leaflet 10. Tissue anchor 320 is coupled to a first, leading end of longitudinal member 28. As tissue anchor 320 passes through leaflet 10, a first portion of longitudinal member 28 passes through leaflet 10 via tissue-anchor-delivery tool 322 and into the ventricle. Tissue anchor 320 is advanced via tissue-anchor-delivery tool 322 toward docking element 312 implanted at muscle 14. Tissue-anchor-delivery tool 322 comprises an oversheath 323. Tissue anchor 320 comprises one or more expandable protrusions 324 which are compressed within oversheath 323 during passing of tissue anchor 320 toward docking element 312.

Docking element 312 has an outer diameter that is at least 1.2 times greater than an outer diameter of tissue anchor 320. For some applications, docking element 312 has an outer diameter that is at least 1.5 times greater than an outer diameter of tissue anchor 320. As such, docking element 312 and tissue anchor 320 are delivered to papillary muscle 14 in different stages so as to effect minimal damage to tissue of leaflet 10. That is, since the outer diameter of docking element 312 is larger than the outer diameter of tissue anchor 320, docking element 312 is not delivered through the tissue of leaflet 10, rather, docking element 312 is delivered between the leaflets in order to avoid passing a larger diameter element through the tissue of leaflet 10. Only the element with the smaller diameter, i.e., tissue anchor 320, is delivered through tissue of leaflet 10. As shown in FIG. 27B, tissue anchor 320 approaches docking element 312 already implanted in papillary muscle 14.

Figure 27C:
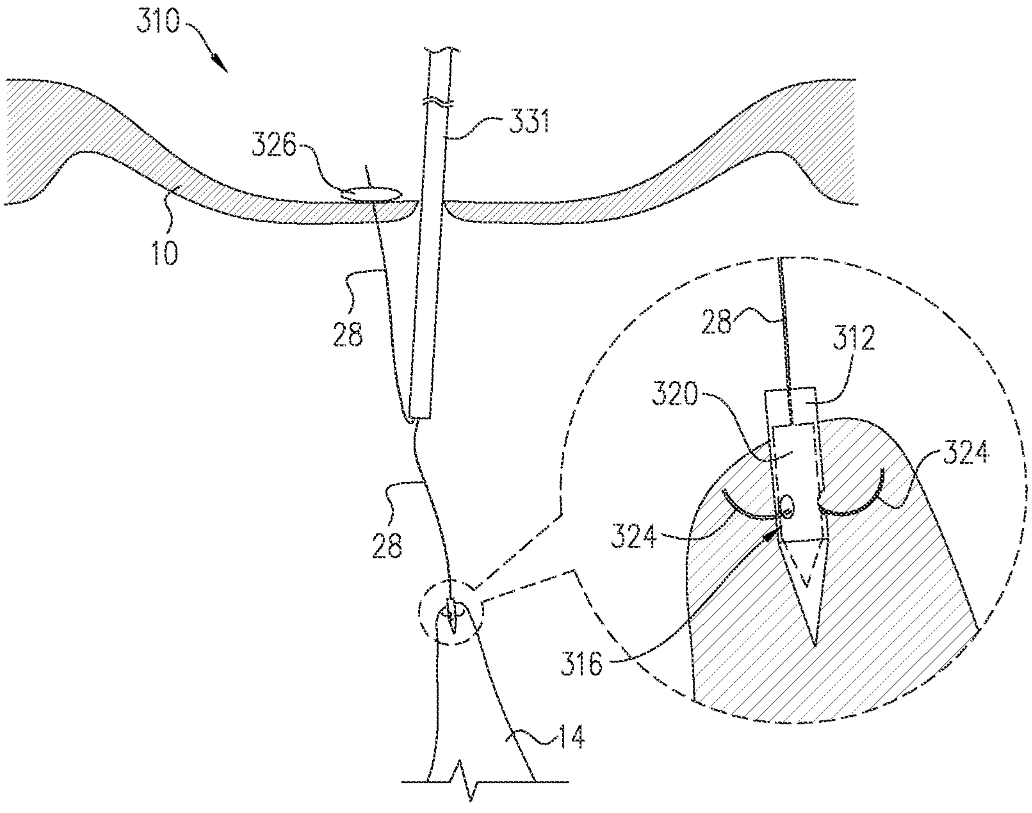

In FIG. 27C, tissue anchor 320 is advanced within the receptacle of docking element 312. Advancing tissue anchor 320 within docking element 312 couples tissue anchor 320 and the first end of longitudinal member 28 to docking element 312. During the coupling, the one or more protrusions 324 of tissue anchor 320 are aligned with the one or more openings 316 of docking element 312. Once aligned, protrusions 324 are enabled to expand through the one or more openings 316 so as to lock tissue anchor 320 to docking element 312. Once expanded, protrusions 324 function as barbs in order to facilitate anchoring of tissue anchor 320 to tissue of muscle 14.

A second end of longitudinal member 28 is coupled to leaflet 10. As shown, a locking element 326, e.g., a pledget, is used to couple the second end of longitudinal member 28 to the atrial surface of leaflet 10. It is to be noted that locking element 326 can comprise any suitable lock, e.g., a bead or a crimp. For some applications, longitudinal member 28 is sutured to or otherwise knotted to leaflet 10. For some applications, by the coupling and locking of longitudinal member 28 to leaflet 10, tension of longitudinal member 28 is adjusted. For example, longitudinal member 28 is pulled to a desired tension, and the tension is maintained by locking longitudinal member 28 in place using locking element 326.

For some applications, subsequently to the locking in place of longitudinal member 28 to leaflet 10, tension of longitudinal member 28 is adjusted. As shown in FIG. 27C, a tension-adjusting tool 331 is advanced between the leaflets of the valve and engages longitudinal member 28, e.g., with a snare. Longitudinal member 28 is pulled using tension-adjusting tool 331 until a desired level of tension of longitudinal member 28 is reached. Tension-adjusting tool 331 cinches and crimps longitudinal member 28.

Figure 27D:
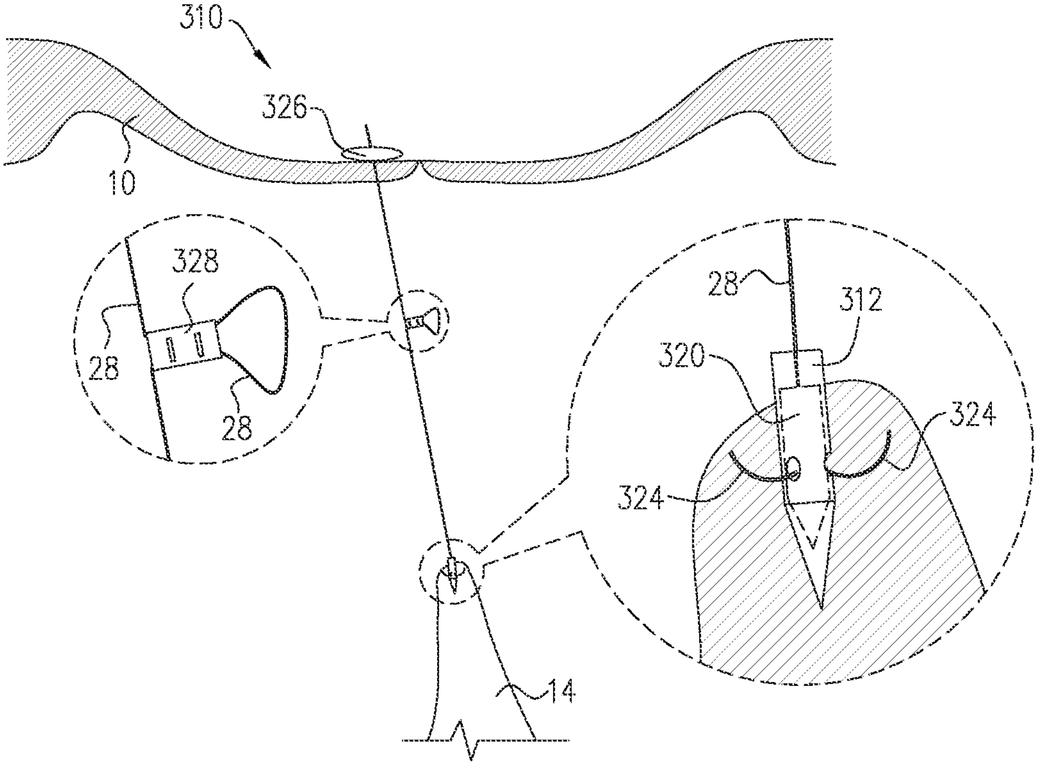

FIG. 27D shows the locking in place of longitudinal member 28 in order to secure the tension applied to longitudinal member 28. As shown, longitudinal member 28 is locked in place using a crimp 328.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Figure 30A:
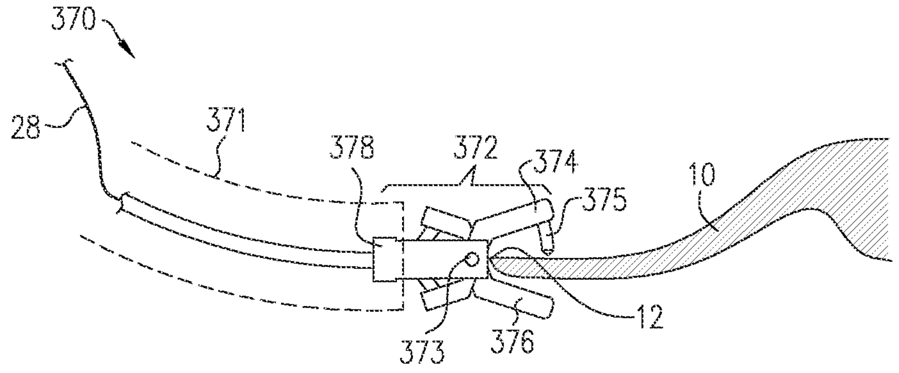
FIGS. 30A-C are schematic illustrations of an example of a leaflet-grasping element comprising a clamp which is configured to clamp and puncture the leaflet, in accordance with some applications.
Figure 30B:
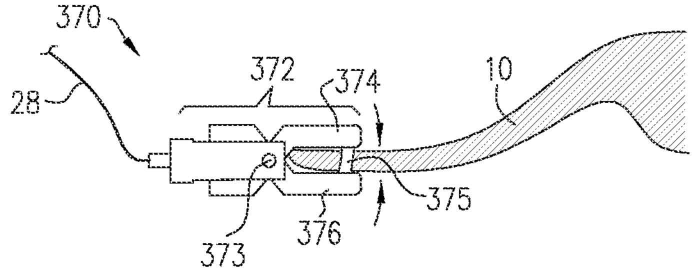
Figure 30C:
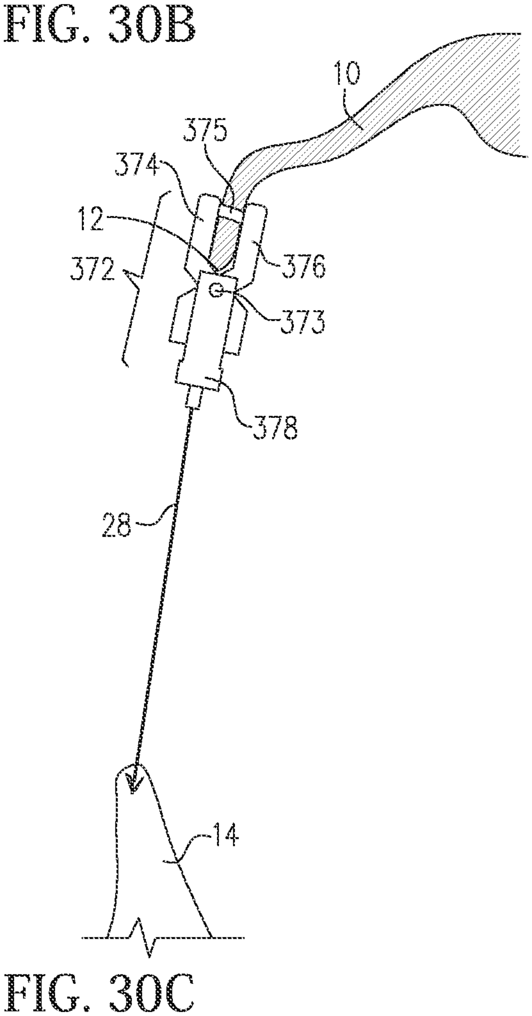

Reference is now made to FIGS. 30A-C, which are schematic illustrations of a system 370 comprising a leaflet-grasping element 372 which is configured to hold and grasp leaflet 10, in accordance with some applications. Leaflet-grasping element 372 is configured to be passed between leaflets of an atrioventricular valve and grasp edge 12 of leaflet so as to hold and grasp leaflet 10, e.g., by clamping the leaflet, and/or puncturing the leaflet. Leaflet-grasping element 372 an upper clamping element 374 and a lower clamping element 376 which are connected together by a hinge 373, which facilitates movement of upper and lower clamping elements 374 and 376. As shown in FIG. 30A, upper and lower clamping elements 374 and 376 are distanced from each other in order to enable positioning of edge 12 of leaflet 10 between upper and lower clamping elements 374 and 376. As shown in FIG. 30B, upper and lower clamping elements 374 and 376 are moved together in order to enable grasping of edge 12 of leaflet 10 between upper and lower clamping elements 374 and 376. This movement can be controlled by the operating physician outside the body of the patient.

Upper clamping element 374 comprises a pointed post 375 which has a pointed distal tip configured to puncture and pass through tissue of leaflet 10. Lower clamping element 376 is shaped so as to define an opening or a receiving element configured for receiving pointed post 375. It is to be noted that lower clamping element 376 can comprise pointed post 375 while upper clamping element 374 is shaped so as to define the opening or the receiving element to receive pointed post 375.

Hinge 373 is operatively controlled by a control structure 378 which is coupled to a tube 379. Control structure 378 is positioned to maintain clamping elements 374 and 376 in an open state, as shown in FIG. 25A. Pulling on tube 379 pulls on control structure 378 which operates hinge 373 to clamp together clamping elements 374 and 376, as shown in FIG. 30B.

Longitudinal member 28 is coupled at a first end to leaflet-grasping element 372. As shown in FIG. 25C, once leaflet-grasping element 372 is clamped to leaflet 10 in order to grasp leaflet 10, longitudinal member 28 is pulled into the ventricle and a second end of longitudinal member 28 is coupled to tissue surrounding the ventricle, e.g., papillary muscle 14, as shown. The second end of longitudinal member 28 is coupled to muscle 14 using any suitable anchor, e.g., a helical anchor or a barb. By pulling on longitudinal member 28, tension is applied to longitudinal member 28. Once sufficient tension is applied, the coupling of the second end of longitudinal member 28 to muscle 14 maintains the tension applied to longitudinal member 28. Maintaining tension on longitudinal member 28 maintains leaflet-grasping element 372 in the clamped and closed state, as shown in FIG. 30C. Application of tension to longitudinal member 28 prevents leaflet-grasping element 372 from opening, as tension is applied to longitudinal member and maintained.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Figure 28A:
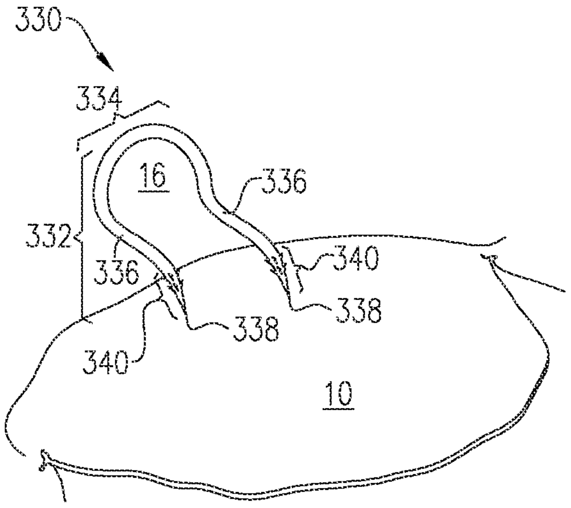
FIGS. 28A-C are schematic illustrations of an example of a curved cardiac-tissue-penetrating element, in accordance with some applications.
Figure 28B:
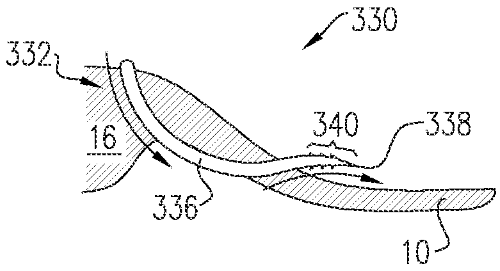
Figure 28C:
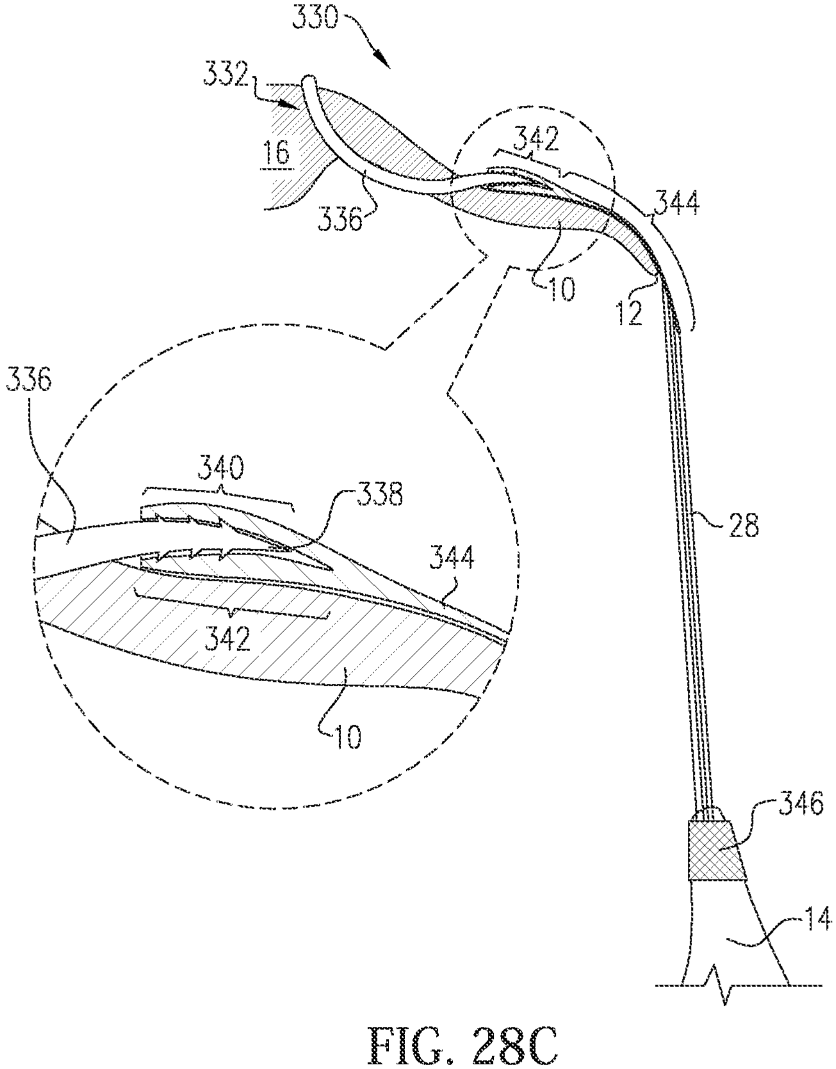

Reference is now made to FIGS. 28A-C, which are schematic illustrations of a system 330 comprising a curved, cardiac-tissue-penetrating element 332 configured to facilitate leaflet augmentation and repair of chordae tendineae, in accordance with some applications. Curved, cardiac-tissue-penetrating element 332 comprises at least one curved rigid element 336. As shown, curved, cardiac-tissue-penetrating element 332 comprises two curved rigid elements 336 coupled together by a bridge 334. Each curved rigid element 336 has a distal pointed tip 338 comprising a plurality of barbs 340. In some applications, curved rigid element 336 is shaped so as to define an "S" shaped curve. For some applications, curved rigid element 336 is shaped so as to define a stretched "S" shaped curve. For some applications, curved, cardiac-tissue-penetrating element 332 comprises a metal, e.g., nitinol or stainless steel, and is rigid.

As shown in FIG. 28A, curved, cardiac-tissue-penetrating element 332 punctures cardiac tissue from an atrial surface of an atrioventricular valve of a heart of a patient with distal pointed tips 338 of curved rigid elements 336. In some applications, distal pointed tips 338 of curved rigid elements 336 puncture tissue of an annulus 16 of the valve. Puncturing tissue of annulus 16 facilitate efficient and strong coupling of curved, cardiac-tissue-penetrating element 332 because annulus 16 is thicker than tissue of leaflet 10 and withstands tension forces of curved, cardiac-tissue-penetrating element 332 on annulus 16.

Distal pointed tips 338 are passed through tissue of annulus 16 toward a ventricular surface of the atrioventricular valve.

As shown in FIG. 28B, a ventricular surface of leaflet 10 is punctured by pointed distal tips 338 such that tips 338 pass through leaflet 10 from the ventricular surface and the atrial surface of the atrioventricular valve, e.g., toward the atrial surface of leaflet 10, as shown. For some applications, the operating physician manually maneuvers curved, cardiac-tissue-penetrating element 332 through the cardiac tissue in accordance with the curved shape of curved, cardiac-tissue-penetrating element 332. For some applications, curved, cardiac-tissue-penetrating element 332 has shape-memory which enables tips 338 of curved, cardiac-tissue-penetrating element 332 to self-penetrate the atrial surface of the atrioventricular valve, pass through to the ventricular surface, penetrate the ventricular surface of leaflet 10 and emerge at the atrial surface of leaflet 10.

As shown in FIG. 28B, passing of a portion of curved, cardiac-tissue-penetrating element 332 through annulus 16 enable a firm coupling between curved, cardiac-tissue-penetrating element 332 and the cardiac tissue. Additionally, tissue of annulus 16 can withstand the pulling forces by curved, cardiac-tissue-penetrating element 332. Once curved, cardiac-tissue-penetrating element 332 is anchored to annulus 16, the plurality of barbs 340 are exposed at the atrial surface of leaflet 10.

In FIG. 28C, a prosthetic leaflet patch 344 is coupled to barbs 340 and to pointed tips 338 of curved, cardiac-tissue-penetrating element 332. Patch 344 comprises a biocompatible material that resembles native tissue of leaflet 10 in a manner in which patch 344 can augment leaflet 10 and enhance the function of leaflet 10 and coaptation of leaflet 10 with the adjacent leaflet. For some applications, patch 344 comprises tissue, e.g., pericardial tissue. For some applications, patch 344 comprises a sheet of polyethylene, expanded polytetrafluoroethylene, or polyethylene terephthalate. For some applications, patch 344 comprises organic and/or inorganic material that collectively provide the characteristics of flexibility, shape-memory durability, impermeability, and peri-implant tissue growth stimulation.

For some applications, barbs 340 ensnare material of prosthetic leaflet patch 344. For some applications, patch 344 comprises a coupling 342 which are ensnared by barbs 340. For some applications, coupling 342 comprises respective sockets which surround pointed distal tips 338 and barbs 340 of each curved rigid element 336.

A first end of at least one longitudinal member 28, e.g., respective first ends of a plurality of longitudinal members 28, is coupled to an edge of patch 344. Longitudinal member 28 is extended from patch 344 into the ventricle of the heart of the patient. A second end of the at least one longitudinal member 28, e.g., respective second ends of a plurality of longitudinal members 28, is coupled to tissue surrounding the ventricle. As shown, the second end of longitudinal member 28 is coupled to papillary muscle 14. It is to be noted that the second end of longitudinal member 28 can be coupled to tissue of a wall of the ventricle. The second end of longitudinal member 28 is coupled to a tissue anchor 346 that is coupled to papillary muscle 14. Tissue anchor 346 couples together all ends of each of the plurality of longitudinal members 28. As shown, tissue anchor 346 surrounds muscle 14. For example, tissue anchor 346 comprises a cuff which surrounds muscle 14. For some applications, tissue anchor 346 comprises a pointed tip which penetrates the tissue surrounding the ventricle.

Anchor 346 can comprise any suitable anchor, e.g., the tubes shown hereinabove with reference to FIG. 9. Once longitudinal member 28 is anchored to muscle 14, tension of member 28 can be adjusted, and longitudinal member 28 is locked in place with respect to muscle 14, e.g., using a bead or a lock or a crimp. As such, system 330 provides devices, apparatuses, and methods for leaflet augmentation and repair/replacement of chordae tendineae. Curved, cardiac-tissue-penetrating element 332 can be viewed under imaging guidance to help facilitate proper positioning of the elements of system 330. Coupling of element 332 of annulus 16 provides a system which can be easily imaged and does not require grasping of leaflet 10 from an edge of leaflet 10. Coupling of element 332 of annulus 16 provides a system with increased ability to withstand tensile forces of patch 344 and longitudinal members 28 on cardiac tissue. Additionally, the "S"-shape of element 332 prevents element 332 from damaging surrounding vasculature during implantation. The shape of element 332 as well as coupling 342 minimize forces upon leaflet 10, enabling leaflet 10 to generally maintain its native orientation and curve.

Longitudinal members 28 function as artificial chordae tendineae. For some applications, longitudinal members 28 comprise a suture. Longitudinal members 28 comprise a flexible and/or superelastic material, e.g., ePTFE, nitinol, PTFE, polyester, stainless steel, or cobalt chrome. In some applications, longitudinal members 28 are coated with polytetrafluoroethylene (PTFE) or with PTFE. In some applications, longitudinal members 28 comprise at least one wire/suture portion and at least one portion that comprises an elongate tensioning coil. For example, longitudinal members 28 can each comprise an elongate coil between two wire/suture portions.

Figure 29A:
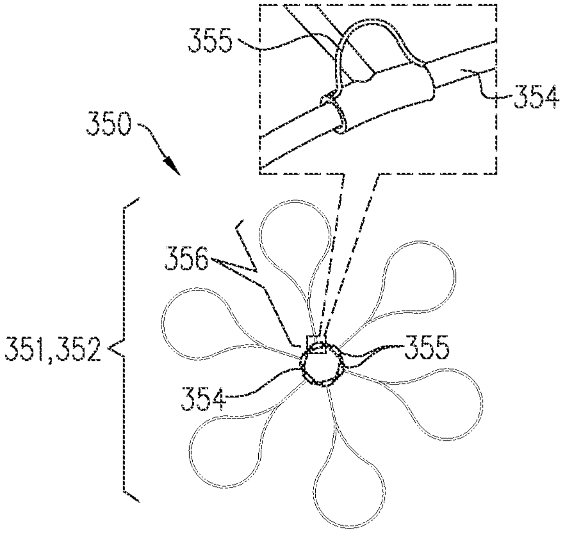
FIGS. 29A-C are schematic illustrations of an example of a papillary muscle anchor, in accordance with some applications.
Figure 29B:
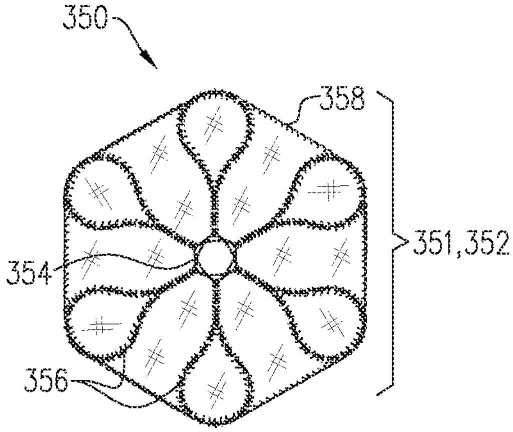
Figure 29C:
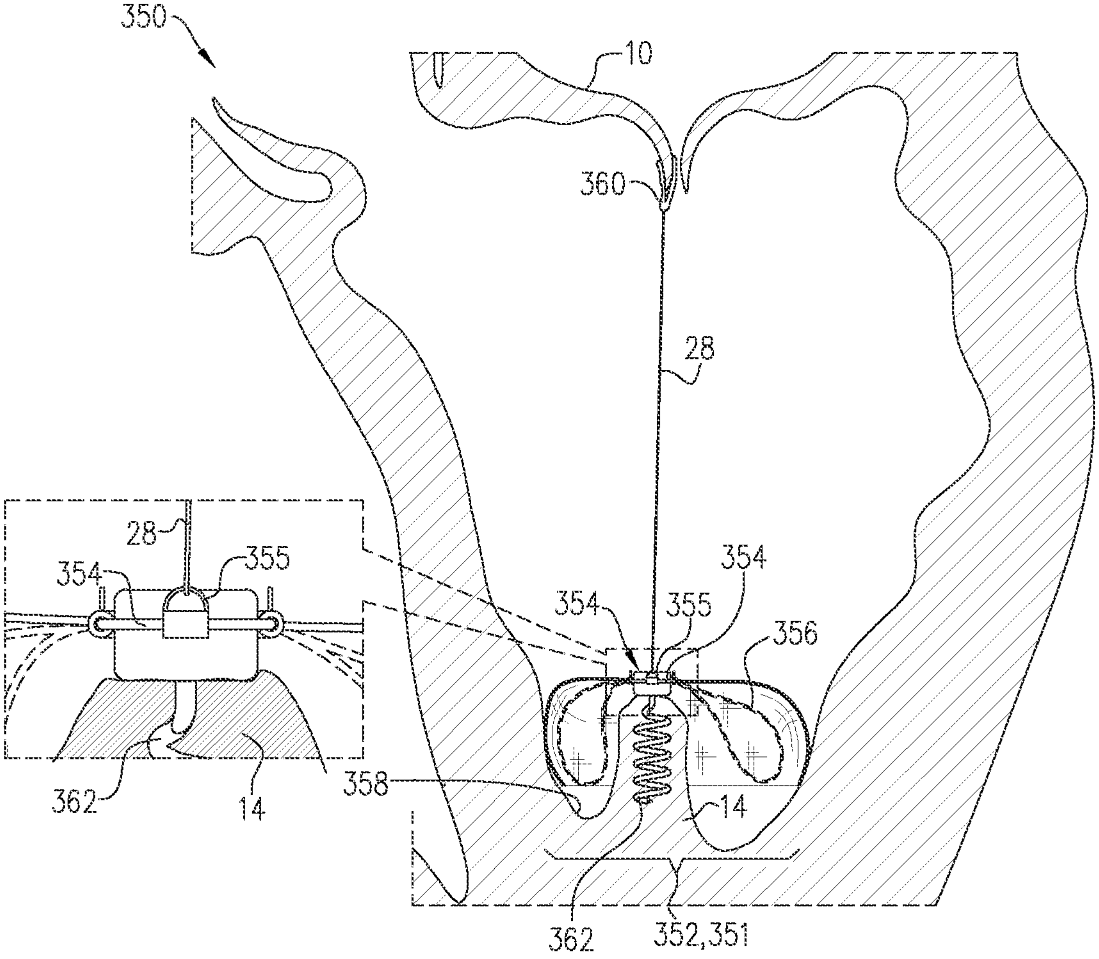

FIGS. 29A-C are schematic illustrations of a system 350 comprising a papillary-muscle-anchor 352 comprising a frame 351 coupled to a flexible sheet (e.g., comprising a fabric and/or a polymer) 358, in accordance with some applications. As shown in FIG. 29A, frame 351 of papillary-muscle-anchor 352 comprises a central ring 354 coupled to a plurality of struts 356 arrange circumferentially with respect to central ring 354. As shown, each strut 356 is shaped so as to define a petal shape. As shown, frame 351 is shaped so as to define a star or an asterisk. For some applications, frame 351 comprises a metal, e.g., nitinol or stainless steel. In some applications, frame 351 has shape-memory. For some applications, frame 351 has shape-memory to assume a collapsed state. For some applications, frame 351 has shape-memory to assume an expanded state. Central ring 354 is shaped so as to define, or is coupled to a plurality of loops 355, extending away from a circumference of central ring 354, for coupling of one or more longitudinal members 28 to central ring 354.

For some applications, polymer sheet 358 comprises an absorbent material, e.g., at a perimeter of sheet 358, which helps facilitate sealing of sheet 358 to tissue and prevent ingress of blood under sheet 358.

As shown in FIG. 29B, polymer sheet 358 is coupled to frame 351, e.g., by being sewn to frame 351 or otherwise adhered or attached. Polymer sheet 358 comprises a non-porous, biocompatible polymer, e.g., a fabric. The braided and porous outlay of polymer sheet 358 facilitate tissue growth in order to enable additional coupling between papillary-muscle-anchor 352 and cardiac tissue.

As shown in FIG. 29C, papillary-muscle-anchor 352 is designated for coupling to papillary muscle 14. It is to be noted, however, that anchor 352 can be coupled to any suitable tissue other than papillary muscle 14. For example, anchor 352 can be coupled to a portion of a wall of the ventricle. Papillary-muscle-anchor 352 comprises a tissue anchor 362, or a tissue-engaging member, which is coupled to cardiac tissue. As shown, anchor 362 comprises a helical tissue by way of illustration and not limitation. Anchor 362 can comprise a barb or any other suitable anchor known in the art. Anchor 362 is coupled to central ring 354.

Anchor 352 is delivered into the ventricle within a sheath such that frame 351 and sheet 358 are in a collapsed state, and anchor 352 is in a collapsed state. Anchor 352 is deployed from within the sheath and allowed to expand. For some applications, frame 351 has shape memory such that anchor 352 self-expands once exposed from within sheath. For some applications, frame 351 has a tendency to collapse, is manually held open during implantation of anchor 362, and then is allowed to self-collapses in order to hug tissue within which anchor 362 is implanted. In the collapsed state, frame 351 and polymer sheet 358 sandwich tissue between (i) anchor 362 and (ii) frame 351 and polymer sheet 358. Sheet 358 increases contact between frame 351 and papillary muscle 14.

Together, frame 351 and sheet 358 function as an umbrella which hugs tissue to which anchor 362 is implanted.

In either example in which frame 351 has a tendency to expand or collapse, the porosity of polymer sheet 358 is small enough that it facilitates tissue growth and endothelialization, while also providing resistance to blood in the ventricle in a manner in which pressure from blood in the ventricle helps facilitate force applied to sheet 358 and frame 351 in a vector toward tissue anchor 362. That is, frame 351 and sheet 358 are maintained in a configuration of sustained hugging of muscle 14 due to pressure of the blood and of the ventricle, in a downward direction, i.e., in a direction that is perpendicular with respect to a surface of tissue within which anchor 362 is implanted.

As shown in FIG. 29C, once anchor 352 is implanted at papillary muscle 14, longitudinal member 28, which is coupled at a first end thereof to ring 354 of anchor 352, is extended upward and a second end of longitudinal member 28 is coupled to leaflet 10, e.g., by a leaflet-tissue-anchor 360 coupled to the second end of longitudinal member 28. It is to be noted that leaflet-tissue-anchor 360 can comprise any leaflet-grasping element described herein, or any other leaflet anchor known in the art. For some applications, longitudinal member 28 is suture or knotted to leaflet 10. It is to be noted that anchor 352 can be coupled to a plurality of longitudinal members 28. For such application, central ring 354 comprises a plurality of loops 355 (shown in FIG. 29A) around its circumference, and each longitudinal member 28 is coupled to a respective loop 355. For some applications, as described hereinabove with reference to FIGS. 5A-B, 6A-C, and 7A-B, longitudinal members 28 are distributed with respect to leaflet 10.

Frame 351 is collapsible around the tissue anchor upon a force applied to frame 351, e.g., by sheet 358, in a vector toward the tissue anchor. Alternatively or additionally, frame 351 is collapsible upon application of tension to central ring 354. For some applications, tension is applied to ring 354 by longitudinal member 28. For some applications, as longitudinal member 28 is being coupled to leaflet 10, tension is applied to longitudinal member 28 which helps apply a force to ring 354 in order to help further collapse frame 351 around muscle 14. Once tension is applied to longitudinal member 28, longitudinal member 28 is locked in place to maintain tension, e.g., by using anchor 360. For some applications, tension can be applied to longitudinal member 28 subsequently to coupling longitudinal member 28 to leaflet 10, e.g., using a crimp or a ratchet.

Longitudinal member 28 functions as artificial chordae tendineae. For some applications, longitudinal member 28 comprises a suture. Longitudinal member 28 comprises a flexible and/or superelastic material, e.g., ePTFE, nitinol, PTFE, polyester, stainless steel, or cobalt chrome. In some applications, longitudinal member 28 is coated with polytetrafluoroethylene (PTFE) or with PTFE. In some applications, longitudinal member 28 comprises at least one wire/suture portion and at least one portion that comprises an elongate tensioning coil. For example, longitudinal member 28 can comprise an elongate coil between two wire/suture portions.

Anchor 352 eliminates the need for deep penetration of cardiac tissue, since frame 351 and sheet 358 provide enhance coupling between anchor 352 and tissue. Additionally, due to downward forces acting upon frame 351 and sheet 358, e.g., pressure of the ventricle during systole, frame 351 and sheet 358 continually grip the cardiac tissue, thereby minimizing the possibility of decoupling of anchor 352 from tissue.

Reference is again made to FIGS. 1A-30C. It is to be noted that systems described herein above with reference to grasping leaflets in FIGS. 1A-8, 10A-16C, 20A-28C, and 30A-C can be used in combination with any anchor used to grasp tissue surrounding the ventricle, e.g., papillary muscle 14, described hereinabove with reference to FIGS. 9, 11A-14C, and 29A-C.

Reference is again made to FIGS. 1A-30C. It is to be noted that systems described herein above with reference to grasping leaflets in FIGS. 1A-8, 10A-16C, and 20A-30C can be used in combination with any leaflet-stabilizing element described hereinabove with reference to FIGS. 17A-19B.

Reference is again made to FIGS. 1A-30C. It is to be noted that tension of longitudinal members 28 and 64 can be adjusted using tension-adjusting tools 217 and 331 or any other tension-adjusting tools known in the art during the implanting of longitudinal members 28 and 64 and/or subsequently thereto.

Reference is now made to FIGS. 31A-B, 32A-Q, 33A-B, and 34A-C, which are schematic illustrations of a system 500, and techniques for using the system to treat a heart 4 of a subject, in accordance with some applications. In particular, system 500 is used to reduce (e.g., eliminate) regurgitation through an atrioventricular valve 7 of the heart, caused by suboptimal coaptation of the leaflets of the valve. System 500 comprises an implant 550, and a delivery tool 800 for delivering and implanting the implant.

Figure 31A:
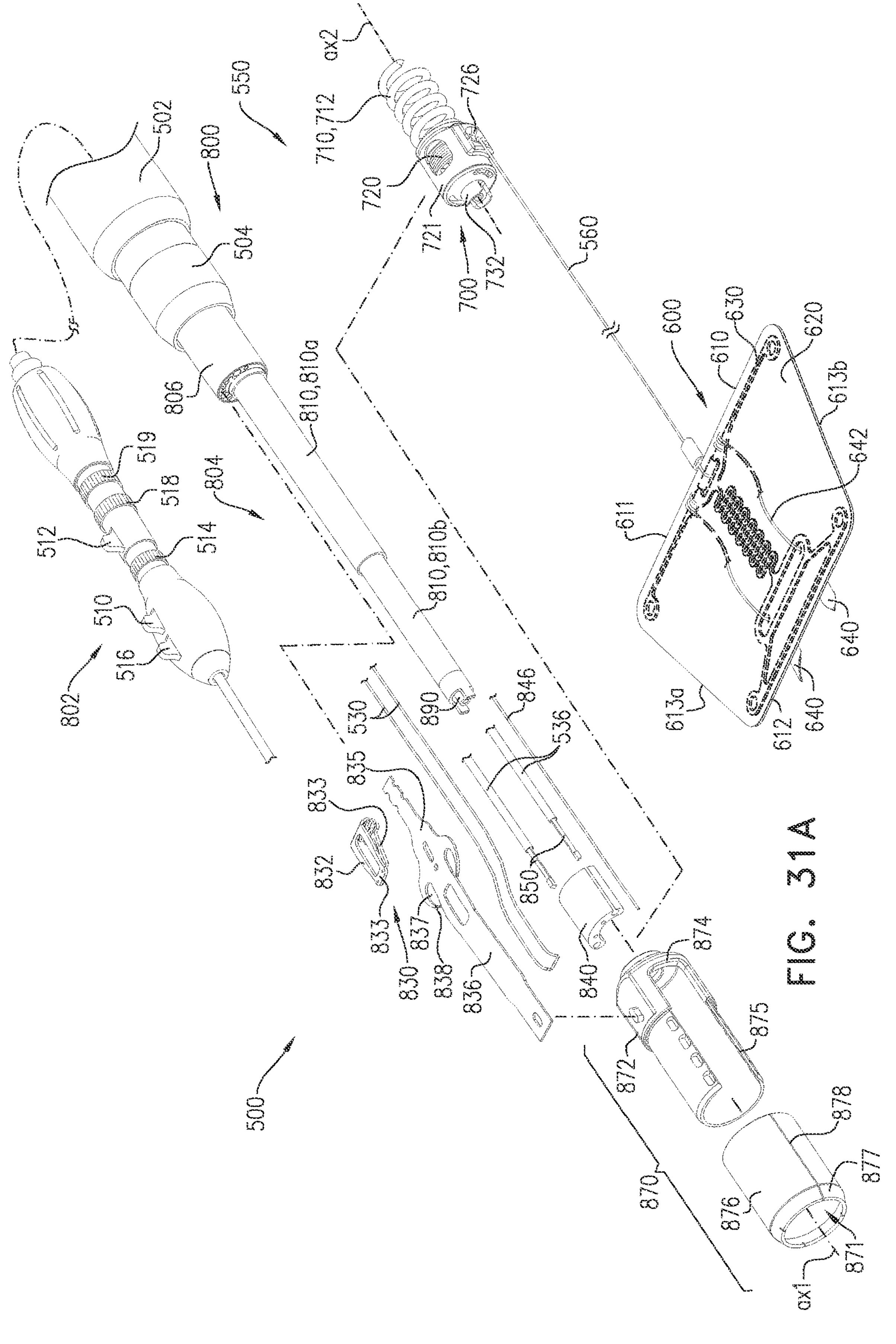
FIGS. 31A-B, 32A-Q, 33A-B, and 34A-C are schematic illustrations of a system, and techniques for using the system to treat a heart of a subject, in accordance with some applications.
Figure 31B:
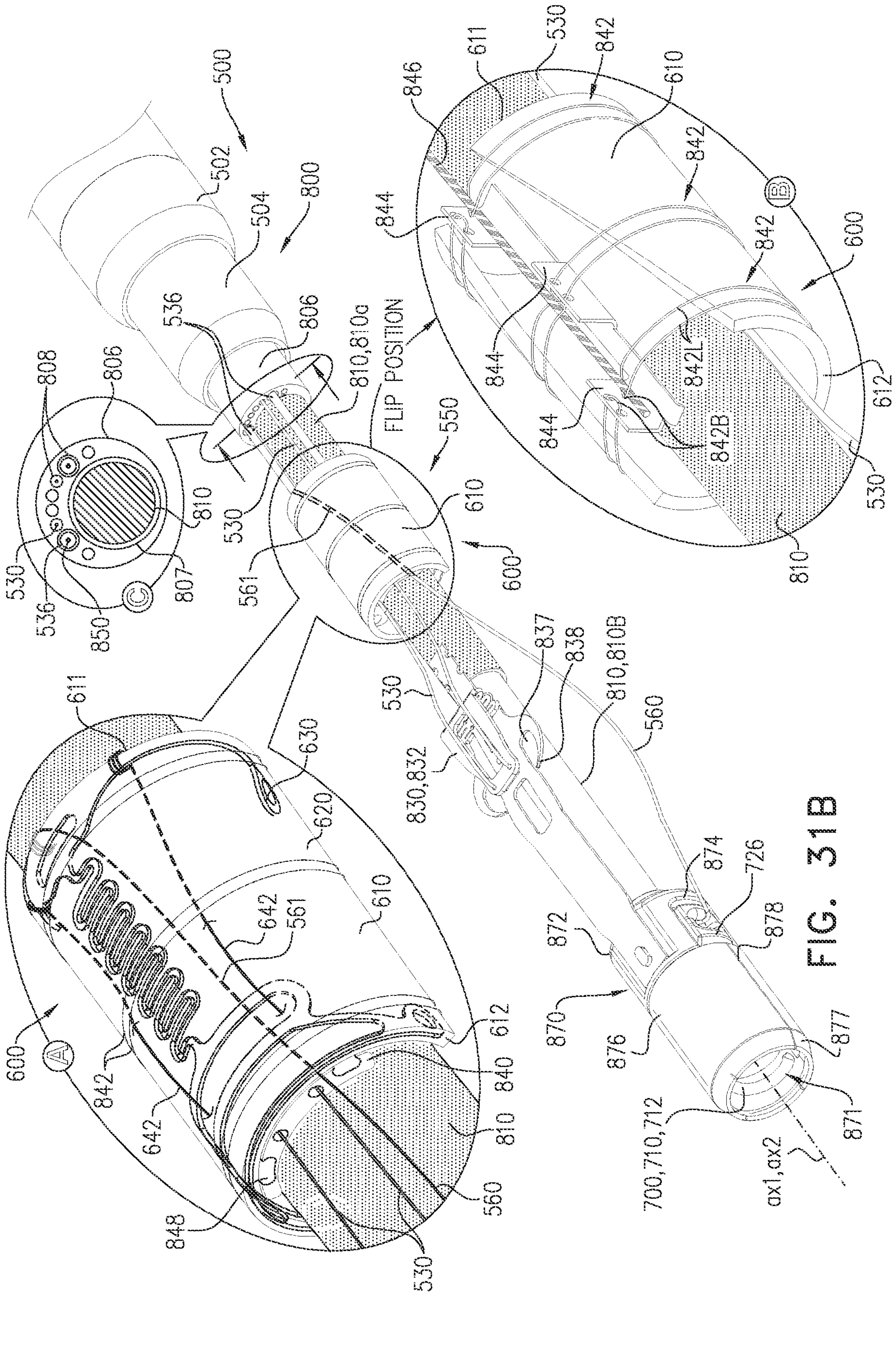

FIG. 31A shows system 500 with implant 550 separate from delivery tool 800, and with an exploded view of the delivery tool. FIG. 31B shows system 500 assembled, with implant 550 loaded onto delivery tool 800. Implant 550 comprises a patch 610, and at least one patch anchor 640. Patch 610 and patch anchor 640 can be considered to be components of an upstream assembly 600 of implant 550. Implant 550 further comprises a downstream assembly 700, and a tether 560 that tethers the downstream assembly to upstream assembly 600. Thus, for some applications, system 500 (e.g., implant 550 thereof) has some features in common with system 270 described hereinabove.

For some applications, tether 560 comprises a suture. For some applications, tether 560 comprises a flexible and/or superelastic material, e.g., ePTFE, nitinol, PTFE, polyester, stainless steel, or cobalt chrome. In some applications, tether 560 is coated with polytetrafluoroethylene (PTFE).

Inset frame A of FIG. 31B uses transparency to illustrate frame 630 within patch 610, whereas inset frame B, for the sake of clarity, does not. Inset B is a view of the opposite side of the apparatus than that shown in inset A. Inset frame C of FIG. 31B shows a cross-section through tool 800. It is to be noted that, for the sake of simplicity, in this cross-section shaft 810 is shown as solid, even though it is tubular, and other components such as a driveshaft subassembly 890 (e.g., driveshafts of the driveshaft subassembly) extend through it.

Patch 610 comprises a flexible sheet 620 and can further comprise at least one frame 630 to which the sheet is attached. Frame 630 can provide patch 610 with mechanical properties that would not be provided by sheet 620 alone. Such properties are described in more detail hereinbelow. Although the present disclosure generally refers to sheet 620 in the singular, patch 610 can comprise more than one sheet, arranged in layers, e.g., with frame 630 disposed between the sheets. (This can alternatively be described as sheet 620 comprising multiple layers, i.e., being a multi-layer sheet.)

For some applications, patch 610 shares characteristics with patch 280 and/or flap 281 thereof, mutatis mutandis.

Implant 550 (e.g., upstream assembly 600 thereof) can be provided with at least one patch anchor 640 coupled to patch 610, e.g., as shown. However, for some applications (e.g., for some variants of implant 550 and/or of system 500) anchoring of the patch can include coupling a patch anchor to the patch (e.g., driving the patch anchor through the patch), e.g., as described elsewhere herein.

Downstream assembly 700 comprises a winch 720, and a winch anchor 710 coupled to the winch. Winch anchor 710 has a tissue-engaging element 712, which is configured to be driven into tissue along an anchor axis ax2 of the winch anchor. In the example shown, tissue-engaging element 712 is a helical tissue-engaging element, configured to be screwed into tissue along axis ax2. However, it is to be noted that winch anchor 710 can comprise a different type of tissue-engaging element such as a dart, a staple, and/or as described hereinbelow with reference to FIGS. 54A-59C mutatis mutandis.

Winch 720 comprises a spool 722 (e.g., see FIGS. 33A-34C) that, as shown, can be mounted such that it and/or its axis of rotation is colinear with anchor axis ax2. However, other spool orientations are possible, e.g., as described with reference to FIG. 60.

Tether 560 can be coupled to patch 610, and extends therefrom to winch 720, thereby tethering the winch to the patch. As shown, tether 560 can enter winch 720 via a lateral aperture 726 in a housing 721 of the winch, and/or can reach spool 722 in an orientation that is substantially orthogonal to anchor axis ax2. Although housing 721 is referred to as the housing of winch 720, for some applications it can be considered to be the housing of downstream assembly 700.

Tether 560 is operatively coupled to winch 720, such that actuation of the winch can adjust an effective length of the tether, i.e., a length of the tether between the winch and patch 610.

Delivery tool 800 has a distal portion 804 that is transluminally (e.g., transfemorally) advanceable to the heart, and can have an extracorporeal proximal portion 802 that can comprise handles and/or controls via which the operator (e.g., the physician) can control (e.g., steer, actuate, etc.) components at the distal portion of the tool, e.g., in order to deliver and implant implant 550. Delivery tool 800 comprises a shaft 810, a clasp 830, and at least one driver 850. For some applications, shaft 810 can have features and/or functions similar to those of tube 271 of system 270, mutatis mutandis.

Delivery tool 800 can comprise an overtube 806 defining a primary lumen 807 through which shaft 810 extends. Overtube 806 can also define one or more auxiliary lumens 808 that provide communication to distal portion 804, e.g., for one or more other components of delivery tool 800 to extend therethrough.

Shaft 810 defines a longitudinal axis ax1 of delivery tool 800. For some applications, and as shown, shaft 810 (and lumen 807 through which it extends) is eccentric with respect to overtube 806, and therefore even if longitudinal axis ax1 is central with respect to shaft 810, it may not be central with respect to delivery tool 800 as a whole. In the example shown, auxiliary lumens 808 are disposed generally on one side of primary lumen 807, e.g., they are distributed circumferentially around less than 220 degrees (e.g., less than 200 degrees, such as 180 degrees) around the primary lumen. This arrangement may advantageously facilitate efficient inclusion of clasp 830 within the overall diameter of delivery tool 800. For example, and as shown, clasp 830 can be disposed on the same side of shaft 810 as secondary lumens 808 are disposed.

Shaft 810 (e.g., a distal end thereof) is advanceable into the ventricle 8 downstream of valve 7 (e.g., as described in more detail hereinbelow). As shown in FIG. 31B, shaft 810 (e.g., the distal end thereof) is coupled to downstream assembly 700 of implant 550. As described in more detail hereinbelow, this coupling configures delivery tool 800 both (i) to anchor winch anchor 710 to ventricular tissue of the heart by applying an anchoring force to the winch anchor, and (ii) to actuate winch 720. That is, shaft 810 can remain coupled to downstream assembly 700 throughout the anchoring of winch anchor 710 and actuation of winch 720. Furthermore, and as described in more detail hereinbelow, delivery tool 800, and the coupling of shaft 810 to downstream assembly 700, are configured such that the delivery tool can actuate winch 720 independently of applying the anchoring force to winch anchor 710.

Clasp 830 comprises an upstream support 832 and a downstream support 834. Clasp 830 is transitionable between (i) an open state, and (ii) a grasping state (e.g., a closed state). In the open state, upstream support 832 and downstream support 834 are positioned away from each other, such that the clasp is configured to receive a portion of a leaflet (e.g., leaflet 10) of valve 7 between the upstream support and the downstream support. Clasp 830 is configured to grasp the portion of the leaflet between upstream support 832 and downstream support 834 by being transitioned from the open state toward the grasping state while the portion of the leaflet is disposed between the upstream support and the downstream support. In the grasping state, upstream support 832 and downstream support 834 can be closer to each other than in the open state. For some applications, in the grasping state, in the absence of an obstruction (e.g., the portion of the leaflet) upstream support 832 and downstream support 834 are in contact with each other, e.g., press against each other.

Driver 850 is configured to anchor patch 610 to the leaflet (e.g., to the portion of the leaflet grasped between upstream support 832 and downstream support 834) by driving patch anchor 640 through the leaflet. Various configurations of patch anchor 640 and driver 850 are possible, and several such configurations are described hereinbelow. FIGS. 31A-35B show a configuration in which (i) patch anchor 640 is a toggle anchor with a sharpened tip, and (ii) driver 850 is configured to drive the patch anchor through the leaflet by pushing a heel of the patch anchor distally while the patch anchor is substantially colinear with the driver and/or with the vector of pushing, e.g., without the patch anchor being disposed within a needle. However, the scope of the disclosure includes examples (e.g., modifications of system 500) in which a needle is employed, e.g., as described with reference to FIGS. 20A-25F, mutatis mutandis.

For some applications, tool 800 comprises a capsule 870 at a distal end of shaft 810. Capsule 870 is configured to house downstream assembly 700 of implant 550 during delivery and implantation of the implant. In some applications, capsule 870 is dimensioned to conceal tissue-engaging element 712 in order to reduce a likelihood of inadvertently engaging and/or injuring tissue with the tissue-engaging element during transluminal advancement of distal portion 804 of tool 800.

Capsule 870 has an open distal end 871 via which downstream assembly 700 is deployable. For applications in which winch 720 (e.g., housing 721 thereof) has lateral aperture 726 through which tether 560 passes, capsule 870 can define a lateral window 874 in order to allow the tether to reach the winch, e.g., by the capsule housing downstream assembly 700 in an orientation in which lateral window 874 aligns with aperture 726.

Capsule 870 can be a unitary element or, as shown, can comprise a housing 872 and a shroud 876. Shroud 876 can cover a distal part of housing 872 and can even extend distally beyond the housing to form a rim 877. Shroud 876 can be formed from a material that is softer and/or more flexible than that of housing 872 (e.g., the shroud can comprise a resilient material such as a polymer or a silicone), so as to reduce a potential for injuring tissue. For applications in which shroud 876 extends distally beyond the housing to form rim 877, the rim can therefore serve as an atraumatic tip, which may be particularly advantageous for placement of capsule 870 against ventricular tissue during driving of tissue-engaging element 712 of anchor 710 into the ventricular tissue.

For some applications in which capsule 870 comprises housing 872 and shroud 876, the housing can define an elongate lateral opening 875 that extends proximally from a distal opening of the housing, e.g., is open to the distal opening of the housing. For such applications, and as shown, shroud 876 can substantially cover a distal region of elongate lateral opening 875, such that window 874 is defined by a proximal region of the elongate lateral opening, i.e., proximally from the shroud. For some such applications, shroud 876 defines a narrow slit 878 that extends between a distal opening of the shroud (which can serve as open distal end 871 of capsule 870) and window 874. Slit 878 can be in alignment with elongate lateral opening 875.

Elongate lateral opening 875 and/or slit 878 can be substantially parallel with axis ax1.

Narrow slit 878 is configured to facilitate tether 560 passing therethrough during deployment of downstream assembly 700 from capsule 870, but also is hypothesized to reduce a likelihood of a deleterious interaction with tissue during advancement of the capsule to the ventricle, such as inadvertent capture of a chorda tendinea within elongate lateral opening 875, compared with an otherwise similar capsule that has only elongate lateral opening 875.

Narrow slit 878 is narrower than elongate lateral opening 875 and can be less than 1 mm wide. For some applications, narrow slit 878 is closed at rest, e.g., its sides are in contact with each other, and are configured to transiently part as tether 560 passes therebetween during deployment of downstream assembly 700 from capsule 870.

While implant 550 is loaded on delivery tool 800, upstream assembly 600 is disposed proximally from downstream assembly 700 and can be secured laterally from shaft 810. For some applications, and as shown, upstream assembly 600 is mounted on a mount 840 that can be disposed laterally from shaft 810. For such applications, this mounting of upstream assembly 600 can be such that patch 610 lies against a surface of mount 840. For some such applications, mount 840 can have a convex outer surface (e.g., the mount can be substantially arc-shaped, curving partway around shaft 810), and patch 610 can lie in a curve against the convex outer surface of the mount, e.g., as shown. For some applications, patch 610 is held against mount 840 in this manner by one or more wraps 842 wrapped around the patch and the mount. For some such applications, and as shown, wraps 842 also wrap around shaft 810, thereby holding patch 610 to the shaft. As described in more detail hereinbelow, mount 840 is configured to carry patch 610 toward clasp 830.

For some applications, and as shown (e.g., in inset B of FIG. 31B), each wrap 842 comprises a flexible loop (e.g., a closed loop) that itself is looped around patch 610 so as to form (i) a pair of longitudinal portions 842L that extend around the patch, and (ii) two bights 842B, each bight connecting an end of one of the longitudinal portions of the pair to an end of the other longitudinal portion of the pair. For each wrap 842, one of the bights is secured to a bracket 844, and a rod 846 extends through the other one of the bights, thereby holding the wrap looped around the patch. Brackets 844 can be spring-loaded, thereby holding wraps 842 taut. For some applications, and as shown, the orientation in which wraps 842 and brackets 844 are arranged alternates, so that rod 846 is held in place. To release wraps 842 (e.g., to release patch 610 from being held against mount 840 by the wraps), rod 846 is retracted. This is described, in the context of implantation of implant 550, with reference to FIG. 32I.

As shown, tether 560 can be attached (e.g., fixedly attached) to a lip region of patch 610, e.g., at or proximate a lip 611 of the patch. As described in more detail hereinbelow, lip 611 is the edge of the patch that, after implantation, is disposed furthest from the root of the leaflet to which the patch is secured. For example, lip 611 can be close to the lip of the leaflet to which the patch is secured, or can overhang the lip of the leaflet (e.g., can be disposed in the ventricle downstream of the valve being treated). Patch 610 can also be considered to have a root region, e.g., at or proximate a root edge 612 of patch. Root edge 612 is the edge of the patch that is opposite lip 611, and that, as described in more detail hereinbelow, after implantation, is disposed closes to the root of the leaflet to which the patch is secured. Patch 610 can also have two lateral edges 613*a* and 613*b*, on opposite sides of the patch, extending between lip 611 and root edge 612.

For some applications, and as shown, patch 610 is wider (e.g., a distance between lateral edges 613*a* and 613*b* is greater) toward (e.g., at) lip 611 than toward (e.g., at) root edge 612. For example, patch 610 can approximate a trapezoid (e.g., an isosceles trapezoid) in shape, with lip 611 being the longer base of the trapezoid, and root 612 being the shorter base of the trapezoid.

While implant 550 is loaded on delivery tool 800, patch 610 can be oriented with lip 611 proximal from root 612, e.g., as shown. In this orientation, for applications in which tether 560 is attached to the lip region of patch 610, the tether therefore can extend past root edge 612 and alongside the patch on its route to the lip region. For example, and as shown, a portion 561 of tether 560 can extend alongside the patch, on the side of the patch that faces shaft 810 (e.g., on the concave side of the patch). For applications in which delivery tool 800 comprises mount 840, portion 561 of tether 560 can be disposed (e.g., sandwiched) between the match and the mount, e.g., as shown in FIG. 31B.

For some applications, alternatively or in addition to patch 610 being held against the surface of mount 840 (e.g., by wraps 842), the patch can be secured to the mount by patch anchors 640. For example, mount 840 can be shaped to house (or can comprise one or more components that are configured to engage) patch anchors 640. In the example shown, mount 840 is shaped to define grooves 848 shaped to receive patch anchors 640 (e.g., one groove per patch anchor). As shown, grooves 848 can be defined in the lateral/convex surface of mount 840, i.e., the surface against which patch 610 is typically disposed. Grooves 848 can be shaped to allow patch anchors 640 to slide along the groove but to obstruct the patch anchors from exiting the groove laterally. Thus, for applications in which implant 550 is provided with patch anchors 640 coupled to patch 610, disposition of patch anchors 640 within grooves 848 secures the patch to mount 840. The relevance of this is discussed hereinbelow with reference to FIGS. 32I-K.

For some applications in which implant 550 is provided with patch anchors 640 coupled to patch 610, this coupling is provided by cords 642, e.g., each patch anchor is coupled to the patch by a respective cord. For some such applications in which patch anchors 640 are disposed in grooves 848, and in which the grooves are shaped to inhibit the patch anchors from exiting the groove laterally, each cord 642 extends away from its patch anchor to patch 610 by exiting the groove laterally, thereby securing patch 610 to mount 840. This is visible in FIG. 32I. This can be facilitated by each groove 848 being narrower at the surface of the mount than deeper into the mount. For example, each groove 848 can have a cross-sectional shape of a major circular segment, with its chord being open at the surface of the mount, e.g., as shown.

For some applications, and as shown, patch anchor 640 can be provided with a retrieval eyelet 641 to which a retrieval line (not shown) can be releasably attached. This retrieval line, and use thereof, can be as described for pull member 388 of system 270 and/or as described for retrieval line 908, mutatis mutandis.

Figure 32A:
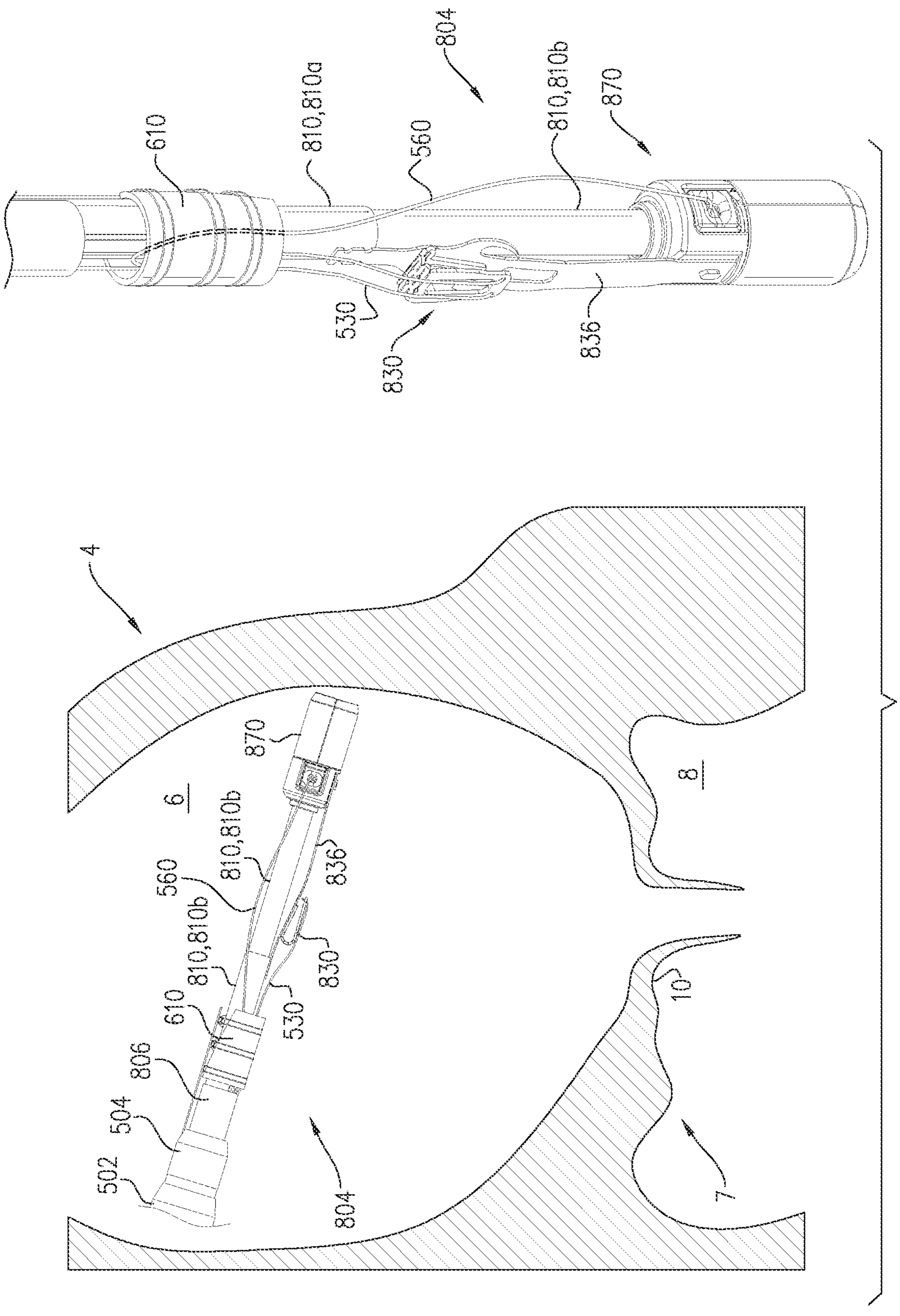

In some applications, delivery tool 800 is configured such that mount 840 is movable between a retracted position and a primed position. FIG. 31B shows mount 840 in its retracted position, which is typically also the position of the mount during transluminal advancement of distal portion 804 of tool 800, e.g., as shown in FIG. 32A. In the primed position (FIG. 32J), mount 840 is closer to clasp 830 than in the retracted position and can be in contact with the clasp (e.g., with upstream support 832 thereof). As described in more detail hereinbelow, drivers 850 can be configured to drive patch anchors 640 through the leaflet while the mount is in the primed position, e.g., as shown in FIG. 32K.

For applications in which wraps 842 are used, the wraps can hold patch 610 against mount 840 while the mount is in its retracted position. For some applications, and as shown in FIG. 32I, wraps 842 are released prior to mount 840 moving into its primed position.

Figure 32B:
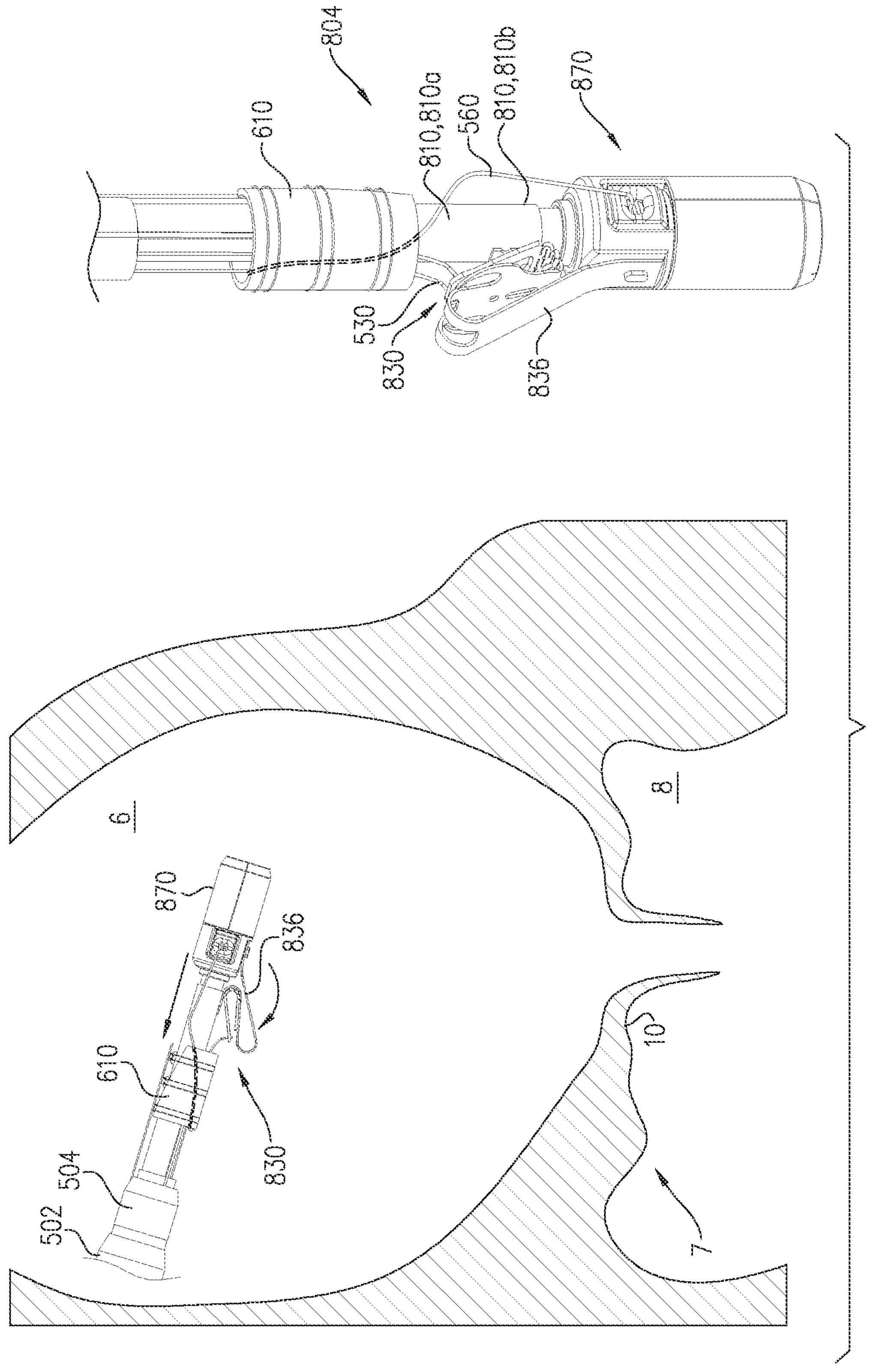
Figure 32C:
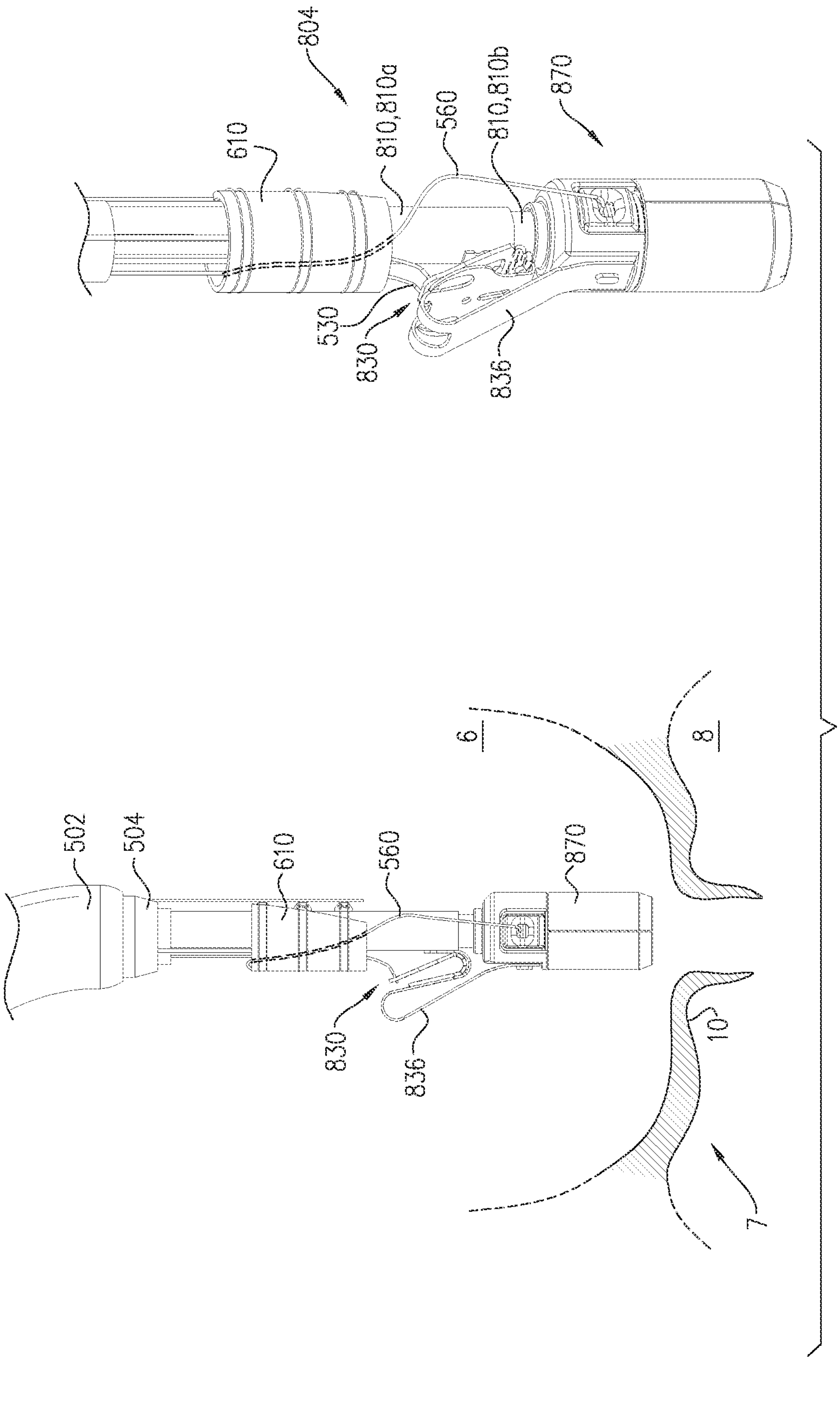

In some applications, and as shown, in the loaded state of tool 800 shown in FIG. 32B, grooves 848 are substantially parallel with axis ax1.

For some applications in which patch anchor 640 is disposed in groove 848, driver 850 is configured to anchor the patch to the leaflet (described hereinbelow) by driving the patch anchor out of a distal end of the groove. For some such applications, driver 850 enters the groove via a proximal end of the groove. For some applications, delivery tool 800 is provided with a distal end (e.g., a driver head) of driver 850 already disposed within groove 848. For some applications, driver 850 merely abuts patch anchor 640, whereas for other applications the driver head is configured to engage and/or grip the anchor (e.g., the driver head and/or the anchor comprise features that facilitate engagement and/or gripping of the anchor by the driver head).

As described hereinabove, delivery tool 800 comprises at least one driver 850. In the example shown, tool 800 comprises one driver 850 per patch anchor 640, e.g., two drivers.

Extracorporeal proximal portion 802 can comprise one or more controllers. The representation of these controllers in FIG. 31A is purely schematic, and each of these controllers can be, or can comprise, a knob, wheel, lever, slider, or other control element or interface via which the operator (e.g., the physician) can operate tool 800 to deliver and implant implant 550, e.g., using the techniques described herein.

For some applications, proximal portion 802 comprises a clasp controller 510, which is operatively coupled to clasp 830 (e.g., to upstream support 832 thereof) such that operation of the clasp controller transitions the clasp between its open and grasping (e.g., closed) states. This operative coupling can be provided by a wire 530 that is coupled to upstream support 832. In the example shown, two wires (e.g., parallel with each other) are used—although, as shown, these could be formed from a single length of wire that loops through upstream support 832 and turns back on itself. Operating clasp controller 510 to pulling on wire 530 transitions clasp 830 between its open and grasping states by moving (e.g., deflecting) upstream support 832 with respect to downstream support 834, and typically also with respect to shaft 810.

For some applications, proximal portion 802 comprises a driver controller 512, which is operatively coupled to drivers 850 such that operation of the driver controller induces the driver to drive patch anchor 640 through the leaflet to which upstream assembly 600 is to be anchored. In the example shown, operating driver controller 512 pushes drivers 850 distally such that each driver pushes the heel of a respective patch anchor 640 distally.

Proximal portion 802 can comprise a mount controller 516, operatively coupled to mount 840 such that operation of the mount controller moves the mount between its retracted position and its primed position. This operative coupling can be provided by one or more mount-control rods 536, a distal end of which can be fixed to mount 840. For some applications, mount-control rods 536 extend through dedicated auxiliary lumens 808. For some applications, each mount-control rod 536 can be tubular, and can share an auxiliary lumen with another control component of tool 800, e.g., with the other control component extending through the tubular mount-control rod. For example, and as shown, drivers 850 can extend through mount-control rods 536.

For some applications, within distal portion 804 shaft 810 has a proximal part 810*a* and a distal part 810*b*, which are axially slidable with respect to each other, e.g., in a telescopic arrangement, as shown. For some such applications, proximal portion 802 comprises a shaft controller 514 (e.g., a shaft extender), operatively coupled to shaft 810 such that operation of the shaft controller reversibly extends the distal part of the shaft distally from the proximal part of the shaft. It is to be noted that distal part 810*b* can extend proximally at least as far as proximal part 810*a*, but is nonetheless referred to as the "distal" part because it extends further distally than the proximal part.

It is to be noted that the functions of the various controllers of proximal portion 802 can be separated into single-function controllers or combined into multi-function controllers.

Proximal part 810*a* can be tubular, e.g., to house distal part 810*b*. Distal part 810*b* can be tubular, e.g., to house one or more driveshafts that control distal assembly 700, e.g., as described hereinbelow.

For some applications, clasp 830 (e.g., downstream support 834 thereof) is coupled to shaft 810 such that extension of distal part 810*b* distally from proximal part 810*a* moves (e.g., deflects) downstream support 834 with respect to the shaft. For example, delivery tool 800 can comprise one or more frame elements 836 that are coupled to shaft 810, and that cooperate with the shaft to define a mechanical linkage that moves (e.g., deflects) downstream support 834 with respect to the shaft. In the example shown, a single frame element 836, preconfigured to bend or articulate in a particular manner (e.g., by the use of flexure joints), provides this function. One end of the frame element is coupled to proximal part 810*a* of the shaft, and the other end of the frame element is coupled to distal part 810*b* of the shaft. It is to be noted that a similar effect can be achieved by using multiple frame elements articulatably (e.g., hingedly) coupled to each other.

For some applications, and as shown, a unitary piece of stock material defines upstream support 832, downstream support 834, and a flexure joint 833 that articulatably couples the upstream support to the downstream support. For such applications, and as further shown, downstream support 834 is fixed to a region 835 of frame element 836. However, it is to be understood that for other applications downstream support 834 can simply be defined by region 835, e.g., a unitary piece of stock material can define frame element 836 and downstream support 834. For such other applications, upstream support 832 can be formed from a separate piece of material, and articulatably coupled to downstream support 834.

For some applications, in the absence of tension on wire 530, axial movement of distal part 810*b* with respect to proximal part 810*a* moves (e.g., deflects) both downstream support 834 and upstream support 832 with respect to shaft 810. For example, clasp 830 can be biased toward being in its grasping state, and can remain in that state (e.g., a disposition between upstream support 832 and downstream support 834 can remain constant) as the downstream support moves (e.g., deflects) with respect to shaft 810.

For some applications, and as shown, clasp 830 defines one or more slots 837 via which driver 850 is configured to drive patch anchors 640 (e.g., one slot per patch anchor). In some applications, it is downstream support 834 (whether as part of a unitary piece of stock material that also defines upstream support 832, or whether defined by part of frame element 836) that defines slots 837. That is, downstream support 834 provides an opposing force during driving of patch anchors 640 through the leaflet, and the patch anchors are positioned to pass through the downstream support at slots 837, e.g., as described in more detail with reference to FIGS. 32K-L. As also described in more detail hereinbelow, this results in cord 642 threaded through slot 837. In order to allow cord 642 to exit slot 837 laterally, but to obstruct tissue (e.g., a chorda tendineae) from entering and becoming trapped in the slot, clasp 830 (e.g., downstream support 834 thereof) can define or comprise a slot guard 838. For some applications, and as shown, slot guard 838 is resilient, has a resting position in which it covers an entrance to the slot, thereby obstructing tissue of the heart from entering the slot, and is transiently deflectable away from the slot by the cord, thereby facilitating exiting of the cord from the slot, e.g., as described with reference to FIGS. 32L, and 63. Examples of other slot guards that can be used are described with reference to FIGS. 64 and 65A-B.

It is to be noted that the scope of the present disclosure includes a variant of system 500 in which (i) delivery tool 800 comprises one or more needles, similar to and/or generally corresponding to needle 278 described hereinabove, mutatis mutandis, (ii) patch anchor 640 may not have a sharpened tip, and (iii) rather than the patch anchor being driven through the leaflet directly, the needle penetrates the leaflet, and the patch anchor is subsequently advanced out of the needle.

Figure 32D:
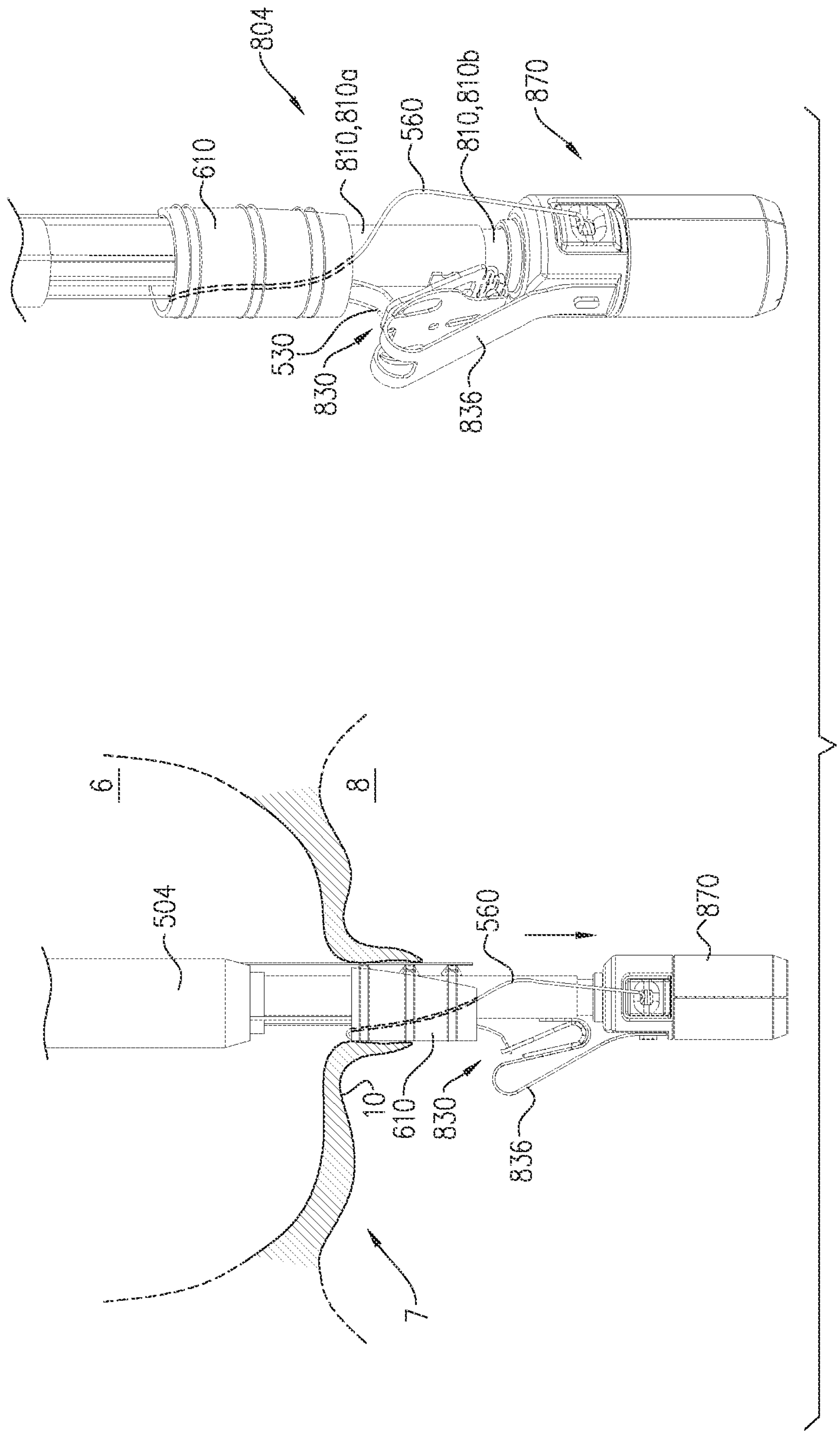
Figure 32E:
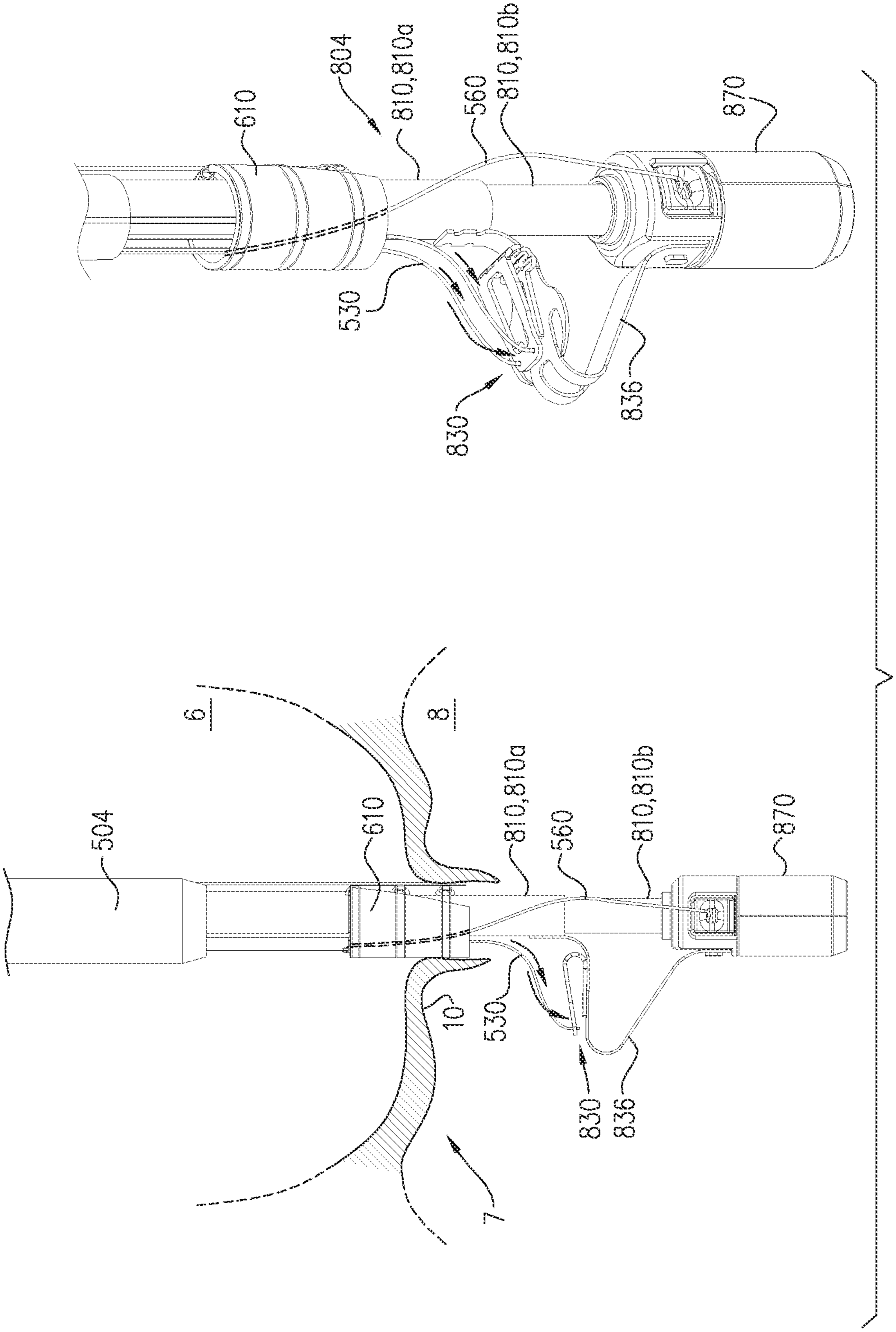
Figure 32F:
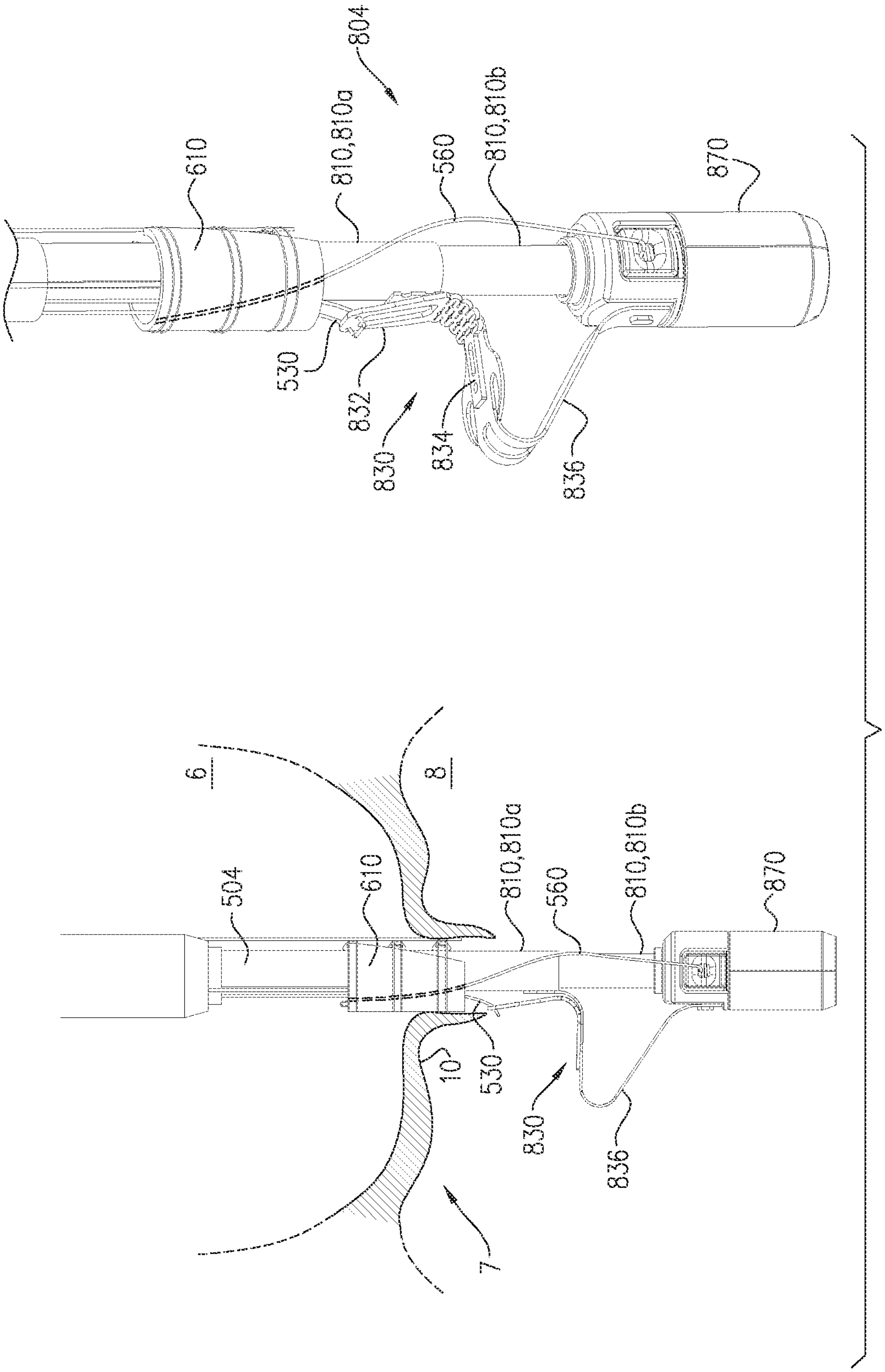
Figure 32G:
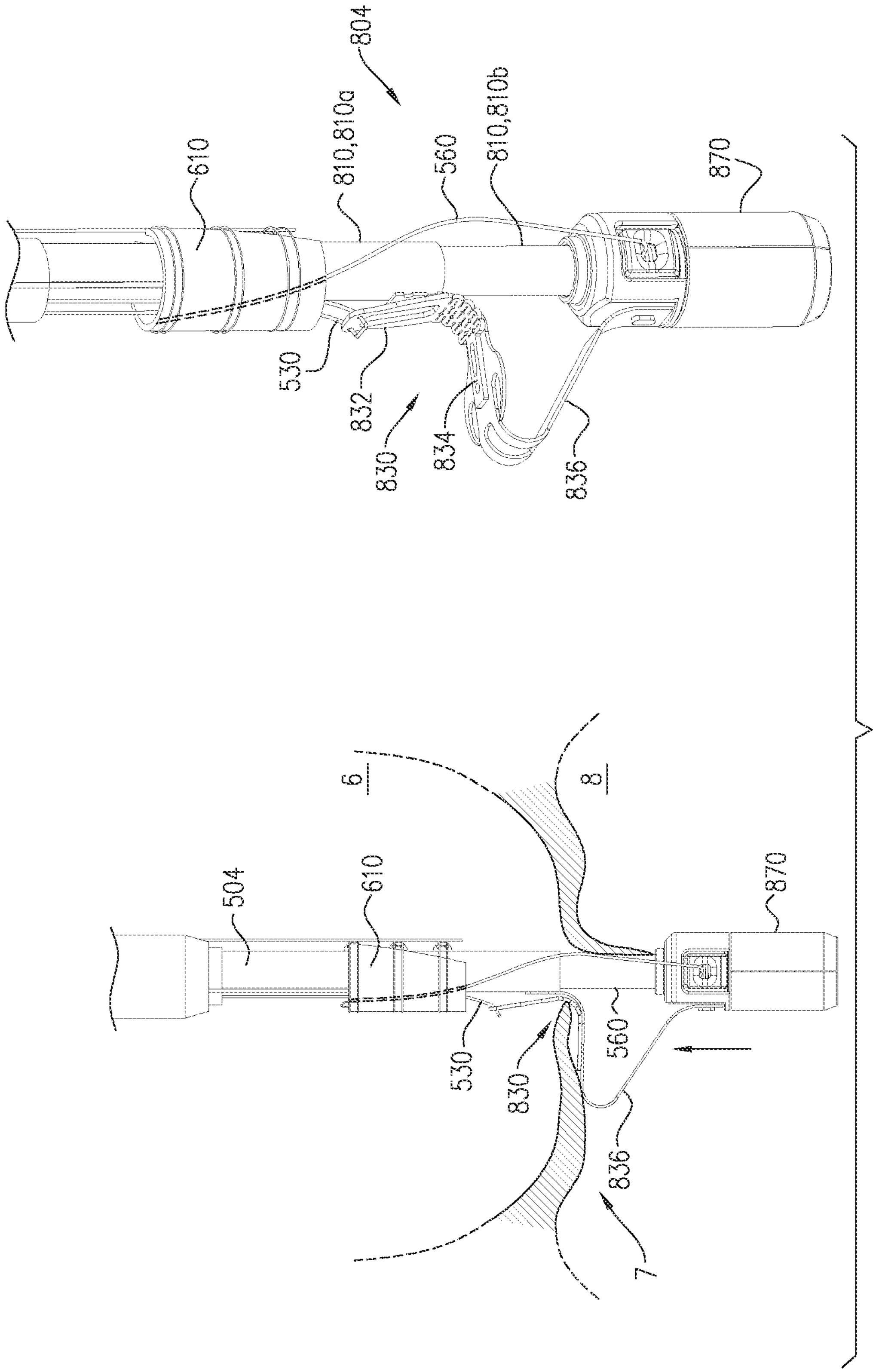
Figure 32H:
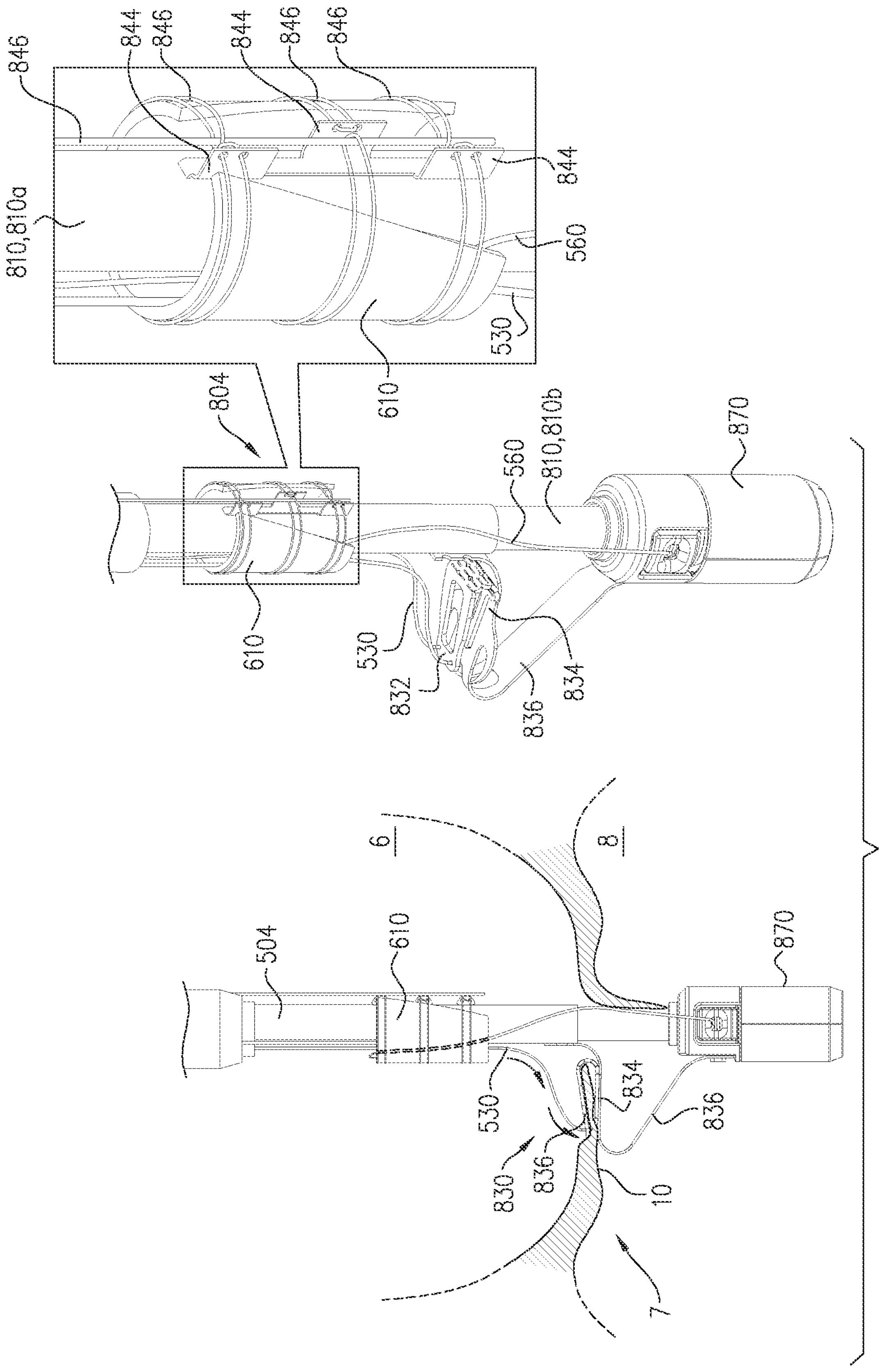
Figure 32I:
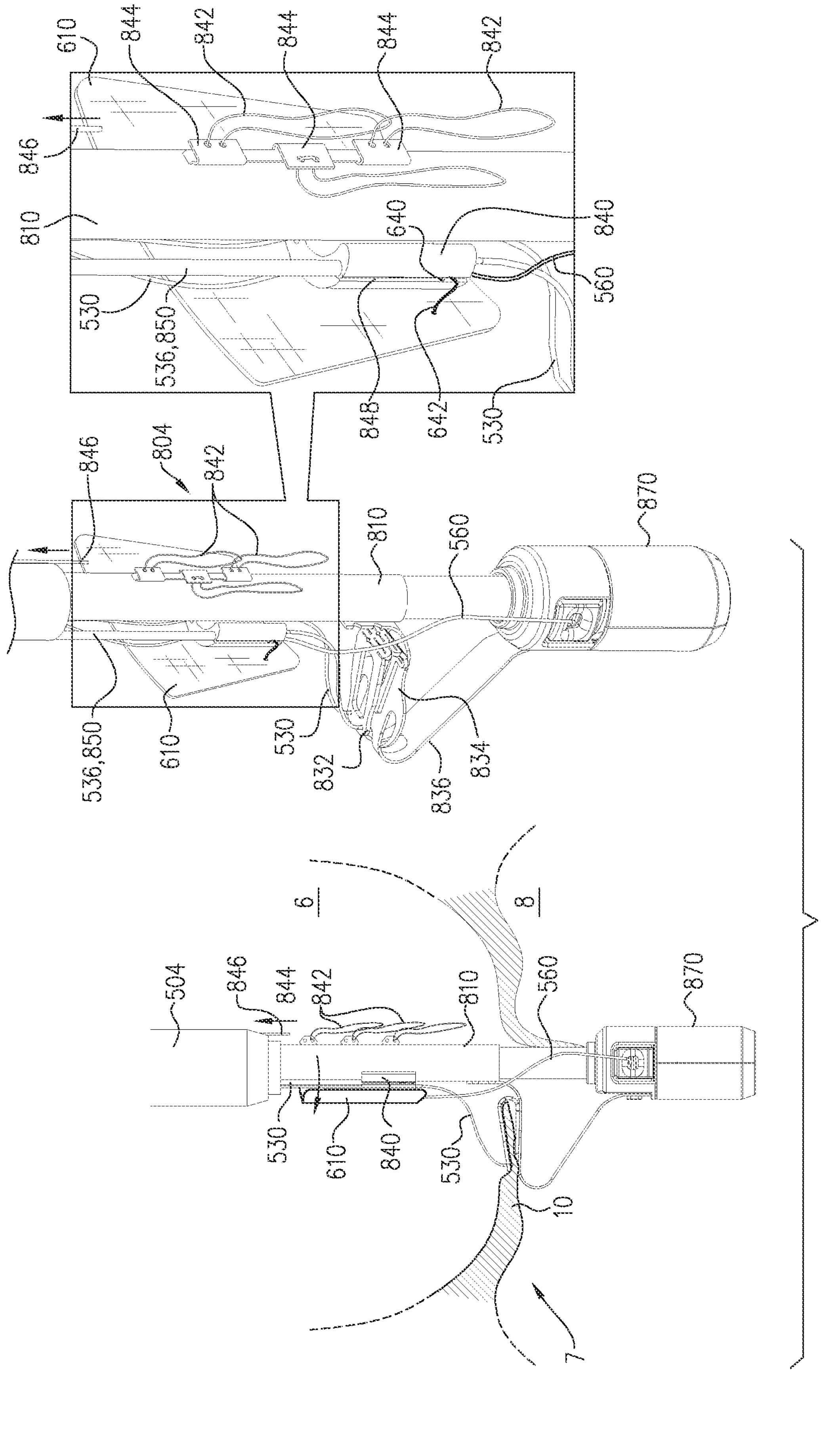
Figure 32J:
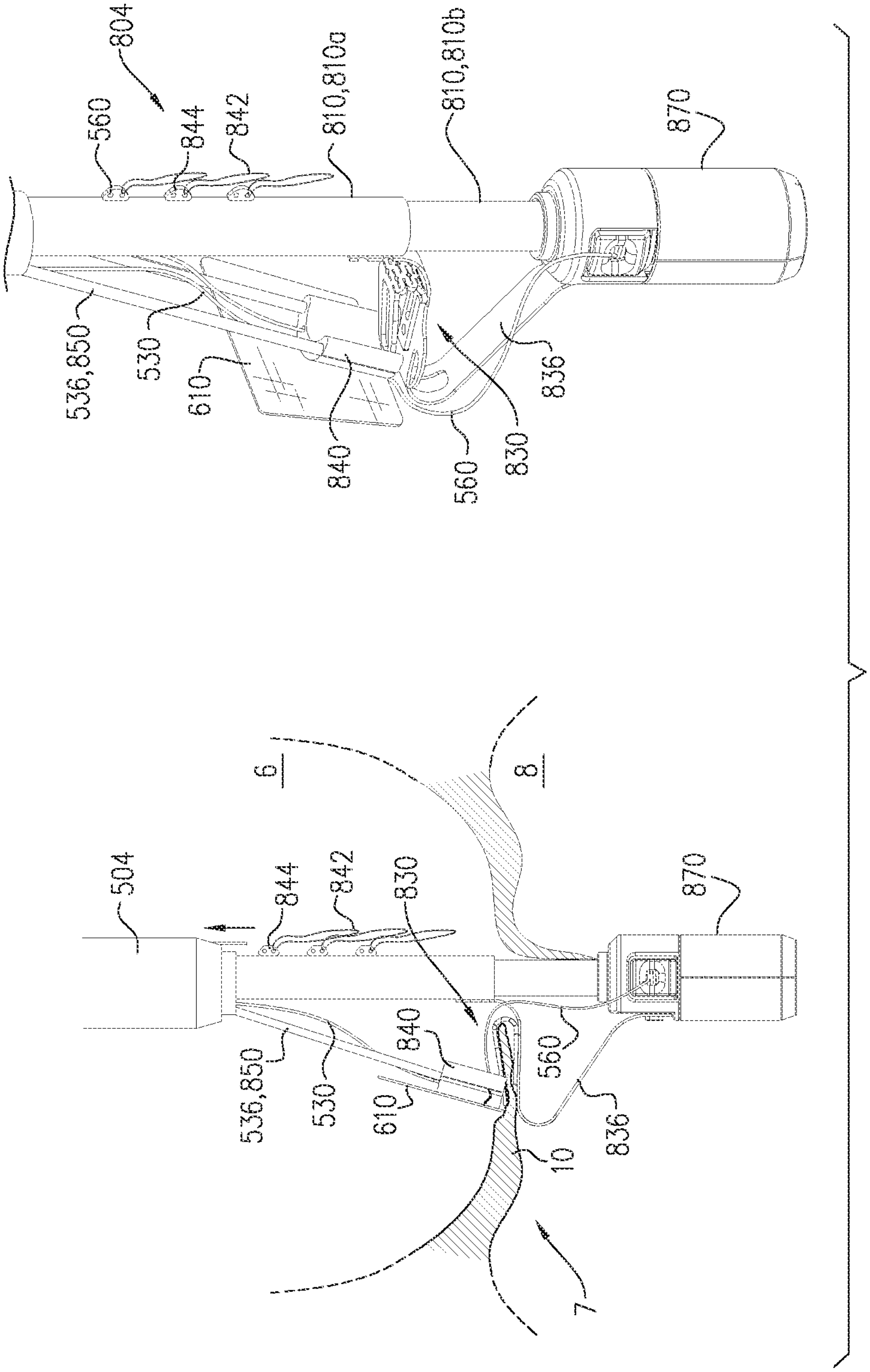
Figure 32K:
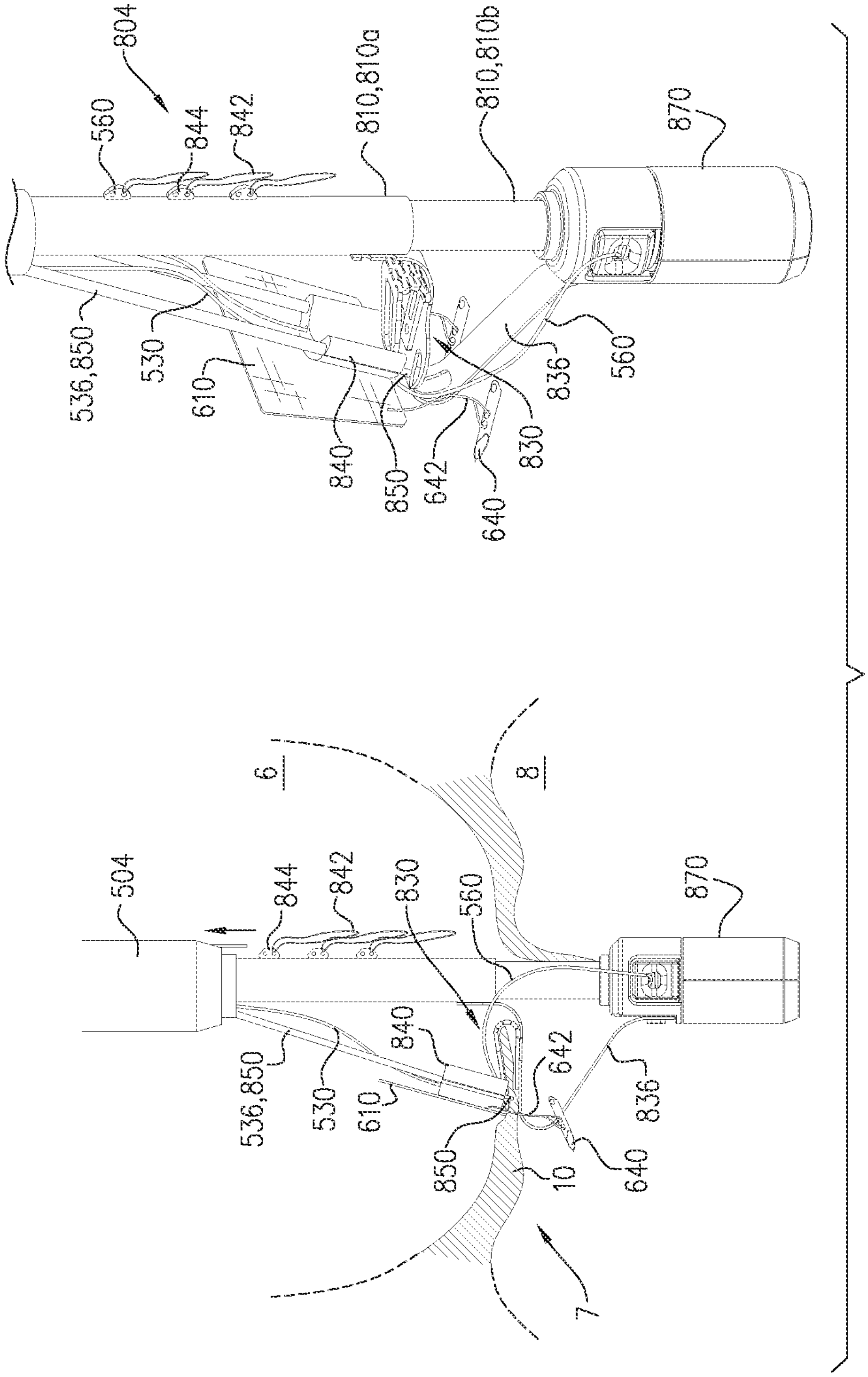
Figure 32L:
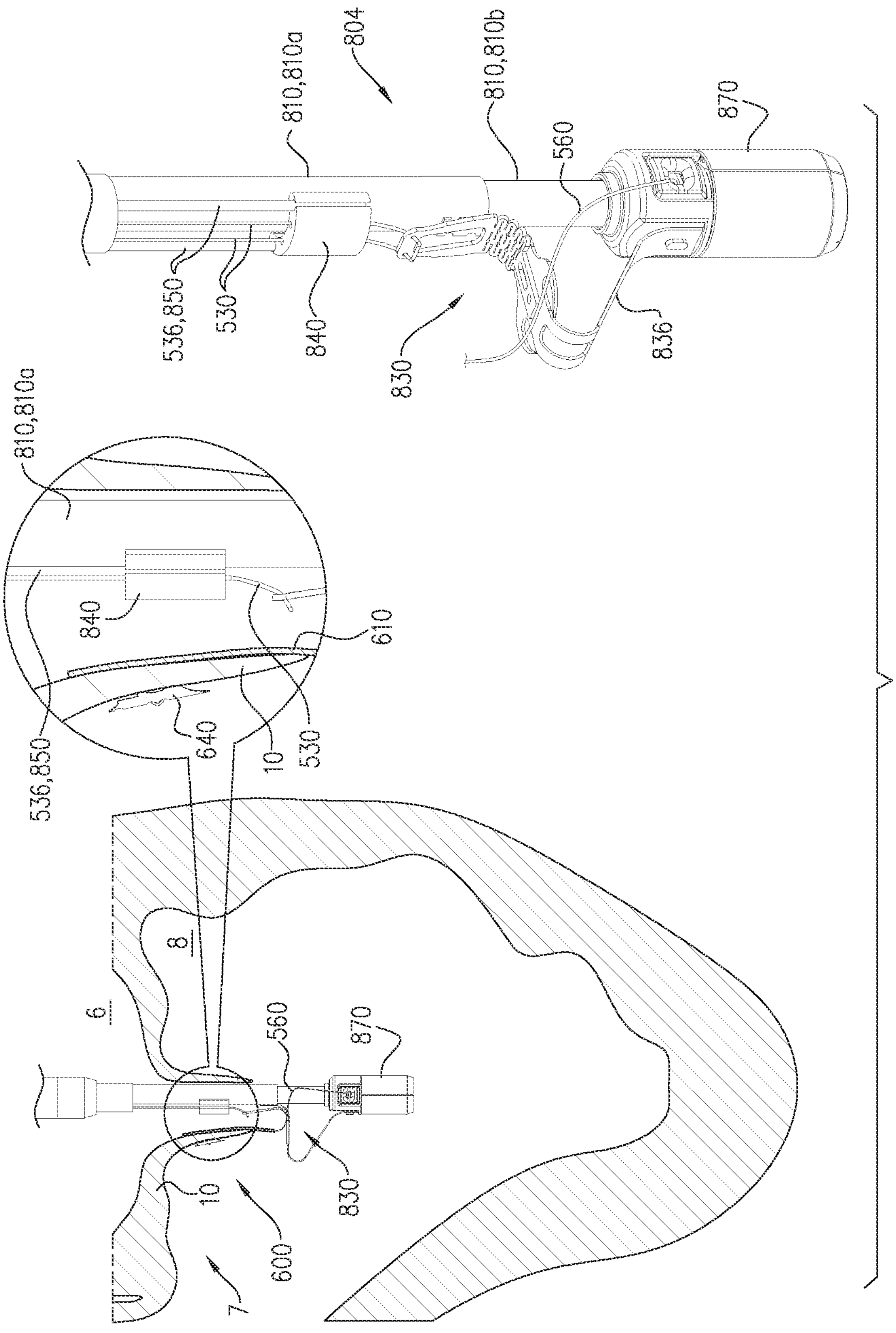
Figure 32M:
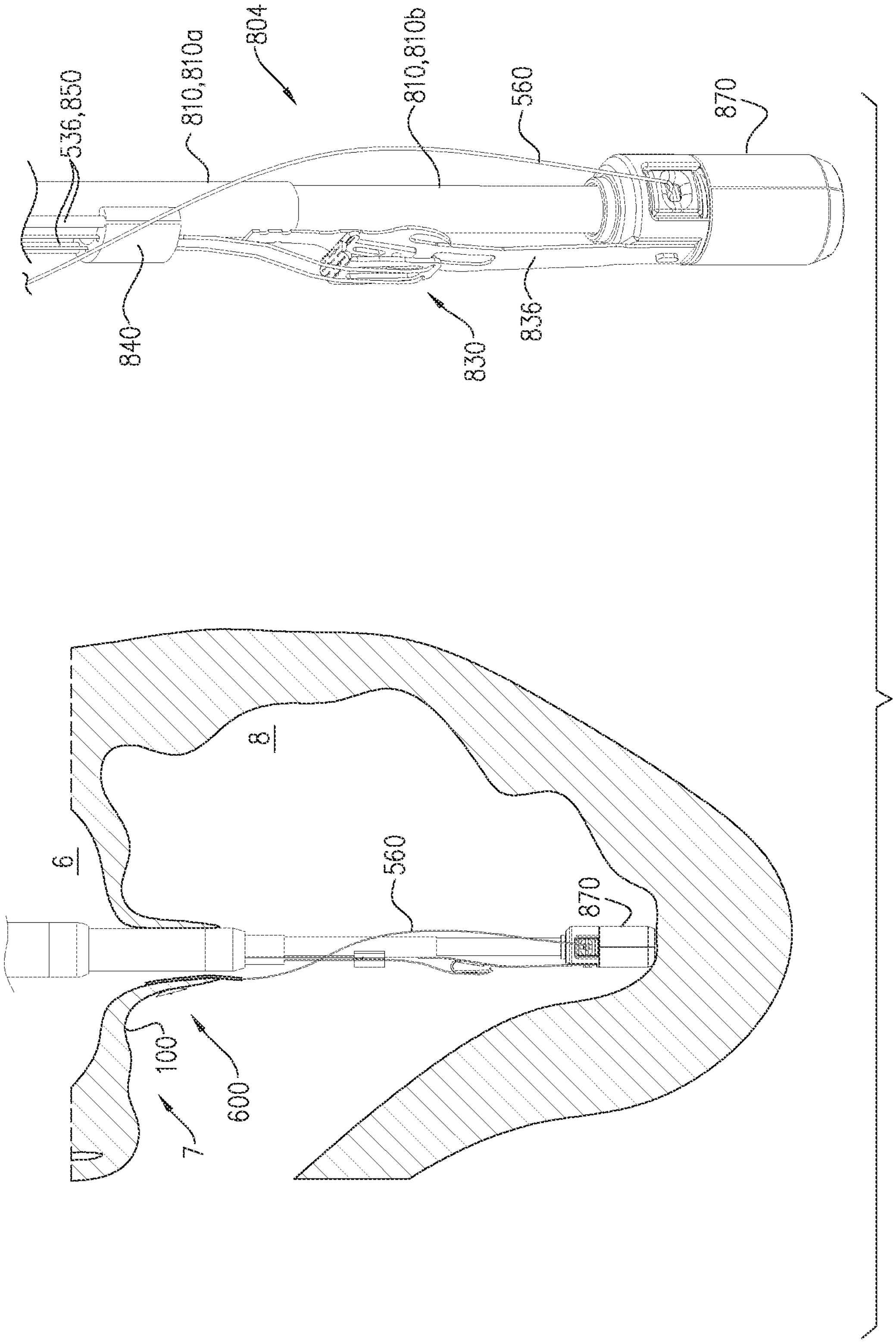
Figure 32N:
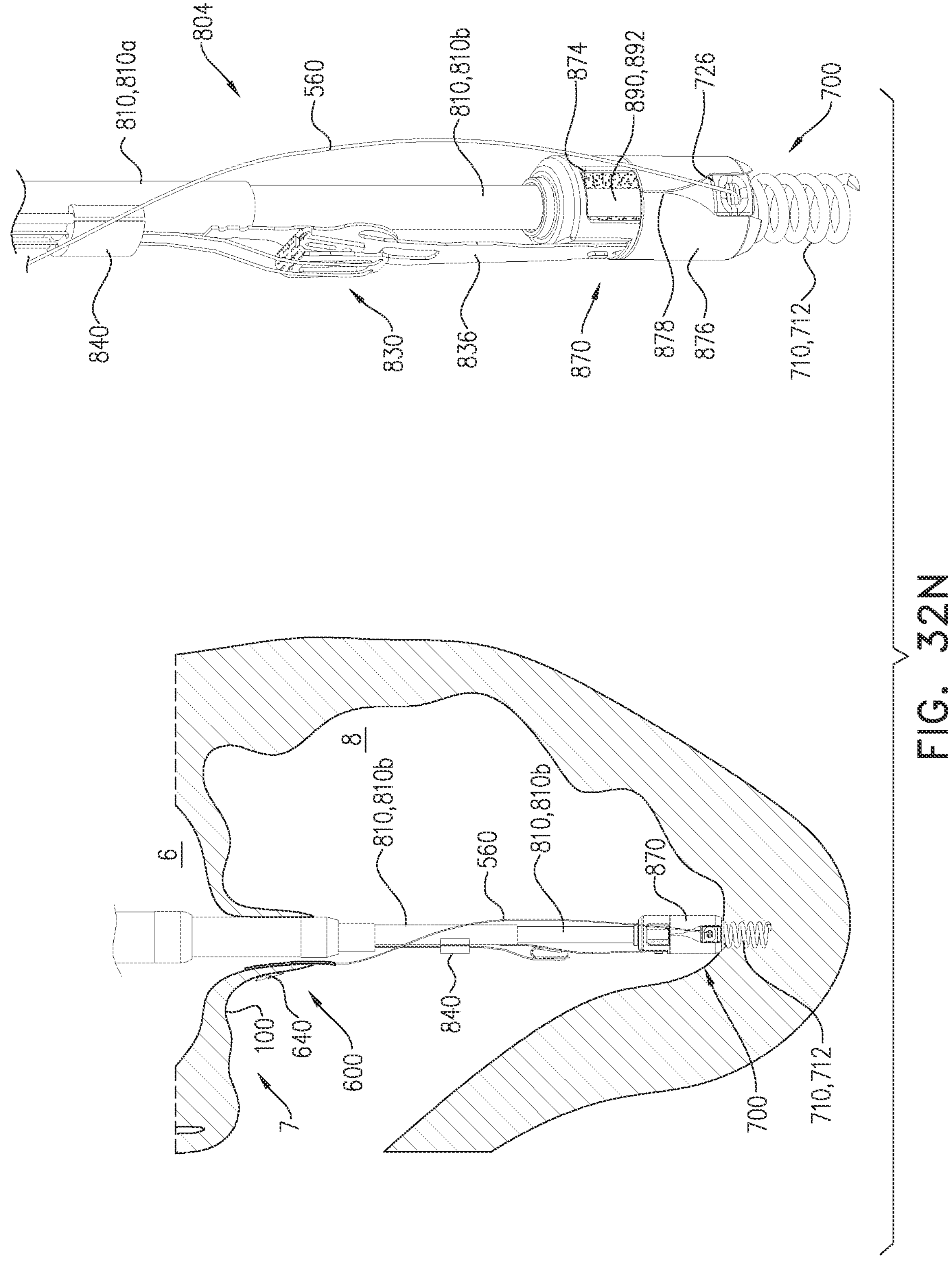
Figure 32O:
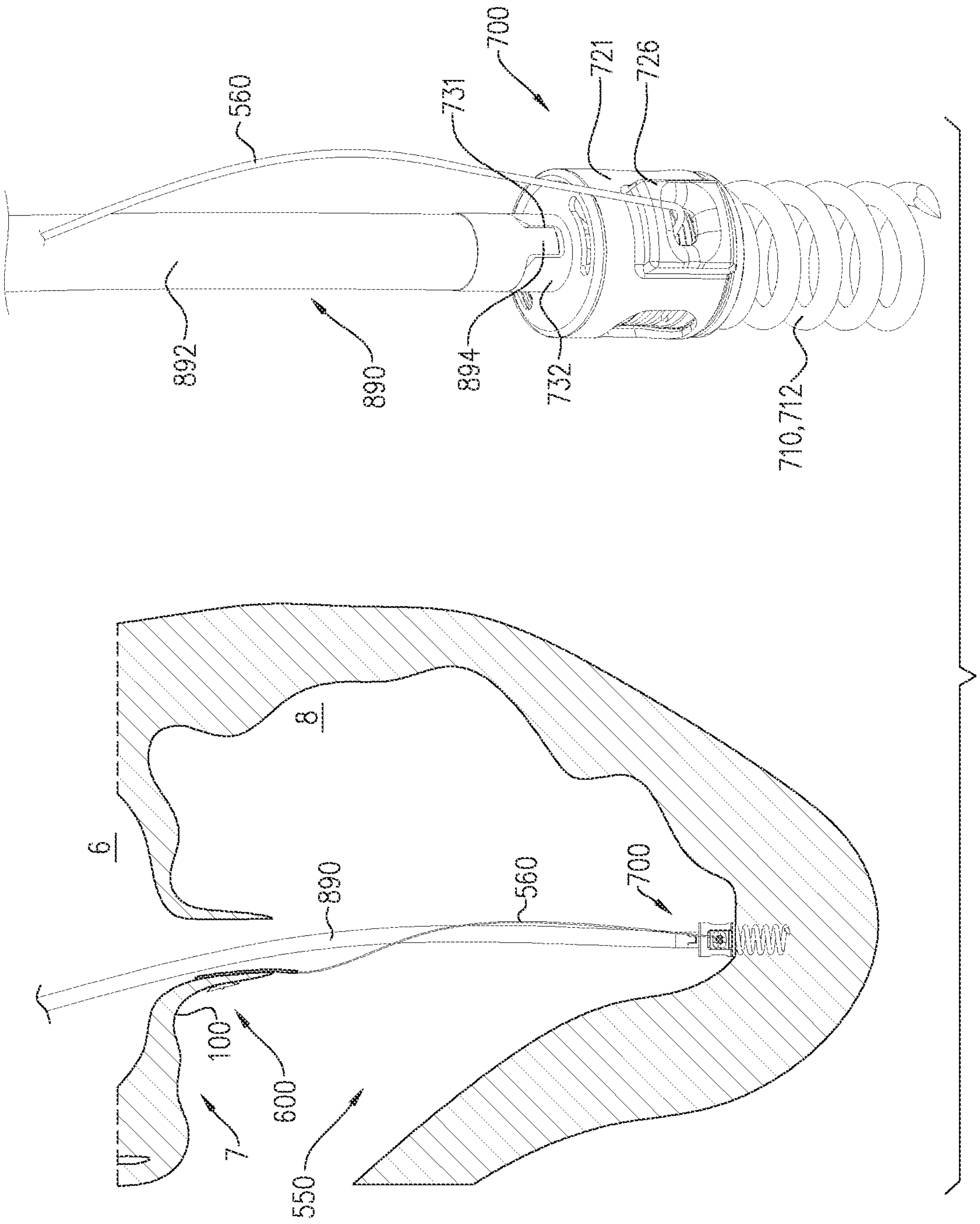
Figure 32P:
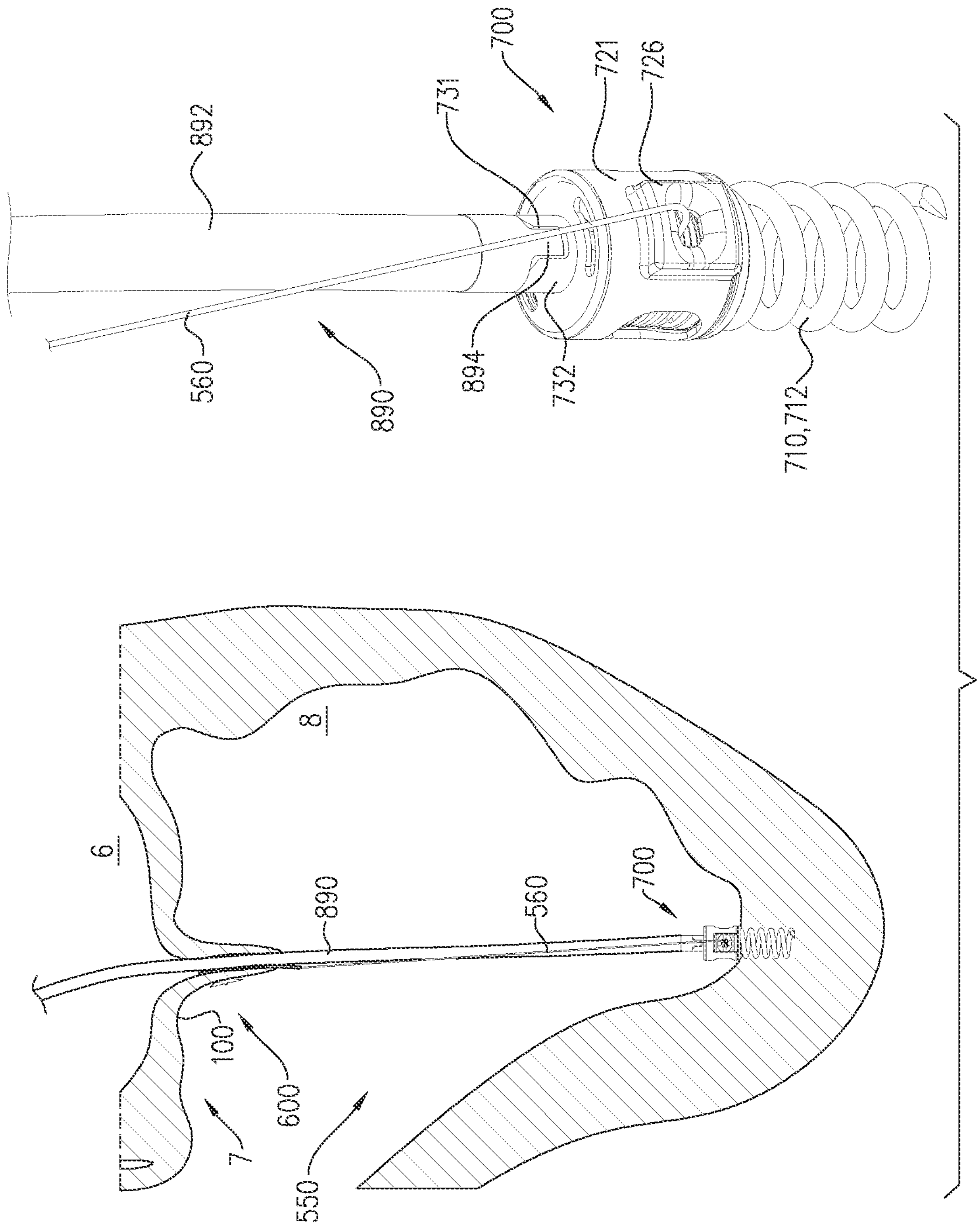
Figure 32Q:
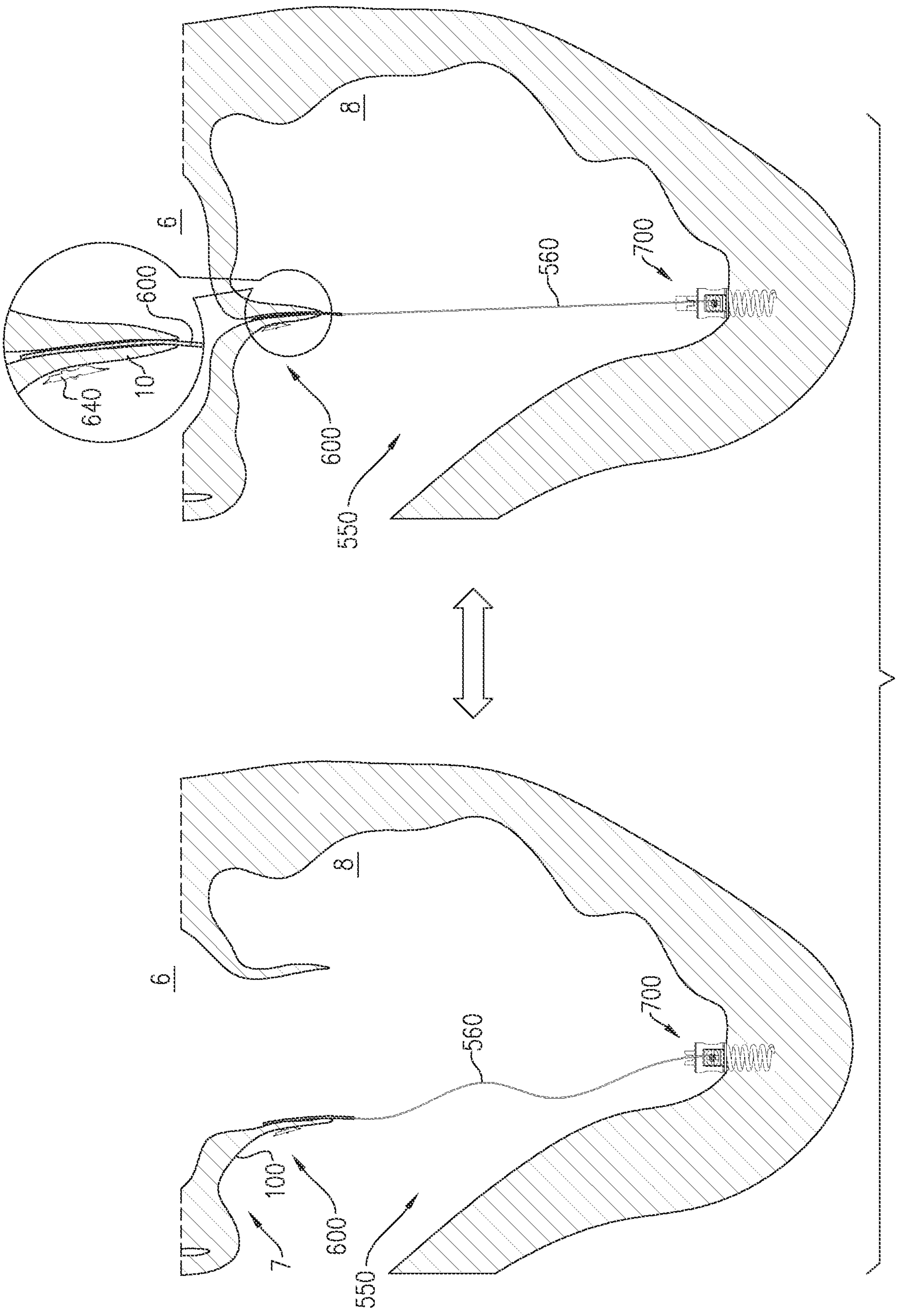

Reference is now made to FIGS. 32A-Q, which are schematic illustrations showing at least some steps in a technique for treating valve 7 of a heart of a subject, in accordance with some applications. Although the technique is shown for use with system 500, for some applications variants of system 500 (e.g., comprising variants of implant 550 and/or of tool 800), and/or other systems can be used instead. In each of FIGS. 32A-P, the left-side frame illustrates the position and/or interaction of system 500 with the heart, while the right-side image emphasizes the state of the system itself.

With implant 550 loaded on distal portion 804 of delivery tool 800, the distal portion is transluminally advanced to heart 4 of the subject, e.g., to an atrium 6 upstream of valve 7. For example, and as shown, distal portion 804 can be transluminally and transseptally advanced into the left atrium of the heart (FIG. 32A).

In the example shown, transluminal advancement of tool 800 is facilitated by one or more catheters 502, 504, one or more of which can be steerable (i.e., actively steerable, e.g., using pull-wires or other components known in the art). For example, catheter 502 and/or catheter 504 can be advanced to the atrium, and tool 800 can be subsequently advanced through the catheter(s). In the example shown, tool 800 is transluminally advanced while in a delivery state.

In the delivery state, patch 610 can be held against mount 840 and/or shaft 810 by wraps 842, e.g., to facilitate smooth advancement, and/or to protect the patch. For some applications, and as shown, in the delivery state, clasp 830 is in a low-profile state. For such applications, in the low-profile state clasp 830 is typically closed (i.e., is in its grasping state) but is deflected distally (i.e., the clasp faces distally, with both upstream support 832 and downstream support

834 deflected distally), e.g., such that downstream support 834 is disposed adjacent to and substantially parallel with shaft 810 (e.g., distal part 810*b* thereof). As described hereinabove, this is achieved by extending distal part 810*b* of shaft 810 from proximal part 810*a* (i.e., telescopically extending the shaft), thereby straightening frame element 836. For some applications, in the low-profile state clasp 830 can be over-opened, e.g., such that upstream support 832 is substantially collinear with downstream support 834 (e.g., by extending distal part 810*b* while also tensioning wires 530).

The low-profile state is advantageous for transluminal advancement, but in some instances may be disadvantageous for maneuvering within the heart due to the relatively large overall length of distal portion 804. Thus, for some applications, once distal portion 804 is disposed (e.g., entirely disposed) within atrium 6, distal portion 804 is transitioned into a contracted state, e.g., by withdrawing distal part 810*b* of shaft 810 into proximal part 810*a* (i.e., telescopically contracting the shaft), such as by operating shaft controller 514 (FIG. 32B). Clasp 830 is also typically closed in the contracted state of distal portion 804, but deflected proximally (i.e., the clasp faces proximally). Thus, the widest part of distal portion 804 in the contracted state (at the level of clasp 830) is wider than the widest part in the low-profile configuration, but the shorter overall length of the distal portion advantageously facilitates a smaller "turning circle" as the distal portion is steered within the heart.

Distal portion 804 (e.g., in its contracted state) is then turned toward valve 7 (FIG. 32C), and through the valve into ventricle 8 downstream of the valve (FIG. 32D). It is to be noted that, in this position, the leaflets of valve 7 may coapt against distal portion 804. Subsequently, clasp 830 is transitioned into its open state in which upstream support 832 and downstream support 834 are positioned away from each other, and in which the clasp is configured to receive a portion of a leaflet of the valve between the upstream support and the downstream support.

For some applications, this is performed as discrete steps of: (i) while the clasp remains closed, deflecting the entire clasp (e.g., in a downstream direction) so that the clasp (or at least downstream support 834 thereof) is substantially orthogonal to shaft 810, and therefore protrudes maximally laterally, such as by operating shaft controller 514 (FIG. 32E); and (ii) subsequently, transitioning clasp into its open state by deflecting upstream support 832 (e.g., by tensioning wire 530) while downstream support 834 remains stationary, such as by operating clasp controller 510 (FIG. 32F). However, it is to be understood that the scope of the disclosure includes other ways of transitioning clasp 830 into its open state within ventricle 8, such as by deflecting downstream support 834 in a downstream direction while keeping upstream support 832 stationary.

The deflection of clasp 830 in the transition between FIG. 32E and FIG. 32F shows the clasp being deflected by partial extension of distal part 810*b* of shaft 810 in a manner that maintains capsule 870 substantially stationary relative to the anatomy and retracts patch 610 proximally/upstream relative to the anatomy. However, it is to be understood that this deflection could also be achieved in a manner that maintains patch 610 substantially stationary relative to the anatomy and advances capsule 870 distally/deeper into the ventricle.

While clasp 830 remains in its open state, distal portion 804 is manipulated to move clasp to receive a portion of leaflet 10 (FIG. 32G). For example, and as shown, distal portion 804 can be moved proximally until leaflet 10 rests upon downstream support 834. While the portion of leaflet 10 remains between upstream support 832 and downstream support 834, the clasp is closed (is transitioned toward its grasping state), thereby grasping the portion of the leaflet (FIG. 32H).

For applications in which tool 800 comprises wraps 842, the wraps can be released at this stage, if not earlier. The inset of FIG. 32H shows wraps 842 holding patch 610 securely against mount 840 (not visible). As described hereinabove, and as shown in FIG. 32H, for some applications wraps 842 can extend around shaft 810. For such applications, wraps 842 should therefore be released so as to facilitate subsequent steps in which patch 610, carried by mount 840, is moved away from shaft 810. FIG. 32I shows wraps 842 having been released by retraction of rod 846, and patch 610 responsively unwrapping from around shaft 810. Brackets 844 are shown as having changed shape in response to the release of tension on wraps 842.

For some applications, such unwrapping of patch 610 can be passive, e.g., following its release, merely in response to movement of blood. For some applications, e.g., for applications in which patch 610 comprises a frame 630, the frame can comprise a spring or otherwise be biased to open up the patch.

While the portion of leaflet 10 remains grasped by clasp 830, mount 840 is advanced toward clasp 830, e.g., upstream support 832 thereof (FIG. 32J). This new position of mount 840 can be considered to be a "primed" position, whereas the previous position of the mount can be considered to be a "retracted" position. As shown, the advancement of mount 840 into its primed position can be performed by operating mount controller 516 to advance mount-control rods 536 to push the mount over and along wires 530 (FIG. 32J).

It is to be noted that, as described hereinabove, despite the unwrapping of patch 610 from around shaft 810 and/or mount 840, for applications in which the patch is coupled to the mount via anchors 640, the patch typically remains coupled to the mount at this stage, e.g., as shown in the inset of FIG. 32I. Therefore, as mount 840 is advanced toward clasp 830, the mount carries patch 610 toward the clasp.

It is to be noted that the movement of mount 840, and thereby of patch 610, toward clasp 830 can include distal and/or downstream movement. It is also to be noted that this movement can also include lateral movement, i.e., movement away from shaft 810, toward the opening end of clasp 830. As shown in FIG. 32H, for applications in which wires 530 are used to operate clasp 830, the articulation of upstream support 832 during closure of the clasp can pull the wires laterally. Thus, for some such applications in which, additionally, mount 840 is slid along wires 530, the wires serve as rails that guide the mount not just distally, but obliquely (e.g., distolaterally) to the clasp.

While (i) the portion of leaflet 10 remains grasped by clasp 830, and (ii) mount 840 is disposed at the clasp (i.e., in its primed position), drivers 850 are used to drive patch anchors 640 through the leaflet (e.g., through the grasped portion of the leaflet), such as by operating driver controller 512, thereby anchoring patch 610 to the leaflet (FIGS. 32I-J). For example, and as shown, patch anchors 640 can be driven out of the end of grooves 848, and through leaflet 10 and slot 837. It is hypothesized that lateral portion of the movement of mount 840 and patch 610 prior to anchoring advantageously positions patch anchors 640 (and typically the patch) away from the lip of leaflet 10, i.e., toward the root of the leaflet, and that this advantageously enhances the positioning of the patch and/or the reliability of its anchoring.

Clasp 830 is then reopened, and distal portion 804 is moved away from patch 610 and the leaflet 10 to which it is anchored (FIG. 32L). It is to be noted that this is facilitated by (i) patch 610 becoming automatically released from mount 840 upon patch anchors 640 exiting the mount, and (ii) cords 642, which became disposed through slots 837 during anchoring, exiting the slots laterally, e.g., due to transient deflection of slot guards 838 as the cords slip through as clasp 830 is moved away.

For some applications, patch 610 is anchored to leaflet 10 in a manner in which the patch (e.g., lip 611 thereof) overhangs the lip of the leaflet, e.g., extends further into ventricle 8 than does the leaflet. It is hypothesized that, for some applications, this advantageously facilitates coaptation with the opposing leaflet.

In some applications, subsequently to anchoring patch 610 to leaflet 10, downstream assembly is anchored to tissue of ventricle 8. In some applications, shaft 810 is extended in order to reach the ventricular tissue, e.g., by operating shaft controller 514 (FIG. 32M). As shown, this can return clasp 830 to its low-profile state. For some applications, tether 560 is released (e.g., unspooled) from winch 720 at generally the same time, in order to accommodate the increased distance between upstream assembly 600 (e.g., patch 610 thereof) and downstream assembly 700 (e.g., the winch thereof).

Figure 33A:
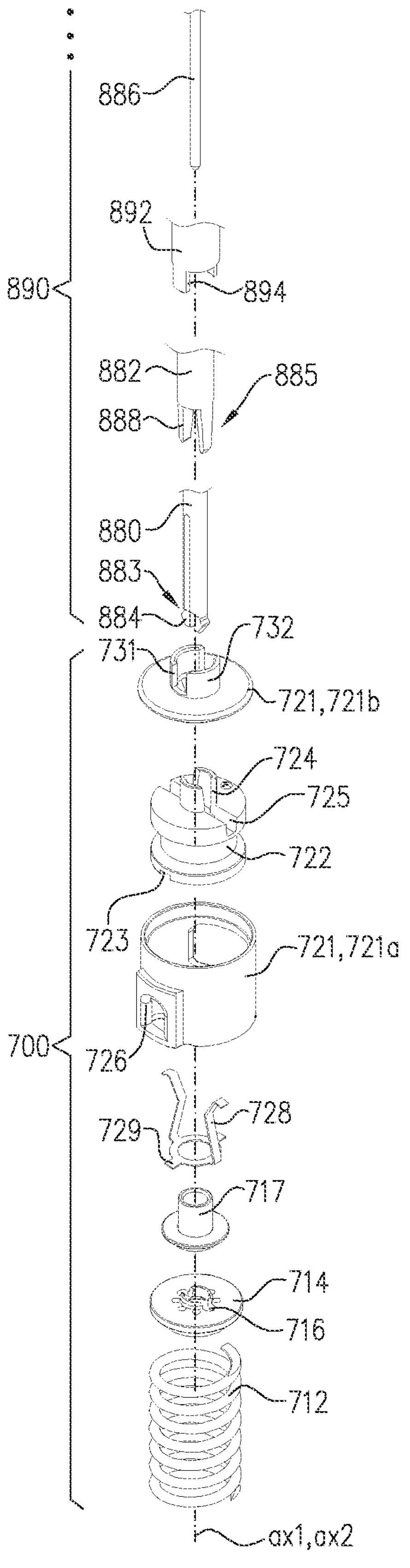
Figure 33B:
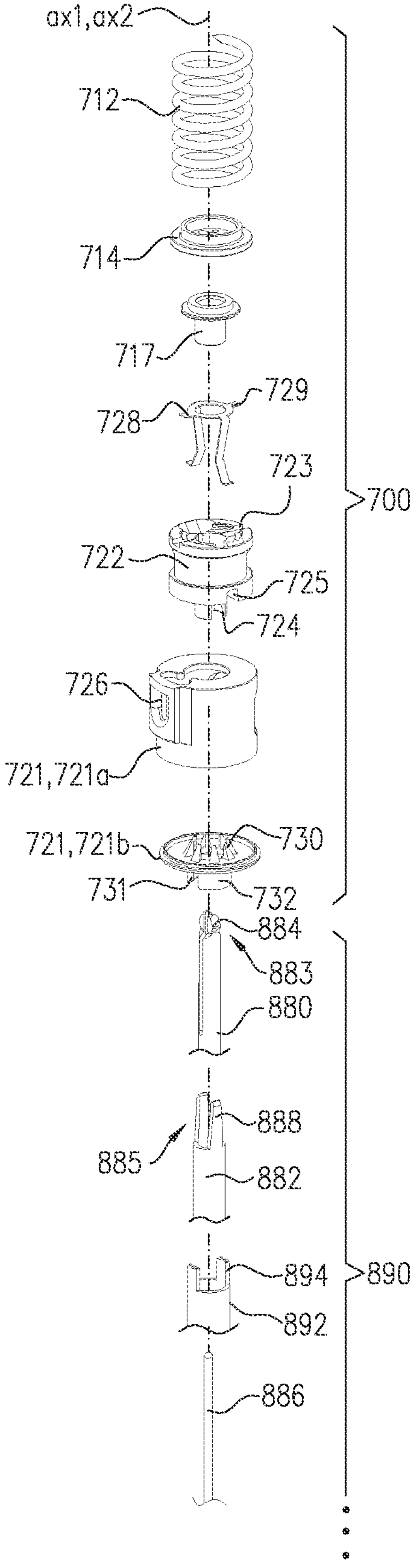
Figure 34C:
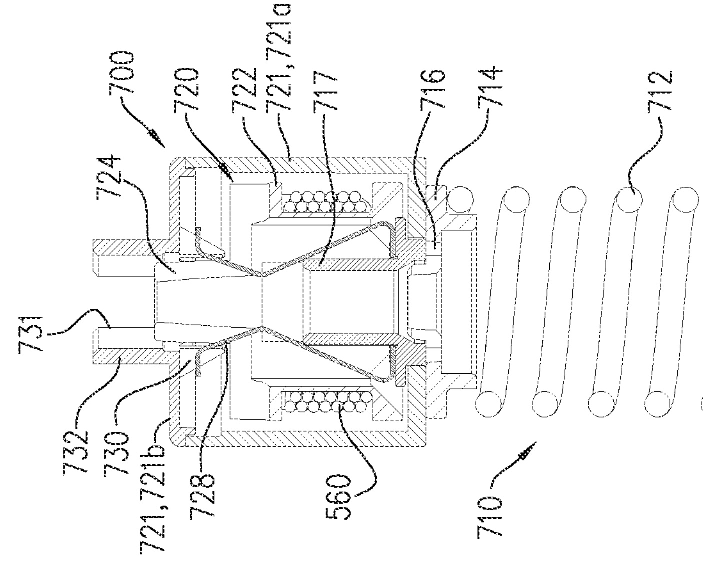
Figure 34B:
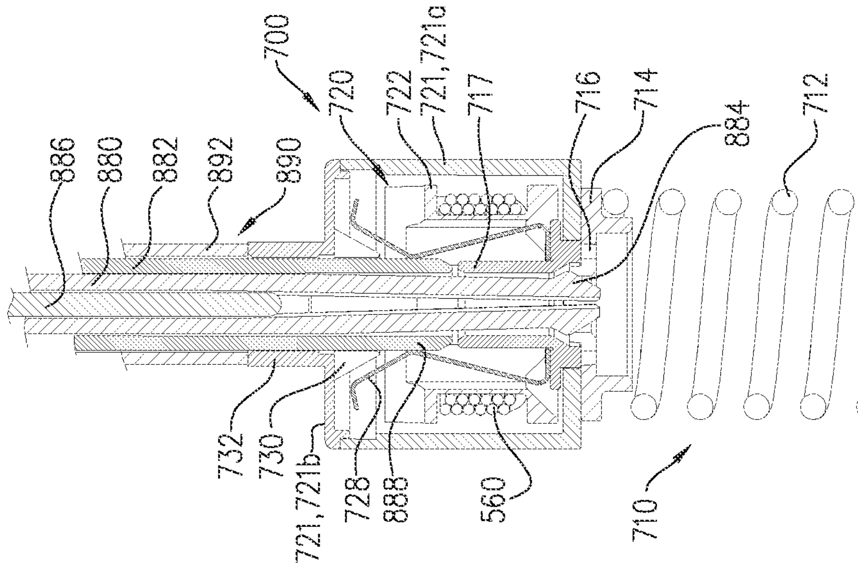
Figure 34A:
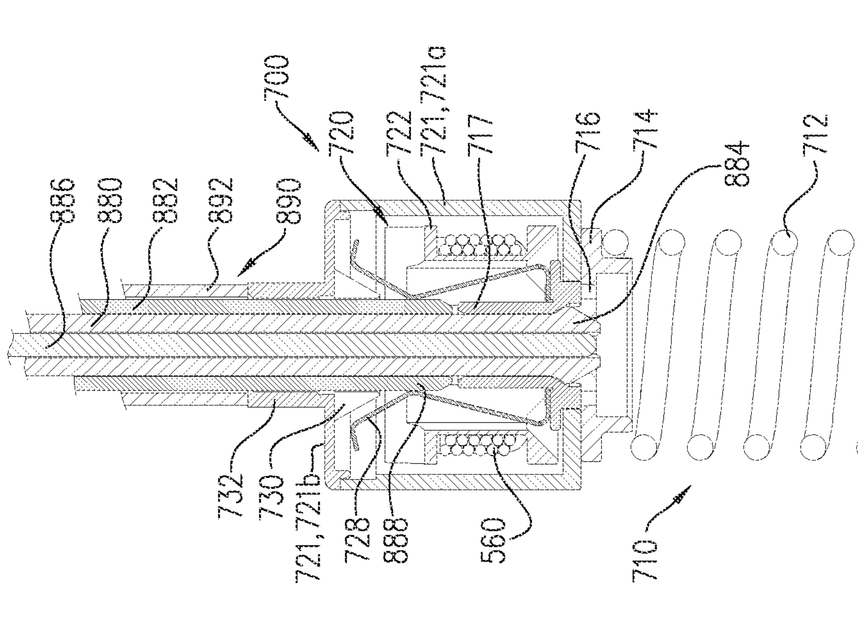

At this point, reference is additionally made to FIGS. 33A-B and 34A-C. FIG. 33A is a schematic illustration showing an exploded view of (i) some components of driveshaft subassembly 890 at a distal end of distal portion 804 of delivery tool 800, and (ii) downstream assembly 700. FIG. 33B is an inverted version of FIG. 33A, showing an inverted view of each component. FIGS. 34A-C show the components that are shown in FIGS. 33A-B, but assembled (e.g., in the manner shown in FIG. 31B) and in cross-section.

Once a site in the ventricle has been selected, downstream assembly 700 is anchored to the site by anchoring winch anchor 710 to the tissue, e.g., by driving tissue-engaging element 712 into the tissue (FIG. 32N). This can be achieved by operating an anchor controller 518 at proximal portion 802. Anchor controller 518 is operatively coupled to winch anchor 710 such that operation of the anchor controller applies an anchoring force to the winch anchor (FIG. 34A). For example, delivery tool 800 can comprise an anchor-control driveshaft 880 that operatively couples anchor controller 518 to winch anchor 710. For some applications, and as shown, the anchoring force is (or includes) torque, which is applied via engagement between anchor-control driveshaft 880 and winch anchor 710. Winch anchor 710 can comprise a driver interface 716 that is a component of, is defined by, or is fixedly coupled, to head 714 of the winch anchor. Driveshaft 880 engages driver interface 716 and applies torque to the driver interface via this engagement. For example, and as shown, driveshaft 880 can comprise or define, at a distal end of the driveshaft, a drive head 883 that comprises one or more (e.g., two) spurs 884 that are held in engagement with driver interface 716 by a lock-rod 886. That is, lock-rod 886 locks the engagement between drive head 883 and driver interface 716.

For some applications, and as shown by the transition from FIG. 32M to FIG. 32N, capsule 870 (e.g., rim 877 of shroud 876 of the capsule) is placed against the ventricular tissue prior to winch anchor 710 being advanced out of the capsule, such that at no time is tissue-engaging element 712 exposed from the capsule, thereby advantageously reducing a likelihood of ensnaring and/or injuring tissue.

Driving winch anchor 710 into the tissue advances the entire of downstream assembly 700 distally through capsule 870 toward the surface of the tissue. For applications in which capsule 870 (e.g., housing 872 thereof) defines elongate lateral opening 875 (described with reference to FIGS. 31A-B), as downstream assembly moves distally through the capsule, aperture 726, which typically protrudes from housing 872, protrudes into lateral opening 875 and moves axially along the lateral opening, rotationally restricted by the lateral opening. That is, lateral opening 875 can serve as a linear track along which winch 720 (e.g., housing 721 thereof) can slide as winch anchor 710 is driven into the tissue. Such a configuration allows capsule 870 to provide a reference force to winch housing 721 continuously throughout the anchoring of anchor 710, such that the winch housing does not rotate along with the anchor. (Such rotation of the housing might otherwise deleteriously wrap tether 560 about tool 800, e.g., shaft 810 thereof.) For applications in which capsule 870 comprises shroud 876, as downstream assembly moves distally through the capsule, tether 560 enters slit 878 from window 874, and extends from aperture 726 out of progressively more downstream parts of slit 878. Depending on the extent to which aperture 726 protrudes from housing 872, the aperture can transiently separate shroud 876 at slit 878 as it moves along the lateral opening 875 and the slit. FIG. 32N shows anchor 710 fully anchored, with aperture 726 separating shroud 876 at a part of slit 878 close to the open distal end of the capsule, and tether 560 extending therefrom.

Once winch anchor 710 has been anchored, the effective length of tether 560 (i.e., the length of the tether between winch 720 and patch 610) can be adjusted in order to achieve optimal hemodynamics, e.g., minimal regurgitation between the leaflets of valve 7. Although patch 610 itself is a leaflet-augmenting patch that itself may improve coaptation between the leaflets by providing a surrogate coaptation surface, it is hypothesized that tether 560—especially when of an optimal length—can further improve coaptation, e.g., by directing and/or limiting movement of the patch, and the leaflet to which it is anchored, during the heart cycle. This length adjustment can be achieved by operating a winch controller 519 at proximal portion 802.

In some applications, prior to the length adjustment, most of tool 800 is withdrawn out of ventricle, e.g., out of the heart, and/or out of the body of the subject entirely (FIG. 32O). Such withdrawal primarily consists of withdrawing shaft 810, to which mount 840, clasp 830, and capsule 870 remain attached. This leaves behind a driveshaft subassembly 890 of tool 800 extending through valve 7 to downstream assembly 700, to which it remains coupled. It is hypothesized that this advantageously facilitates accurate hemodynamic monitoring during adjustment of the effective length of tether 560 (described hereinbelow), due to driveshaft subassembly 890 typically being slimmer and/or more flexible than shaft 810, or tool 800 as a whole, thereby being less likely to create significant hemodynamic artifacts by (i) pressing on downstream assembly 700 and the ventricular tissue to which it is anchored, (ii) obstructing leaflet movement and coaptation, and/or (iii) directly obstructing or causing turbulence in blood flow. In this state, the leaflets of valve 7 can coapt around driveshaft subassembly 890.

For some applications, the length adjustment is performed while shaft 810 and capsule 870 remain in place.

Driveshaft subassembly 890 comprises at least one driveshaft, and often further comprises a reference-force tube 892, e.g., as described hereinbelow.

Winch controller 519 is operatively coupled to winch 720 such that operation of the winch controller actuates the winch (FIG. 34A). For example, delivery tool 800 (e.g., driveshaft subassembly 890 thereof) can comprise a winch-control driveshaft 882 that operatively couples winch controller 519 to winch 720. In some applications, and as shown, actuation of winch 720 is achieved by applying torque to the winch, e.g., via engagement between winch-control driveshaft 882 and winch 720. Winch 720 can comprise a driveshaft interface 724 that is defined by, is a component of, or is fixedly coupled to, spool 722 of the winch. Driveshaft 882 engages driveshaft interface 724 and applies torque to the driveshaft interface via this engagement. For example, and as shown, driveshaft 882 can comprise or define, at a distal end of the driveshaft, a drive head 885 that comprises one or more (e.g., two) projections 888 that extend into recesses defined by interface 724, e.g., the torque can be applied to spool 722 via these projections. This engagement can be maintained indirectly via the locking, by lock-rod 886, between drive head 883 and driver interface 716, e.g., due to preloading between driveshafts 880 and 882. For example, irrespective of advancement of tool 800 through the vasculature, and throughout steps of the implantation procedure, driveshaft 880 can be kept under a limited amount of tension while driveshaft 882 can be kept under a limited amount of axial compression.

A reference force tube 892 is also engaged with downstream assembly 700. As shown, this engagement can be with housing 721. For example, reference force tube 892 (e.g., a distal end thereof) and housing 721 can comprise or define complimentary couplings (e.g., mating surfaces) 894 and 731, respectively. Downstream assembly 700 (e.g., housing 721 thereof) can therefore be considered to comprise or define a reference-force-tube interface 732 that comprises one or more couplings (e.g., mating surfaces) 731, reference force tube 892 engaging the reference-force-tube interface. The engagement between reference force tube 892 and reference-force-tube interface 732 can rotationally lock the reference force tube to the reference-force-tube interface, allowing the reference force tube to provide a reference force during rotation of winch 720. Inter alia, this rotational locking and reference force facilitate rotation of spool 722 without rotation of housing 721 (or revolution of aperture 726 about axis ax2), which is hypothesized to be advantageous due to the presence of tether 860 extending between downstream assembly 700 and upstream assembly 600. For example, were housing 721 to revolve during rotation of spool 722, tether 560 might become wrapped around driveshaft subassembly 890.

For some applications, the engagement between reference force tube 892 and housing 721 can be maintained indirectly via the locking, by lock-rod 886, between drive head 883 and driver interface 716, e.g., due to preloading between driveshaft 880 and reference force tube 892. For example, irrespective of advancement of tool 800 through the vasculature, and throughout steps of the implantation procedure, driveshaft 880 can be kept under a limited amount of tension while reference force tube 892 can be kept under a limited amount of axial compression.

FIG. 32P shows tether 560 after its length has been adjusted. This is represented by tether 560 appearing slack in FIG. 32O and taut in FIG. 32P, although it is to be understood that this is schematic and is not intended to be limiting with respect to the adjustment of the length of the tether.

Once an optimal effective length of tether 560 has been achieved, driveshaft subassembly 890 is disengaged from downstream assembly 700, and thereby from implant 550 as a whole (FIGS. 32Q, and FIGS. 34B-C). For example, and as shown, lock-rod 886 can be withdrawn at least sufficiently to allow disengagement of driveshaft 880 from interface 716 via medial deflection of spurs 884 (FIG. 34B). Once disengaged, driveshaft 880, and driveshaft subassembly 890 as a whole, can be withdrawn from downstream assembly 700 (FIG. 34C). Upon this withdrawal of driveshaft subassembly 890 from downstream assembly 700, and more specifically upon withdrawal of winch-control driveshaft 882 (e.g., projections 888 thereof) from winch 720 of the downstream assembly, one or more spring-loaded detents 728 can responsively move to engage housing 721 in a manner that locks spool 722 from rotating with respect to the housing (i.e., locks winch 720) such that tension on tether 560 cannot unspool the tether, thereby fixing the effective length of the tether. For some applications, winch 720 comprises a number of detents 728 that is equal to the number of projections 888, each of the projections retaining a respective one of the detents from engaging housing 721 until the projection is withdrawn.

For some applications, and as shown, this movement of detents 728 is a medial movement. For some applications, housing 721 defines a set of ridges 730 between which detents 728 can become disposed (and/or recesses into which the detents can become disposed) upon withdrawal of driveshaft 882.

For some applications, housing 721 comprises at least two subcomponents that are secured to each other during manufacture, such as a first subcomponent (e.g., an annular or circumferential subcomponent) 721*a* and a second subcomponent (e.g., a lid subcomponent) 721*b*. For some such applications, and as shown, ridges 730 are defined by second subcomponent 721*b*. For some such applications, reference-force-tube interface 732 is defined by second subcomponent 721*b*.

For some applications, within downstream assembly 700, tissue-engaging element 712, head 714, and driver interface 716 are rotationally fixed with respect to each other and are collectively rotatably coupled to housing 721 and to spool 722.

For some applications, within downstream assembly 700, detents 728 (e.g., a frame defining the detents) are, even while unlocked by the presence of driveshaft 882, rotationally fixed with respect to spool 722, e.g., (i) via one or more tongues 729 defined by the frame that defines the detents being disposed in one or more recesses 723 defined in spool 722 (or vice versa), and/or (ii) due to detents 728 being disposed in slots 725 defined by the spool.

For some applications, within downstream assembly 700, spool 722 is rotatably coupled to housing 721, except when detents 728, which are rotationally fixed with respect to the spool, lock to the housing.

Slots 725 can also provide space for detents 728 to deflect between their unlocked and locked states.

For some applications, and as shown, downstream assembly 700 can comprise a hub 717 or axle on which spool 722 and detents 728 (e.g., a frame defining the detents) are mounted, providing at least some of the rotatable couplings described hereinabove.

For some applications, housing 721 is mounted to be rotatable (e.g., freely rotatable) with respect to anchor 710. It is hypothesized that this can advantageously allow the housing to naturally find a rotational orientation in which lateral aperture 726 is optimally positioned, e.g., in response to movement and tension of tether 560.

Figure 35A:
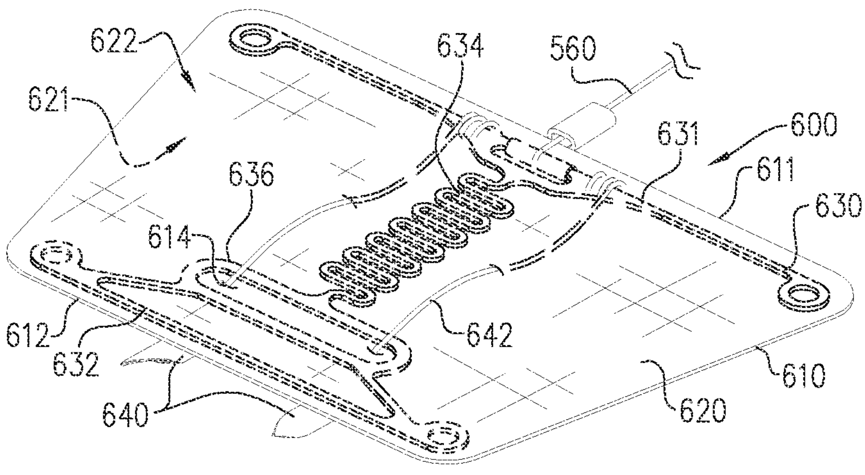
FIGS. 35A-B are schematic illustration of an upstream assembly, in accordance with some applications.
Figure 35A:
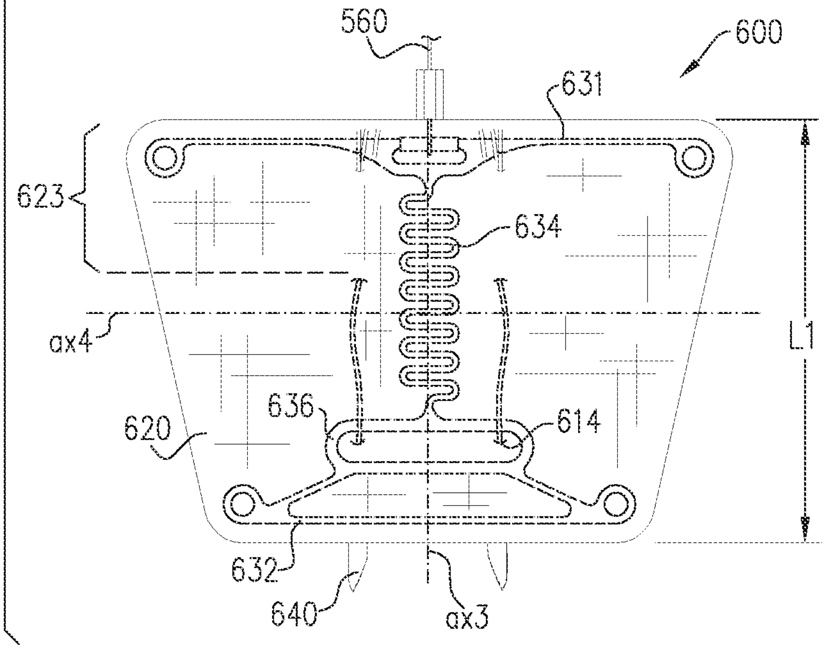
Figure 35B:
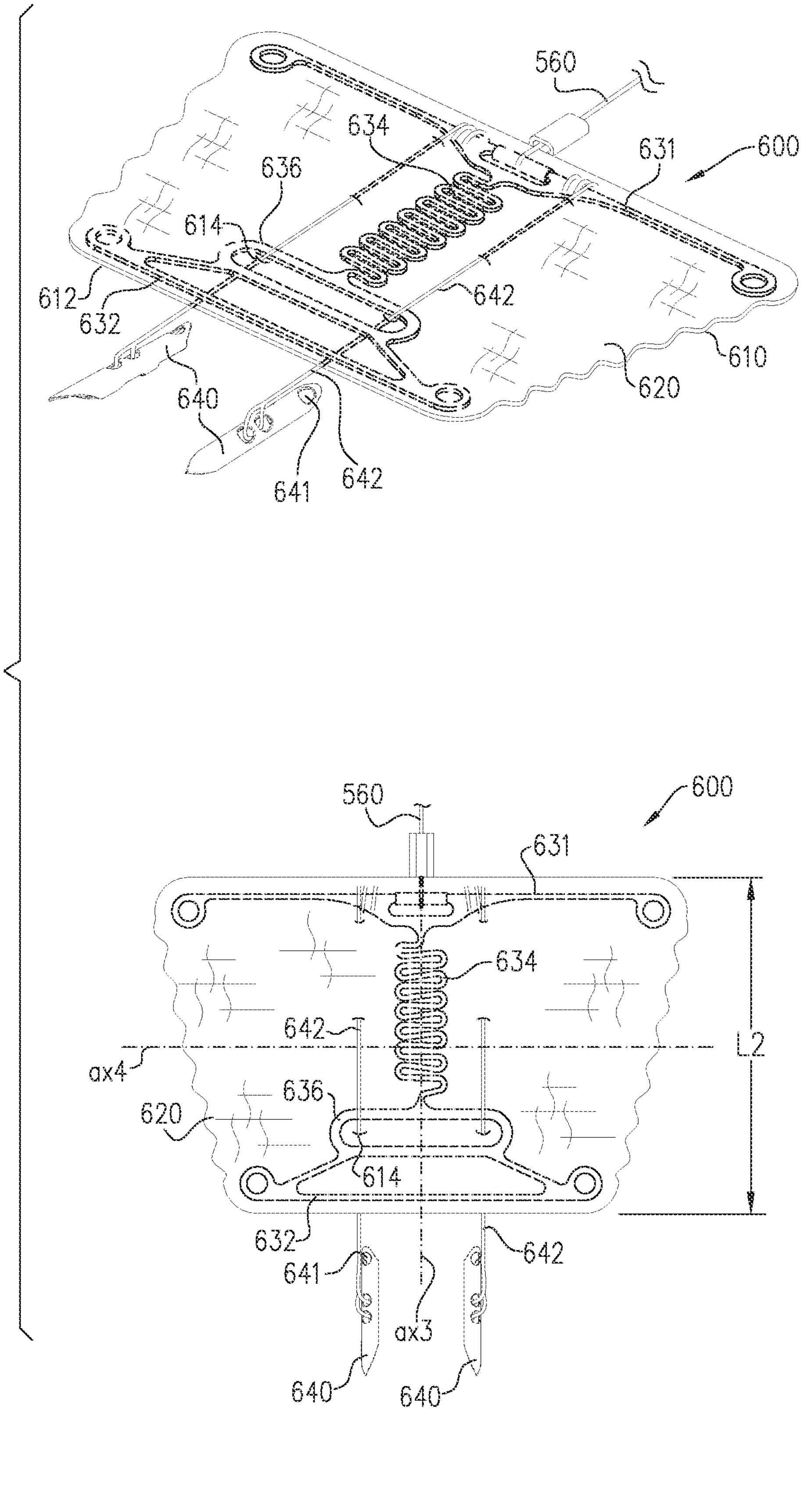

Reference is now made to FIGS. 35A-B, which are schematic illustration of an upstream assembly 600, in accordance with some applications. As described hereinabove, patch 610 can comprise a flexible sheet 620 and at least one frame 630 supporting the sheet. As further described hereinabove, upstream assembly 600 can be provided with at least one patch anchor 640 coupled to patch 610.

Frame 630 supports sheet 620, thereby providing patch 610 with a shape. However, frame 630 can be flexible, such that patch 610 can be responsive to conditions in the heart, e.g., to the shape of one or both leaflets, in order to facilitate optimal coaptation. For some applications, frame 630 (and thereby patch 610) is configured to be more flexible on one axis than on another axis. For example, frame 630 can provide greater flexibility along a root-to-lip axis ax3 of patch 610 (e.g., with lip 611 moving with respect to root 612), than along a mediolateral axis ax4 of the patch, transverse to the root-to-lip axis (e.g., with one lateral edge 613 moving with respect to the other lateral edge). This higher mediolateral rigidity can facilitate patch 610 opening upon release from wraps 842, and/or can advantageously inhibit the patch from folding in on itself after implantation. This characteristic of root-to-lip flexibility being greater than mediolateral flexibility is also shared by other patches described hereinbelow (which, for some applications, can be considered variants of patch 610).

Frame 630 can comprise a root brace 632, which can comprise a beam that extends along root 612, e.g., from one lateral edge 613 to the other. Frame 630 can also define a lip brace 631, which can comprise a beam that extends substantially along lip 611, e.g., from one lateral edge 613 to the other. Lip brace 631 and root brace 632 can provide patch 610 with a degree of mediolateral rigidity, e.g., as described in the preceding paragraph.

Frame 630 comprises a spring 634, which can run between lip brace 631 and root brace 632. In the example shown, spring 634 runs substantially along a root-to-lip midline of patch 610 (e.g., along axis ax3, if axis ax3 is a central root-to-lip axis).

Spring 634 can provide the root-to-lip flexibility described hereinabove. However, spring 634 also provides patch-anchor tightening functionality, which is also a feature of several other patches described hereinbelow.

FIG. 35A shows face-on and isometric views of patch 610 in a resting state thereof, e.g., prior to loading onto delivery tool 800. For some applications, other than the curvature of patch 610 around mount 840 and shaft 810 while loaded on delivery tool 800, FIG. 35A can also represent the state of the patch during the initial stages of delivery.

As described hereinabove, cords 642 couple patch anchors 640 to patch 610. For example, and as shown, each patch anchor can be coupled to the patch by a respective cord. However, rather than each cord 642 being secured to patch 610 (e.g., frame 630 thereof) close to a point 614 at which the cord reaches the patch, the cord passes through the patch at point 614, and extends along the patch (e.g., in a root-to-lip direction, such as substantially parallel with axis ax3) to lip brace 631, to which it is secured.

For some applications, and as shown, at point 614 cord 642 passes through patch 610 (e.g., sheet 620 thereof), from a contact face 621 of the patch (i.e., the face that is placed against leaflet 10 when the patch is anchored to leaflet 10) to an opposing face 622 of the patch. For some such applications, and as shown, from point 614 cord 642 extends alongside opposing face 622 partway to lip 611, passes back through patch 610, and from there extends alongside contact face 621 to lip brace 631. Thus, cord 642 is slidably coupled to patch 610 at point 614, which can be at or proximate to root 612, and is fixedly attached to the patch at lip brace 631, which can be at or proximate to lip 611.

By cord 642 extending back through the patch to opposing face 622 partway along the patch, the cord is absent from opposing face 622 within a region 623 of the opposing face closest to lip 611 (e.g., a region between the lip and the point at which the cord extends back through the patch), thereby making region 623 smooth. Region 623 can therefore be referred to as a smooth region of opposing face 622. It is hypothesized that this smoothness can be advantageous inter alia in creating optimal coaptation between the patch and the opposing leaflet.

In FIG. 35A, cords 642 are shown as relatively slack. As patch anchors 640 are driven through to the far (e.g., downstream) side of leaflet 10 by drivers 850 (e.g., as described hereinabove with reference to FIGS. 32J-K), the patch anchors are pushed away from patch 610, which remains on the near (e.g., upstream) side of the leaflet. This tensions cords 642, which thus pull lip brace 631 toward root brace 632, placing spring 634 under stress (FIG. 35B). This is represented in FIGS. 35A-B by linear compression of spring 634 and patch 610, temporarily reducing a root-to-lip length L1 of the patch (FIG. 35A) to a reduced length L2 (FIG. 35B), i.e., linearly contracting the patch. Upon the release of patch anchors 640 from drivers 850, spring 634 returns toward its original (e.g., resting) state, pulling the patch anchors back toward patch 610, and thereby securing the patch to the leaflet by sandwiching the leaflet between the patch anchors and the patch, e.g., as illustrated by the transition from FIGS. 32K and 35B to FIGS. 32L and 35A. It is hypothesized that providing the upstream assembly with self-tightening patch anchors such as these (e.g., by including the patch with a spring that is biased to draws the patch anchors tight) can advantageously obviate a need for a discrete tightening or locking step to be performed, and/or for a discrete locking component to be included.

For some applications, and as shown, frame 630 defines at least one patch-anchor support 636, which can be positioned and shaped to partially or completely surround point 614. For some applications, and as shown, spring 634 can be coupled to root brace 632 via patch-anchor support 636. Patch-anchor support 636 can advantageously provide one or more of the following benefits: (1) to serve to reinforce the patch at point 614, e.g., to protect against cord 642 cutting through sheet 620; (2) to serve as a bearing surface over which cord 642 slides as it moves through point 614; and/or (3) to provide opposition (e.g., an opposing force) against which patch anchors 640 can press the leaflet, thereby improving sandwiching of the leaflet between the patch anchors and patch 610, e.g., compared to a similar patch in which the patch anchors press the leaflet against part of the patch in which sheet 620 is not supported by frame 630.

As described hereinabove, the tether that tethers the upstream assembly to the downstream assembly can be attached to a lip region of the patch. For applications in which the patch comprises a frame that defines a lip brace, the tether can be attached to the lip brace. As shown in FIGS. 35A-B, for patch 610 tether 560 is attached to lip brace 631 (e.g., to an eyelet defined by the lip brace), at the middle of lip 611. It is to be noted that, although tether 560 and cords 642 are both attached to lip brace 631, they act at least partly independently, e.g., with spring 634 tensioning cords 642 irrespective of tension on the lip brace. Furthermore, lip brace 631 can be configured to distribute at least some of the force exerted on patch 610 by tether 560 (e.g., during ventricular systole) across the width of the patch. Nonetheless, the finite length of cords 642 can limit the degree to which such force is experienced by patch 610 itself (e.g., by sheet 620), e.g., preventing the patch from being stretched deleteriously. That is, once cord 642 pulls its patch anchor tight against the leaflet, firmly sandwiching the leaflet against contact face 621 of patch 610, the cord inhibits further distancing of lip brace 631 from root brace 632.

Reference is now made to FIGS. 36A-K, and 37A-G which are schematic illustrations of various patches (e.g., leaflet-augmentation patches), in accordance with some applications. Each of these patches can be used in place of patch 610, mutatis mutandis, e.g., as a component of implant 550 or an implant similar thereto, mutatis mutandis. For some applications, each of these patches can be considered to be a variant of patch 610. Furthermore, delivery tool 800 or a variant thereof, mutatis mutandis, can be used to implant such an implant using techniques described herein, mutatis mutandis. Each of these patches has been assigned reference numeral 610 with a respective suffix, to indicate its correspondence to patch 610.

Figure 36A:
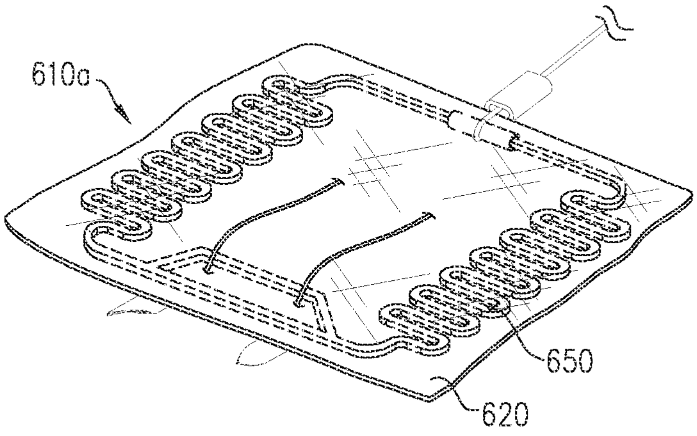

FIG. 36A shows a patch 610*a* whose frame defines two springs 650, one running along each lateral side of the patch, (i.e., two lateral springs) in contrast to the single spring 634 running along the midline of patch 610 (i.e., a midline spring). In addition to providing anchoring-tightening functionality, it is hypothesized that lateral springs can further provide the patch with a shape and/or bias the patch to be unfolded and open. Patch 610*a* is substantially rectangular (e.g., its lip and root are substantially equal in length)—and it is to be noted that the scope of the disclosure includes any other of the patches described herein being modified to be rectangular.

Figure 36B:
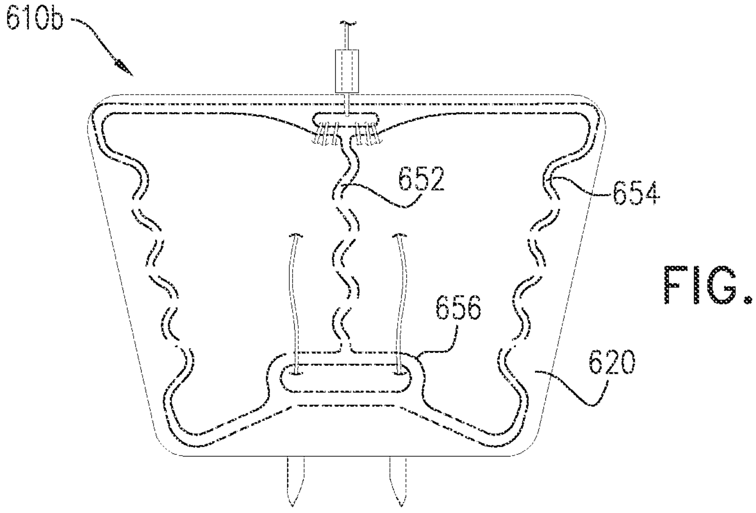

FIG. 36B shows a patch 610*b* whose frame defines both a midline spring 652 (which can be identical or different to spring 634) and two lateral springs 654 (which can be identical or different to springs 650). Midline spring 652 can be connected to the root brace via a patch-anchor support 656 (e.g., as described for patch 610, mutatis mutandis), whereas the lateral springs are connected to the root brace directly.

Figure 36C:
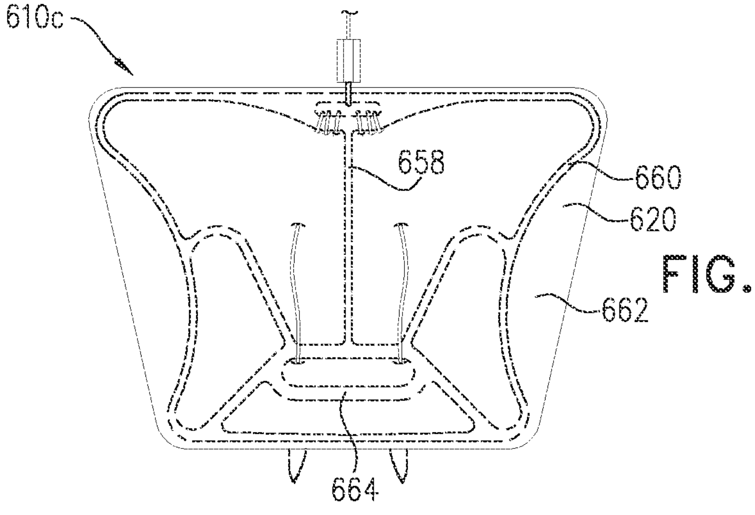

FIG. 36C shows a patch 610*c* whose frame defines a midline strut 658 and two lateral struts 660. For some applications, the lateral struts and/or midline strut can serve as springs, e.g., as described for spring 634 of patch 610, mutatis mutandis. Midline strut 658 can be connected to the root brace via a patch-anchor support 664, whereas lateral struts 660 can be connected to the root brace directly. However, for some applications, the frame of patch 610*c* also defines connecting struts 662 that connect patch-anchor support 664 to partway along lateral struts 660.

Figure 36D:
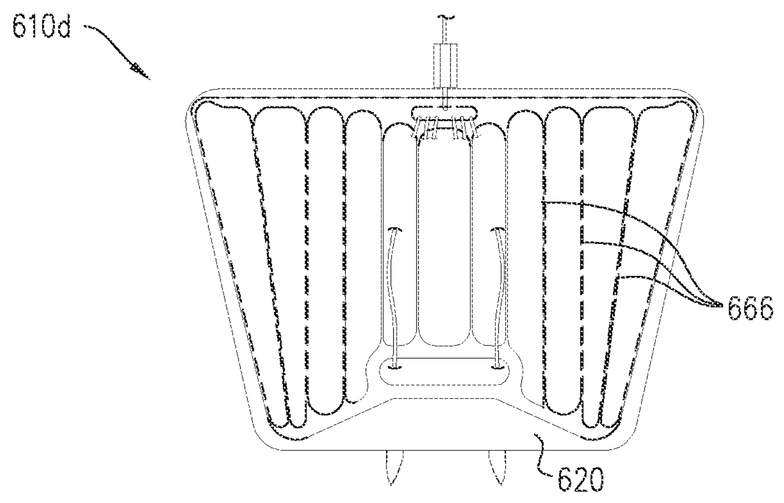

FIG. 36D shows a patch 610*d* whose frame defines a plurality of struts 666 (e.g., 6-15 struts, e.g., 8-14 struts, e.g., 10-12 struts, e.g., exactly 12 struts), extending between the lip brace and the root brace of the patch, either directly or via a patch-anchor support of the frame. For some applications, the struts can serve as springs, e.g., as described for spring 634 of patch 610, mutatis mutandis.

While the midline spring of patch 610, the lateral springs of patch 610*a*, and the midline and lateral springs of patch 610*b* can be serpentine springs, for applications in which the struts of patches 610*c* and 610*d* serve as springs, each of these struts can behave like a bow or a cantilever spring bending in response to being axially compressed from both ends.

Figure 36E:
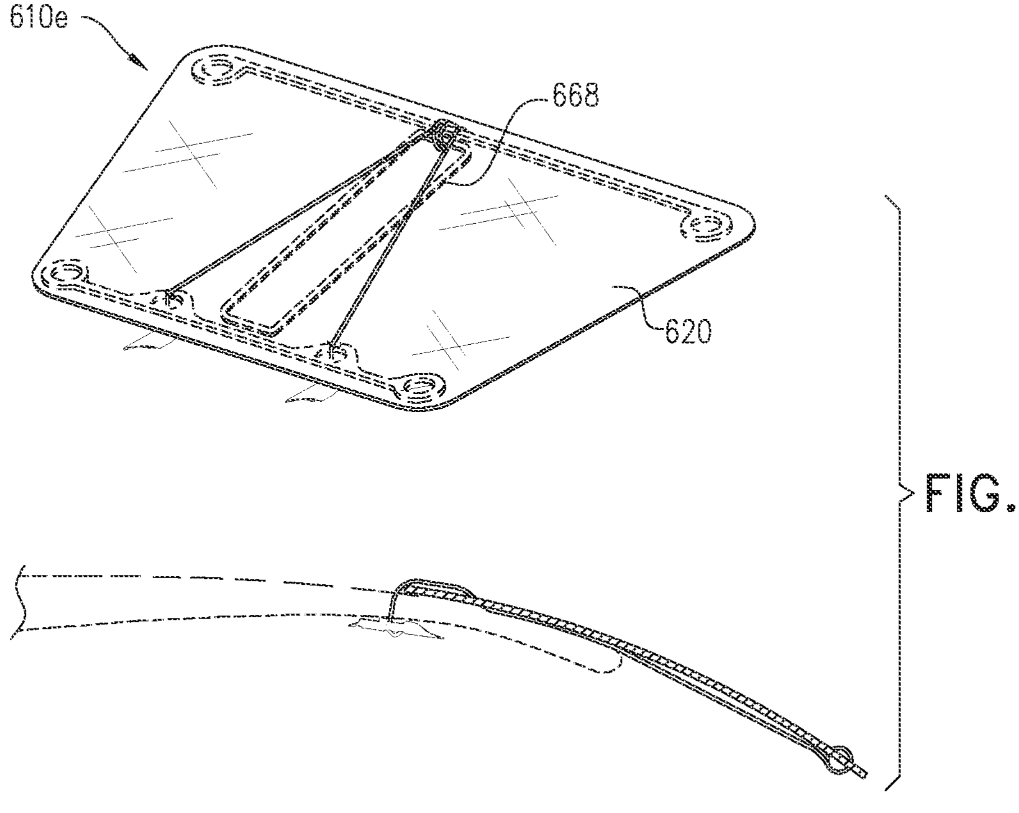

FIG. 36E shows a patch 610*e* whose frame structure can be provided as multiple discrete frame components. A midline spring 668 is shown as a generally rectangular frame component, but can take the shape of any of the other springs described herein, or any other shape suitable for its function. Spring 668 is, in effect, coupled to the other frame components (which define the lip brace and the root brace of the patch) via the sheet of the patch.

Patch 610*e* has a different anchor and cord arrangement than some other patches described herein. Rather than passing though the sheet of the patch twice (once at point 614 or the equivalent thereof, and once partway between there and the lip of the patch), the cords of patch 610*e* pass primarily alongside the contact face of the patch (which, in the upper image of FIG. 36E is facing upward), passing through the patch only once, to the opposing face, close to the root of the patch. To reach the leaflet, rather than passing through the patch a second time, the cords extend around the root of the patch. It is hypothesized that this arrangement can advantageously provide a larger smooth region on the opposing face of the patch, compared to other arrangements described hereinabove.

It is to be noted that patch 610*e* also differs from patch 610 and patches 610*a-d* in that, rather than having two cords that extend in parallel with each other, the cords of patch 610 converge toward each other as they approach the lip of the patch, and are attached to the lip brace close to each other.

It is to be noted that the scope of the present disclosure includes applying one or more of the features of the arrangements of the cords of patch 610*e* to the other patches described herein, mutatis mutandis.

Figure 36F:
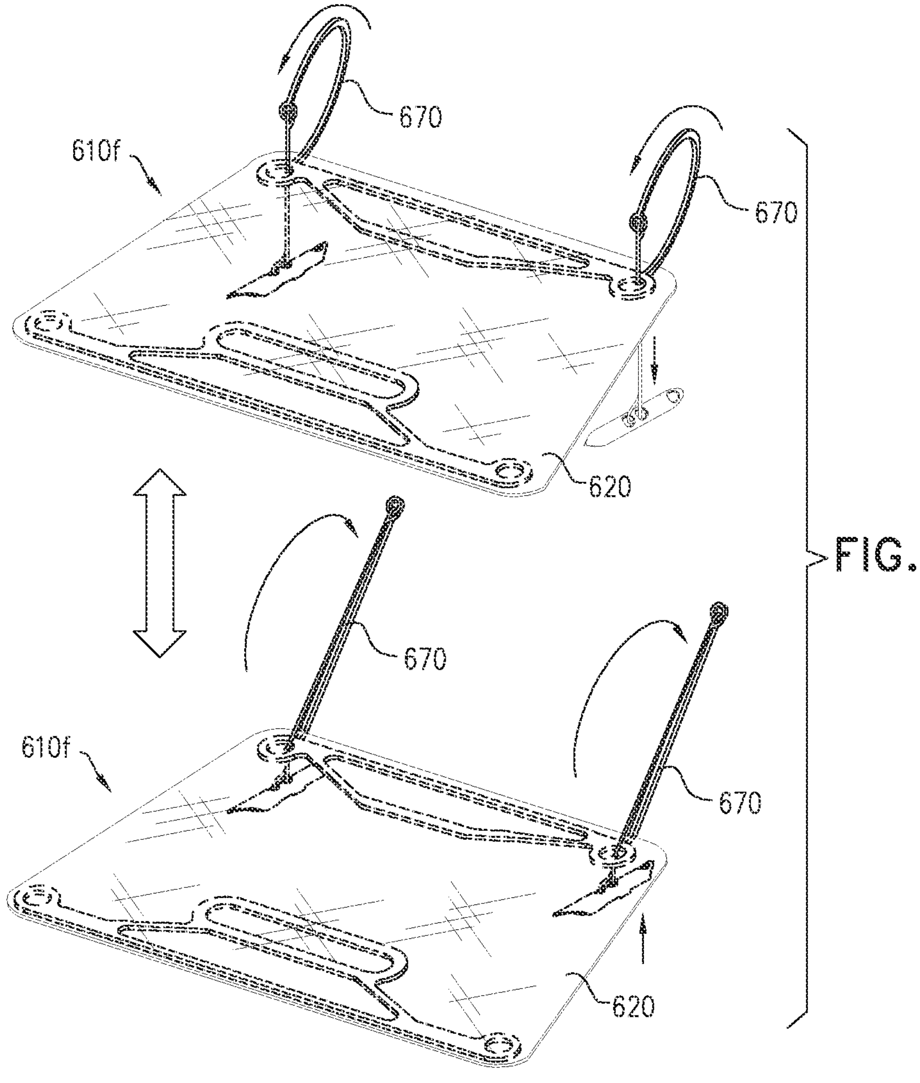

FIG. 36F shows a patch 610*f* in two states. Patch 610*f* (e.g., a frame thereof) comprises one or more springs 670 that provide anchor/cord-tightening functionality similarly to that described for springs of other patches described hereinabove. However, unlike other springs described herein (e.g., spring 634 and spring 674) springs 670 (and typically also the cords of the patch) extend beyond the sheet of the patch, and/or extend out of the plane of the patch. It is hypothesized that, for at least some applications, the resulting vector of the cords is more similar (than that of cords of other patches described herein) to the vector in which the patch anchors move during anchoring, and may therefore advantageously reduce rubbing of the cord on the sheet and/or frame of the patch.

It is to be noted that the frame and cord arrangement of patch 610*f* also differs in another respect from that of other patches described herein. The frame (e.g., springs and/or struts thereof) of other frames described hereinabove extend substantially from the root to the lip of the patch. This can subject the springs and/or struts to tradeoffs between (i) characteristics beneficial to tightening of the patch anchors (e.g., strong spring force) and (ii) characteristics beneficial to the behavior of the patch once implanted (e.g., flexibility and compliance with the leaflets). In contrast, the frame of patch 610*f* is disposed entirely in the vicinity of the root of the patch, i.e., at the end of the patch at which the patch anchors are disposed. Thus, regions of the patch closer to the lip, which are the regions that typically contact the opposing leaflet, can be optimized solely for characteristics beneficial therefore, e.g., without taking into account requirements for patch anchor tightening.

For some applications, patch 610*f* comprises an additional frame in the vicinity of the lip of the patch, defining a lip brace. However, even for such applications, patch 610*f* can be absent of frame components between the frame at the root and the lip brace, enabling the patch to be highly flexible despite the potential for springs 670 to be strong.

Another feature of note of patch 610*f* is that the length of tether that is (or can be) taken up by spring 670 is, compared to patches 610 and 610*a-e*, more independent of the length of the patch. That is, for patches 610 and 610*a-e*, the length of the patch decreases as the anchors are pushed away from the patch and through the leaflet. This decrease in patch length can be proportional (and perhaps equal) to the distance by which the patch anchors are be pushed away from the patch. Furthermore, for some applications, the overall nature of a given patch can mechanically limit the amount by which its patch length can be decreased, and can therefore limit the distance by which the patch anchors can be pushed away from the patch. The increased independence between tether-length take-up and patch dimensions that is characteristic of patch 610*f* is hypothesized to advantageously allow tether-length take-up to be optimized without tradeoffs with patch dimensions. The potentially advantageous characteristics of patch 610*f* described in this paragraph also apply, mutatis mutandis, to patches 610*g*-*k*, described hereinbelow.

Figure 36G:
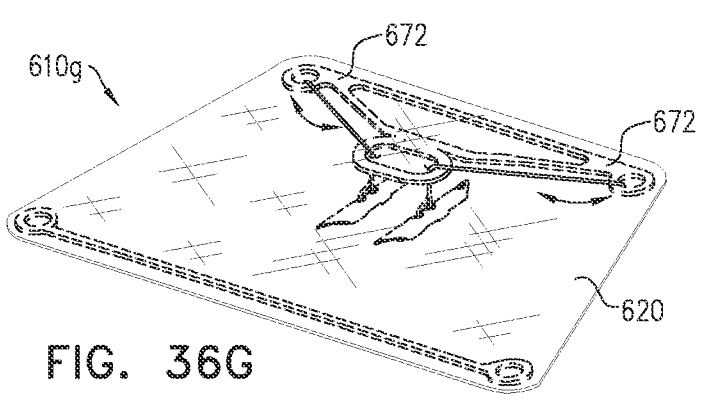

FIG. 36G shows a patch 610*g* which, similarly to patch 610*f*, comprises anchor/cord-tightening springs that do not extend across to the lip of the patch, and which are substantially independent of the length of the patch. However, in contrast to the protruding springs of patch 610*f*, springs 672 of patch 610*g* are disposed within the patch. More specifically, springs 672 are defined by the root brace of the patch. Cords 642 extend diagonally across the patch toward the lateral edges and root of the patch to their attachment sites on springs 672. At rest, these attachment sites can be at the lateral edges of patch 610*g*. For example, and as shown, these attachment sites can be at the lateral extremities of the root of the patch.

Springs 672 are configured to elastically deflect medially and toward the lip of the patch in response to the tensioning of cords 642 upon the pushing of the patch anchors away from the patch, and to subsequently pull in the opposite direction so as to tighten the anchors against the leaflet, e.g., as indicated by the double-headed arrows.

Figure 36H:
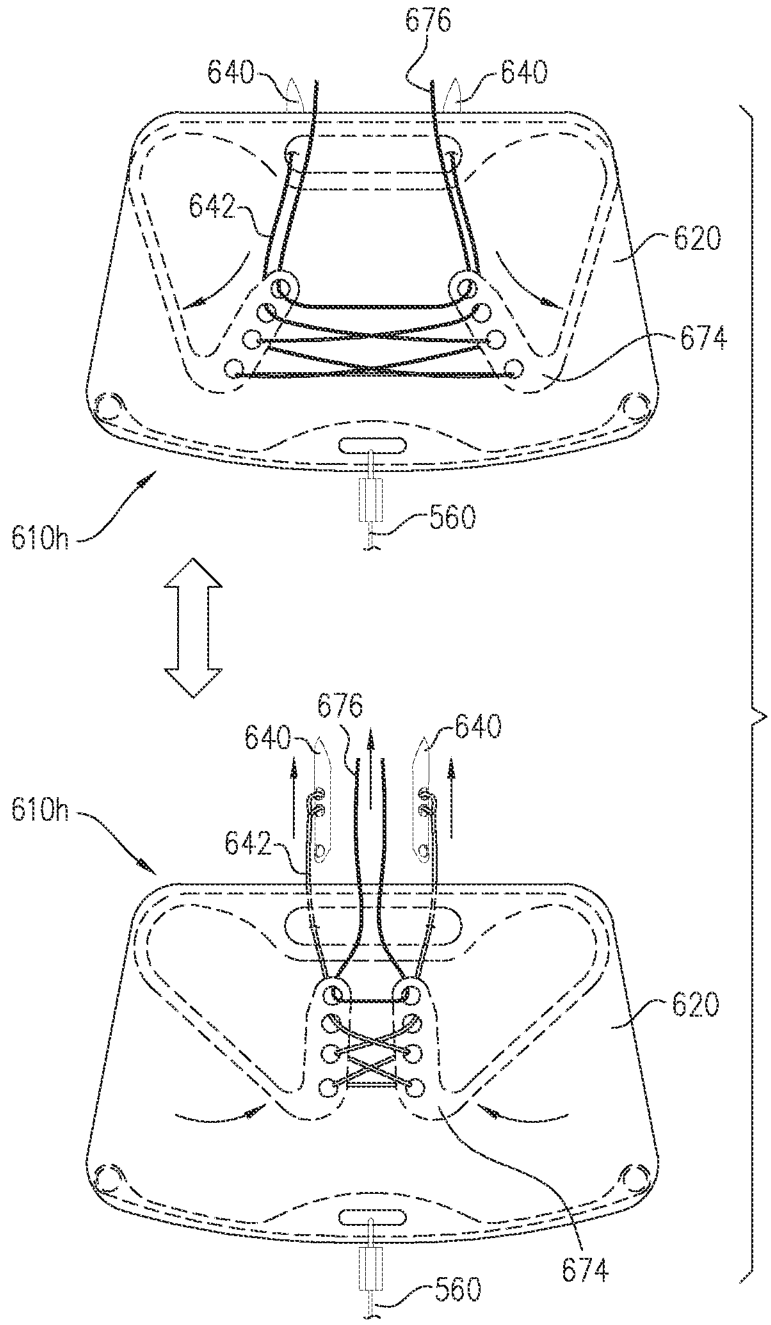

FIG. 36H shows a patch 610*h* that comprises springs 674 which, similarly to springs 672 of patch 610*f*, do not extend across to the lip of the patch, are substantially independent of the length of the patch, and which are disposed within the patch. Also, similarly to springs 672, springs 674 are cantilever springs. Further similarly to springs 672, springs 674 are configured to elastically deflect medially in response to tensioning of cords 642 upon the pushing of the patch anchors away from the patch (lower image), and to subsequently pull in the opposite direction so as to tighten the anchors against the leaflet (upper image).

In patch 610*h*, each of cords 642 is coupled to both springs 674. In some applications, and as shown, each cord extends back-and-forth between springs 674, to which it is slidably coupled. For example, and as shown, cords can be threaded through eyelets defined by the springs, e.g., in a manner that resembles a shoelace. Each cord can extend to its respective patch anchor from a respective one of the springs. For each cord 642, an end of the cord can be fixed to one of the springs. In some applications, and as shown, both cords 642 can be defined by a single length of cord that extends from one patch anchor, through patch 610*h* and springs 674, and back out to the other patch anchor.

This back-and-forth arrangement of cords 642 of patch 610*h* multiplies the length of cord taken up by springs 674 relative to the distance that the springs move. For example, if the distance between springs 674 increases by x mm, the length of each cord taken up can be twice, three times, four times x, or more. It is hypothesized that this advantageously enables greater movement of the patch-anchors relative to the size of the patch.

For some applications, patch 610*h* (e.g., the upstream assembly that comprises the patch) is provided with a straining line 676, coupled to both of springs 674. For example, and as shown, straining line 676 be slidably coupled to both of the springs, e.g., by being looped through each of the springs, such as by being threaded through an eyelet of each of the springs. For applications in which patch 610*h* is provided with straining line 676, once the patch is disposed in the heart of the subject, the straining line extends back out of the heart (e.g., out of the subject). That is, a bight of the straining line is slidably coupled to both springs 674, while the ends of the straining line are disposed outside of the heart (e.g., outside of the subject). Tensioning straining line 676 (e.g., by pulling from outside of the subject) draws springs 674 together, stressing the springs. This this can be used to facilitate anchoring of patch 610*h*, such as by reducing the required pushing force required to be applied by drivers 850 to patch anchors 640, e.g., to overcome resistance from springs 674.

After patch 610*h* has been anchored, straining line 676 can be decoupled from the patch and removed from the body, e.g., by releasing one end and pulling on the other end, such that it unloops from springs 674.

Figure 36I:
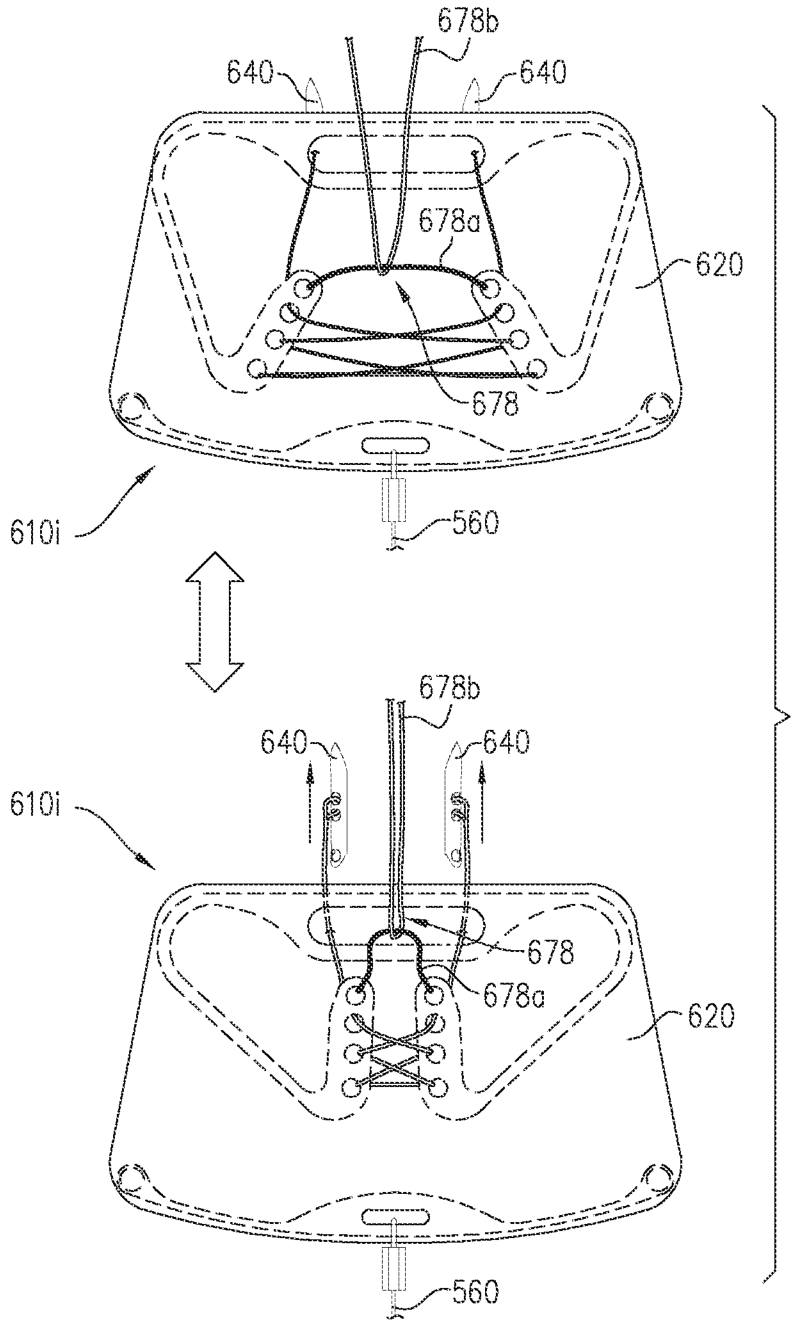

FIG. 36I shows a patch 610*i* that is identical to patch 610*h* except that it is provided with a straining line 678 that comprises two subcomponents: A first subcomponent 678*a*, each end of which is fixedly attached to a respective one of springs 674; and a second subcomponent 678*b* that is slidably coupled to subcomponent 676*a* (e.g., by being looped around subcomponent 676*a*).

Once patch 610*i* is disposed in the heart of the subject, subcomponent 678*b* extends back out of the heart (e.g., out of the subject). That is, a bight of subcomponent 678*b* is slidably coupled springs 674 by being slidably coupled to subcomponent 678*a*, while the ends of subcomponent 678*b* are disposed outside of the heart (e.g., outside of the subject). Tensioning subcomponent 678*b* (e.g., by pulling from outside of the subject) draws springs 674 together by pulling on subcomponent 678*a*.

Straining line 678 of patch 610*i* can be used in generally the same manner and for the same purpose as straining line 676 of patch 610*h*.

After patch 610*i* has been anchored, subcomponent 678*b* can be decoupled from the patch and removed from the body, e.g., by releasing one end and pulling on the other end, such that it unloops from subcomponent 678*a*. Subcomponent 678*a* remains behind as part of patch 610*i*.

Figure 36J:
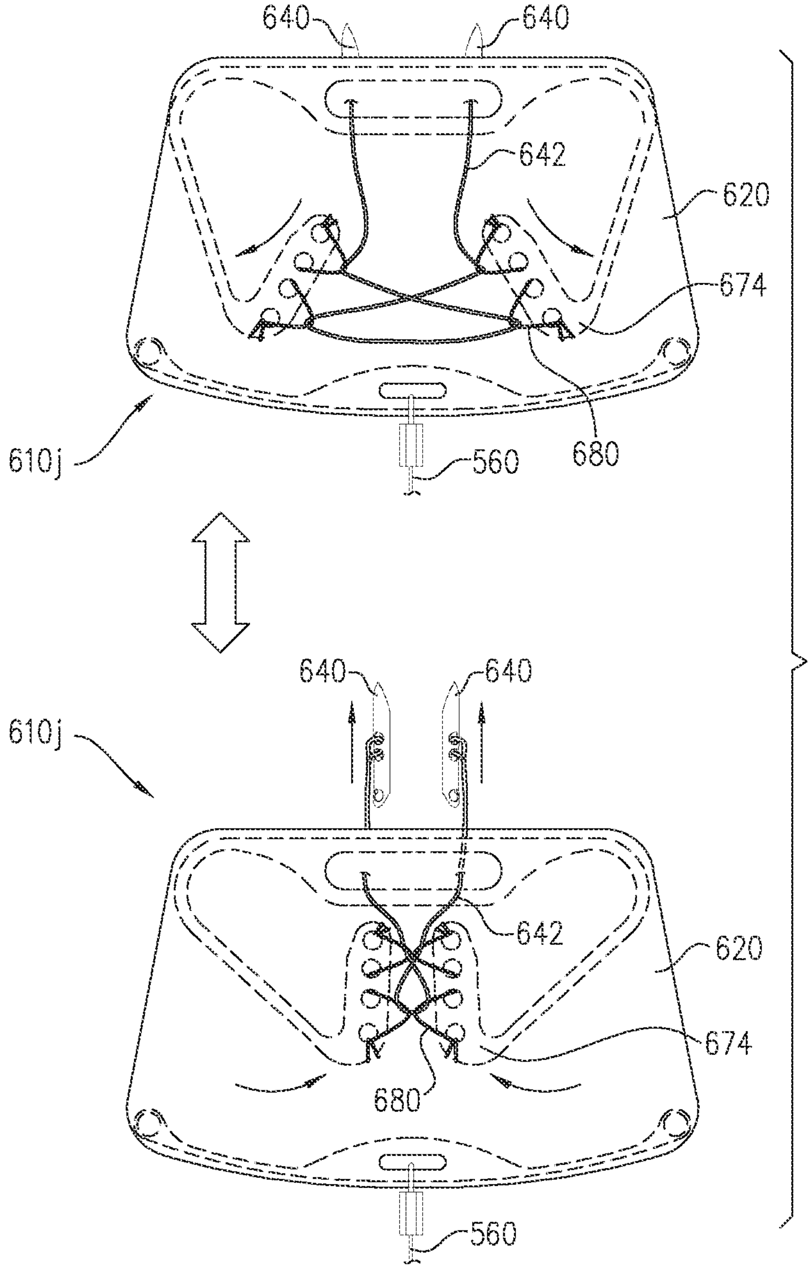

FIG. 36J shows a patch 610*j*, which is identical to patch 610*h* except that, rather than cords 642 being slidably coupled to springs 674 directly, threads 680 are attached to the springs (e.g., by being secured to eyelets defined by the springs), and cords 642 are slidably coupled to the springs by being looped around bights of the threads. It is hypothesized that, for some applications, this may advantageously reduce friction between cords 642 and springs 674, thereby facilitating the tightening of the cords by the springs. Although not shown, patch 610*j* can be provided with a straining line such as straining line 676 or straining line 678, mutatis mutandis.

Figure 36K:
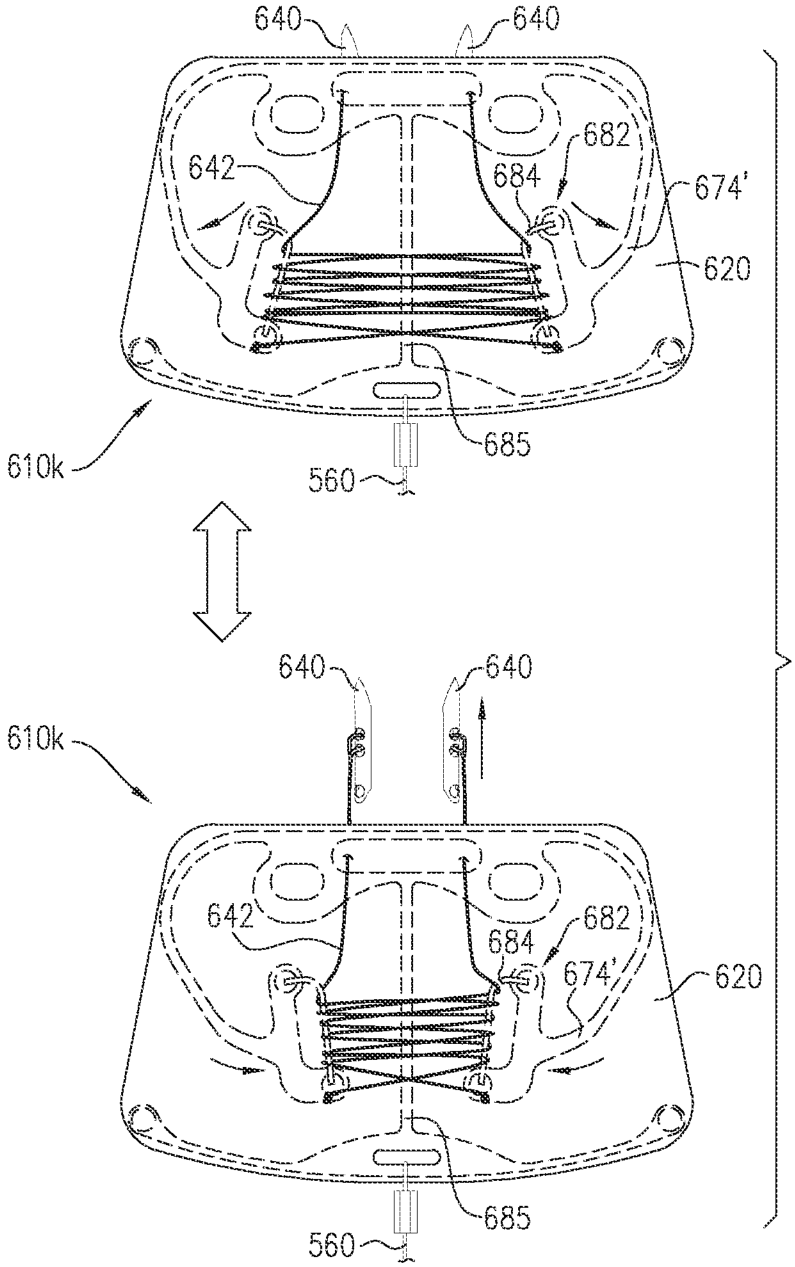

FIG. 36K shows a patch 610*k*, which is identical to patch 610*h* except that springs 674 have been replaced with a variant: springs 674'. Springs 674' are similar to, and perform the same role, as springs 674, but whereas springs 674 are shown as defining multiple eyelets (e.g., with one loop of cord 642 per eyelet), each springs 674' has a common connector region 682 at which both cords can be slidably coupled to the spring multiple times. For example, and as shown, connector region 682 can comprise a smooth bar 684 (or a flexible tie in the same position) about which both cords are looped multiple times. It is hypothesized that, for some applications, this configuration advantageously allows for smoother sliding of cords 642.

Another difference between of springs 674' and with springs 674 is their angle of deflection. Compared with springs 674, when springs 674' are drawn together by the tensioning of cords 642 resulting from pushing of the patch anchors, a larger proportion of their movement is in a medial direction and a smaller proportion of their movement is toward the root of the patch. In contrast, at least for some applications springs 674 can be describable as being articulated where they join the root brace, and their movement can thereby be more like a swing in a medial and root-ward direction.

Although not shown, patch 610*k* can be provided with a straining line such as straining line 676 or straining line 678, mutatis mutandis.

FIG. 36K also shows that, even for patches whose springs do not extend to the lip brace of the patch, the frame of the patch can include a midline strut 685 that extends from the root brace to the lip brace, e.g., to provide the patch with desirable mechanical properties.

As described hereinabove, the sheet of patch 610 (and variants thereof) can comprise two layered sheets, with the frame of the patch disposed therebetween. For some applications in which this is the case for patches 610 and 610*a-k*, each cord 642 can be disposed entirely between the layers of the sheets except for the part of the cord that extends away from the patch to its patch anchor.

Similarly, for some such applications the spring of these patches can be disposed between the layers of the sheets. For some applications in which the spring is disposed between the layers of the sheets, the spring functionality can be facilitated by the spring being free to move with respect to the sheet. Thus, although the root brace and the lip brace (when present) of each of patches 610 and 610*a-k* can be secured (e.g., stitched) to sheet 620 of the patch, the spring can be free to move (e.g., slide) between the layers of the sheet (or, for applications in which the sheet is a single-layer sheet, to move across the surface of the single layer).

While patches 610 and 610*a-k* comprise springs that provide patch-anchor tightening functionality, FIGS. 37A-G are schematic illustrations of patches 610*l-r*, which typically do not. It is to be noted that the shape of patches 610*l-r* (e.g., sheet 620 thereof) can be as shown in FIGS. 37A-G, or can be as shown for any of patches 610 and/or 610*a-k*, mutatis mutandis. Similarly, for some applications, patches 610 and 610*a-k* can be modified to the shape of any of patches 610*l-r*, mutatis mutandis.

Patches 610*l-r* are shown without patch anchors or cords for patch anchors. For some applications, patches l-r can nonetheless be provided with patch anchors secured to the patch via cords, e.g., as described hereinabove, mutatis mutandis. However, patches l-r can be provided without patch anchors secured via cords. For example, any of these patches can be provided with a different patch anchor secured thereto in a different way, e.g., as described hereinbelow with reference to FIGS. 43-50C. For some applications, patches l-r can be provided without any patch anchor secured thereto, and instead a patch anchor can be coupled to the patch during anchoring of the patch, e.g., as described hereinbelow with reference to FIGS. 51A-52B.

Furthermore, for the sake of simplicity, patches 610*l-r* are shown without tether 560 attached thereto. However, it is to be noted that for different applications tether 560 can be attached to different parts of the patch.

FIG. 37A shows a patch 610*l* which comprises a root brace and a lip brace, and no other frame elements therebetween. It is hypothesized that this provides patch 610*l* with flexibility particularly along its root-to-tip axis.

FIG. 37B shows a patch 610*m* which comprises lateral struts that can, as shown, each define a chevron whose apex extends medially across the patch. It is hypothesized that this provides patch 610*m* with flexibility particularly along its mediolateral axis, e.g., allowing the lateral sides of the patch to deflect with respect to each other, optionally while providing some rigidity to each of the lateral sides individually.

FIGS. 37C and 37D show patches 610*n* and 610*o*, which are similar to patch 610*m* except that the apices of the chevrons are hingedly coupled to each other, such that the chevrons can articulate with respect to each other. For example, and as shown, this hinged coupling can be achieved by the apices simply passing around each other (patch 610*n*) or looping around each other multiple times (patch 610*o*).

FIG. 37E shows a patch 610*p* whose frame is substantially X-shaped, with a central node and four arms extending from the central node toward the corners of the patch where the root and the lip meet the lateral sides.

FIG. 37F shows a patch 610*q*, which is similar to patch 610*p*, but with an additional two arms extending from its central node toward the lateral sides of the patch. Additionally, patch 610*q* comprises a perimeter frame element that circumscribes the perimeter of the patch. The arms of patch 610*q* can be hingedly coupled to this perimeter frame element.

FIG. 37G shows a patch 610*r* that comprises a spine 686, which can be along its midline. For some applications, spine 686 serves a similar role to one or more of the midline struts described hereinabove. However, spine 686 can be formed from a plurality of vertebrae, stacked in series.

Spine 686 provides patch 610*r* with compressive strength (i.e., resistance to crumpling along its root-to-tip axis), while allowing flexibility along its root-to-tip axis, e.g., similarly to the role of the spine of vertebrates. For some applications, and as shown, these vertebrae can be shaped to mate with each other, e.g., to resist lateral translation with respect to each other.

For some applications, and as shown, the vertebrae of spine 686 can be flexibly coupled to each other via a laminate 688 comprising two laminate layers between which the vertebrae are sandwiched. Laminate 688 can comprise a polymer and/or can be applied by heat treatment. Laminate 688 can be applied prior to the attachment of sheet 620.

Although patches 610*l-r* are shown as discrete examples, it is to be noted that the scope of the present disclosure includes combinations of the frame features of one or more of these patches with those of one or more other of these patches, or with those of one or more of patches 610 and 610*a-k*, mutatis mutandis.

Figure 38:
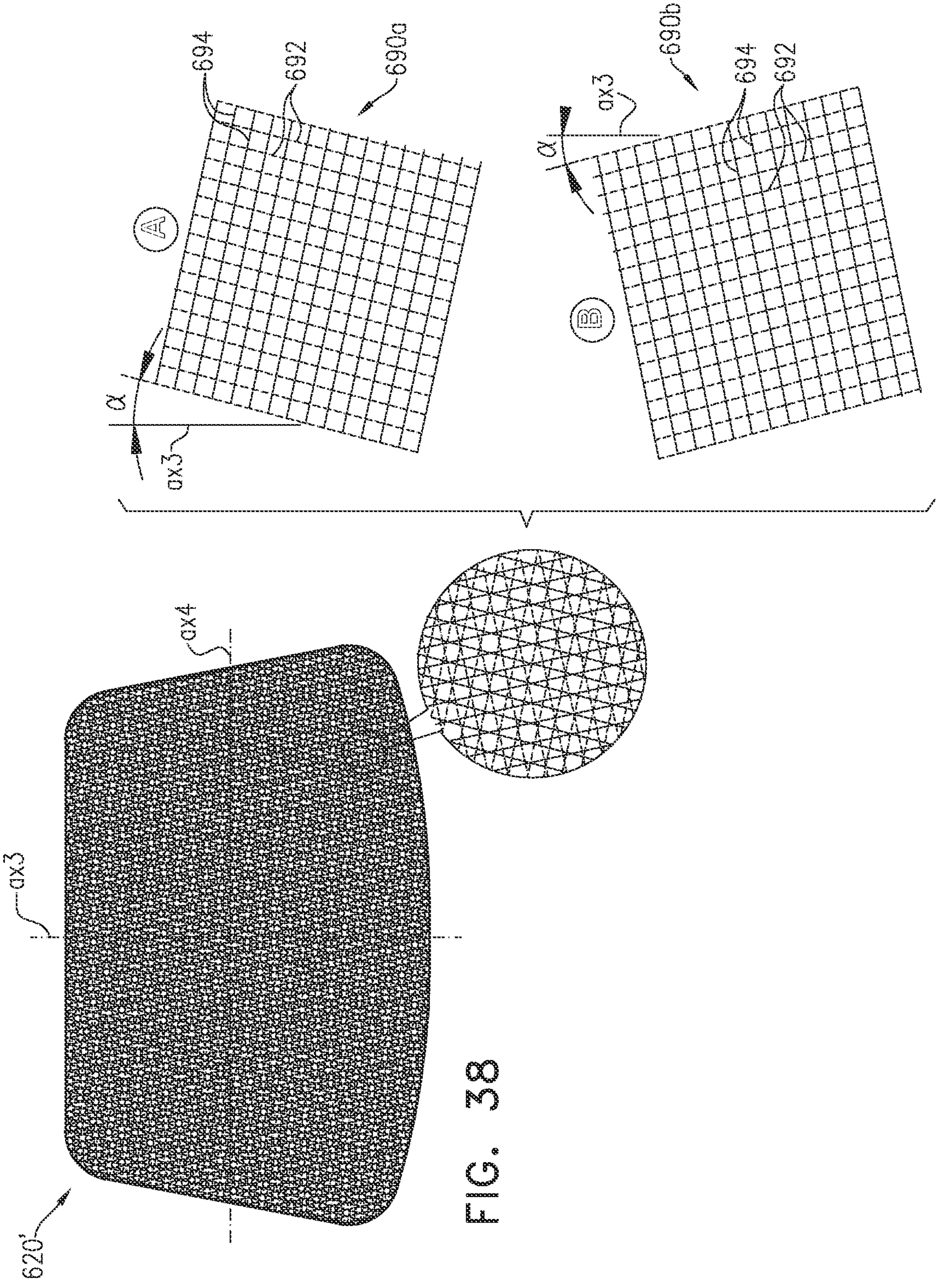
FIG. 38 is a schematic illustration of a sheet for a leaflet-augmentation patch, in accordance with some applications.

Reference is made to FIG. 38, which is a schematic illustration of a sheet 620' for a leaflet-augmentation patch such as patch 610, in accordance with some applications. As described hereinabove, frame 630 (and variants thereof) can provide patch 610 (and variants thereof) with structural characteristics, including having different flexibility in different regions. The nature of sheet 620 itself can also be modified to provide the patch with structural characteristics. Sheet 620' is anisotropic. Sheet 620' can be oriented within patch 610 to confer different flexibility on its root-to-lip axis ax3 (e.g., bending around its mediolateral axis ax4) than on its mediolateral axis (e.g., bending around its root-to-lip axis). For example, for some applications, it can be advantageous to confer on a patch greater flexibility on its root-to-lip axis ax3 (e.g., to facilitate curving downstream toward the ventricle during ventricular systole) and greater rigidity on its mediolateral axis ax4 (e.g., to prevent curling of its lateral edges medially). However, for other applications, it can be advantageous to confer greater flexibility on the mediolateral axis (e.g., to facilitate wrapping of the patch around the delivery tool for delivery).

Sheet 620' can be considered a variant of sheet 620 and can be used in any of the patches described herein, in combination with any of the patch frames described herein, or even in a frame-free patch.

Sheet 620' comprises a first layer 690*a* and a second layer 690*b*, e.g., sheet 620' is a bilayer sheet (although for some applications this bilayer can be repeated). It is to be noted that this is distinct from the above-described use of multiple layers of sheet 620 in a given patch, e.g., with a layer on either side of the patch frame. Moreover, multiple layers of sheet 620' can be used in a patch that has multiple sheet layers, e.g., with one bilayer sheet 620' on one side of the patch frame, and another bilayer sheet 620' on the other side of the patch frame. Alternatively or additionally, a given patch can comprise one or more layers of bilayer sheet 620' and one or more layers of another type of sheet.

Inset A shows first layer 690*a*, and inset B shows second layer 690*b*. Each of these layers is a woven fabric comprising weft yarns 692 and warp yarns 694. Weft yarns 692 are represented in FIG. 38 by broken lines, and warp yarns 694 by solid lines. Within each layer, weft yarns 692 can be substantially orthogonal to warp yarns 694.

Within sheet 620' (e.g., within the patch that comprises sheet 620'), layers 690*a* and 690*b* are oriented such that both their weft yarns and their warp yarns are offset from both the root-to-lip axis ax3 of the patch and the mediolateral axis ax4 of the patch. Furthermore, this offset is typically not an offset of 45 degrees. Rather, for each layer 690*a* and 690*b*, the offset is typically such that weft yarns 692 or warp yarns 694 are offset from root-to-lip axis ax3 by 5-40 degrees; with the offset of layer 690*a* being in an opposite direction to that of layer 690*b*. For some applications, and as indicated by the angle alpha, weft yarns 692 are offset from root-to-lip axis ax3, but to a lesser degree than warp yarns 694. For example, weft yarns 692 can be offset from root-to-lip axis ax3 by 5-30 degrees, e.g., by 5-20 degrees (e.g., by 5-15 degrees or by 10-20 degrees) or by 10-40 degrees, e.g., by 20-40 degrees or by 10-30 degrees (e.g., by 15-30 degrees, e.g., by 20-30 degrees).

In some applications, the offset of layer 690*a* is equal (albeit in an opposite direction) to that of layer 690*b*. However, for some applications, the offset of layer 690*a* can be different to that of layer 690*b*.

The offset of layers 690*a* and 690*b* can also be described as an offset of one layer with respect to the other. For some applications, weft yarns 692 of layer 690*a* are offset from the weft yarns of layer 690*b* by 5-30 degrees, e.g., by 5-20 degrees (e.g., by 5-15 degrees or by 10-20 degrees) or by 10-30 degrees (e.g., by 15-30 degrees, such as by 20-30 degrees).

Alternatively or additionally to the angular offset described in the preceding paragraphs, for some applications, within a given layer, the warp yarns closer to the lip of the patch can have a different flexibility to those closer to the root of the patch, e.g., to provide greater rigidity in the region of the patch that is anchored to the leaflet, and/or to provide greater flexibility in the region of the patch that is to coapt with the opposing leaflet.

Reference is now made to FIGS. 39, 40, 41A-B, 42A-D, 43A-C, 44, 45A-C, 46A-B, 47A-C, 48A-B, 49A-D, 50A-C, 51A-E, 52A-B, and 53A-B, which are schematic illustrations of various patch anchors and techniques for use therewith, in accordance with some applications. Each of these patch anchors can be used in place of patch anchor 640, mutatis mutandis, e.g., as a component of upstream assembly 600 (e.g., patch 610 thereof) or a variant thereof (e.g., a variant described hereinabove), and/or a component of implant 550 or an implant similar thereto, mutatis mutandis. Each of these patch anchors can, for some applications, be considered to be a variant of patch anchor 640. Delivery tool 800 or a variant thereof, mutatis mutandis, can be used to anchor these patch anchors to a heart valve leaflet using techniques described herein, mutatis mutandis. Each of these patch anchors has been assigned reference numeral 640 with a respective suffix, to indicate its similarity with, and correspondence to, patch anchor 640.

It is to be further noted that each of these patch anchors can, for some applications, be used independently of a leaflet-augmenting patch such as patch 610, e.g., for anchoring a different component or implant to a heart valve leaflet, or for anchoring to tissue other than a heart valve leaflet.

Figure 39:
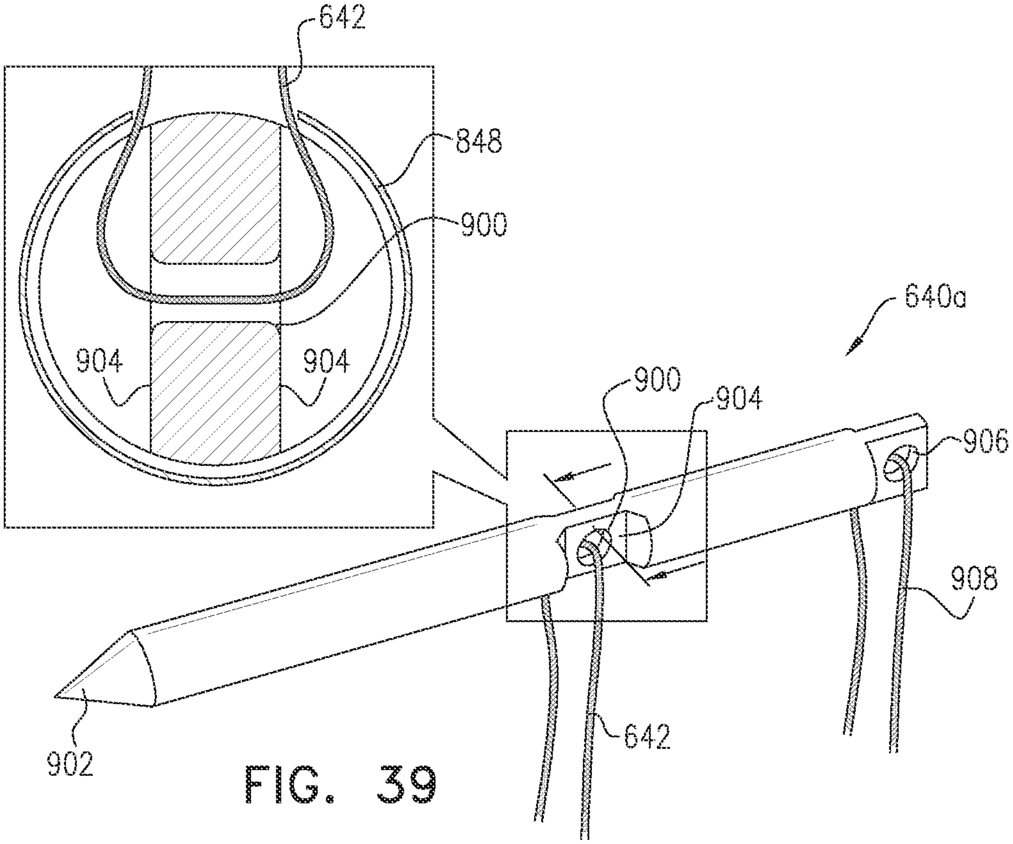

FIG. 39 shows a patch anchor 640*a* that is a toggle anchor defining a cord eyelet 900 partway (e.g., approximately midway) along the length of the anchor, via which cord 642 is connected to the patch anchor. In the example shown, patch anchor 640*a* has a sharpened tip 902, configuring the patch anchor to be pushed through the leaflet, but for other applications patch anchor 640*a* can have a blunt tip, the patch anchor being configured to be advanced through the leaflet within a needle.

Cord eyelet 900 extends entirely through the width of patch anchor 640*a*, and thus cord 642 passes into one side of the patch anchor and out of the other side.

For some applications, and as shown, patch anchor 640*a* defines a recess 904 on each side, with cord eyelet 900 extending between the recesses such that the cord eyelet is sunken below the general lateral surface of the patch anchor. For applications in which patch anchor 640*a* is disposed within a groove 848 of mount 840, this sinking of cord eyelet 900 allows cord 642 to extend from eyelet 900 on both side of the patch anchor, and out of the groove to patch 610, without the cord becoming trapped between the patch anchor and the inner wall of the groove—thus allowing the patch anchor to slide through and out of the groove, e.g., as described hereinabove with reference to FIGS. 32I-J.

For some applications, patch anchor 640*a* is delivered via a needle. For such applications, the C-shaped structure in FIG. 39A (which is referred to above as groove 848 of mount 840) can instead represent a C-shaped needle. For such applications, the sinking of cord eyelet 900 allows cord 642 to extend from eyelet 900 on both side of the patch anchor, and laterally out of the C-shaped needle to patch 610, without the cord becoming trapped between the patch anchor and the inner wall of the C-shaped needle.

For some applications, patch anchor 640*a* further comprises a retrieval eyelet 906 at the heel of the patch anchor, via which a retrieval line 908 can be connected to the patch anchor. During anchoring of patch anchor 640*a* (e.g., during implantation of a patch to which it belongs), retrieval line 908 extends from retrieval eyelet 906. Should it be determined, during the course of implantation, that the patch anchor should be retrieved, pulling on retrieval line 908 facilitates retrieval (e.g., de-anchoring) of the patch anchor.

Because retrieval eyelet 906 is disposed at the heel of the patch anchor, it is hypothesized that pulling on retrieval line 908 will (i) reorient the patch anchor axially (e.g., in alignment with the vector along which it was advanced, such as in alignment with a hole in the leaflet through which it was passed), and (ii) withdraw the patch anchor proximally.

Although retrieval eyelet 906 and retrieval line 908 are described with reference to patch anchor 640*a*, other patch anchors described herein—especially toggle anchors—can be modified to include a retrieval eyelet. For example, and as shown, patch anchor 640 can be provided with a retrieval eyelet 641. Similarly, system 500 (e.g., delivery tool 800 thereof) can be modified to accommodate retrieval line 908, and to facilitate use thereof.

For some applications, retrieval eyelet 906 is sunk similarly to as described for cord eyelet 900, for the same reasons.

Although cord 642 and line 908 are each shown as being simply looped through their respective eyelet such that two lengths of the cord/line extend away from the eyelet, other types of connections can be used, e.g., connections in which only one length of the cord/line extends away from the eyelet, such as the cord/line extending through the eyelet and being hitched thereto, or the cord/line having a knot or bead at one end preventing that end from passing through the eyelet.

Figure 40:
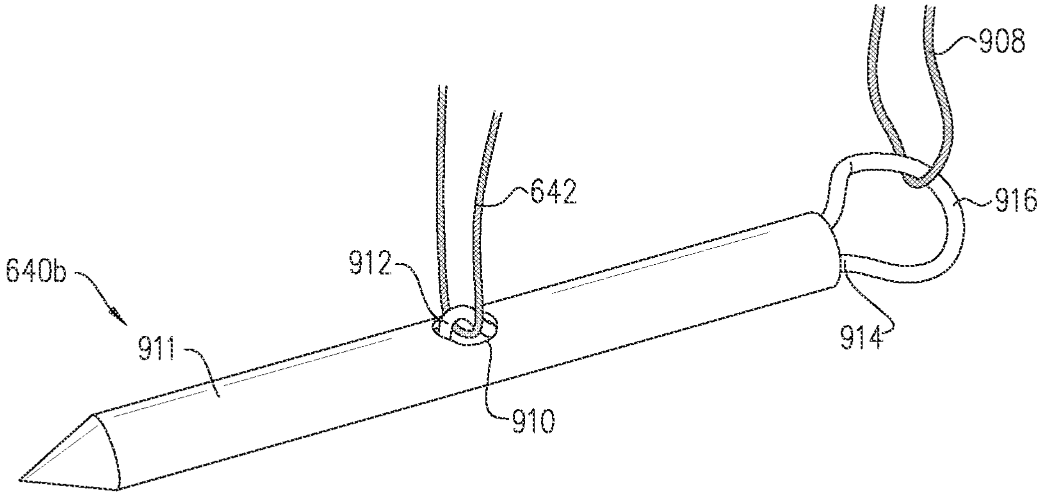

FIG. 40 shows a patch anchor 640*b* that is a toggle anchor. In the example shown, patch anchor 640*b* has a sharpened tip 902, configuring the patch anchor to be pushed through the leaflet, but for other applications patch anchor 640*b* can have a blunt tip, the patch anchor being configured to be advanced through the leaflet within a needle.

Whereas patch anchor 640*a* can be substantially solid (e.g., cut from a solid rod), patch anchor 640*b* is generally tubular (e.g., cut from a tubular rod). That is, patch anchor 640*b* can comprise a tubular body 911. Patch anchor 640*b* has a lateral eyelet 910 that can extend only between the lumen of the patch anchor and the outside, rather than transversely entirely through the patch anchor. Thus, cord 642 does not pass into one side of patch anchor 640*b* and out of the other side. Furthermore, lateral eyelet 910 does not serve as a cord eyelet of anchor 640*b*. Rather, a cord eyelet 912 extends across lateral eyelet 910, optionally protruding laterally from the lateral eyelet. Cord 642 is connected to the cord eyelet, e.g., as described for cord eyelet 900, mutatis mutandis.

For some applications, and as shown, cord eyelet 912 is formed from a shaped spring wire 914 that is advanced into the lumen of the patch anchor (e.g., via an open heel of the patch anchor), until a part of the spring wire that defines cord eyelet 912 arrives at lateral eyelet 910 and serves as a crosspiece that defines eyelet 912, at which point the spring wire can snap into place.

For some applications, spring wire 914 further defines a retrieval eyelet 916 at a heel of the implant. For example, spring wire 914 can include a hairpin turn that both (i) defines retrieval eyelet 916, and (ii) provides spring functionality that allows the spring wire to snap into place with cord eyelet 912 pressed against lateral eyelet 910. That is, the spring functionality of spring wire 914 secures it in place.

Figure 41A:
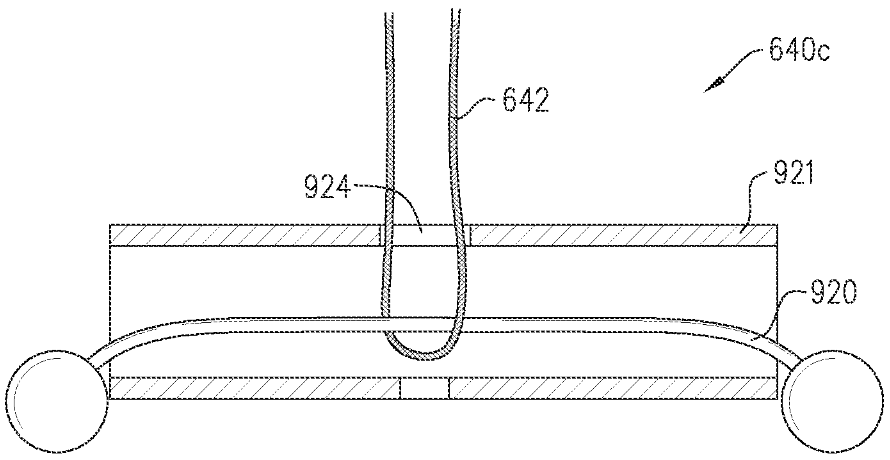
Figure 41B:
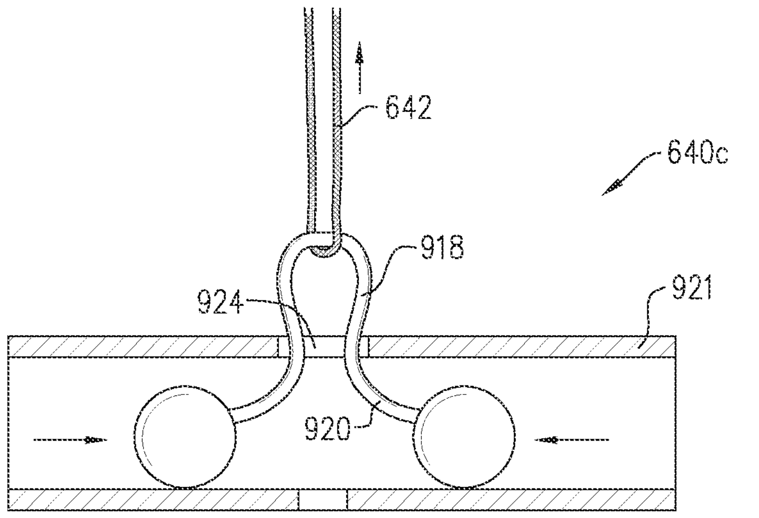

FIGS. 41A-B show a patch anchor 640*c* that is a toggle anchor. Patch anchor 640*c* can be similar in structure and function to patch anchor 640*b*, except for how its cord eyelet 918 is fashioned. A wire 920 with a bead 922 (or other relatively wide element, such as a knot) on either end is advanced into a tubular body 921, such that it extends past a lateral eyelet 924 in the tubular body (FIG. 41A). Beads 922 can be dimensioned to fit through an open end of tubular body 921, but to not fit through lateral eyelet 924. Cord 642 is then passed into lateral opening 924, looped around wire 920, and then pulled out of the lateral opening, pulling the wire out of the lateral opening such that it forms cord eyelet 918 (FIG. 41B).

For some applications, another lateral eyelet disposed opposite lateral eyelet 924 is provided, to facilitate passage and looping of cord 642.

For some applications, cord eyelet 918 is formed by pulling wire 920 out of lateral eyelet 924 using a wire, a snare, a hook, or similar, and cord 642 is connected to the cord eyelet only once the cord eyelet has been formed.

In the example shown, patch anchor 640*c* does not have a sharpened tip, e.g., it is configured to be advanced through the leaflet within a needle. However, for other applications, patch anchor 640*c* can have a sharpened tip such as that of patch anchor 640*a* or 640*b*, thereby configuring the patch anchor to be pushed through the leaflet.

For some applications, patch anchor 640 or a variant thereof has two lateral holes adjacent each other (e.g., arranged in a line parallel with a central axis of the toggle anchor, or arranged in the same longitudinal position along the toggle anchor but at different positions around the circumference of the toggle anchor). This can be particularly applicable to hollow/tubular toggle anchors. For such applications, the cord eyelet of the toggle anchor is, in effect, defined by the part of the wall of the toggle anchor between the two lateral holes, with cord 642 extending into one of the lateral holes and out of the other one of the lateral holes. An example of such a configuration is provided by the schematic illustrations of patch anchor 640, e.g., FIG. 35B.

Figure 42A:
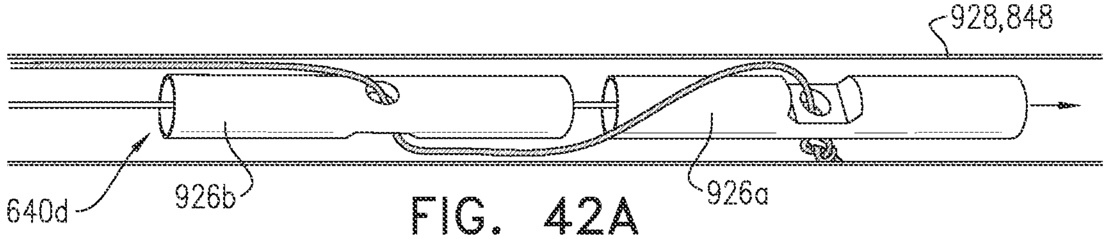
Figure 42B:
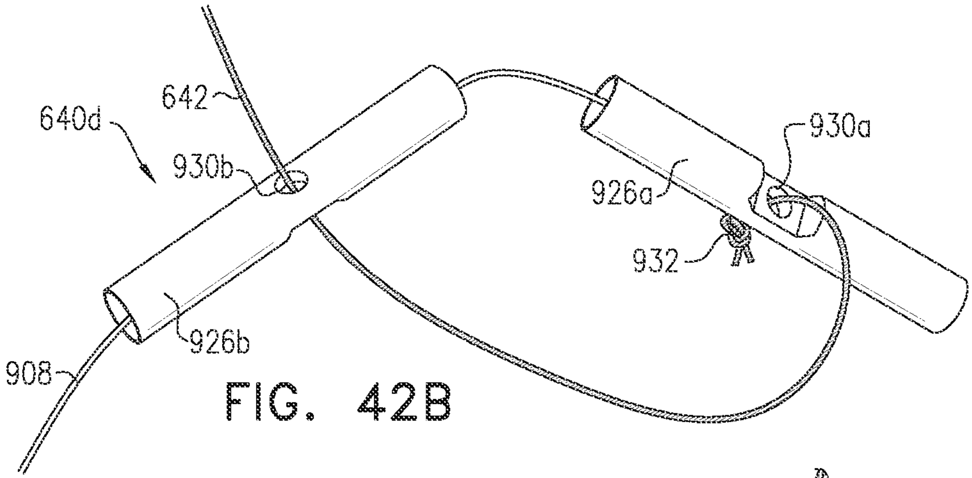

FIGS. 42A-D show a toggle anchor 640*d* that comprises two toggles: a first toggle 926*a*, and a second toggle 926*b*. During delivery, the toggles are collinear, with toggle 926*a* is disposed distally from second toggle 926 (FIG. 42A). Pushing of second toggle 926*b* pushes both toggles out of the needle 928 or groove 848 within which they are delivered (FIG. 42B).

Cord 642 extends through a cord eyelet 930*a* of toggle 926*a* and a cord eyelet 930*b* of toggle 926*b*. In some applications, each of the cord eyelets is approximately midway along its toggle, and further typically extends entirely through its toggle such that cord 642 passes laterally through each of the toggles. Cord 642 is slidable through eyelet 930*b*, but has limited movement with respect to eyelet 930*a*, e.g., an end of the cord can be secured to cord eyelet 930*a* by a knot 932, bead, or other means.

Figure 42C:
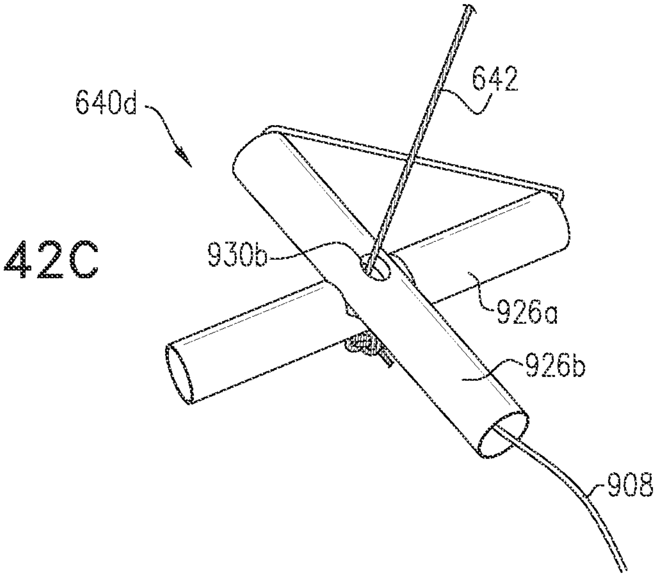
Figure 42D:
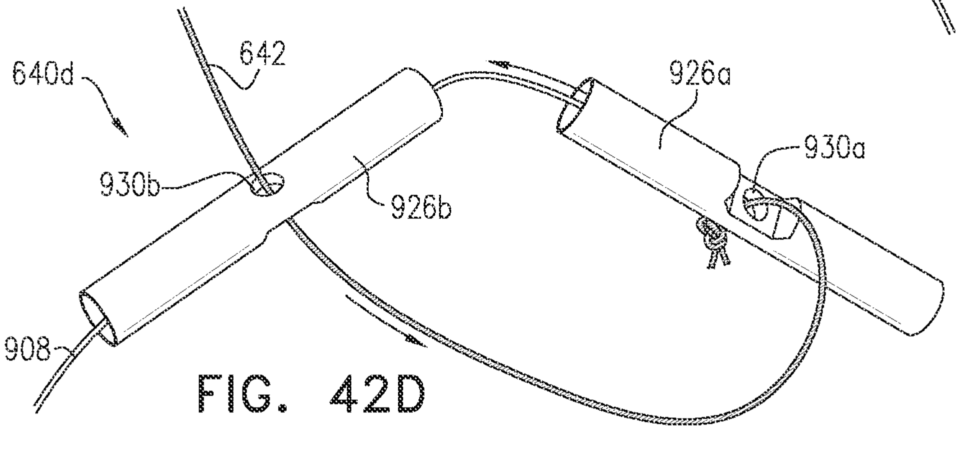

Upon deployment on the far side of the leaflet (e.g., at the downstream side of the leaflet), tensioning of cord 642 (e.g., by a spring in the patch to which the cord is attached) pulls cord eyelet 930*a* to meet cord eyelet 930*b*. In some applications, one or both of the cord eyelets is sunken on at least one side. This, along with the generally cylindrical shape of the toggles, encourages the sunken sites to engage with each other, arranging the two toggles into a cross (FIG. 42C). It is hypothesized that, for some applications, this resulting cross-shape distributes force across a greater surface area of the leaflet compared to a single toggle, and may therefore be less injurious to the leaflet for a given amount of tension on cord 642.

For some applications, retrieval line 908 extends through a longitudinal lumen of toggle 926*b* (e.g., from a heel to a tip of the toggle), to toggle 926*a* to which it is secured, often at the heel of the toggle. Should it be determined, during the course of implantation, that patch anchor 640*d* should be retrieved, pulling on retrieval line 908 (e.g., with sufficient force to overcome tension on cord 642, and/or accompanied by relieving tension on cord 642) slides the retrieval line through the lumen of toggle 926*b*, pulling the heel of toggle 926*a* toward the tip of toggle 926*b*, thereby returning the two toggles toward collinearity. Further pulling on retrieval line 908 can then retrieve the patch anchor.

FIGS. 43A-48B show patch anchors that each comprise a resilient (e.g., shape-memory) structure that is shaped to define a frame and at least one arm (e.g., two arms). For applications in which such anchors are used, patch 610 (or a variant thereof) can be provided with the frame affixed (e.g., stitched) to the patch. For some applications the frame is affixed to the contact face of the patch, and for other applications the frame is affixed to the opposing face of the patch. The anchor is configured to anchor the patch to the leaflet by the arm being driven through the leaflet while constrained in a strained state, and, in response to being released on the far side of the leaflet, to automatically move to press against the far side of the leaflet.

FIGS. 43A-C show a patch anchor 640*e* that comprises a resilient frame that is shaped to define a frame 934 and two arms 936. Frame 934 is affixed (e.g., stitched) to patch 610. In some applications, frame 934 at least partly frames a window is cut in the patch, and arms 936 are disposed within the framed area (e.g., within the window). In the example shown, frame 934 comprises two substantially parallel beams that are affixed to long edges of the window.

Each arm 936 is disposed between the two substantially parallel beams of frame 934 and at rest is typically substantially parallel to the beams. Thus, at rest, patch anchor 640*e* is typically substantially in-plane with patch 610.

For some applications, arms 936 typically point away from each other when at rest. However, for other applications the arms point toward each other when at rest. Each arm can be pivotably connected to both beams of frame 934, such that it can be pivoted from its rest orientation into an anchoring orientation in which it points away from patch 610, and it which it can be advanced through leaflet 10. In its anchoring orientation, the arm can be substantially orthogonal to its rest orientation, to frame 934, and/or to sheet 620.

FIG. 43B shows an example in which each arm 936 is retained in its anchoring orientation by being disposed within a hollow needle 938. Needle 938 has lateral slits parallel with the axis of the needle, which accommodate sliding of the connections between arm 936 and the beams of frame 934. These lateral slits and the connections between the arms and the beams are not visible in the particular cross-section of FIG. 43B. Another artifact of this particular cross-section is that arms 936 appear to hover freely within needles 938.

In FIG. 43B, needles 938 have been driven through the leaflet until patch 610 is disposed against leaflet 10. Needles 938 are then retracted, allowing arms 936 to return toward their resting state, pressing against the far side of the leaflet, thereby anchoring patch 610 to the leaflet (FIG. 43C).

Although patch anchor 640*e* is shown and described as being used with needles that penetrate the leaflet, for some applications the patch anchor can optionally be used with tubes, channels, or grooves that restrain arms 936 in their anchoring orientations but that do not pierce the leaflet. For example, patch anchor 640*e* can be used with a mount similar to mount 840, mutatis mutandis. For such applications, the tip of the arm can be sharpened, the tube/channel/groove can be placed against the leaflet, and the arm can be driven out of the tube/channel/groove and directly through the leaflet, returning toward its rest state on the far side of the leaflet.

For some applications, patch anchor 936*e* (e.g., each arm 936 thereof) is provided with a line 940 that can serve as a straining line and/or as a retrieval line. For such applications, each arm has (i) an anchoring portion 936*a* that includes the tip of the arm, and that will be advanced through the leaflet, and (ii) a lever portion 936*b* that includes a heel of the arm. The pivotable connection of the arm to frame 934 is disposed between the anchoring portion and the lever portion. Line 940 is attached to lever portion 936*b*, such that pulling (i.e., tensioning) the line causes the arm to pivot about its pivotable connection, with the lever portion moving in the direction of the pulling, and the anchoring portion moving towards its anchoring orientation. That is, tensioning of line 940 causes arm 936 to act as a class I lever with its fulcrum being the point of pivotable connection to frame 934.

For some applications, line 940 is used to move arms 936 toward their anchoring orientation in order to anchor the patch anchor to leaflet 10. For some such applications, a needle or a tube is therefore not required.

For some applications, line 940 is used to move arms 936 toward their anchoring orientation in order to de-anchor and retrieve the anchor and the patch. For example, pulling on line 940 can both (i) pivot the arms toward their anchoring orientation, and (ii) pull the arms out of leaflet 10, thereby de-anchoring patch anchor 640*e* and patch 610.

Figure 44:
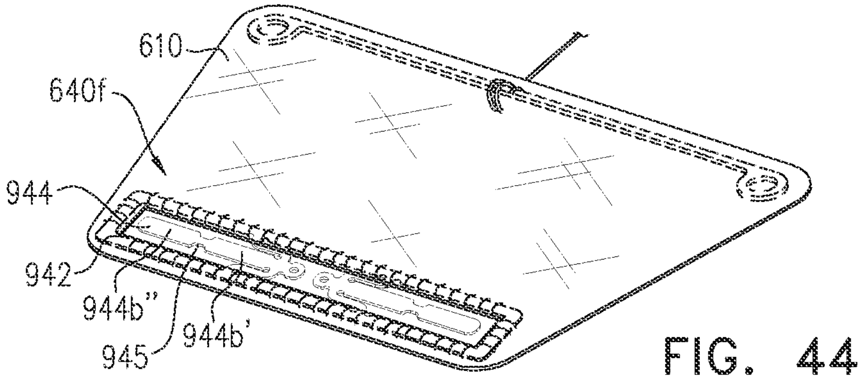

FIG. 44 shows a patch anchor 640*f* that is similar to patch anchor 640*e*, except that (i) its frame 942 is a closed rectangle rather than just two parallel beams, and (ii) the anchoring portion of its arms is divided into two articulated sub-portions 944*b*' and 944*b*" connected at a flexure 945 which allow the second portion to be folded and advanced through the leaflet flexure-first (e.g., within a needle).

FIGS. 45A-C and 46A-B show a patch anchor 640*g*, whose arms 946 are defined by two sides of a four-sided mechanical linkage 948, the other two sides being struts 950. Struts 950 are articulatably coupled to each other, and each is also articulatably coupled to a respective one of arms 946.

Patch anchor 640*g* further comprises a frame 952 that is affixed (e.g., stitched) to patch 610, e.g., to opposing face 622. In some applications, linkage 948 is disposed on the opposite side of the patch from frame 952, e.g., on the side of contact face 621.

For some applications, and as shown, arms 946, struts 950, and frame 952 are all (e.g., patch anchor 640*g* is entirely) defined by a single continuous elongate and linear piece of stock material that has been folded and heat set to define the arms, struts, and frame. For some such applications, and as shown, (i) at a medial region of the elongate piece are two regions that define struts 950 and that are articulatably coupled to each other at a strut-strut articulation 949, (ii) lateral to the struts are two regions that define arms 946, and that are each articulatably coupled, at a respective strut-arm articulation 947, to a respective one of the regions that define the struts, and (iii) the lateral ends of the elongate piece define respective beams that collectively define frame 952, and that are each articulatably coupled, at a respective arm-frame articulation 951, to a respective one of the regions that define the arms. (It is to be understood that, in this paragraph, medial and lateral refer to relative positions along the elongate and linear piece of stock material from which patch anchor 940*g* can be formed, not to relative positions within the fully-formed patch anchor.)

In some applications, in a resting state of patch anchor 940*g* (FIGS. 45A and 45C) strut-strut articulation 949 is disposed at a midline of patch anchor 940*g*, strut-arm articulations 947 are disposed laterally from the midline (e.g., at or close to lateral extremes of the patch anchor), arm-frame articulations 951 are disposed close to the midline, and the beams that define frame 952 are disposed collinearly, both pointing laterally outward, terminating at or close to lateral extremes of the patch anchor.

Figure 45A:
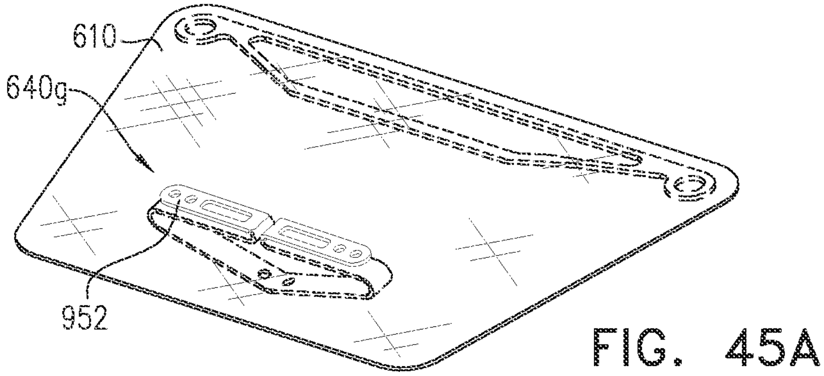
Figure 45B:
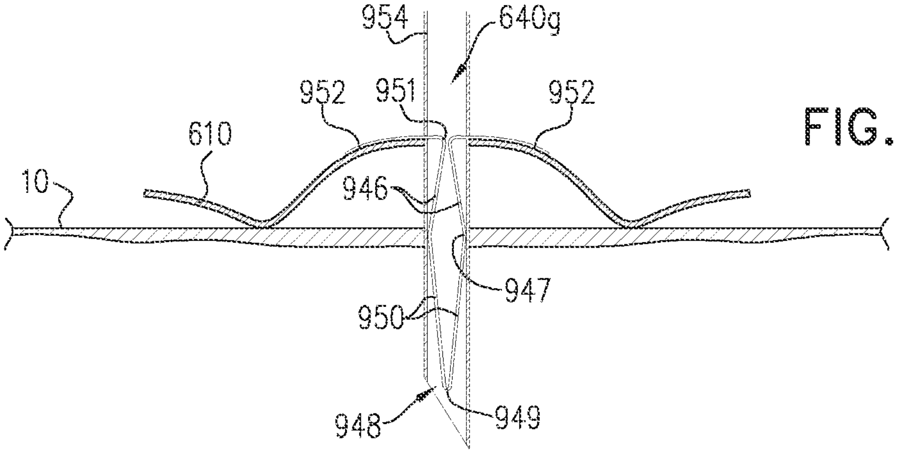

FIG. 45B shows an example in which mechanical linkage 948 is constrained in its anchoring state by being advanced through leaflet 10 within a hollow needle 954. In the anchoring state, mechanical linkage 948 is narrowed, with strut-arm articulations 947 close to each other and forming obtuse angles, and strut-strut articulation 949 forming an acute angle.

Needle 954 can have lateral slits parallel with the axis of the needle, which accommodate sliding of the connections between arms 946 and the beams of frame 952.

Figure 45C:
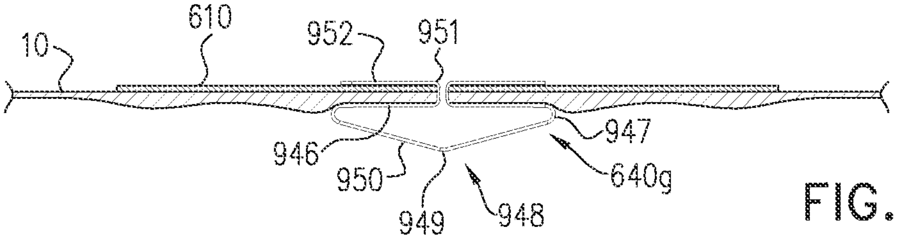

Needle 954 is then retracted, allowing patch anchor 640*g* to return toward its resting state, in which mechanical linkage 948 is widened, with strut-arm articulations 947 distanced from each other and forming acute angles, strut-strut articulation 949 forming an obtuse angle, and arms 946 pressing against the far side of the leaflet (e.g., sandwiching the leaflet between the arms and frame 952), thereby anchoring patch 610 to the leaflet (FIG. 45C).

As shown, struts 950, arms 946, and frame 952 can all lie in a common plane, both when constrained in the delivery state of patch anchor 640*g*, and in its resting state.

Figure 46A:
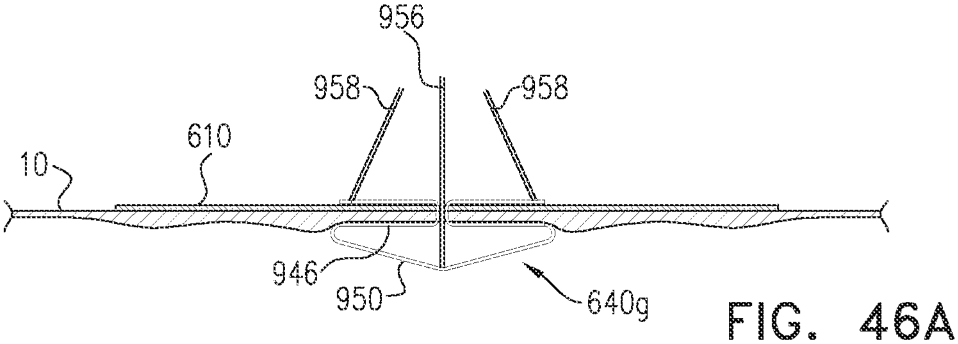
Figure 46B:
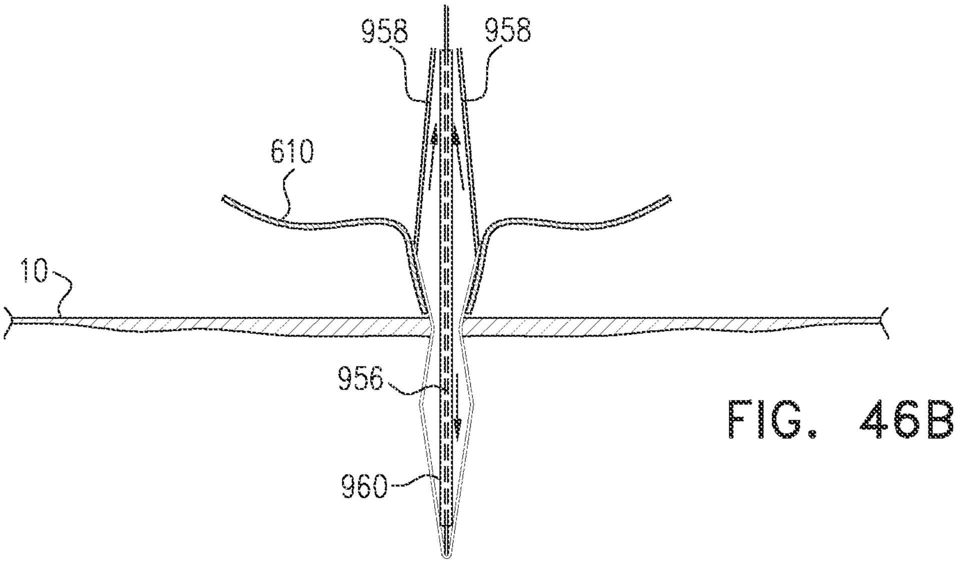

FIGS. 46A-B shows an option in which patch anchor 640*g* is provided with retrieval functionality. The patch anchor is provided with three lines connected thereto, which remain in place during anchoring. FIG. 46A shows the state after anchoring. A central line 956 is connected at strut-strut articulation 950, and a respective lateral line 958 is connected at the ends of the beams that define frame 952. Should it be determined, during the course of implantation, that patch anchor 640*g* should be retrieved, a prop (e.g., a pusher tube) 960 is advanced over central line 956 so as to apply a pushing force against strut-strut articulation 950, while pulling on lateral lines 958, thereby returning the patch anchor toward its delivery state (FIG. 46B). The patch anchor can then be retrieved (e.g., de-anchored) by pulling it proximally.

Figure 47A:
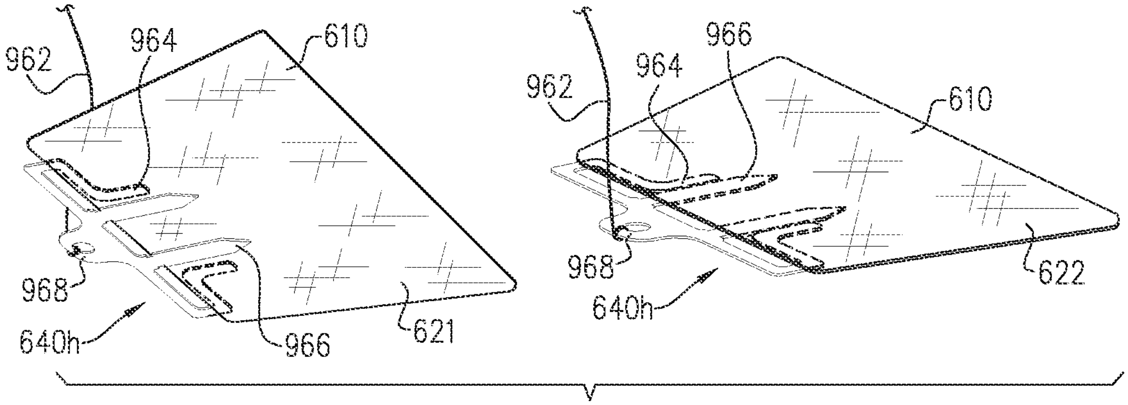
Figure 47B:
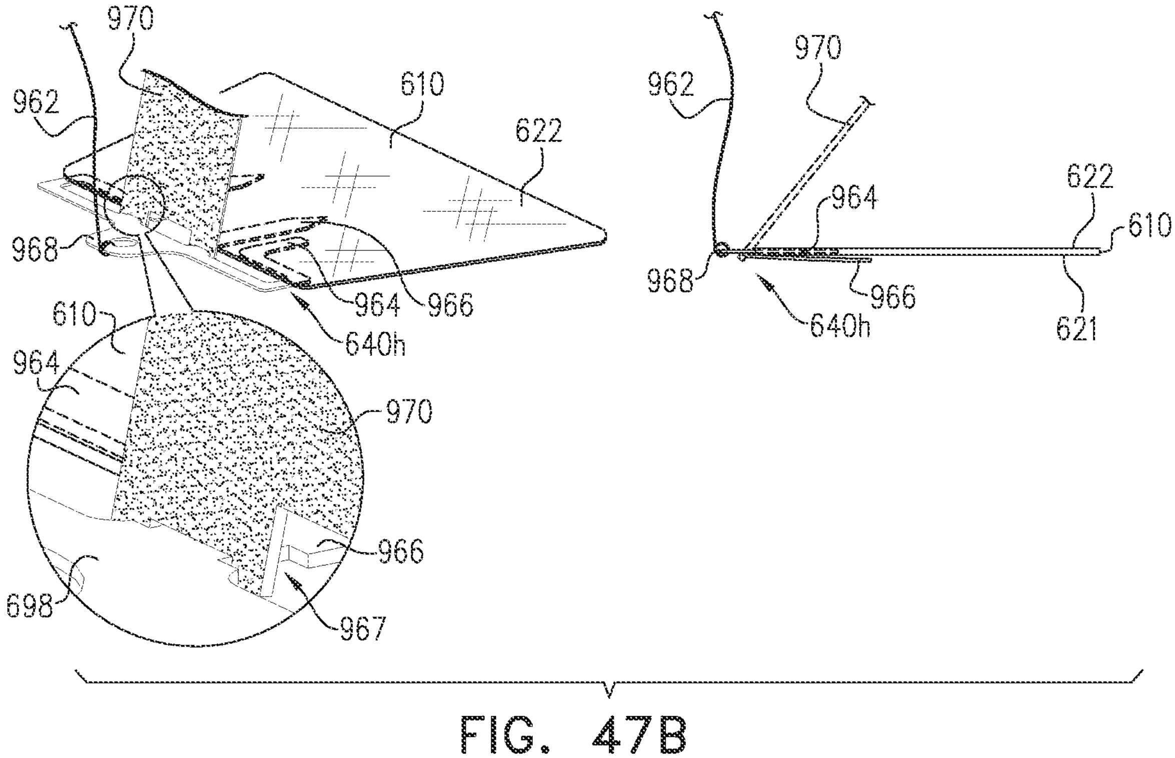
Figure 47C:
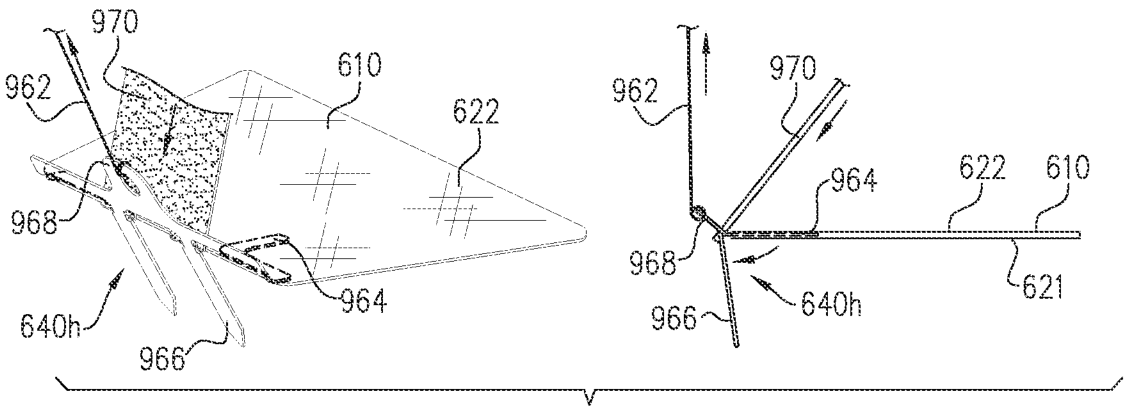

FIGS. 47A-C show a patch anchor 640*h*, attached to patch 610, being used to anchor the patch. Whereas patch 640*g* can be provided with lines that facilitate retrieval, anchor 640 is provided with a line 962 that is used in the anchoring process, and if relevant, also for retrieval.

Similarly to patch anchors 640*e* and 640*f*, patch anchor 640*h* comprises (i) a frame 964 that is attached (e.g., stitched) to patch 610, substantially coplanar with the patch, and (ii) arms 966 that, in a resting state of the patch anchor, are disposed substantially coplanar or parallel with the frame, that are pivotable into an anchoring orientation in which they point away from the frame and the patch, and that are biased toward returning to their resting orientation. However, whereas for anchors 640*e* and 640*f* the axis of pivoting is transverse to a long axis of the frame, for anchor 640*h* the axis of pivoting is parallel with (or even lies on) the long axis of frame 964. As shown, patch anchor 640*h* (e.g., frame 964 thereof) extends beyond the root of patch 610, such that the axis of pivoting is at or beyond the root of the patch, typically parallel with the root of the patch.

Patch anchor 640*h* defines a lever portion 968, which, as shown, can be common to all (e.g., both) arms 966. Line 962 is connected to patch anchor 640*h* at lever portion 968.

Each arm 966 has a sharpened tip and is configured to be advanced directly through the leaflet, i.e., to pierce the leaflet. In a resting state of patch anchor 640*h*, arms 966 point generally toward the lip of the patch.

In the example shown, frame 964 is disposed within patch 610, e.g., between layers of sheet 620. For other patch anchors, the frame is shown and/or described as lying against opposing face 622 of the patch. It is to be noted that, in most instances, these two configurations are interchangeable.

At rest, arms 966 are disposed close to or against contact face 621 of patch 610 (FIG. 47A).

For applications in which patch 610 comprises patch anchor 640*h*, the patch can be advanced to valve 7 with a prop (e.g., a pusher plate) 970 engaged with the patch anchor (FIG. 47B). Prop 970 can engage patch anchor 640*h* at or close to the axis of pivoting of the patch anchor. For example, and as shown, prop 970 can define one or more recesses shaped to receive arms 966, e.g., at or close to where the arms join frame 964. For some applications, and as shown, arms 966 can also define a notch 967 dimensioned to engage prop 970, e.g., to prevent the prop from slipping along the arms.

In order to anchor patch anchor 640*h* to the leaflet, line 962 is tensioned while a reference force is provided by prop 970, thereby causing arms 966 to pivot about their pivotable connection, with lever portion 968 moving in the direction of the pulling, and the arms moving (e.g., pivoting) away from patch towards their anchoring orientation (FIG. 47C). While arms 966 are in their anchoring orientation they are pushed through leaflet 10 (e.g., by pushing the root of patch 610 against the leaflet). To secure the patch to the leaflet, tension on line 962 is released, allowing arms 966 to pivot back toward the patch, thereby sandwiching leaflet tissue between the arms and the patch.

Should it be determined, during the course of implantation, that patch anchor 640*h* should be retrieved, line 962 can be used again to pivot arms 966, with or without the use of prop 970. While arms 966 remain pivoted, the patch anchor can then be retrieved (e.g., de-anchored) by pulling it proximally.

Figure 48A:
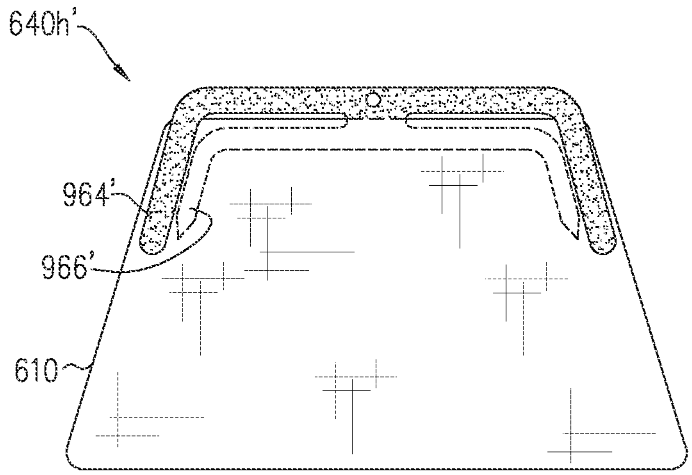
Figure 48B:
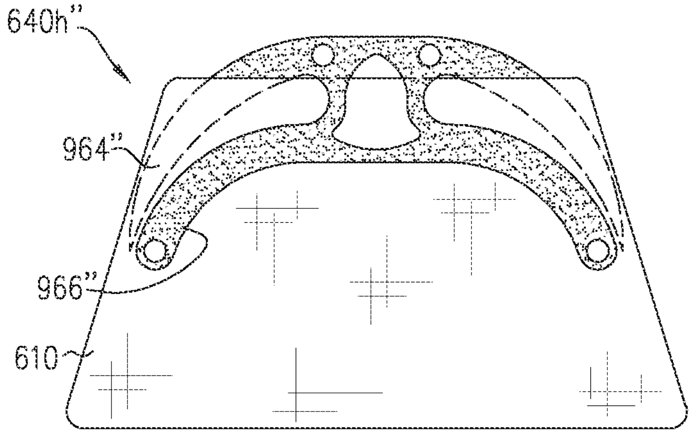

FIGS. 48A-B show patch anchor 640*h*' and patch anchor 640*h*", which are variants of patch anchor 640*h*.

Whereas, at rest, both frame 964 of patch anchor 640*h* and frame 964' of patch anchor 640' comprise frame members that extend substantially alongside the arms of the patch anchor (e.g., pointing toward the lip of patch 610), these frame members are closer to the lateral edges of the patch in patch anchor 640', e.g., serving to keep the patch unfurled.

Whereas, at rest, arms 966 of patch anchor 640*h* and arms 966' of patch anchor 640*h*' are disposed medially from the frame members of their corresponding frames, arms 966" of patch anchor 640*h*" are disposed laterally from the frame members of frame 964" of patch anchor 640". Additionally, in some applications, the frame members and arms of patch anchor 640" extend laterally and then curve toward the lip of patch 610, whereas those of patch anchors 640*h* and 640*h*' are typically not curved in this manner.

It is to be noted that patch anchor 640*h*, and variants 640*h*' and 640*h*" thereof, can serve as root braces in addition to patch anchors.

Figure 49A:
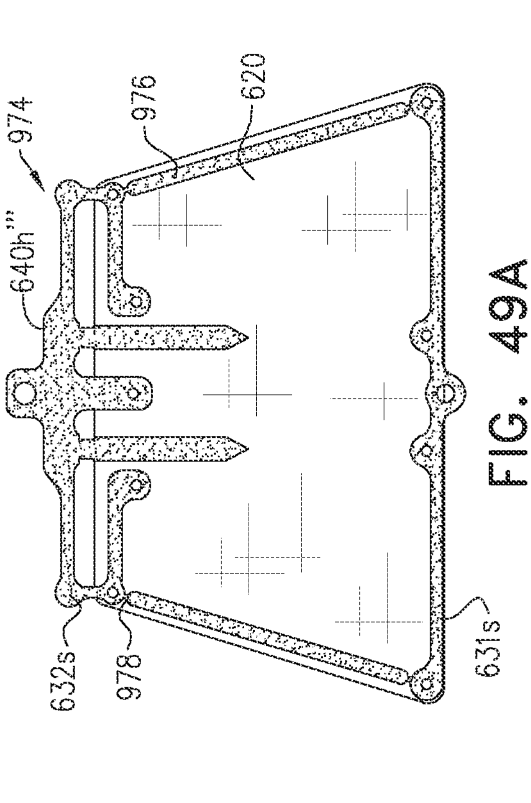
Figure 49B:
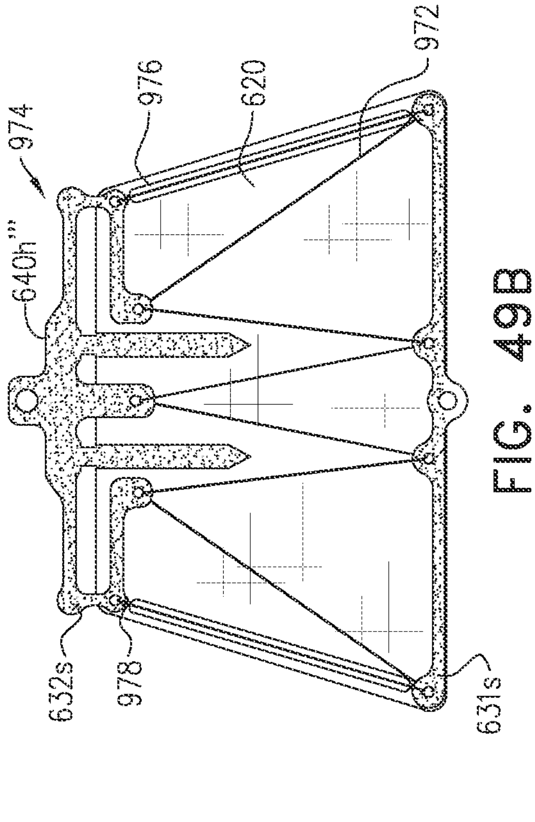
Figure 49C:
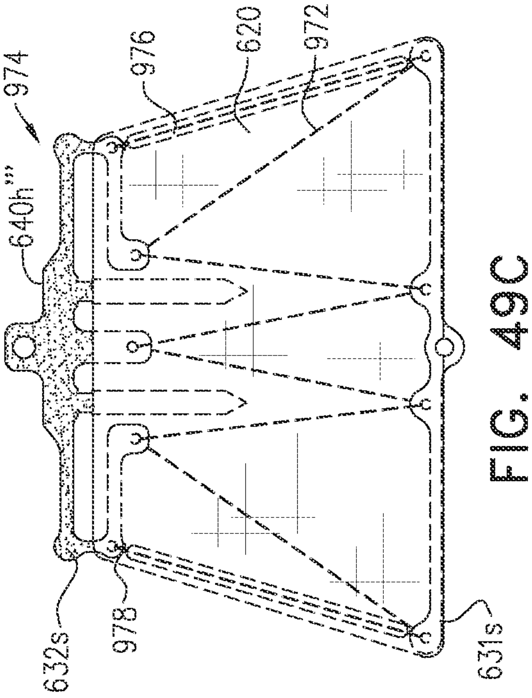

FIGS. 49A-C are schematic illustrations of at least some steps in a technique for assembling an upstream assembly comprising a patch 610*s* that comprises a root brace 632*s* and a lip brace 631*s*. This technique is particularly applicable for patches that do not have a frame component with compressive strength connecting the root brace to the lip brace. In the example shown, root brace 632*s* is defined by a patch anchor 640*h*''', but the technique is applicable, mutatis mutandis, to patches whose root brace is not defined by a patch anchor.

Patch anchor 640*h*''' which is a variant of patch anchor 640*h* that includes eyelets to which ties 972 can be secured. Lip brace 631*s* also includes eyelets. In patch 610*s* ties 972 connect root brace 632*s* to lip brace 631*s*, providing tensile strength but little or no compressive strength. Ties 972 also provide this tensile strength without substantially reducing flexibility of the patch. This tensile strength is hypothesized to reduce and/or even out tension on sheet 620 after implantation by transferring some of the tension from lip brace 631*s* to root brace 632*s* via ties 972, bypassing the sheet. However, because patch 610*s* does not have a frame component with compressive strength connecting the root brace to the lip brace, it may be challenging to correctly and/or consistently size ties 972 and/or sheet(s) 620 with respect to the root brace, the lip brace, and the gap therebetween. Therefore, a provisional frame assembly 974 is provided, comprising root brace 632*s*, lip brace 631*s*, and one or more splints 976 connecting the root brace to the lip brace at a predefined relative position (e.g., a predefined distance from each other).

Sheet 620 is attached (e.g., sutured) to root brace 632*s* and lip brace 631, e.g., extending therebetween with no slack or tension in the sheet (FIG. 49A). In the example shown, splints 976 extend along the lateral edges of the provisional frame assembly, e.g., so as to be positioned approximately at the lateral edges of sheet 620. Ties 972 are similarly attached to the root brace and the lip brace (FIG. 49B). It is to be noted that ties 972 can be attached before or after sheet 620 is attached.

For applications in which sheet 620 is a two-layer sheet between which the braces and ties will be disposed, the second layer of the sheet can be attached to the root brace and the lip brace at this stage, again with no slack or tension in the second layer of the sheet (FIG. 49C).

Figure 49D:
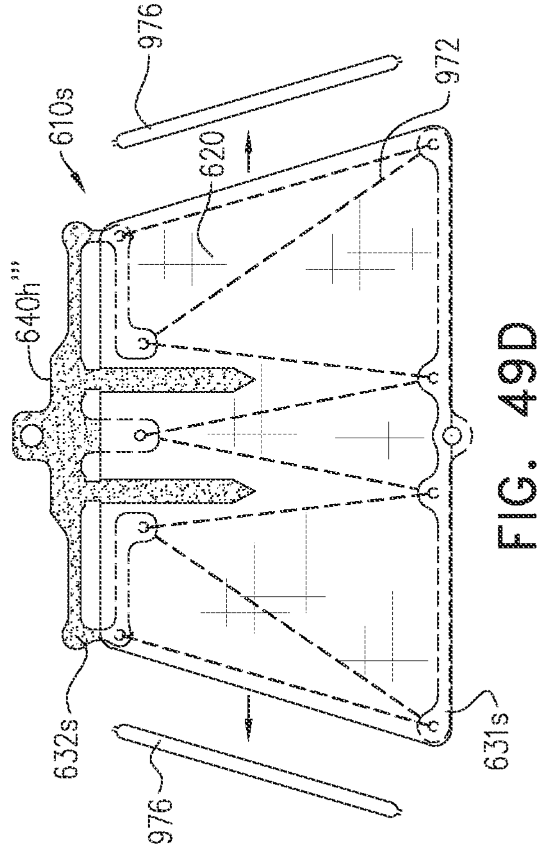

Subsequently, splints 976 are removed (FIG. 49D). In some applications, splints 976 are connected to the braces via frangible connections 978, which facilitate removal of the splints. For applications in which sheet 620 is a two-layer sheet, in order to facilitate removal of splints 976 at the lateral edges of the patch the sheets can be left unstitched (represented by broken lines in FIG. 49C) until the splints have been removed, at which point the sheet layers can be stitched together at the lateral edges.

Figure 50A:
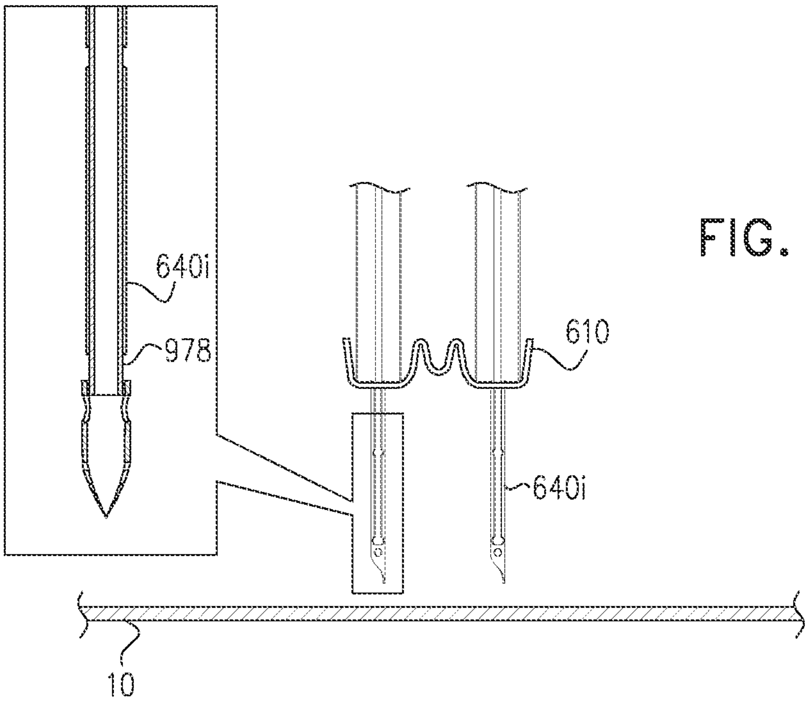
Figure 50B:
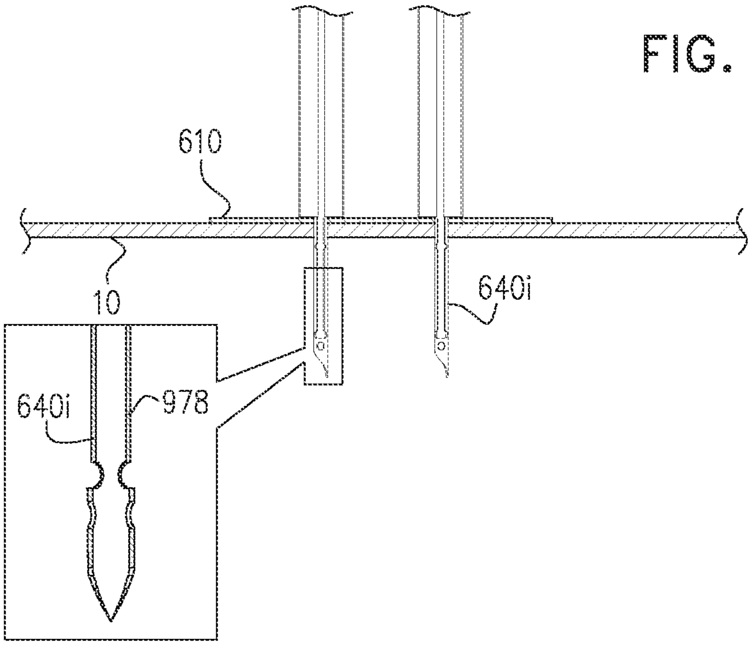
Figure 50C:
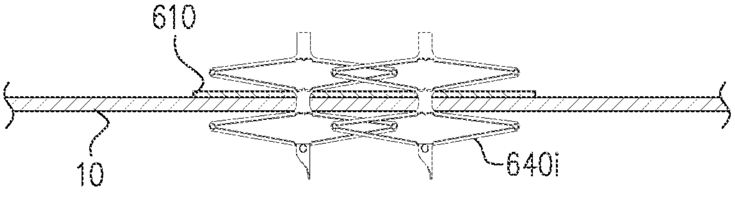

FIGS. 50A-C show patch anchors 640*i*, which are expandable tubes, optionally with a sharpened tip. Patch anchors 640*i* are advanced (e.g., with patch 610) toward leaflet 10, while restrained in an elongate state by a rod 978 disposed within the patch anchor. As a distal portion of patch anchor 640*i* is driven through the leaflet, rod 978 is withdrawn from the patch anchor (FIG. 50B). For example, rod 978 can remain on the near side of the leaflet as patch anchor 640*i* is advanced off of the rod and through the leaflet. In response to the withdrawal of rod 978 from the distal portion of the patch anchor, the distal portion of the patch anchor widens and shortens against the far side of the leaflet, in a manner similar to that of a drywall anchor. In response to further (e.g., complete) withdrawal of the rod from the patch anchor, the proximal portion of the patch anchor also widens and shortens—against patch 610 (FIG. 50C).

For some applications, patch anchors 640*i* are restrained by being disposed within a complete or partial tube, rather than by rod 978.

FIGS. 51A-E and 52A-B show a patch anchor 640*j*, which, for some applications can be considered to be a tubular staple. Patch anchor 640*j* is formed from a tube of shape memory material such as nitinol, and is cut to define two lateral openings 980 which separate the tube into a central tubular portion 982, and two lateral tubular portions 984 each connected to a respective end of the central tubular portion by a joint 981 formed from the residual piece of the tube opposite a respective one of the lateral openings. This structure of patch anchor 640*j* is most clearly seen in FIG. 51F, which shows the patch anchor after anchoring is complete.

Figure 51A:
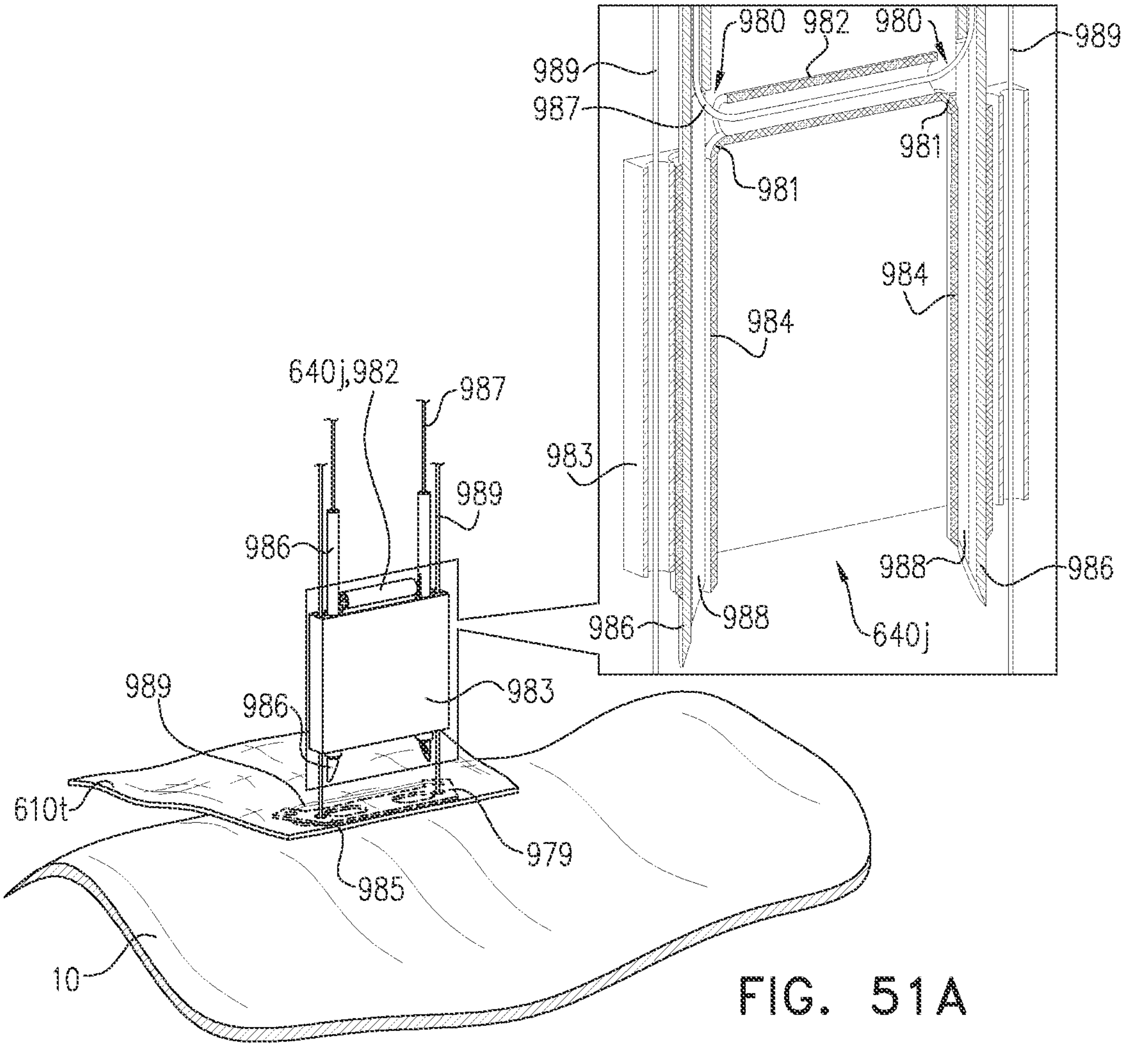
Figure 51B:
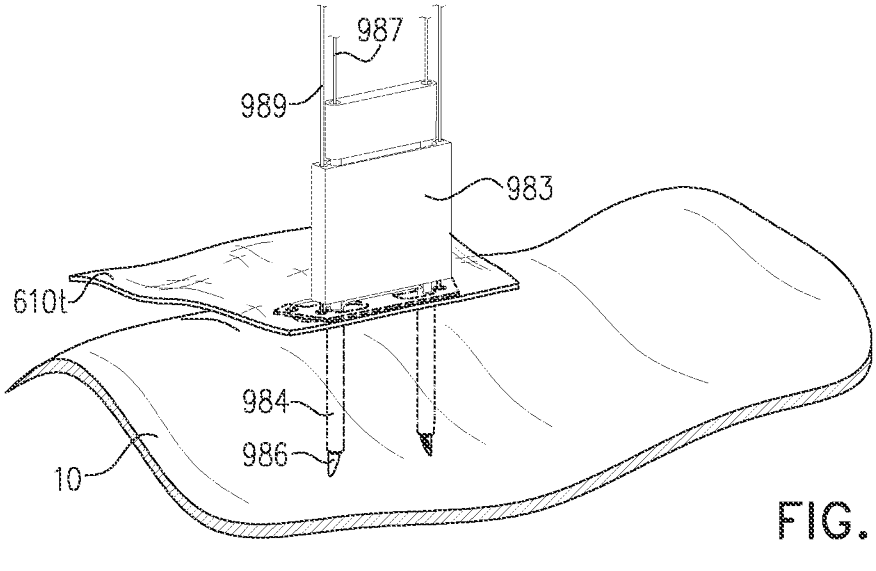

Patch anchor 640*j* is advanced to a patch 610*t* (e.g., a variant of patch 610) while restrained in an anchoring state by a pair of needles 986 disposed through lateral tubular portions 984 (FIG. 51A). As shown, needles are parallel with each other, and thus restrain lateral tubular portions 984 parallel with each other. Lateral tubular portions 984 are advanced (e.g., by a driver, analogous to driver 850) through patch 610*t* (e.g., through premade holes 985 therein), and through leaflet 10 (e.g., with the tips of needles 986 leading and piercing the leaflet) while the patch anchor remains restrained in this state (FIG. 51B). In some applications, the patch anchor is advanced until central tubular portion 982 is disposed against the patch.

Figure 51C:
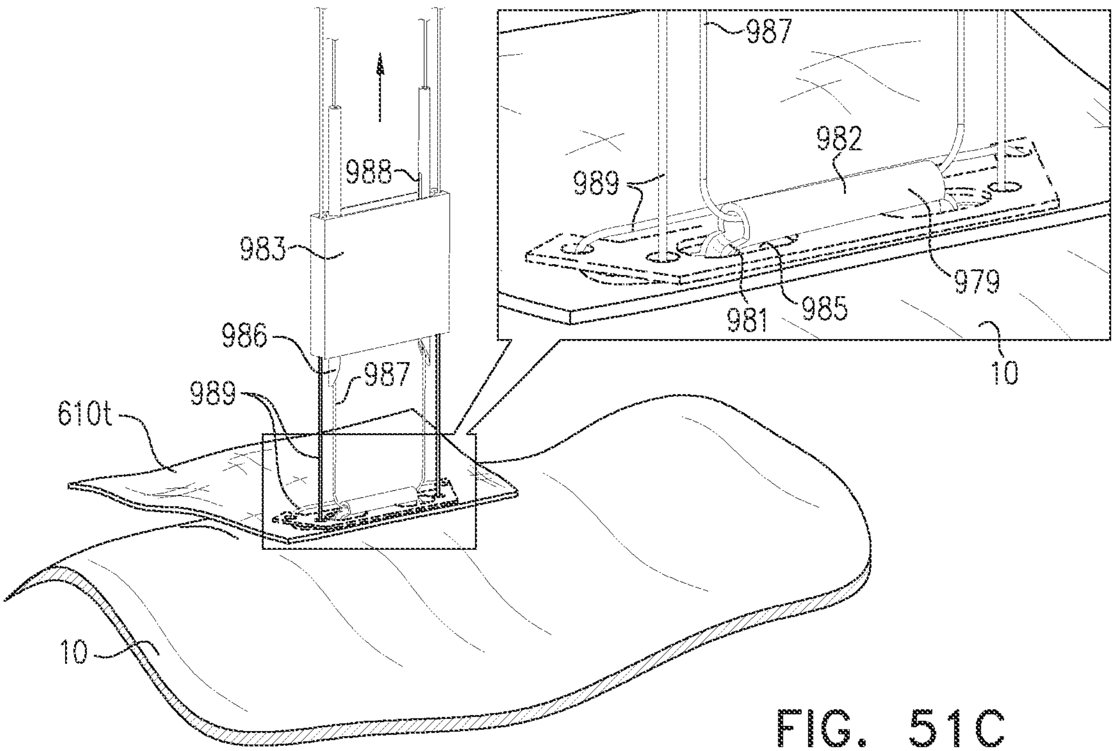
Figure 51D:
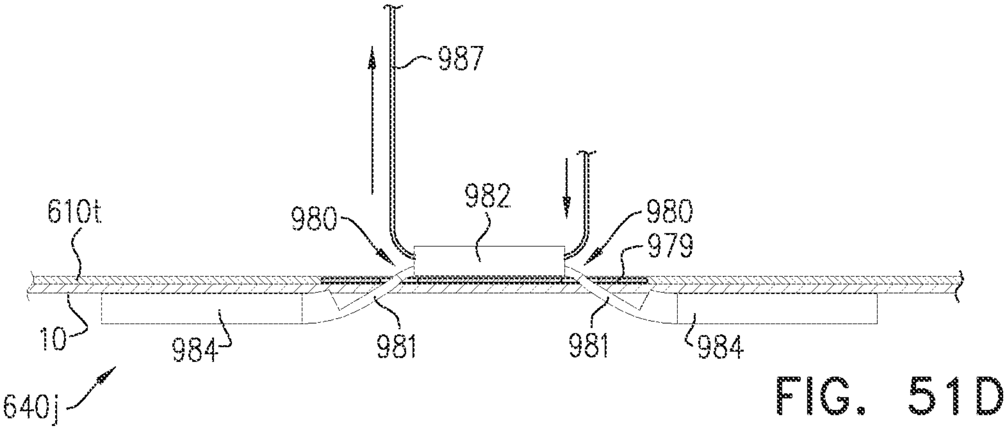
Figure 51E:
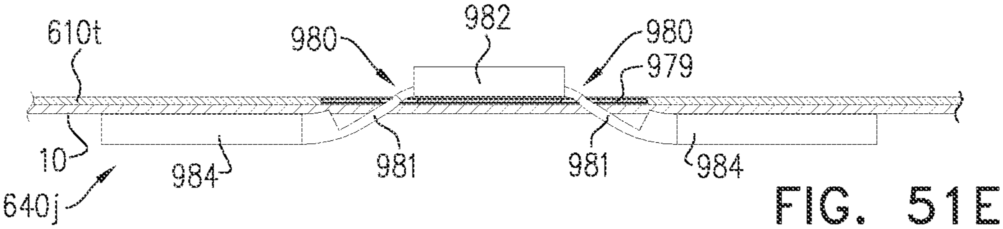

Subsequently, needles 986 are retracted from lateral tubular portions 984, which responsively deflect laterally (e.g., due to the shape memory nature of the material from which patch anchor 640*j* is formed), thereby anchoring patch 610*t* to leaflet 10 (FIGS. 51C and 51E). The anchoring of patch 610*t* to leaflet 10 by patch anchor 640*j* can resemble two pieces of paper stapled together by a stapler whose anvil is set to its sheer setting.

For some applications, patch anchor 640*j* is provided with a retrieval line 987 that extends through one of needles 986 distally to the patch anchor, through central tubular portion 982 from one lateral opening 980 to the other, and back through the other one of the needles away from the patch anchor (see FIG. 51A). That is, retrieval line 987 loops through needles 986 and central tubular portion 982. For such applications, needles 986 are hollow needles, each defining a lateral slit 988 that runs proximally from the tip of the needle parallel with an axis of the needle. Lateral slit 988 allows retrieval line 987 to extend laterally out of the lumen of needles 986 and through central tubular portion 982, even when the needles extend distally beyond the central tubular portion and through lateral tubular portions 984.

Figure 52A:
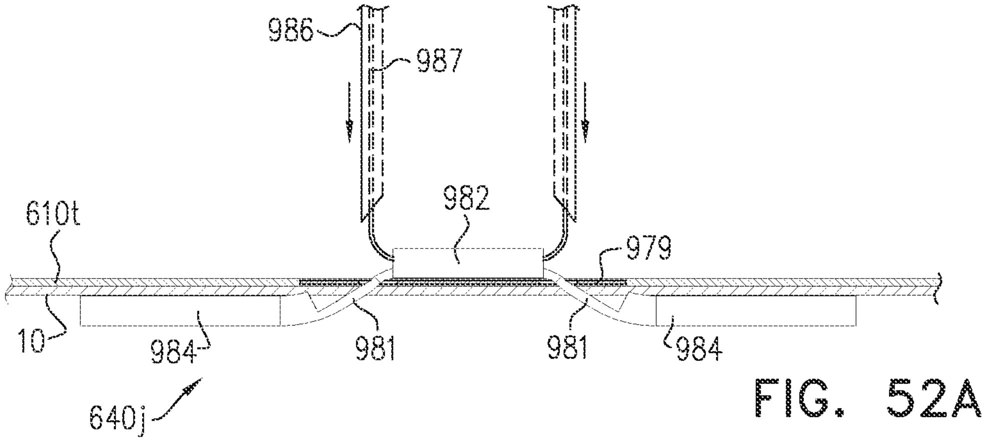
Figure 52B:
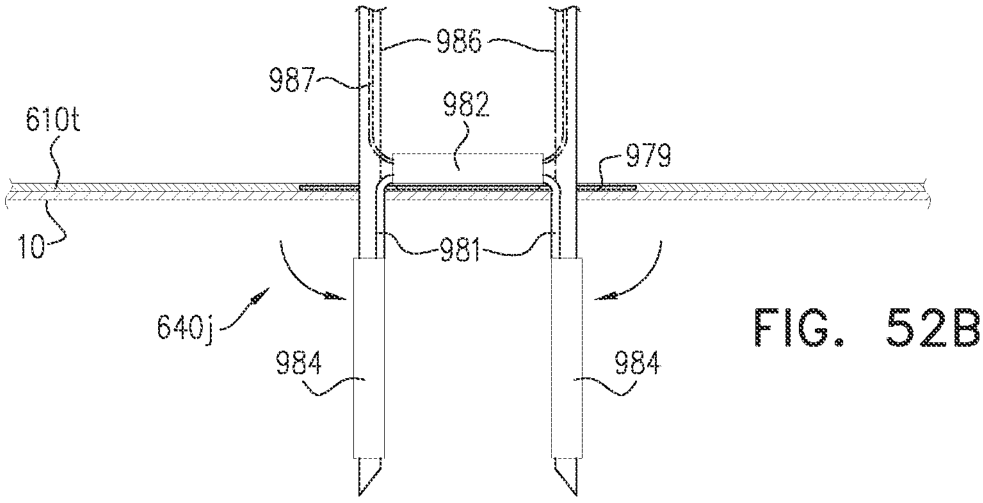

As shown in FIG. 51C, for applications in which retrieval line 987 is used, immediately after anchoring patch anchor 640*j* the retrieval line remains in place, looping through central tubular portion 982. Should it be determined at this point that patch anchor 640*j* should be retrieved, needles 986 can be re-advanced over and along retrieval line 987, to meet the patch anchor at lateral openings 980 (FIG. 52A). Further advancement of needles 986 presses the needles against joints 981 and slides the needles along the joints and into and through lateral tubular portion 984, thereby returning the patch anchor to its original state (FIG. 52B). In this state, the patch anchor can be de-anchored and/or retrieved.

The sliding of needles 986 along joints 981 and into lateral tubular portions 984 can be facilitated by the joints having a concave surface, and/or by the needles having a bevel that faces central tubular portion 982, e.g., as shown.

Whether the initial anchoring of patch anchor 640*j* was successful, or whether it was de-anchored and re-anchored, once the anchoring is determined to be satisfactory, retrieval line 987 is unlooped and withdrawn (FIG. 51D), leaving the anchored patch in place (FIG. 51E).

For some applications, a guide line 989 is provided, to guide the initial advancement of patch anchor 640*j* to the patch. For example, and as shown, the guide line can extend to the patch, loop through and/or across a portion of the patch, and then extend back proximally. For some applications, guide line 989 is utilized by advancing patch anchor 640*j* and needles 986 within a mount 983 that itself is threaded on guide line 989. This may also facilitate the return of needles 986 for de-anchoring if desired. Once anchoring of patch anchor 640*j* is determined to be satisfactory, guide line 989 is unlooped and withdrawn, e.g., similarly to as described for retrieval line 987.

For some applications, mount 983 can generally correspond to mount 840 described hereinabove, or mount 840 can be modified to facilitate the use of patch anchor 640*j*, mutatis mutandis.

For some applications, patch 610*t* (or another patch that is being anchored by patch anchor 640*j*) comprises a patch-anchor support 979, which can be attached (e.g., stitched) to sheet 620 of the patch in the vicinity of the root of the patch, e.g., on one side of the patch, or between multiple sheets of the patch. In some applications, patch-anchor support 979 is shaped and positioned to partially or completely surround holes 985. Patch-anchor support 979 can advantageously provide one or more of the following benefits: (1) to serve to provide opposition (e.g., an opposing force) against which patch anchor 640*j* can press the leaflet, thereby improving sandwiching of the leaflet between the patch anchor and the patch, e.g., compared to a similar patch in which the patch anchors press the leaflet against an unsupported part of sheet 620, and/or (2) to serve to reinforce the holes in the patch, e.g., to protect against patch anchor 640*j* and/or line 989 cutting through sheet 620.

Figure 53A:
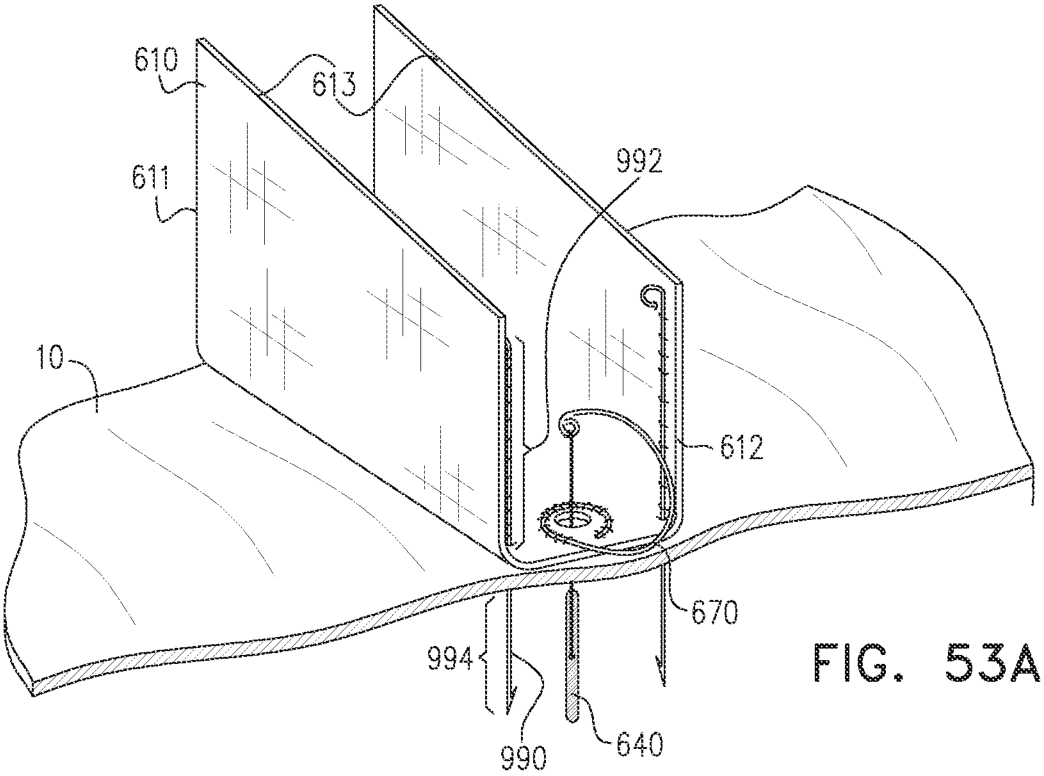
Figure 53B:
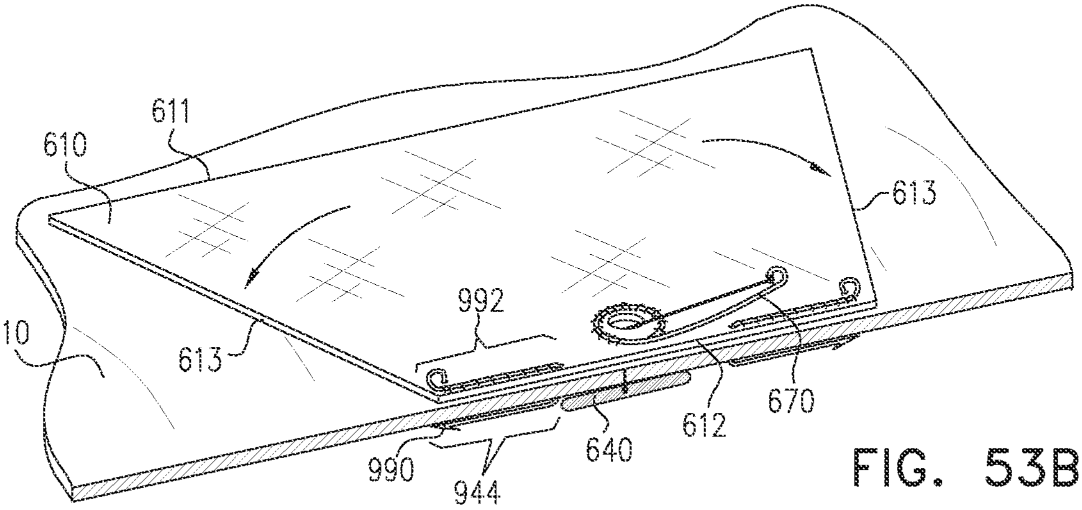

FIGS. 53A-B show auxiliary anchors 990 being used to augment anchoring of a patch 610 to leaflet 10 by a patch anchor (which in this context is referred to as a primary anchor). In the example shown, the primary patch anchor is a single patch anchor 640 connected to the patch via a single spring 670, e.g., as described with reference to FIG. 36F—but disposed approximately midway along root 612 of the patch. However, it is to be understood that auxiliary anchors 990 can be used with any type of anchor Auxiliary anchors 990 are hypothesized to be particularly useful in instances in which a primary patch anchor is disposed approximately midway along the root of the patch. For example, auxiliary anchors 990 can retain the lateral corners of the root anchored to leaflet 10, rather than allowing them to curl or flap medially. This is hypothesized to, for some applications, improve the hemodynamic benefits of the patch, and/or to reduce strain on the primary patch anchor and the surrounding region of the patch and of the leaflet.

Each auxiliary anchor 990 can comprise (e.g., can consist essentially of) a shape-memory wire or ribbon that, at rest, doubles back on itself to form two substantially parallel regions: a support region 992 and an arm region 994. The patch can be provided with: (i) support region 992 attached (e.g., stitched) to the opposing face of the patch, extending from a lateral corner of the root of the patch, medially along the root of the patch toward the primary patch anchor, and/or (ii) the wire or ribbon extending through a pierce point on the patch such that arm region 994 is disposed on the opposite side of the patch.

At rest, arm region 994 extends from the pierce point laterally back toward the lateral corner of the root of the patch.

To utilize auxiliary anchors 990, the patch is advanced to leaflet 10 with arm regions 994 pointing away from the patch and toward the leaflet such that, in conjunction with the anchoring of the primary anchor patch to the leaflet, the arm regions of the auxiliary anchors pierce the leaflet (FIG. 53). This can be performed with the arm regions of the auxiliary anchors being constrained in this state. For example, and as shown, auxiliary anchors can be entirely linear during this step. Furthermore, for some applications, this step is facilitated by performing it while the lateral sides of the patch are folded away from leaflet 10, e.g., as shown.

Subsequently, auxiliary anchors 990 (e.g., arm regions 994 thereof) are released, such that arm regions 994 become substantially parallel with support regions 992, thereby sandwiching tissue of leaflet 10 between the arm regions and the support regions, and holding the lateral corners of the root of the patch against the leaflet.

Reference is now made to FIGS. 54A-B, 55A-C, 56A-B, 57A-B, 58A-C, and 59A-C, which are schematic illustrations of various winch anchors and techniques for use therewith, in accordance with some applications. Each of these patch anchors can be used in place of winch anchor 710, mutatis mutandis, e.g., as a component of downstream assembly 700 or a variant thereof (e.g., a variant described hereinabove), and/or a component of implant 550 or an implant similar thereto, mutatis mutandis. Each of these patch anchors can, for some applications, be considered to be a variant of winch anchor 710. For simplicity, these winch anchors are shown without the winch of downstream assembly 700. Delivery tool 800 (e.g., driveshaft subassembly 890 thereof) or a variant thereof, mutatis mutandis, can be used to anchor these winch anchors to ventricular tissue using techniques described herein, mutatis mutandis. Each of these patch anchors has been assigned reference numeral 710 with a respective suffix, to indicate its correspondence to, winch anchor 710.

It is to be further noted that each of these winch anchors can, for some applications, be used independently of a winch such as winch 720, e.g., for anchoring a different component or implant to ventricular tissue, or for anchoring to tissue other than ventricular tissue.

FIGS. 54A-B, 55A-C, and 56A-B show winch anchors 710*a*, 710*b*, and 710*c*, respectively. Each of these winch anchors has a respective tissue-engaging element that comprises radially-expandable barbs and a lance, relative axial movement between the barbs and the lance inducing radial expansion of the barbs.

Figure 54A:
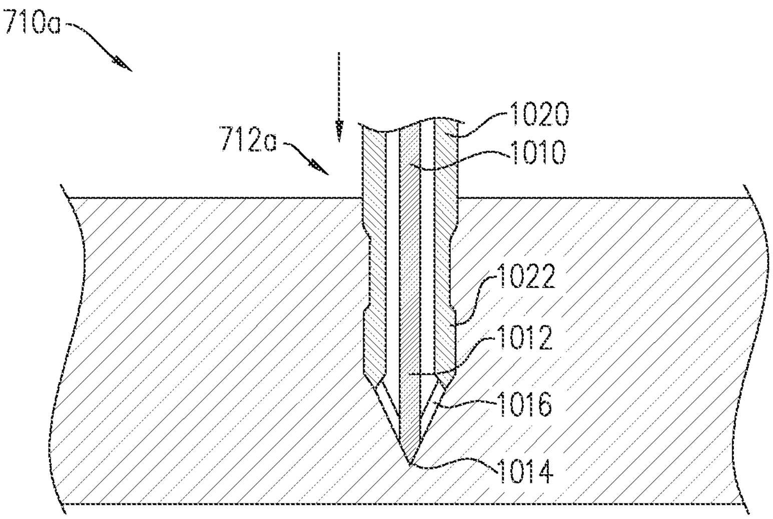
FIGS. 54A-B, 55A-C, 56A-B, 57A-B, 58A-C, and 59A-C are schematic illustrations of various winch anchors and techniques for use therewith, in accordance with some applications.
Figure 54B:
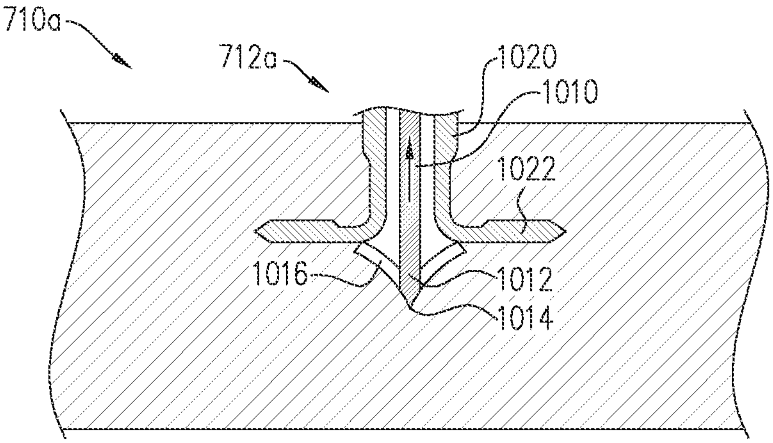

Winch anchor 710*a* of FIGS. 54A-B has a tissue-engaging element 712*a* that comprises (i) a lance structure 1010 that comprises a lance 1012 that has a pointed tip 1014 and spurs 1016, and (ii) a barb structure 1020 that comprises multiple barbs 1022.

Tissue-engaging element 712*a* is advanced distally into tissue with tip 1014 leading, and barb structure 1020 in a retracted position in which barbs 1022 are medially retracted and typically point axially in the direction of advancement (FIG. 54A). In some applications, there is no relative movement between lance structure 1010 and barb structure 1020 during this advancement. For some applications, and as shown, barbs 1022 and spurs 1016 can coapt to provide tissue-engaging element 712*a* with a streamlined profile for axial advancement into the tissue. For example, the tips of barbs 1022 can meet spurs 1016 in a manner that presents, to the tissue, a substantially seamless outer surface.

Once tissue-engaging element 712*a* has been advanced into the tissue, lance structure 1010 is retracted with respect to barb structure 1020, e.g., by retracting the lance structure (e.g., as shown), or by advancing the barb structure. This pushes spurs 1016 proximally against barbs 1022, urging the barbs to deflect radially outward (FIG. 54B), thereby securing the tissue-engaging element in the tissue. For some applications, and as shown, spurs 1016 can also responsively deflect radially outward.

It is hypothesized that, due to the complimentary opposite curvatures of spurs 1016 and barbs 1022 (the spurs curving proximally and outward, and the barbs curving distally and outward), the spurs support the barbs in their radially-expanded state, thereby resisting de-anchoring of the anchor. For applications in which spurs 1016 also become expanded, it is hypothesized that the spurs and barbs 1022 cooperate to become mutually supportive in their radially-expanded states.

For some applications, a discrete locking step can be performed to prevent further relative axial movement between lance structure 1010 and barb structure 1020.

For some applications, winch anchor 710*a* (e.g., tissue-engaging element 712*a* thereof) is de-anchorable (e.g., retrievable) by returning lance structure 1010 to its original extended position with respect to barb structure 1020, thereby allowing barbs 1022 to responsively return medially.

Figure 55A:
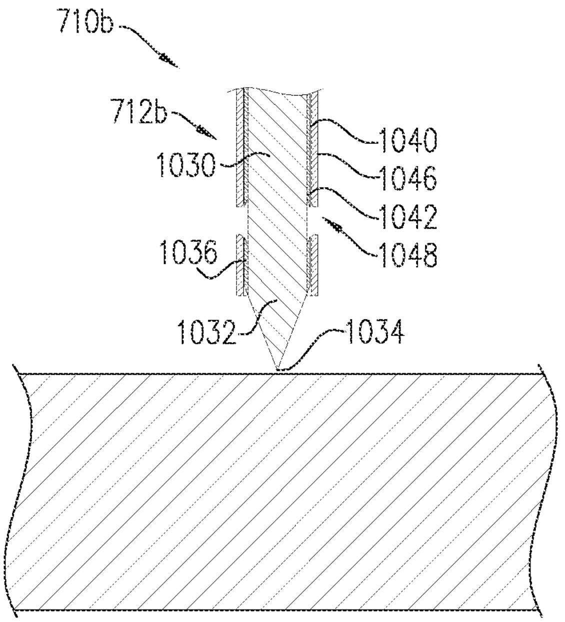
Figure 55B:
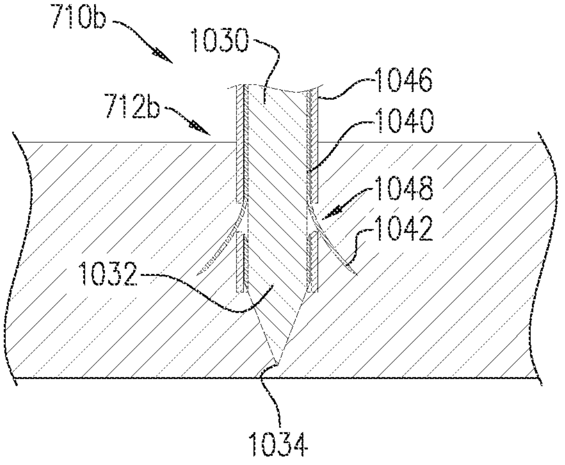
Figure 55C:
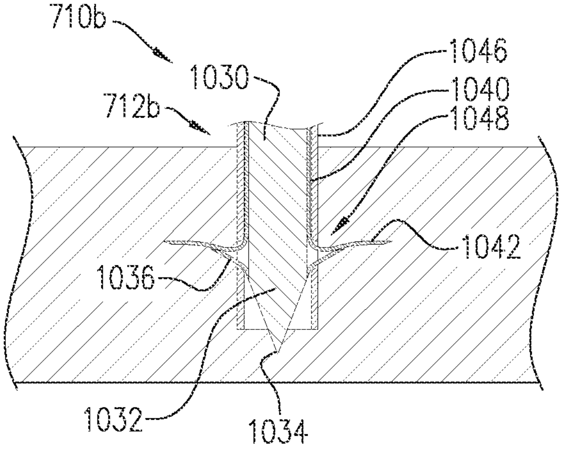

Winch anchor 710*b* of FIGS. 55A-C is similar to winch anchor 710*a*, except primarily for the addition of an overtube 1046 within which its lance structure and barb structure are disposed and axially slidable, and the resulting order of steps in the anchoring of the winch anchor. Winch anchor 710*b* has a tissue-engaging element 712*b* that comprises (i) a lance structure 1030 that comprises a lance 1032 that has a pointed tip 1034 and spurs 1036, and (ii) a barb structure 1040 that comprises multiple barbs 1042.

Tissue-engaging element 712*b* is advanced distally into tissue with tip 1034 leading, barb structure 1040 in a retracted position in which barbs 1042 are medially retracted and typically point axially in the direction of advancement, and lance structure in an advanced position in which spurs 1036 are medially retracted and typically point axially away from the direction of advancement, e.g., pointing toward barbs 1042 (FIG. 55A). In this configuration, barbs 1042 and/or spurs 1036 are generally constrained medially (e.g., constrained against lance 1032) by overtube 1046. In some applications, there is no relative movement between lance structure 1030, barb structure 1040, and overtube 1046 during this advancement.

Once tissue-engaging element 712*b* has been advanced into the tissue, barb structure 1040 is advanced distally with respect to overtube 1046 (and typically also with respect to lance structure 1030), such that barbs 1042 extend out of lateral openings 1048 in the overtube (FIG. 55B). Barbs 1042 can extend in a substantially lateral direction, in a lateroproximal direction (i.e., laterally and proximally toward the surface of the tissue), or, as shown, in a laterodistal direction (i.e., laterally and distally) away from the surface of the tissue. This can be facilitated by barbs 1042 having shape-memory.

Subsequently, lance structure 1030 is retracted proximally with respect to overtube 1046 and barb structure 1040 (e.g., without further relative movement between the overtube and the barb structure), such that spurs 1036 protrude out of lateral openings 1048 and push proximally against barbs 1042 (FIG. 55C). In the example shown, this deflects barbs 1042 in a proximal direction, e.g., such that they extend laterally or lateroproximally from openings 1048. This deflection can pull tissue-engaging element 712*b* deeper into the tissue.

It is hypothesized that spurs 1036 support barbs 1042 in their radially-expanded state, thereby resisting de-anchoring of the winch anchor.

For some applications, a discrete locking step can be performed to prevent further relative axial movement between lance structure 1030, barb structure 1040, and/or overtube 1046.

For some applications, winch anchor 710*b* (e.g., tissue-engaging element 712*b* thereof) is de-anchorable (e.g., retrievable) by returning lance structure 1030 and barb structure 1040 to their original positions with respect to overtube 1046, thereby medially retracting spurs 1036 and barbs 1042.

Figure 56A:
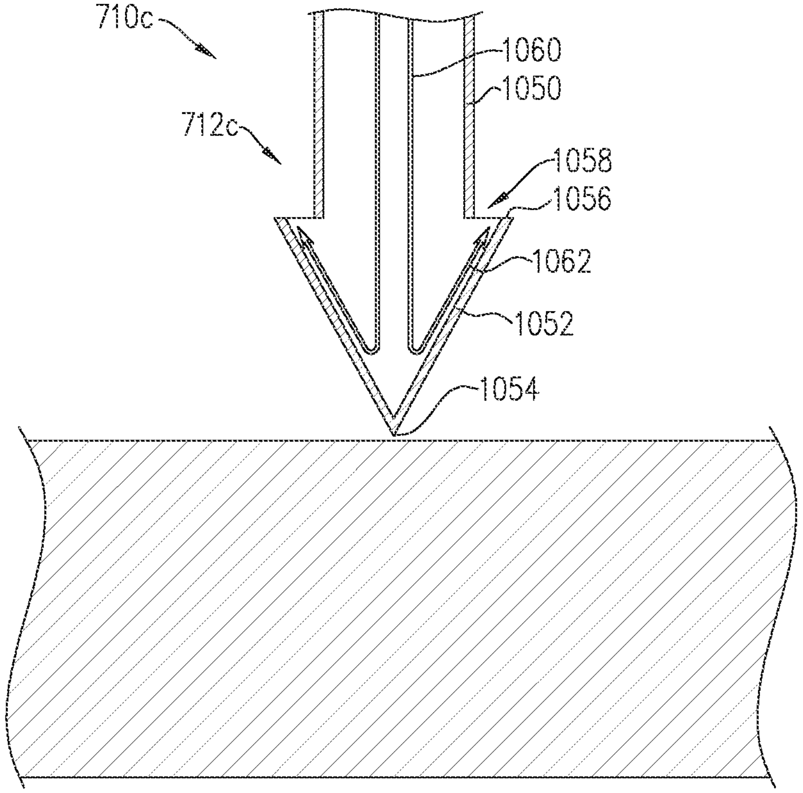
Figure 56B:
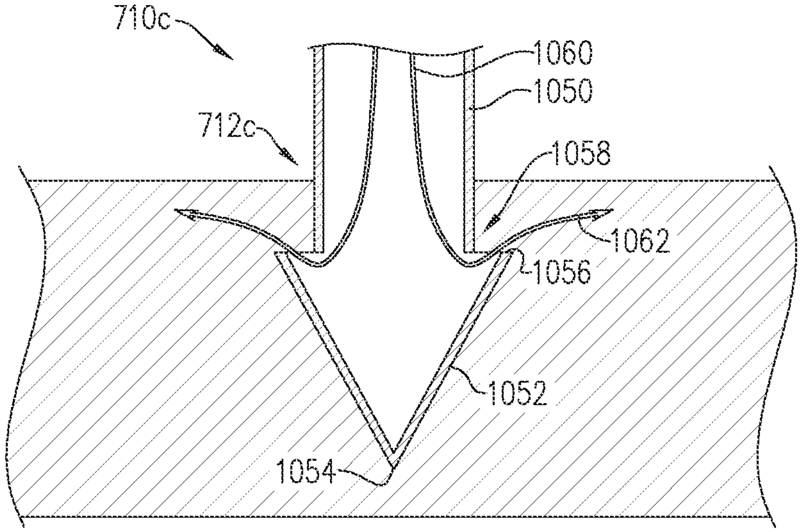

FIGS. 56A-B show a winch anchor 710*c* that has a tissue-engaging element 712*c* that comprises (i) a lance structure 1050 that comprises a lance 1052 that has a pointed tip 1054, and (ii) a barb structure 1060 that comprises multiple barbs 1062. Whereas, for each of winch anchors 710*a* and 710*b*, the lance structure is disposed substantially within the barb structure, barb structure 1060 of winch anchor 710*c* is disposed substantially within its lance structure 1050. Another difference between winch anchor 710*c* and winch anchors 710*a* and 710*b* is that lance structure 1050 of winch anchor 710*c* does not have discrete spurs, but rather a flange 1056. Lance 1052 can be substantially conical, with a proximal rim of the conical lance defining flange 1056.

Tissue-engaging element 712*c* is advanced distally into tissue with tip 1054 leading, and barb structure 1060 in a distal position in which barbs 1042 are medially retracted within lance structure 1050 (e.g., within lance 1052). In this position, barbs 1042 can point in a lateromedial direction away from the direction of advancement, e.g., as shown. In this configuration, barbs 1042 and/or spurs 1036 are generally constrained medially (e.g., constrained against lance 1052, e.g., an inner surface thereof). In some applications, there is no relative movement between lance structure 1050 and barb structure 1060 during this advancement.

Once tissue-engaging element 712*c* has been advanced into the tissue, barb structure 1060 is moved proximally with respect to lance structure 1050, such that barbs 1062 extend out of lateral openings 1058 in the lance structure (FIG. 56B). Barbs 1062 can extend in a substantially lateral direction or in a lateroproximal direction. This can be facilitated by barbs 1062 having shape-memory.

It is hypothesized that flange 1056 support barbs 1062 in their radially-expanded state (e.g., inhibiting them from deflecting in response to a pulling force applied to the winch anchor), thereby resisting de-anchoring of the winch anchor.

For some applications, a discrete locking step can be performed to prevent further relative axial movement between lance structure 1050 and barb structure 1060.

For some applications, winch anchor 710*c* (e.g., tissue-engaging element 712*c* thereof) is de-anchorable (e.g., retrievable) by returning barb structure 1060 to its original position with respect to lance structure 1050, thereby medially retracting barbs 1062 into the lance structure.

Figure 57A:
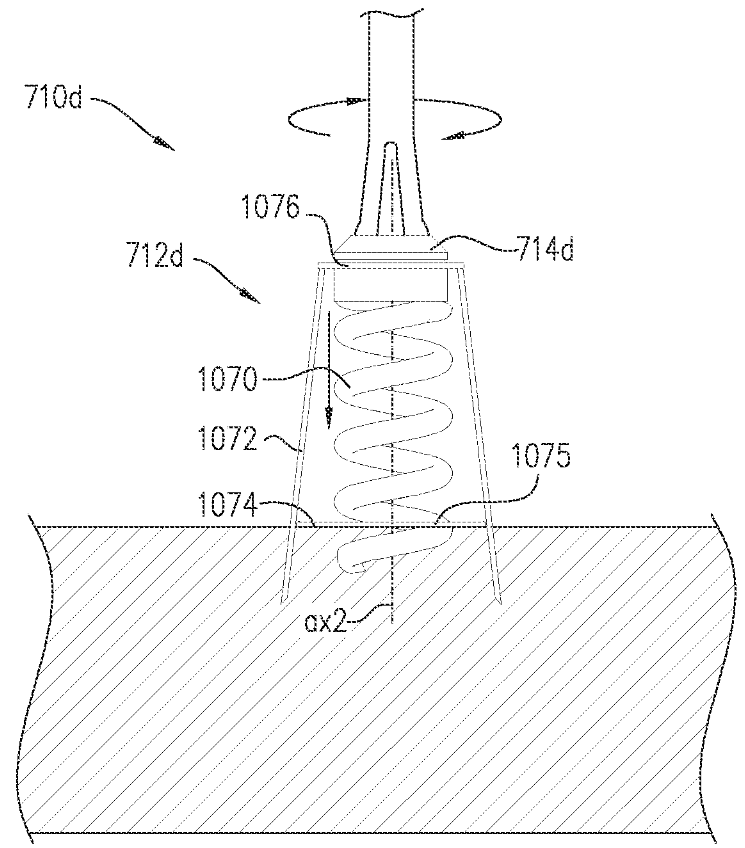
Figure 57B:
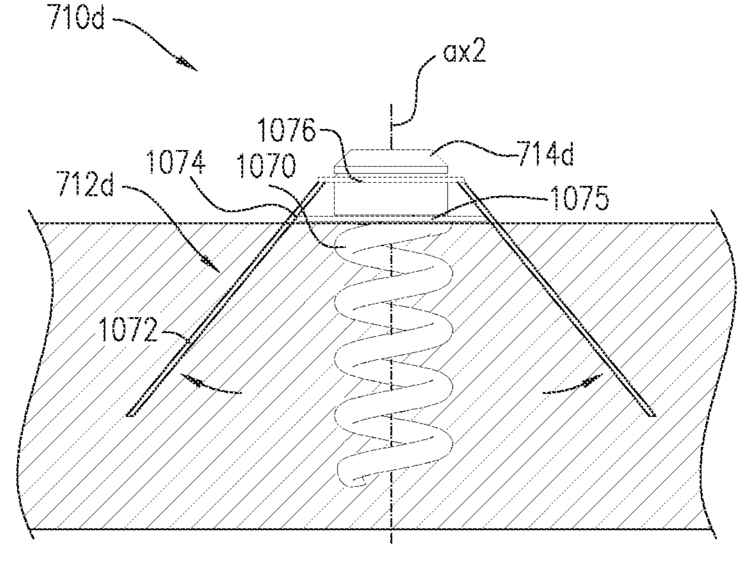

FIG. 57A-B show a winch anchor 710*d* that, like winch anchor 710, has a tissue-engaging element 712*d* that comprises a helical tissue-engaging element 1070. However, winch anchor 710*d* (e.g., tissue-engaging element 712*d* thereof) further comprises auxiliary tissue-engaging elements or friction enhancing elements, which can be in the form of barbs 1072. Barbs 1072 are coupled to a head 714*d* of the winch anchor in a manner that facilitates deflection of the barbs with respect to the head and/or with respect to helical tissue-engaging element 1070. For example, and as shown, barbs 1072 can be articulatably coupled to head 714*d*. Winch anchor 710*d* (e.g., tissue-engaging element 712*d* thereof) further comprises a flange 1074, which can be defined by the rim of a plate 1075. Helical tissue-engaging element 1070 is advanceable (e.g., screwable) past or through flange 1074 (e.g., through the plate whose rim defines the flange), and barbs 1072 are slidable over flange 1074. Helical tissue-engaging element 1070 is rotatable independently of barbs 1072, e.g., by the barbs being articulatably coupled to a ring 1076 that is rotatably coupled to head 714*d*.

As shown in FIGS. 57A-B, as helical tissue-engaging element 1070 is screwed into the tissue, barbs 1072 are also driven into the tissue but plate 1075 remains on the surface of the tissue. As head 714*d* (and ring 1076) approach the tissue, the resulting change in the angle between (i) central longitudinal axis ax2 of the anchor, and (ii) a straight line between (a) the coupling point of barb 1072 to head 714*d* (or ring 1076), and (b) flange 1074, means that as the barb slides over the flange the barb is urged to deflect radially outward. To augment this behavior, flange 1074 can be disposed, from central longitudinal axis ax2 of winch anchor 710*d*, further laterally than the coupling between barbs 1072 and head 714*d*.

Figure 58A:
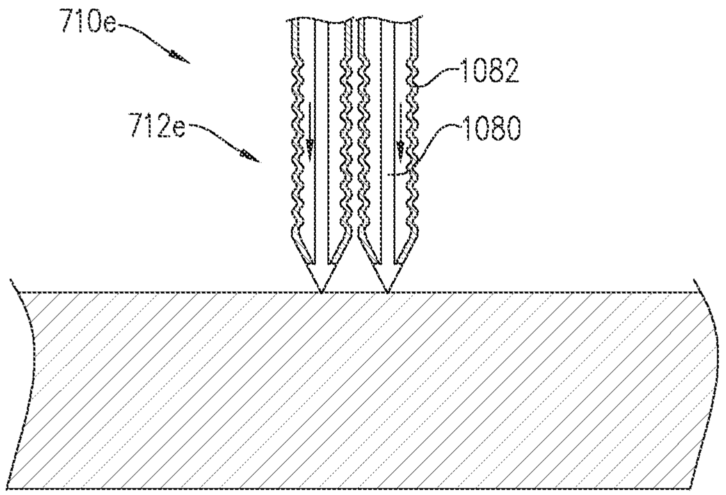
Figure 58B:
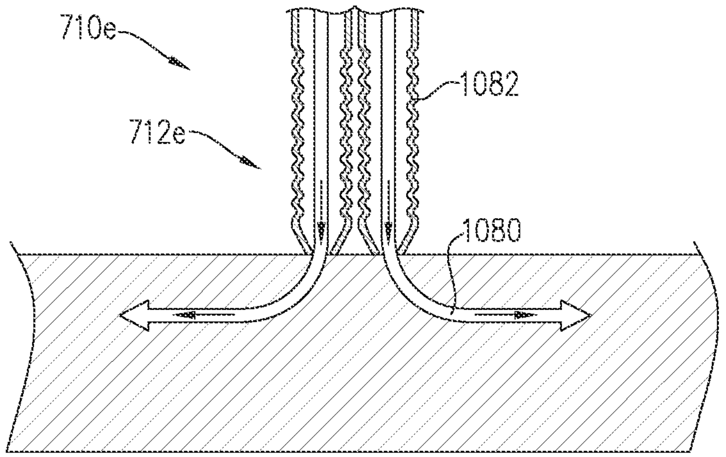
Figure 58C:
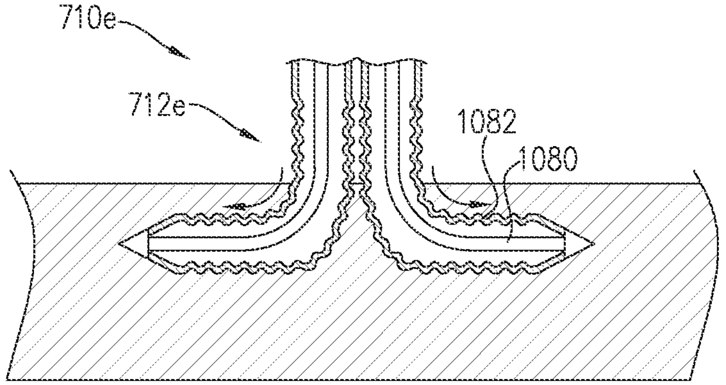

FIGS. 58A-C show a winch anchor 710*e* that has a tissue-engaging element 712*e* that comprises multiple lances 1080 and a corresponding plurality of sleeves 1082. Lances 1080 are first advanced into the tissue, and can automatically deflect laterally (FIGS. 58A-B). Lances 1080 are narrow and rigid relative to sleeves 1082, thereby facilitating their penetration of the tissue. Subsequently, sleeves 1082 are advanced over and along lances 1080, e.g., with the lances serving as rails. Because sleeves 1082 are more flexible than lances 1080, they typically follow the path of the lances without substantially moving the lances within the tissue. Because sleeves 1082 are wider than lances 1080, they are hypothesized to contribute to the anchoring strength of tissue-engaging element 712*e* by increasing a surface area of tissue over which force is distributed, e.g., reducing a likelihood of the tissue-engaging element cutting or tearing out of the tissue in response to being pulled.

For some applications, each sleeve 1082 can comprise a metallic or polymer hypotube, optionally covered and/or lined with a fabric.

Figure 59A:
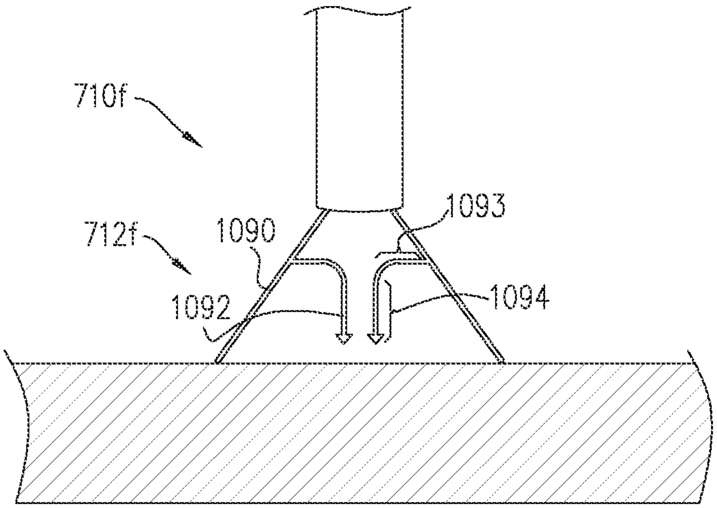
Figure 59B:
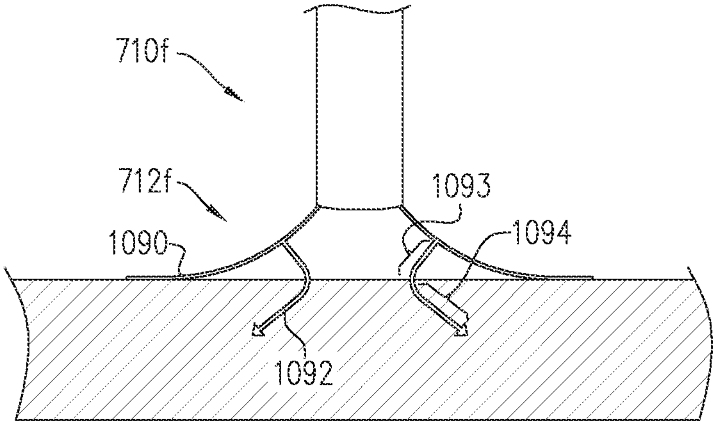
Figure 59C:
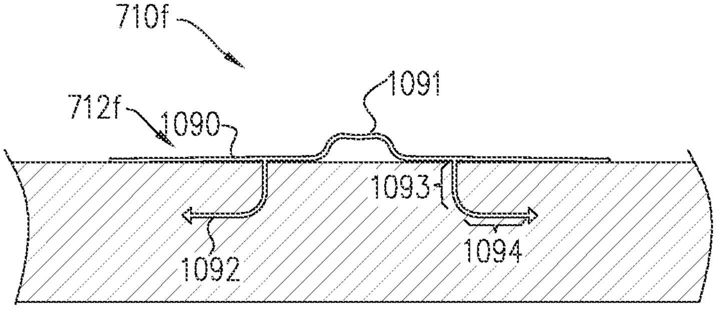

FIGS. 59A-C show a winch anchor 710*f* that comprises a plate 1090 and a tissue-engaging element 712*f* coupled to the plate. Tissue-engaging element 712*f* comprises multiple curved barbs 1092 whose roots are coupled to plate 1090. At least when tissue-engaging element 712*f* is at rest, barbs 1092 extend away from plate 1090 (e.g., such that their roots 1093 are substantially perpendicular to the plate), and curve medially such that tip regions 1094 of the barbs are substantially parallel with the plate (FIG. 59C).

Tissue-engaging element 712*f* is placed against the tissue while constrained in a delivery state in which the tip regions of barbs 1092 point at the tissue (FIG. 59A). As shown, plate 1090 (e.g., the rim thereof) can be in contact with the tissue at this point.

Tissue-engaging element 712*f* is then pushed against the tissue and progressively released, such that plate 1090 becomes disposed progressively flatter against the tissue while barbs 1092 penetrate into the tissue following a curved path, e.g., with the expansion of the plate driving the barbs through the tissue along the curved path.

A central region 1091 of plate 1090 can be configured to facilitate compression and expansion of the plate as described. For example, the central region can serve as a spring.

Features of winch anchor 710*f* can be combined with those of other tissue anchors described herein, such as anchor 352.

Figure 60:
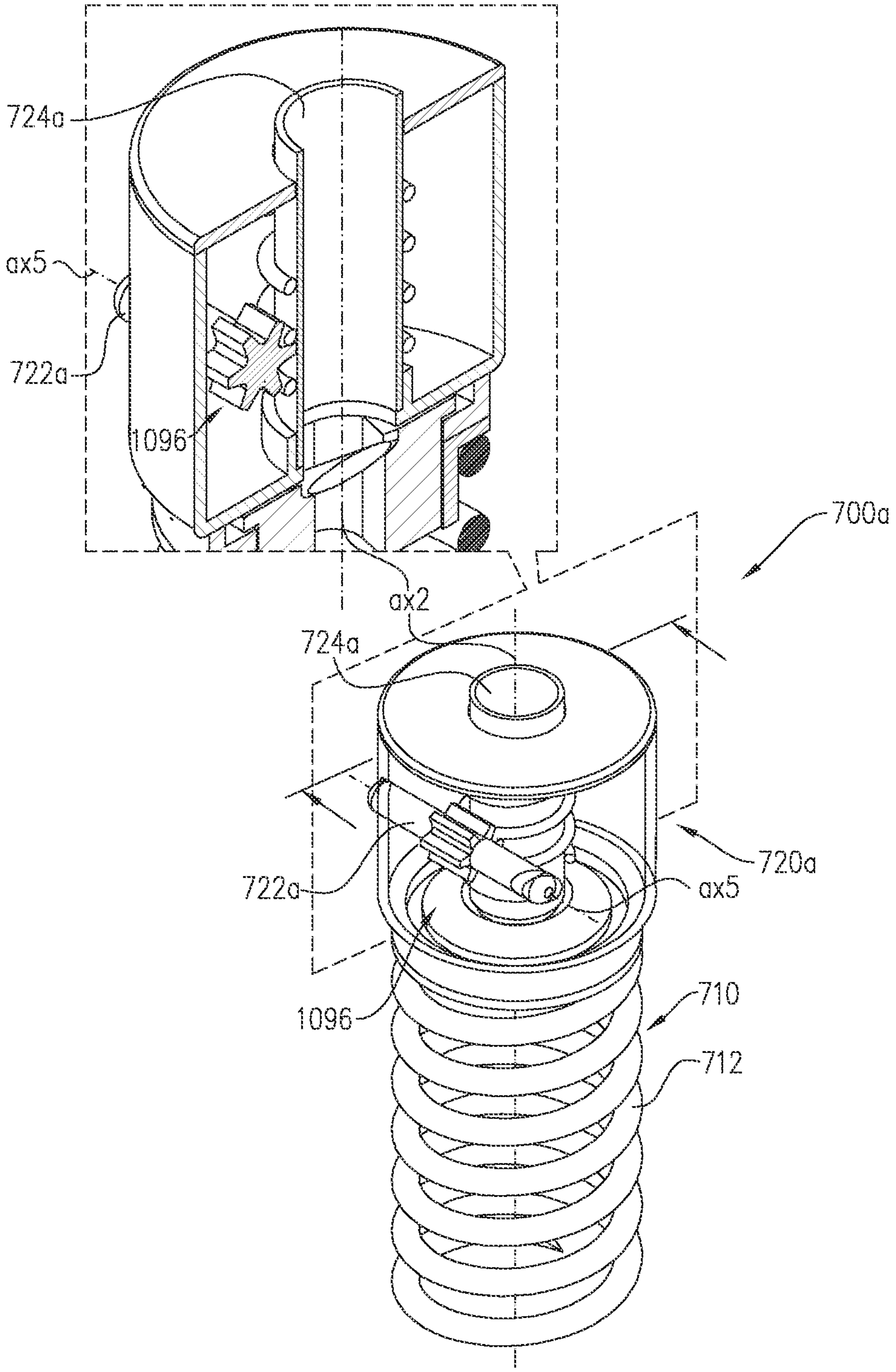
FIG. 60 is a schematic illustration of a downstream assembly, in accordance with some applications.

Reference is now made to FIG. 60, which is a schematic illustration of a downstream assembly 700*a*, in accordance with some applications. Downstream assembly 700*a* can be considered to be a variant of downstream assembly 700, described hereinabove. In some applications, and as shown, downstream assembly 700*a* comprises winch anchor 710 (described hereinabove) and a winch 720*a* coupled thereto. Winch 720*a* can be considered to be a variant of winch 720. As described hereinabove, spool 722 of winch 720 of downstream assembly 700 can be mounted such that it and/or its axis of rotation is colinear with anchor axis ax2. FIG. 60 illustrates that other spool orientations are possible. More specifically. FIG. 60 shows that a spool 722*a* of winch 720*a* can be mounted such that it and/or its axis of rotation is orthogonal to anchor axis ax2. For example, and as shown, winch 720*a* can comprise a driveshaft interface 724*a* that lies on axis ax2 and is actuated by rotation about axis ax2, but that is operatively coupled to spool 722*a* via a worm gear arrangement 1096 that rotates the spool about an axis ax5 that is orthogonal to axis ax2.

Reference is made to FIGS. 61A-B and 62A-D, which are schematic illustrations of a downstream assembly 700*b*, in accordance with some applications. Downstream assembly 700*b* can be considered to be a variant of downstream assembly 700, described hereinabove. In some applications, and as shown, downstream assembly 700*b* comprises a winch anchor 710*b* and a winch 720*b* coupled thereto. Winch anchor 710*b* can be considered to be a variant of winch anchor 710, winch 720*b*, can be considered to be a variant of winch 720, and a spool 722*b* of winch 720*b* can be considered to be a variant of spool 722.

In some applications, downstream assembly 700*b* is broadly as described for downstream assembly 700, mutatis mutandis, except for modifications that enable it to be operated by a driveshaft subassembly 890*b*, which generally corresponds to driveshaft subassembly 890 described hereinabove except that the separate anchor-control driveshaft 880 and winch-control driveshaft 882 have been replaced with a unitary downstream-assembly-control driveshaft 1100. It is hypothesized that, for some applications, replacing two coaxial driveshafts with a single driveshaft can enable driveshaft subassembly 890*b* to be slimmer and/or more flexible than driveshaft subassembly 890, thereby advantageously being even less likely to create significant hemodynamic artifacts during adjustment of the effective length of tether 560.

Figure 61A:
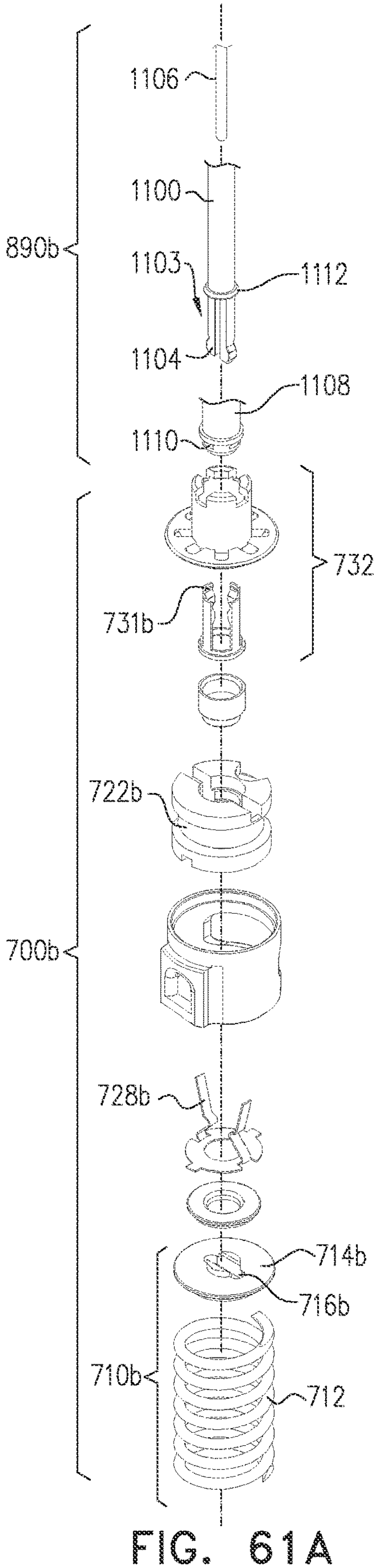
FIGS. 61A-B and 62A-D are schematic illustrations of a downstream assembly, in accordance with some applications.
Figure 61B:
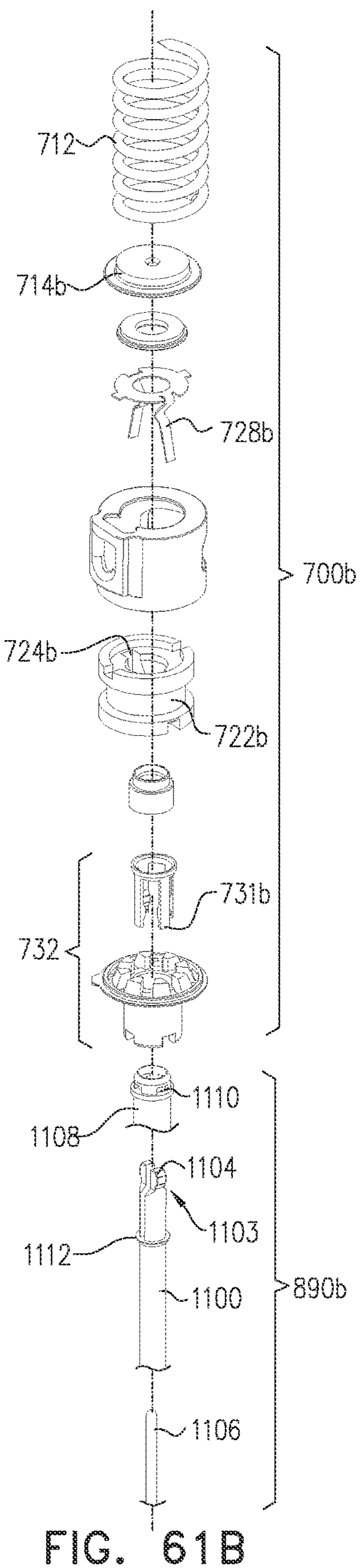

FIG. 61A is a schematic illustration showing an exploded view of (i) some components of driveshaft subassembly 890*b* at a distal end of the driveshaft subassembly, and (ii) downstream assembly 700*b*. FIG. 61B is an inverted version of FIG. 61A, showing an inverted view of each component. FIGS. 62A-D show cross-sections of the same components, assembled and in different states.

Driveshaft 1100 can comprise or define, at a distal end of the driveshaft, a drive head 1103 that comprises one or more (e.g., two) spurs 1104 that are locked to downstream assembly 700*b* by a lock-rod 1106, which can be identical to lock-rod 886.

Winch anchor 710*b* comprises tissue-engaging element 712 (described hereinabove), and can be identical or similar to winch anchor 710 except that its head 714*b* (e.g., a driver interface 716*b* defined by the head) can be modified to be engaged by drive head 1103.

Driveshaft subassembly 890*b* (or the delivery tool of which it is a part) is transitionable between an anchoring state and a winching state such that it (e.g., driveshaft 1100 thereof) can drive winch anchor 710*b* and rotate spool 722*b* independently of each other. Transitioning between the states can be controlled from the extracorporeal control portion (e.g., a controller thereof).

In the anchoring state (FIG. 62A), driveshaft 1100 (e.g., drive head 1103 thereof) is engaged with driver interface 716*b*, enabling the driveshaft to transfer anchoring force (e.g., torque) to winch anchor 710*b*. In some applications, in the anchoring state, driveshaft 1100 is disengaged from winch 720*b*, and cannot rotate spool 722*b*.

In the winching state (FIG. 62B), driveshaft 1100 (e.g., drive head 1103 thereof) is engaged with a driveshaft interface 724*b* that is defined by, is a component of, or is fixedly coupled to, spool 722*b*, enabling the driveshaft to actuate winch 720*b*. In some applications, in the winching state, driveshaft 1100 is disengaged from winch anchor 710*b* (e.g., from driver interface 716*b* thereof), and therefore cannot apply the anchoring force to the winch anchor.

For applications in which driveshaft subassembly 890*b* and downstream assembly 700*b* are used, the anchor controller of the extracorporeal proximal portion of the delivery tool can serve both (i) to drive winch anchor 710*b* when in the anchoring state (e.g., by being operatively coupled to the winch anchor via driveshaft 1100 but operatively uncoupled from winch 720*b*), and (ii) to actuate the winch when in the winching state (e.g., by being operatively coupled to the winch via driveshaft 1100 but operatively uncoupled from the winch anchor). That is, for such applications, the anchor controller can be a downstream-assembly controller with dual functions. For such applications, the winch controller of the extracorporeal proximal portion of the delivery tool can be replaced by a state controller via which the delivery tool (e.g., the driveshaft subassembly thereof) is transitionable between the anchoring state and the winching state.

Figures 62A, 62B, 62C, 62D:
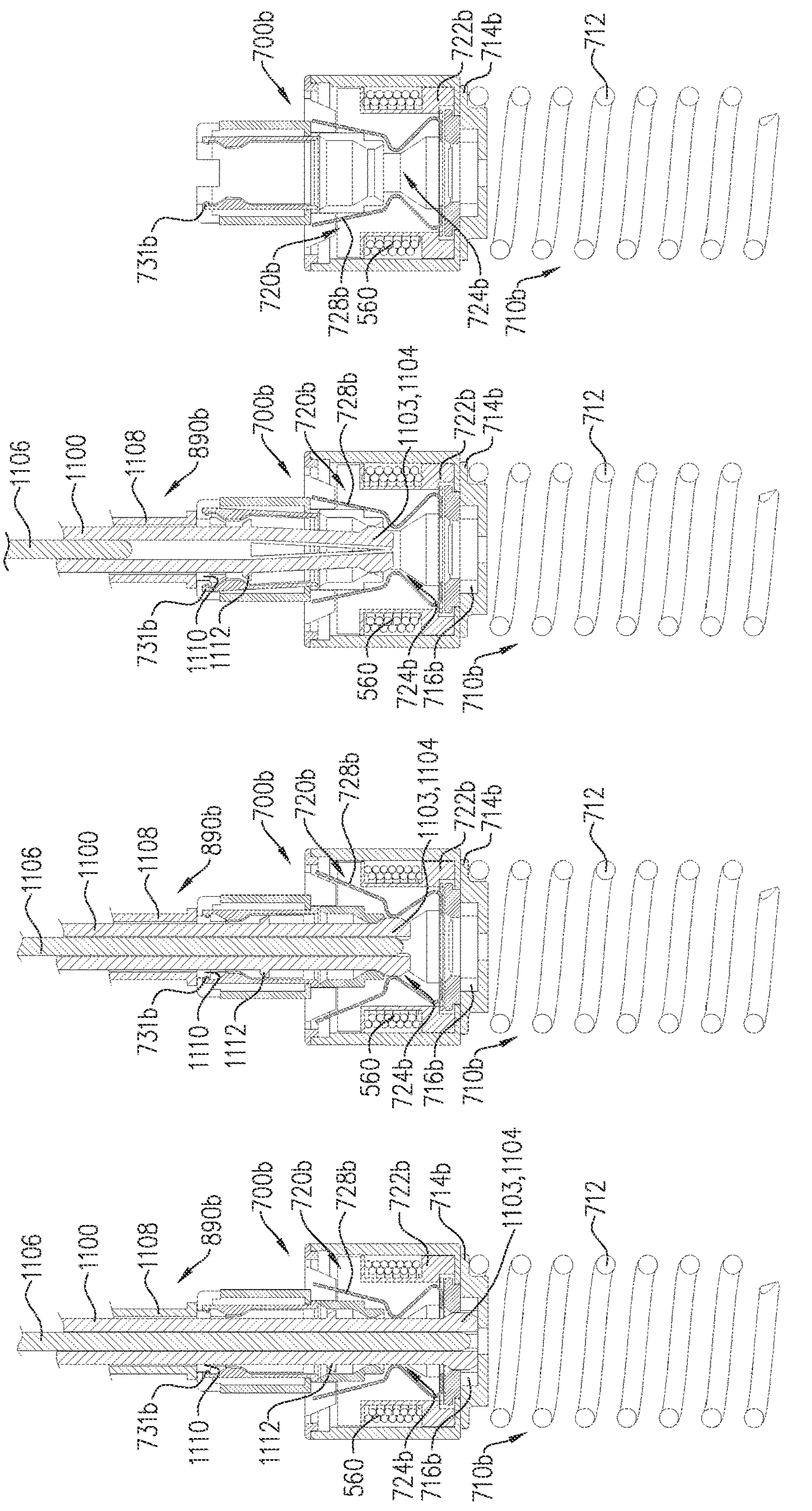

For some applications, and as shown, in the anchoring state driveshaft 1100 is disposed in a first axial position with respect to downstream assembly 700*b* (FIG. 62A), and in the winching state the driveshaft is disposed in a second, different (e.g., more proximal), axial position with respect to the downstream assembly (FIG. 62A). That is, for such applications, the delivery tool (e.g., driveshaft subassembly 890*b* thereof) is transitionable between the anchoring state and the winching state via axial movement of driveshaft 1100 with respect to downstream assembly 700*b*.

In the example shown, driver interface 716*b* and driveshaft interface 724*b* each define a respective slot within which drive head 1103 fits. While lock-rod 1106 remains in place between spurs 1104, drive head 1103 is locked to downstream assembly 700*b* but can nonetheless be moved (e.g., axially) between driver interface 716*b* and driveshaft interface 724*b*, thereby allowing transitioning between the anchoring and winching states. Winch 720*b* (e.g., driveshaft interface 724*b* thereof) is shaped to obstruct movement of drive head 1103 proximally beyond the driveshaft interface while lock-rod 1106 remains in place.

It is to be noted that, whereas winch 720 described hereinabove remains unlocked throughout both anchoring of the winch anchor and actuation of the winch (e.g., is provided unlocked, and remains unlocked until actuation of the winch is complete), winch 720*b* is locked (e.g., due to spring-loaded detents 728*b* engaging the housing of the winch) while driveshaft subassembly 890*b* is in the anchoring state (FIG. 62A), and becomes unlocked (e.g., via deflection of the detents) only upon the driveshaft subassembly transitioning into the winching state, e.g., by being pushed aside by spurs 1104 (FIG. 62B).

Once an optimal effective length of tether 560 has been achieved, driveshaft subassembly 890*b* is disengaged from downstream assembly 700*b*, and thereby from the implant as a whole (FIGS. 62C-D). For example, and as shown, lock-rod 1106 can be withdrawn at least sufficiently to allow disengagement of driveshaft 1100 from driveshaft interface 724*b*, e.g., by medial deflection of spurs 884 allowing drive head 1103 to move proximally beyond the driveshaft interface (FIG. 62C). Responsively, one or more spring-loaded detents 728 move to engage the housing of spool 722*b* in a manner that locks the spool from rotating with respect to its housing (i.e., locks winch 720) such that tension on tether 560 cannot unspool the tether, thereby fixing the effective length of the tether.

Driveshaft subassembly 890*b* can comprise a reference-force tube 1108, which serves a similar function to reference-force tube 892 of driveshaft subassembly 890, mutatis mutandis. However, whereas reference-force tube 892 is maintained in engagement with the downstream assembly via tension on driveshaft 880, reference-force tube 1108 is engaged with downstream assembly 700*b* via locking between complimentary couplings on the distal end of the reference-force tube (couplings 1110) and on a reference-force-tube interface 732*b* of the downstream assembly (couplings 731*b*). For example, couplings 1110 can be recesses, and couplings 732*b* can be latches that protrude into the recesses (e.g., as shown), or vice versa. For some applications, couplings 1110 and 732*b* define a cantilever snap fit. This engagement is maintained irrespective of whether the driveshaft subassembly is in its anchoring state (drive head 1103 engaged with driver interface 716*b*) or in its winching state (drive head 1103 engaged with driveshaft interface 724*b*). However, once lock-rod 1106 is withdrawn, withdrawing driveshaft 1100 such that drive head 1103 moves proximally beyond driveshaft interface 724*b* also moves a flange 1112 of the driveshaft (e.g., circumscribing the driveshaft proximally from the driver head) proximally in a manner that pushes couplings 731*b* out of engagement with couplings 1110, e.g., by transiently pushing couplings 731*b* laterally (FIG. 62C). At this point, driveshaft subassembly 890*b* is disengaged from downstream assembly 700, and can be withdrawn from the downstream assembly (FIG. 62D).

It is hypothesized that, for some applications, this release configuration can advantageously facilitate the use of a single downstream-assembly-control driveshaft that moves axially between anchoring and winching states, e.g., by obviating a need for preloading between the driveshaft and the reference-force tube in order to maintain the reference-force tube engaged with the downstream assembly.

Reference is made to FIGS. 63, 64, and 65A-B, which are schematic illustrations of downstream support 834 and variants 834*a* and 834*b* thereof, in accordance with some applications. As described hereinabove, clasp 830 (e.g., downstream support 834 thereof) can define or comprise a slot guard 838 for each slot 837.

Figure 63:
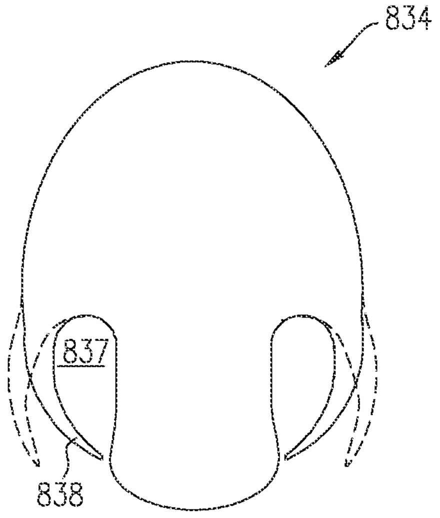
FIGS. 63, 64, and 65A-B are schematic illustrations of various downstream supports, in accordance with some applications.

FIG. 63 schematically illustrates slot guard 838 in more detail. In its resting position (solid line), slot guard 838 covers an entrance to slot 837, thereby obstructing tissue of the heart from entering the slot. Slot guard 838 is resilient, for example, comprising a resilient flap that is transiently pushed out of the way by cord 642 as it exits slot 837. The transiently-deflected position of slot guard 838 is shown in broken lines.

Figure 64:
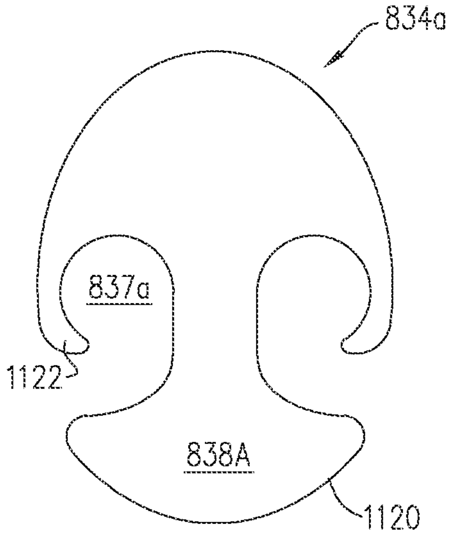

FIG. 64 shows a downstream support 834*a* that defines slots 837*a* that are open to the lateral sides of the support. This could also be viewed as downstream support 834*a* defining a fixed slot guard 838*a* with a curved face 1120 that guides any chordae tendineae around the downstream support past, rather than into, the entrances into slots 837*a*. Furthermore, at the entrances into slots 837*a* the downstream support can further define auxiliary slot guards 1122 that reduce a likelihood of tissue of the heart (e.g., a chorda tendinea) entering slots 837*a* rather than brushing past the entrances into the slots.

Figure 65A:
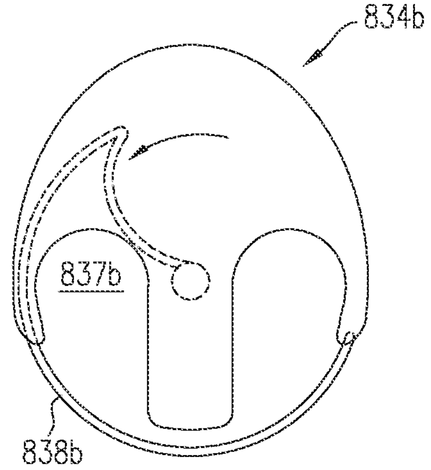
Figure 65B:
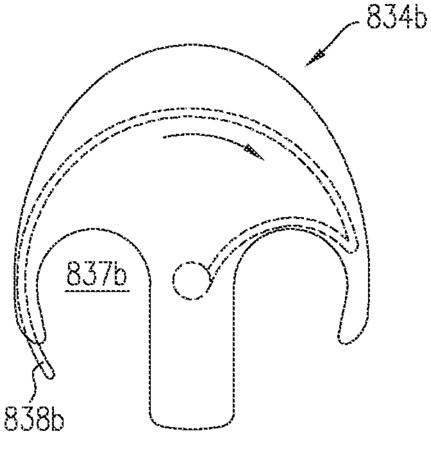

FIGS. 65A-B show a downstream support 834*b* that defines slots 837*b* and that comprises a retractable slot guard 838*b*. During advancement of system 500 and anchoring of patch 610, slot guard 838*b* is typically in its closed position, in which it covers the entrances to slots 837*b* (FIG. 65A), thereby obstructing tissue of the heart (e.g., a chorda tendinea) from entering the slot. Once patch 610 has been anchored, in order to move delivery tool 800 (or a variant thereof) away from the patch and the leaflet to which it is anchored, slot guard 838*b* is retracted from the entrances to slot 837*b* (FIG. 65B), thereby allowing cords 642 to exit the slots. Slot guard 838*b* can then be returned to its closed position for the rest of the implantation procedure. In the example shown, slot guard 838*b* comprises a curved bar. In the example shown, retraction of slot guard 838*b* is achieved via rotation.

Reference is now made to FIGS. 66A-D, which are schematic illustrations of a clasp 830*a*, in accordance with some applications. Clasp 830*a* can be a component of a delivery tool such as tool 272, tool 800, or variants thereof, but for the sake of clarity the clasp is shown independently of other parts of a delivery tool. However, for some applications clasp 830 can be used in such an independent manner. At least for some applications, clasp 830*a* can be considered to be a variant of clasp 830.

In the clasp of tool 272, the upstream support (e.g., needle-stabilizing element 276) and the downstream support (e.g., lower structural element 274) are movable toward each other via axial movement (e.g., translation). In clasp 830 of tool 800, upstream support 832 and downstream support 834 are movable toward each other via articulation (e.g., deflection). Clasp 830*a* comprises a mechanical linkage 1130 that combines these two movements. That is, in clasp 830*a*, the upstream support 832*a* and the downstream support 834*a* are movable toward each other via a combination of translation and deflection—see transition through FIGS. 67A-D. It is hypothesized that this may advantageously combine the benefits of both types of movement.

For some applications, and as shown, clasp 830*a* is actuated via an axial force. A proximally-directed axial movement of a shaft 1132 relative to upstream support 832*a* moves downstream support 834*b* and closes the clasp.

In the example shown, a first end of a link 1134 is hingedly connected to shaft 1132, and the second end of the link is hingedly connected to a lever 1136 that defines downstream support 834*a*. Lever 1136 can be considered to be a class III lever whose fulcrum 1138 is pivotably connected, via a link 1140, to upstream support 832*a* or a component fixed thereto. An additional link 1141 can provide additional pivotable coupling of lever 1136. Proximally-directed axial movement of shaft 1132 pulls the first end of link 1134 axially proximally (e.g., with the hinged connection 1133 between the shaft and the link sliding along a track 1144). This applies a pulling force on lever 1136 at a force-transfer hinge 1137, which is disposed between fulcrum 1138 and downstream support 834*a*, thereby deflecting the downstream support with respect to upstream support 832*a*. The pivotable connection of lever 1136 (e.g., fulcrum 1138 thereof) via link 1140 and/or link 1141 directs some of the force applied to the lever into swinging fulcrum 1138 proximally, thereby augmenting the deflection of downstream support 834*a* with translation of the downstream support toward upstream support 832*a*.

It is to be noted that the swinging of fulcrum 1138 is typically swinging away from upstream support 832*a* and downstream support 834*b*, thereby increasing the lateral "depth" of clasp 830*a*. It is hypothesized that this allows deeper insertion of the leaflet into the clasp as the clasp is closed, thereby advantageously facilitating anchoring further away from the lip of the leaflet.

Although many of the examples described herein (including FIGS. 31A-66D, and the descriptions thereof), relate primarily to (i) implants that comprise an upstream assembly that includes a patch and a patch anchor, a downstream assembly that comprises a winch and a winch anchor, and a tether that tethers the upstream assembly to the downstream assembly, and (ii) delivery tools for implanting such implants, it is to be noted that the scope of the present disclosure includes:

(i) for each of the upstream assemblies and patches described herein, its use as a leaflet-augmentation patch independent from a downstream assembly, e.g., with a tether anchored in the ventricle without a winch, or without a tether at all;

(ii) for each of the patch anchors described herein, its use as a tissue anchor other than for anchoring a leaflet patch to a leaflet, e.g., for anchoring a different implant to a leaflet (such as for anchoring a tether directly to a leaflet, independently from a leaflet patch), or for anchoring to a different tissue;

(iii) for each of the downstream assemblies described herein, its use independently of a leaflet-augmentation patch, e.g., with a tether anchored to a leaflet independently from a leaflet patch, or with a tether anchored to a tissue other than a leaflet; and (iv) delivery tools that comprise only certain components or mechanisms of tool 800, such as (a) only those for interacting with a heart valve leaflet (e.g., for anchoring, to the leaflet, a leaflet-augmentation patch independent from a downstream assembly), (b) only those for interacting with a patch anchor described herein, (c) only those for implanting and/or actuating a downstream assembly independent from a leaflet patch, or (d) a combination of any two of a, b, and c.

Reference is again made to FIGS. 1A-66D. Although the different terms "tether," "cord," "line," and "longitudinal member," are used to distinguish one element from another within the specification and the claims, it is to be understood that the structural, mechanical, and/or chemical properties of these elements can be different to that of the others, or many be the same as that of the others. For example, each of these elements can comprise a natural or synthetic suture, can comprise a metal and/or a polymer, or can be braided or a monofilament.

Figures 66A, 66B, 66C, 66D:
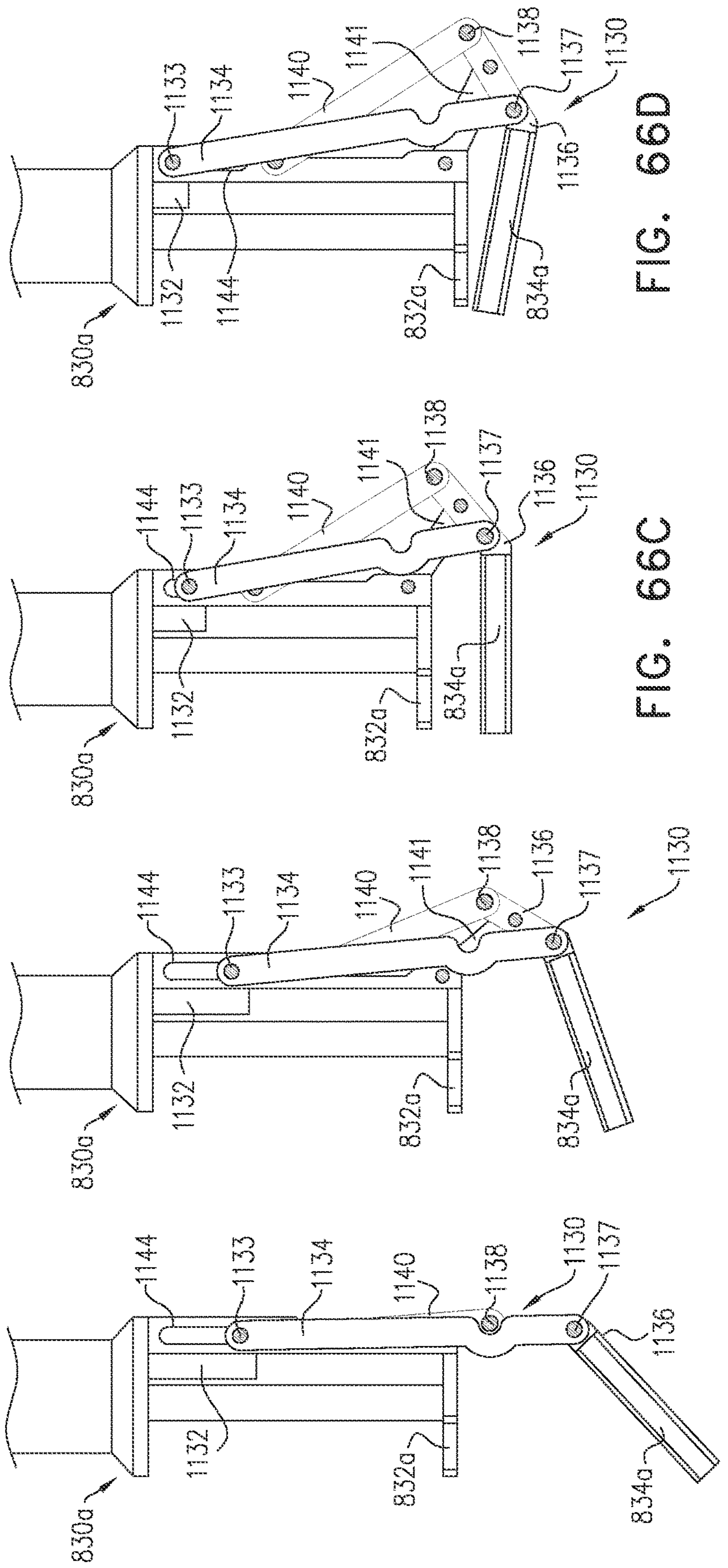
FIGS. 66A-D are schematic illustrations of a clasp, in accordance with some applications.

Reference is now made to FIGS. 1A-66D. Although for some applications ventricular anchoring is shown and/or described as anchoring to a papillary muscle, and for other applications ventricular anchoring is shown and/or described as anchoring to the ventricular wall, it is to be understood that these particular ventricular anchoring sites are by way of illustration and not limitation, e.g., they are interchangeable, mutatis mutandis.

Reference is yet again made to FIGS. 1A-66D. Although the techniques described herein are generally described as being performed on the left ventricle and/or mitral valve, the technique can also be performed on the right ventricle and/or tricuspid valve. Additionally, techniques described herein can be used during open-heart, minimally-invasive, and transcatheter procedures, mutatis mutandis.

The systems, methods, etc. herein can include adjusting a length of the artificial chords (tethers) following initial implantation (i.e., once the delivery tools have been extracted from within the body) in response to the application of energy (e.g., radiofrequency or ultrasound) toward the heart from a source of energy disposed externally to the body of the patient.

As appropriate, techniques described herein can be practiced in conjunction with methods, systems, and apparatuses described in one or more of the following patent applications, all of which are assigned to the assignee of the present application and are incorporated herein by reference for all purposes:

U.S. patent application Ser. No. 12/435,291 to Maisano et al., entitled, "Adjustable repair chords and spool mechanism therefor," filed on May 4, 2009, which issued as U.S. Pat. No. 8,147,542;

U.S. patent application Ser. No. 12/437,103 to Zipory et al., entitled, "Annuloplasty ring with intra-ring anchoring," filed on May 7, 2009, which issued as U.S. Pat. No. 8,715,342;

U.S. patent application Ser. No. 12/548,991 to Maisano et al., entitled, "Implantation of repair chords in the heart," filed on Aug. 27, 2009, which issued as U.S. Pat. No. 8,808,368;

PCT Patent Application PCT/IL2009/001209 to Cabiri et al., entitled, "Adjustable annuloplasty devices and mechanisms therefor," filed on Dec. 22, 2009, which published as PCT Publication WO 2010/073246;

PCT Patent Application PCT/IL2010/000357 to Maisano et al., entitled, "Implantation of repair chords in the heart," filed on May 4, 2010, which published as WO 2010/128502; and/or PCT Patent Application PCT/IL2010/000358 to Zipory et al., entitled, "Deployment techniques for annuloplasty ring and over-wire rotation tool," filed on May 4, 2010, which published as WO 2010/128503.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Further, the various techniques, methods, operations, steps, etc. described or suggested anywhere herein (including in documents incorporated by reference herein) can be performed on a living animal or on a non-living simulation, such as on a cadaver, cadaver heart, simulator (e.g., with the body parts, tissue, etc. being simulated), etc.

The invention claimed is:

1. An apparatus for use with a valve disposed between an atrium and a ventricle of a heart of a subject, the valve having a first leaflet and a second leaflet, and the apparatus comprising an implant that comprises:

a leaflet-augmentation patch comprising:

a flexible sheet, and a frame that supports the flexible sheet and defines a spring;

a patch anchor; and a cord, coupling the patch anchor to the patch in a manner in which anchoring the patch anchor to the first leaflet positions the patch to be a surrogate coaptation surface that moves toward, and coapts with, the second leaflet during ventricular systole, the spring being configured to tension the cord;

wherein the spring extends beyond the sheet of the patch.

2. The apparatus according to claim 1, wherein:

the implant comprises an upstream assembly that comprises the patch and the patch anchor, and the implant further comprises:

a downstream assembly comprising a winch coupled to a winch anchor that is configured to anchor the downstream assembly to tissue of the ventricle; and a tether, tethering the winch to the patch.

3. The apparatus according to claim 1, wherein the spring extends out of a plane defined by the patch.

4. An apparatus for use with a valve disposed between an atrium and a ventricle of a heart of a subject, the valve having a first leaflet and a second leaflet, and the apparatus comprising an implant that comprises:

a leaflet-augmentation patch comprising:

a flexible sheet, and a frame that supports the flexible sheet and defines a spring;

a patch anchor, the patch anchor has a sharpened tip, and is configured to be driven through the first leaflet with the sharpened tip penetrating the first leaflet; and a cord, coupling the patch anchor to the patch in a manner in which anchoring the patch anchor to the first leaflet positions the patch to coapt with the second leaflet during ventricular systole, the spring being configured to tension the cord.

5. The apparatus according to claim 4, wherein the patch anchor comprises a toggle that defines an eyelet substantially midway along the toggle, the cord being attached to the patch anchor at the eyelet, and the apparatus further comprises a retrieval line, coupled to the patch anchor at substantially an end of the toggle, and configured to de-anchor the patch anchor from the first leaflet upon tensioning of the retrieval line.

6. An apparatus for use with a valve disposed between an atrium and a ventricle of a heart of a subject, the valve having a first leaflet and a second leaflet, and the apparatus comprising an implant that comprises:

a leaflet-augmentation patch comprising:

a flexible sheet, and a frame that supports the flexible sheet and defines a spring;

a patch anchor; and a cord, coupling the patch anchor to the patch in a manner in which anchoring the patch anchor to the first leaflet positions the patch to coapt with the second leaflet during ventricular systole, the spring being configured to facilitate driving of the patch anchor through the first leaflet by transiently straining in response to tension applied to the cord by pushing the patch anchor away from the patch and through the leaflet.

7. The apparatus according to claim 6, wherein the spring is a compression spring.

8. The apparatus according to claim 6, wherein the spring is a cantilever spring that is configured to tension the cord by deflecting with respect to the flexible sheet.

9. The apparatus according to claim 6, wherein the spring lies substantially flat with respect to the flexible sheet.

10. The apparatus according to claim 6, wherein the patch anchor is configured to be driven through the leaflet while disposed within a hollow needle.

11. The apparatus according to claim 6, wherein the spring is coupled to the sheet in a manner in which the patch transiently linearly contracts as the spring transiently strains.

12. The apparatus according to claim 6, wherein the spring is coupled to the sheet in a manner in which the spring slides across the sheet as the spring transiently strains.

13. The apparatus according to claim 6, wherein:
- the patch has a lip and a root,
- the cord couples the patch anchor to the patch in a manner in which anchoring the patch anchor to the first leaflet positions the patch such that the lip of the patch extends toward the second leaflet, and
- the frame defines:
  - a lip brace at the lip of the patch, and
  - a root brace at the root of the patch.

14. The apparatus according to claim 13, wherein the frame defines a patch-anchor support coupled to the root brace, the cord extending from the spring, through the patch-anchor support, to the patch anchor.

15. The apparatus according to claim 13, wherein the spring is attached to the root brace.

16. The apparatus according to claim 15, wherein the spring extends from the root brace to the lip brace.

17. The apparatus according to claim 6, wherein the spring is a first spring, and wherein the frame further comprises a second spring, the first spring and the second spring configured to tension the cord by deflection of the first spring and the second spring away from each other.

18. The apparatus according to claim 17, wherein the cord extends back and forth between the first spring and the second spring.

19. The apparatus according to claim 6, wherein the patch anchor comprises a toggle that defines an eyelet substantially midway along the toggle, the cord being attached to the patch anchor at the eyelet, and the apparatus further comprises a retrieval line, coupled to the patch anchor at substantially an end of the toggle, and configured to de-anchor the patch anchor from the first leaflet upon tensioning of the retrieval line.

20. The apparatus according to claim 6, wherein the spring is a tension spring.

21. The apparatus according to claim 6, wherein the spring is a cantilever spring that is configured to pull the cord by deflecting with respect to the flexible sheet.

22. An apparatus for use with a valve disposed between an atrium and a ventricle of a heart of a subject, the valve having a first leaflet and a second leaflet, and the apparatus comprising an implant that comprises:
- a leaflet-augmentation patch comprising:
  - a flexible sheet, and
  - a frame that supports the flexible sheet and defines a spring;
- a patch anchor; and
- a cord:
  - coupling the patch anchor to the patch in a manner in which anchoring the patch anchor to the first leaflet positions the patch to coapt with the second leaflet during ventricular systole, and
  - passing through the sheet to the spring to be tensioned by the spring.

23. The apparatus according to claim 22, wherein the cord is coupled to the sheet in a manner in which the patch transiently linearly contracts as the cord transiently strains.

* * * * *